(12) United States Patent
Chaturvedula et al.

(10) Patent No.: US 7,470,680 B2
(45) Date of Patent: Dec. 30, 2008

(54) CONSTRAINED COMPOUNDS AS CGRP-RECEPTOR ANTAGONISTS

(75) Inventors: Prasad V. Chaturvedula, Cheshire, CT (US); Stephen E. Mercer, Middletown, CT (US); Haiquan Fang, Madison, CT (US); Xiaojun Han, Cheshire, CT (US); Guanglin Luo, Madison, CT (US); Gene M. Dubowchik, Middlefield, CT (US); Graham S. Poindexter, Old Saybrook, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/742,626

(22) Filed: May 1, 2007

(65) Prior Publication Data

US 2007/0259851 A1 Nov. 8, 2007

Related U.S. Application Data

(60) Provisional application No. 60/797,400, filed on May 3, 2006.

(51) Int. Cl.
*C07D 487/04* (2006.01)
*C07D 401/14* (2006.01)
*C07D 519/00* (2006.01)
*A61K 31/55* (2006.01)
*A61P 25/06* (2006.01)

(52) U.S. Cl. .................................. 514/212.06; 540/521
(58) Field of Classification Search ................ 540/522; 514/212.06
See application file for complete search history.

(56) References Cited

U.S. PATENT DOCUMENTS

| | | | |
|---|---|---|---|
| 2004/0229861 | A1 | 11/2004 | Burgey et al. |
| 2005/0256098 | A1 | 11/2005 | Burgey et al. |
| 2006/0094707 | A1 | 5/2006 | Chaturvedula et al. |
| 2006/0135511 | A1 | 6/2006 | Burgey |
| 2006/0148790 | A1 | 7/2006 | Burgey et al. |
| 2006/0194783 | A1 | 8/2006 | Burgey et al. |
| 2006/0229447 | A1 | 10/2006 | Chaturvedula et al. |
| 2007/0225272 | A1 | 9/2007 | Burgey et al. |

FOREIGN PATENT DOCUMENTS

| | | | |
|---|---|---|---|
| WO | WO 2004/082602 A2 | 9/2004 | |
| WO | WO 2004/087649 A2 | 10/2004 | |
| WO | WO 2004/091514 A2 | 10/2004 | |
| WO | WO 2004/092166 A2 | 10/2004 | |
| WO | WO 2004/092168 A1 | 10/2004 | |
| WO | WO 2005/000807 A2 | 1/2005 | |
| WO | WO 2005/013894 A2 | 2/2005 | |
| WO | WO 2005/072308 A2 | 8/2005 | |
| WO | WO 2006/031606 A2 | 3/2006 | |
| WO | WO 2006/041830 A2 | 4/2006 | |
| WO | WO 2006/044449 A2 | 4/2006 | |
| WO | WO 2006/044504 A1 | 4/2006 | |
| WO | WO 2006/047196 A2 | 5/2006 | |
| WO | WO 2006/052378 A1 | 5/2006 | |
| WO | WO 2006/078554 A2 | 7/2006 | |
| WO | WO 2006/099268 A2 | 9/2006 | |
| WO | WO 2007/016087 A2 | 2/2007 | |
| WO | WO 2008/085317 A1 | 7/2008 | |

OTHER PUBLICATIONS

U.S. Appl. No. 11/742,615, filed May 1, 2007, Stephen E. Mercer, et al.
Prasad, C.V.C., et al, "Enantioselective Synthesis of Aminobenzazepinones," Tetrahedron Letters, 48, pp. 2661-2665, 2007.

*Primary Examiner*—Bruck Kifle
(74) *Attorney, Agent, or Firm*—James Epperson

(57) ABSTRACT

The invention encompasses constrained bicyclic and tricyclic CGRP-receptor antagonists, methods for identifying them, pharmaceutical compositions comprising them, and methods for their use in therapy for treatment of migraine and other headaches, neurogenic vasodilation, neurogenic inflammation, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

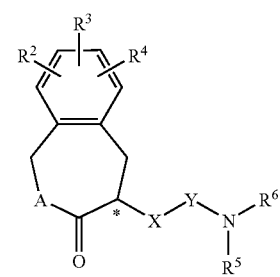

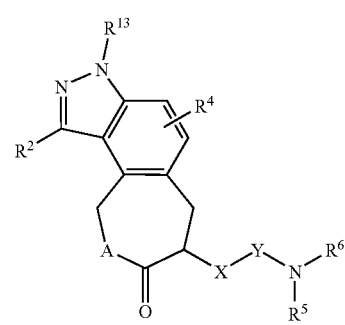

9 Claims, No Drawings

CONSTRAINED COMPOUNDS AS CGRP-RECEPTOR ANTAGONISTS

CROSS REFERENCE TO RELATED APPLICATIONS

This application claims the benefit of U.S. provisional application No. 60/797,400, filed May 3, 2006.

BACKGROUND OF THE INVENTION

Calcitonin gene-related peptide (CGRP) is a naturally occurring 37-amino-acid peptide first identified in 1982 (Amara, S. G. et al, Science 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, Br J Pharmacol 1992, 105, 441-7; Van Valen, F. et al, Neurosci Lett 1990, 119, 195-8). Two classes of CGRP receptors, CGRP1 and CGRP2, have been proposed based on the antagonist properties of the peptide fragment CGRP(8-37) and the ability of linear analogues of CGRP to activate CGRP2 receptors (Juaneda, C. et al. TiPS 2000, 21, 432-438). However, there is lack of molecular evidence for the CGRP2 receptor (Brain, S. D. et al, TiPS 2002, 23, 51-53). The CGRP1 receptor has three components: (i) a 7 transmembrane calcitonin receptor-like receptor (CRLR); (ii) the single transmembrane receptor activity modifying protein type one (RAMP 1); and (iii) the intracellular receptor component protein (RCP) (Evans B. N. et al., J Biol Chem. 2000, 275, 31438-43). RAMP1 is required for transport of CRLR to the plasma membrane and for ligand binding to the CGRP-receptor (McLatchie, L. M. et al, Nature 1998, 393, 333-339). RCP is required for signal transduction (Evans B. N. et al., J Biol Chem. 2000, 275, 31438-43). There are known species-specific differences in binding of small molecule antagonists to the CGRP-receptor with typically greater affinity seen for antagonism of the human receptor than for other species (Brain, S. D. et al, TiPS 2002, 23, 51-53). The amino acid sequence of RAMP1 determines the species selectivity, in particular, the amino acid residue Trp74 is responsible for the phenotype of the human receptor (Mallee et al. J Biol Chem 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001;15(10): 745-53; Williamson, D. J. Microsc. Res. Tech. 2001, 53, 167-178.; Grant, A. D. Brit. J. Pharmacol. 2002, 135, 356-362.). Serum levels of CGRP are elevated during migraine (Goadsby P J, et al. Ann Neurol 1990;28: 183-7) and treatment with anti-migraine drugs returns CGRP levels to normal coincident with alleviation of headache (Gallai V. et al. Cephalalgia 1995;15: 384-90). Migraineurs exhibit elevated basal CGRP levels compared to controls (Ashina M, et al., Pain 2000, 86(1-2):133-8.2000). Intravenous CGRP infusion produces lasting headache in migraineurs (Lassen L H, et al. Cephalalgia February 2002 Feb;22(1):54-61). Preclinical studies in dog and rat report that systemic CGRP blockade with the peptide antagonist CGRP(8-37) does not alter resting systemic hemodynamics nor regional blood flow (Shen, Y-T. et al, J Pharmacol Exp Ther 2001, 298, 551-8). Thus, CGRP-receptor antagonists may present a novel treatment for migraine that avoids the cardiovascular liabilities of active vasoconstriction associated with non-selective 5-HT1B/1D agonists, 'triptans' (e.g., sumatriptan).

DESCRIPTION OF THE INVENTION

The invention encompasses compounds of Formula I which are CGRP antagonists. The invention also encompasses compositions and methods of using these compounds in therapeutic treatment.

One aspect of the invention is a compound of Formula I

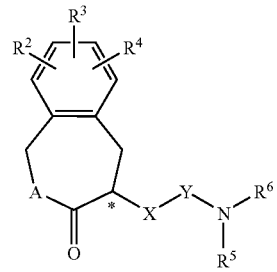

where:

A is O or $NR^1$;

$R^1$ is alkyl, alkenyl, cycloalkyl, $C_{5-7}$ cycloalkenyl, (cycloalkyl)alkyl, haloalkyl, alkoxyalkyl, $(Ar^1)$alkyl, $(NR^7R^8)$alkyl, $N-(R^9)$-pyrrolidinyl or $N-(R^9)$-piperidinyl;

$R^2$ is hydrogen, halo, alkyl or alkenyl;

$R^3$ is hydrogen, halo, alkyl, or alkenyl;

or $R^2$ and $R^3$ taken together is $N(R^{13})N=C(R^4)$;

$R^4$ is hydrogen, halo, alkyl, or alkenyl;

$NR^5R^6$ taken together is

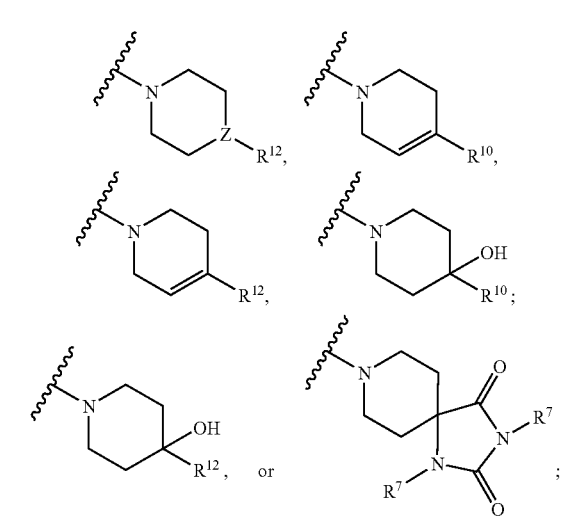

$R^7$ is hydrogen or alkyl;
$R^8$ is hydrogen or alkyl;

or NR⁷R⁸ taken together is selected from the group consisting of pyrrolidinyl, piperidinyl, N—(R⁹)-piperazinyl, morpholinyl, and thiomorpholinyl;

R⁹ is hydrogen, alkyl, alkylcarbonyl, or alkoxycarbonyl;

R¹⁰ is phenyl, naphthyl, pyridinyl, pyridinyl N-oxide, quinolinyl, quinolinyl N-oxide, isoquinolinyl, or isoquinolinyl N-oxide, and is substituted with 0-2 substituents selected from the group consisting of halo, alkyl, haloalkyl, alkoxy, hydroxy, and phenyl;

or R¹⁰ is selected from the group consisting of

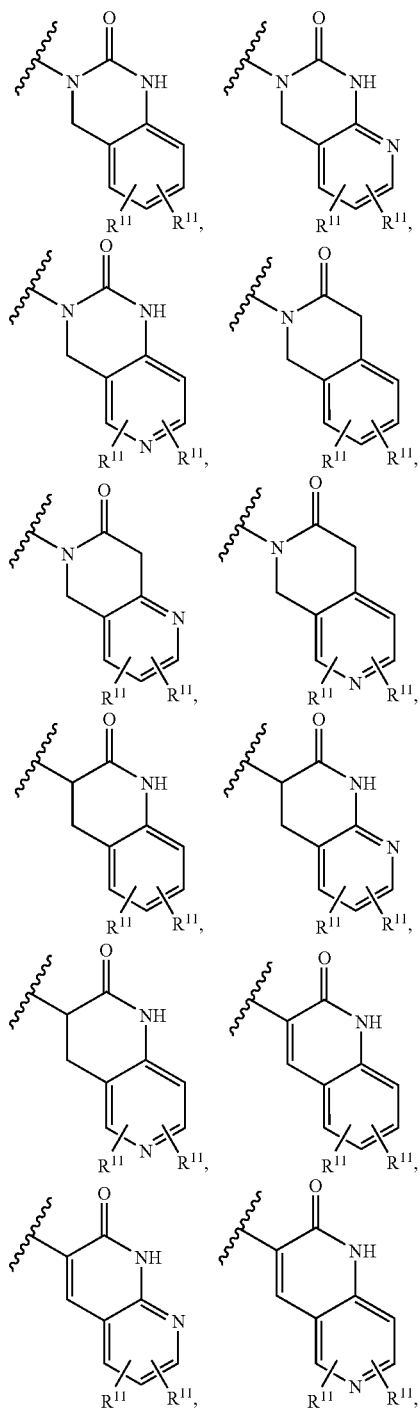

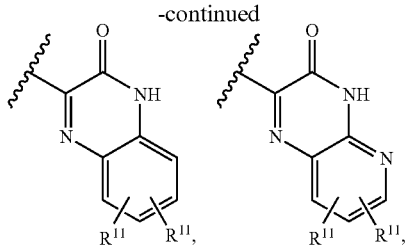

-continued

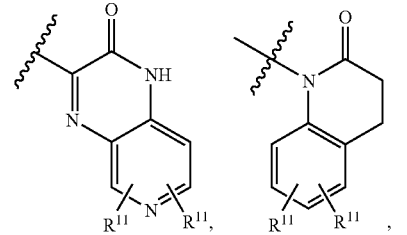

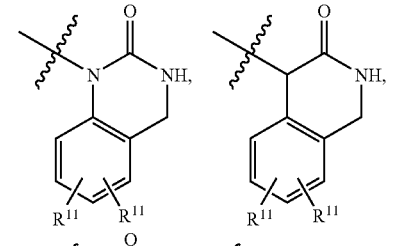

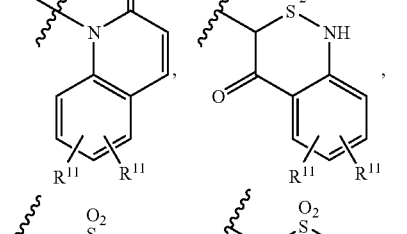

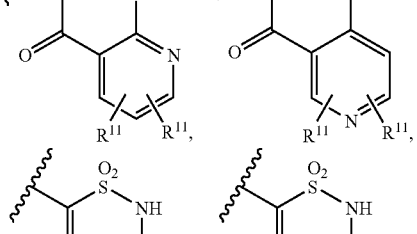

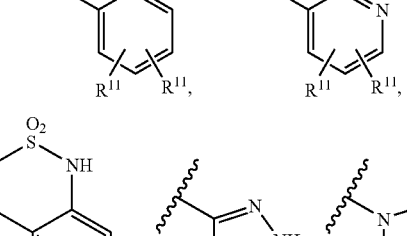

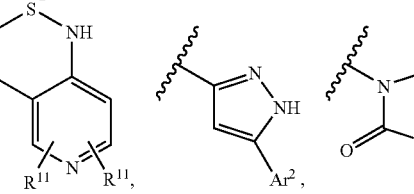

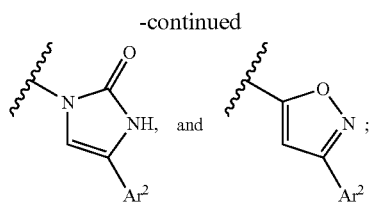

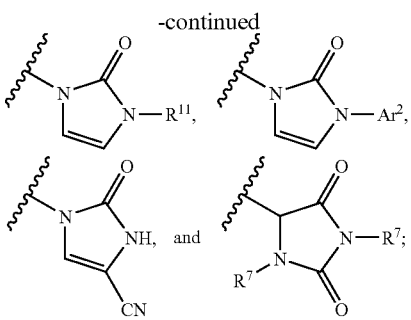

$R^{11}$ is hydrogen, halo, alkyl, haloalkyl, or alkoxy;
$R^{12}$ is selected from the group consisting of

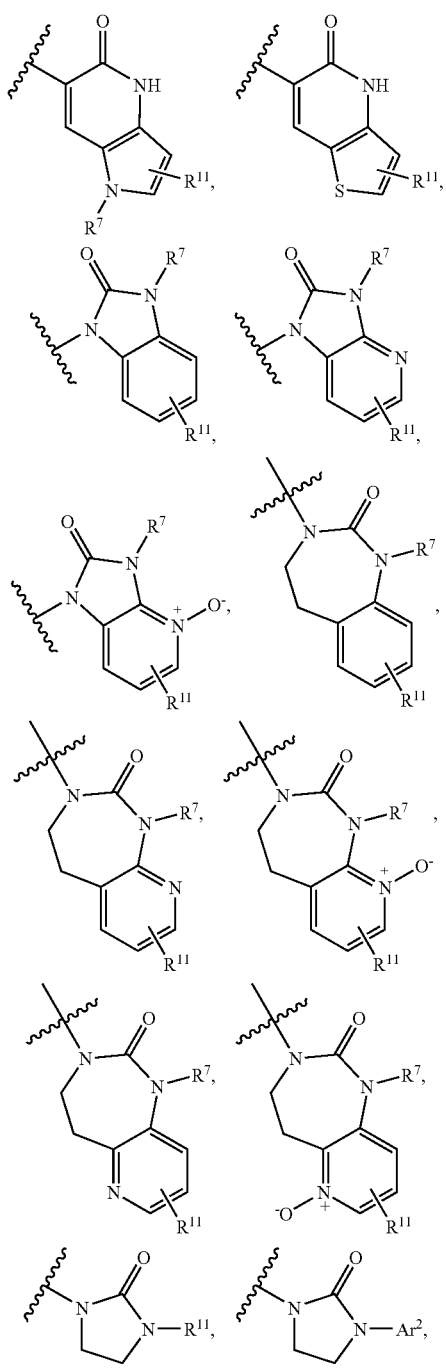

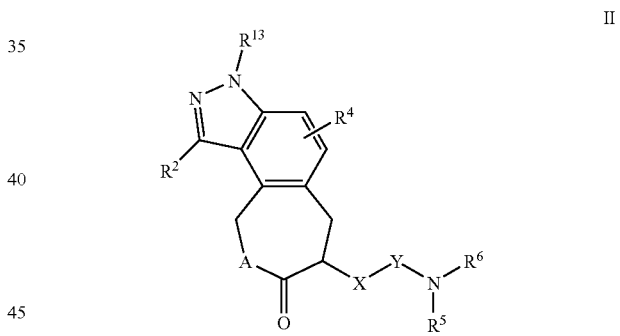

$R^{13}$ is hydrogen, alkyl, alkenyl, alkoxyalkyl, or benzyl;

$Ar^1$ is phenyl, naphthyl, pyridinyl, or imidazolyl, and is substituted with 0-2 substituents selected from the group consisting of halo, alkyl, and haloalkyl;

$Ar^2$ is phenyl, naphthyl, or pyridinyl, and is substituted with 0-2 substituents selected from the group consisting of halo, alkyl, and haloalkyl;

X—Y is aminocarbonyl, oxycarbonyl, methylenecarbonyl, ethylene, or amino(cyano)iminomethyl;

Z is N or CH; and the carbon bearing the asterisk is either the (S) configuration or the (R) configuration;

or a pharmaceutically acceptable salt thereof.

Another aspect of the invention is a compound of formula II

II

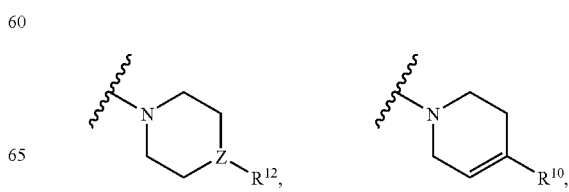

where:

A is O or $NR^1$;

$R^1$ is alkyl, alkenyl, cycloalkyl, $C_{5-7}$ cycloalkenyl, (cycloalkyl)alkyl, haloalkyl, alkoxyalkyl, $(Ar^1)$alkyl, $(NR^7R^8)$alkyl, N—$(R^9)$-pyrrolidinyl or N—$(R^9)$-piperidinyl;

$R^2$ is hydrogen, halo, alkyl, or alkenyl;

$R^3$ is hydrogen, halo, alkyl, or alkenyl;

$R^4$ is hydrogen, halo, alkyl, or alkenyl;

$NR^5R^6$ taken together is

-continued

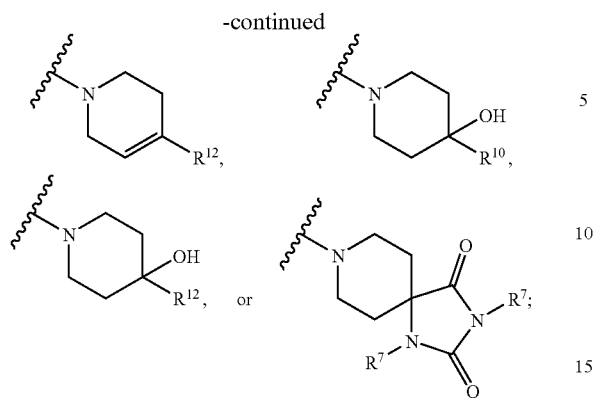

R[7] is hydrogen or alkyl;
R[8] is hydrogen or alkyl;
or NR[7]R[8] taken together is selected from the group consisting of pyrrolidinyl, piperidinyl, N—(R[9])-piperazinyl, morpholinyl, and thiomorpholinyl;
R[9] is hydrogen, alkyl, alkylcarbonyl, or alkoxycarbonyl;
R[10] is phenyl, naphthyl, pyridinyl, pyridinyl N-oxide, quinolinyl, quinolinyl N-oxide, isoquinolinyl, or isoquinolinyl N-oxide, and is substituted with 0-2 substituents selected from the group consisting of halo, alkyl, haloalkyl, alkoxy, hydroxy, and phenyl;
or R[10] is selected from the group consisting of

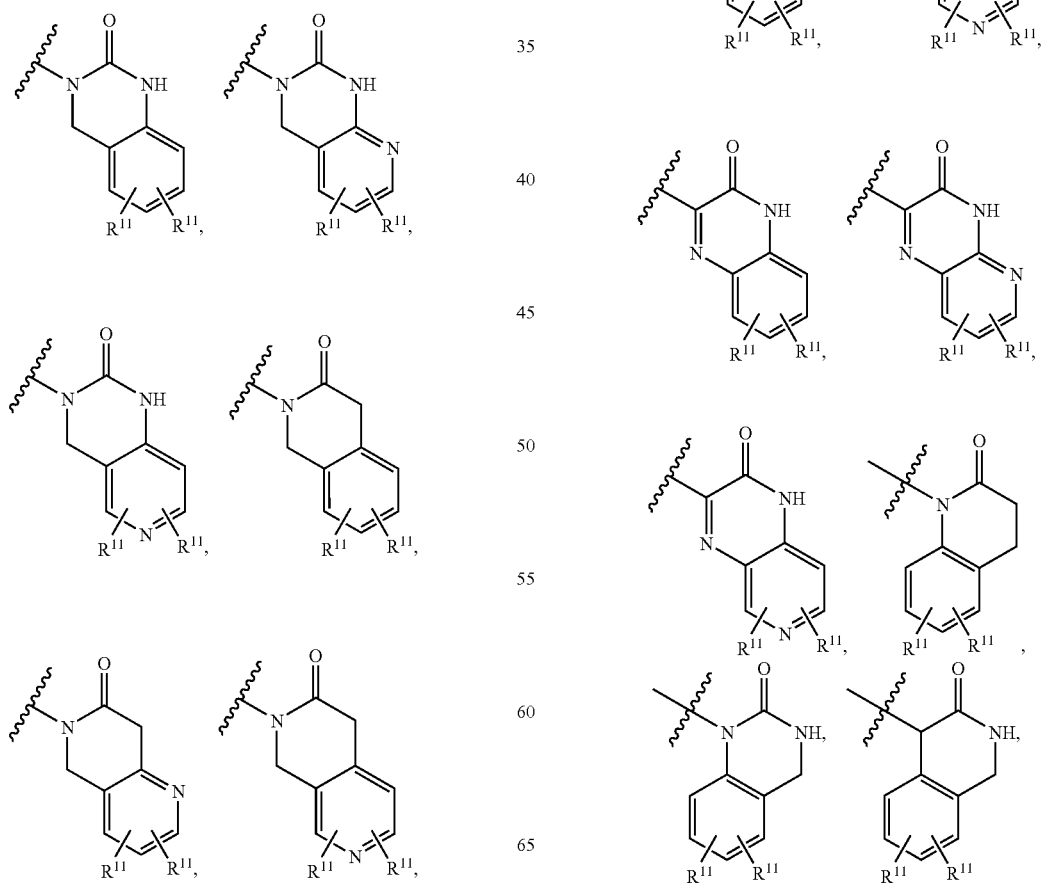

-continued

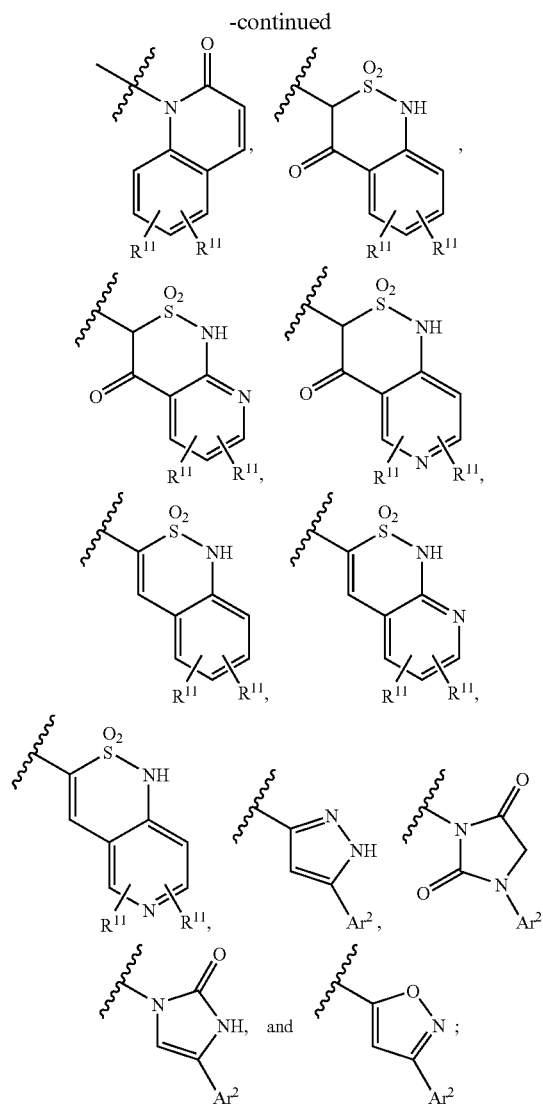

$R^{11}$ is independently hydrogen, halo, alkyl, haloalkyl, or alkoxy;

$R^{12}$ is selected from the group consisting of

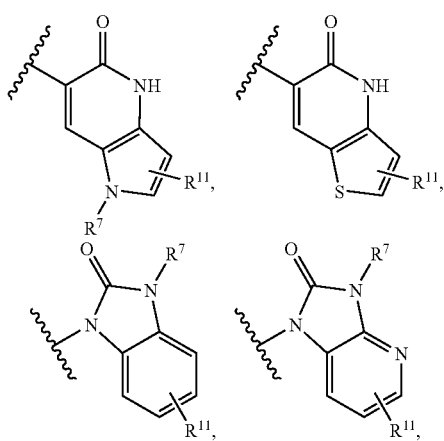

$R^{13}$ is hydrogen, alkyl, alkenyl, alkoxyalkyl, or benzyl;

$Ar^1$ is phenyl, naphthyl, pyridinyl, or imidazolyl, and is substituted with 0-2 substituents selected from the group consisting of halo, alkyl, and haloalkyl;

$Ar^2$ is phenyl, naphthyl, or pyridinyl, and is substituted with 0-2 substituents selected from the group consisting of halo, alkyl, and haloalkyl;

X—Y is aminocarbonyl, oxycarbonyl, methylenecarbonyl, ethylene, or amino(cyano)iminomethyl;

Z is N or CH; and the carbon bearing the asterisk is either the (S) configuration or the (R) configuration;

or a pharmaceutically acceptable salt thereof.

Another aspect of the invention is a compound of the following formula II where A is $NR^1$

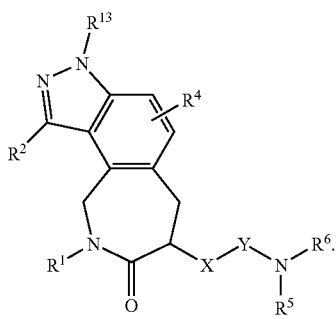

Another aspect of the invention is a compound of Formula II where the carbon marked with an asterisk is of the (S) stereochemistry.

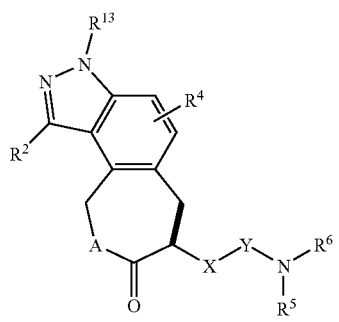

Another aspect of the invention is a compound of Formula II where the carbon marked with an asterisk is of the (R) stereochemistry.

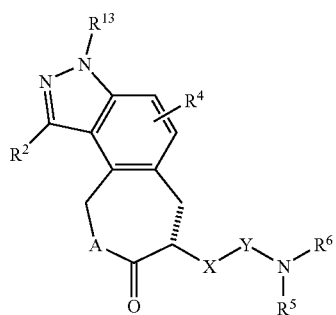

Another aspect of the invention is that any scope of a variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $Ar^1$, $Ar^2$, X—Y, A, and Z, can be used with any scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic ring systems.

"Amino" includes includes primary, secondary, and tertiary amine moieties. "Carbonyl" means CO. "Oxy" means —O—. "Aminocarbonyl" means —N(R)C(=O)—. "Oxycarbonyl" means —OC(=O)—. "Methylenecarbonyl" means —CH$_2$C(=O)—. "Amino(cyano)iminomethyl" means —NHC(=NCN)—. Parenthetic and multiparenthetic terms are intended to clarify bonding relationships to those skilled in the art. For example, a term such as ((R)alkyl) means an alkyl substituent further substituted with the substituent R. A term such as N—(R)-pyrrolidinyl indicates that the nitrogen is substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some compounds of the invention may exist in stereoisomeric forms, one example of which is shown below. The invention includes all stereoisomeric and tautomeric forms of the compounds.

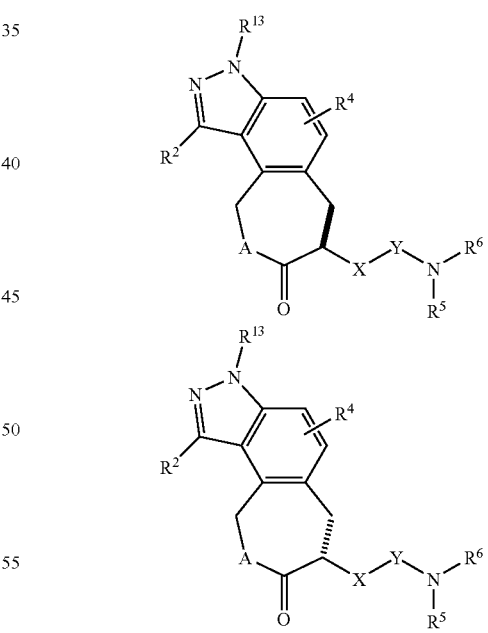

Synthetic Methods

The compounds described in the present invention can be synthesized by methods known in the art some of which are described in Schemes 1-9 as well as other procedures described in the specific embodiments section. Starting materials are commercially available or synthesized by common synthetic procedures. Variations of the compounds and the procedures to make them which are not illustrated are within the skill of the art. The variables describing general structural formulas and features in the synthetic schemes are distinct from and should not be confused with the variables in the claims or the rest of the specification. These variables are meant only to illustrate how to make some of the compounds of the invention.

Scheme 1 describes how to make certain compounds of the invention. Regiospecific introduction of iodine on a appropriately substituted aromatic ring can be accomplished using iodine monochloride. Aryl iodides (II) are good coupling partners in palladium-mediated Heck reactions. The Heck products (III) can be reduced with hydrogen mediated by number of asymmetric catalysts to produce enatiomerically pure materials (IV). Subsequent hydrolysis of acetate functionality with methanolic potassium carbonate followed by treatment of alcohol (V) with thionyl chloride can produce benzylic chlorides (VI). Treatment of benzylic chlorides with various amines in acetonitrile can deliver requisite amines (VII).

The amines (VII) can be converted into desired azepinones (VIII) in refluxing toluene mediated by catalytic acetic acid. The azepinone intermediates VIII (X=NH, $CH_2$, O) can in turn be elaborated into final products. Hydrogenolysis of VIII (X=NH) under 10% Pd on carbon produces amine intermediate IX (Scheme II). The amine functionality can be transformed to the desired urea functionality (X) with the assistance of phosgene or N,N'-disuccinimyl dicarbonate and various amines (Scheme 2). Alternatively, the succinic ester VIII (X=$CH_2$) can be converted to carboxylic acid (XI) with lithium hydroxide, followed by reaction with an appropriate amine under TBTU coupling conditions to give desired amides (XII) (Scheme 3).

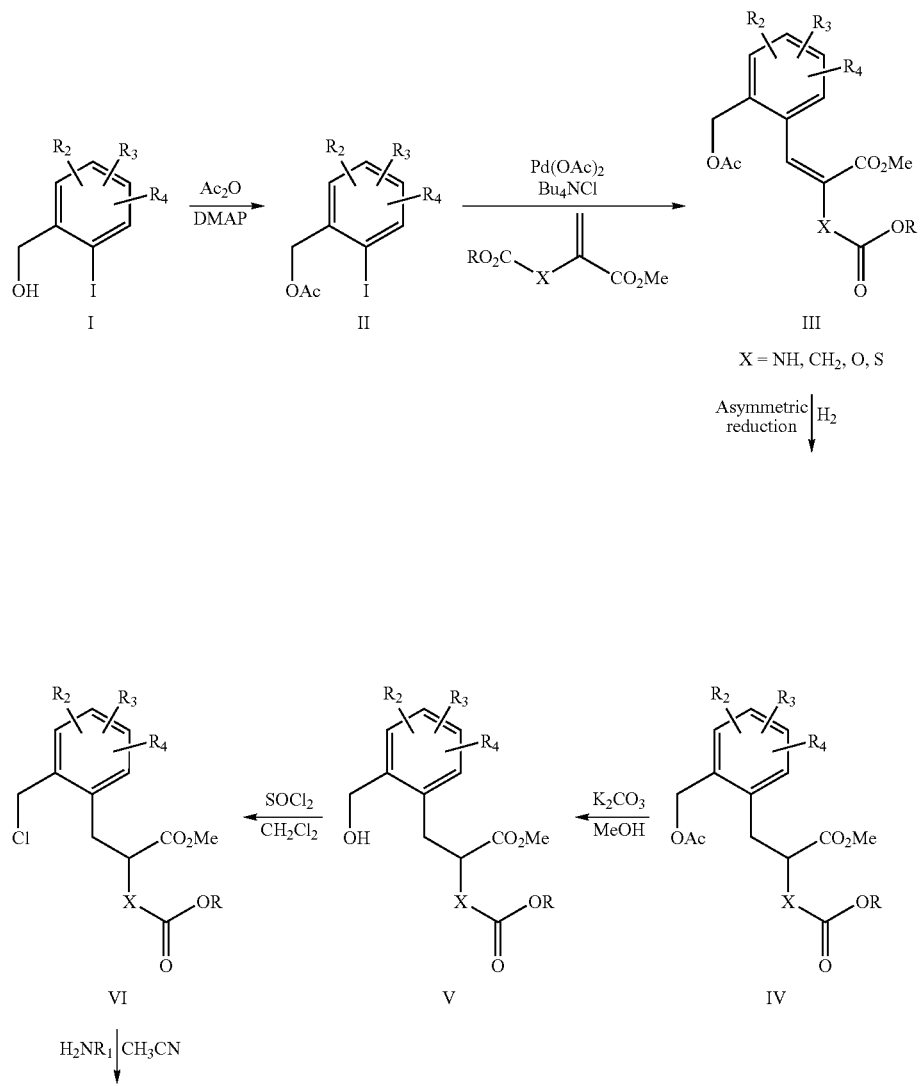

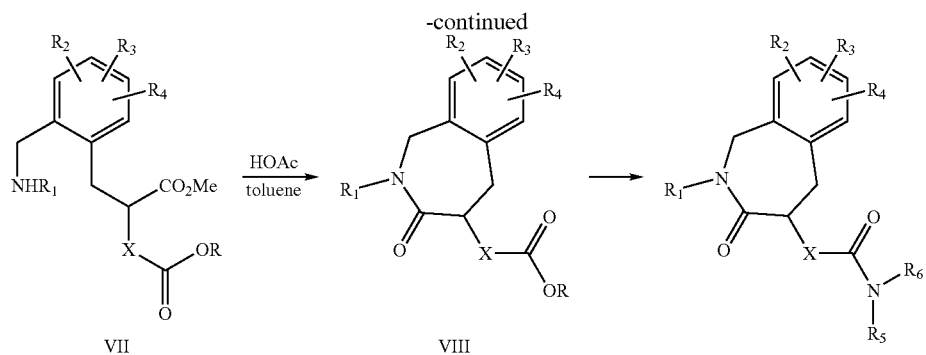
Scheme 2.
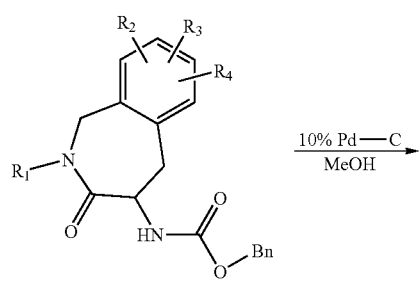
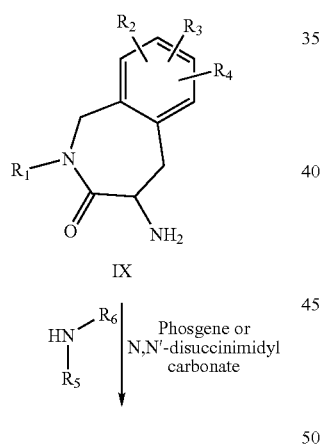
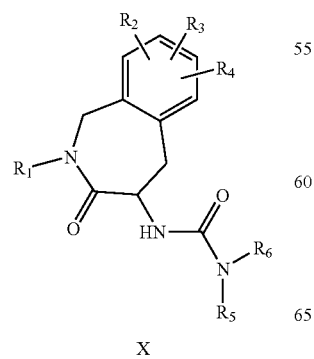
Scheme 3.
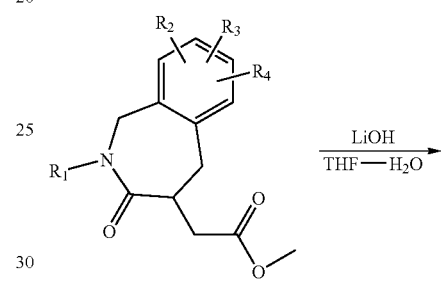
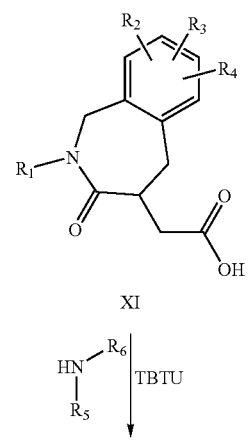

In a manner similar to urea formation, cyanoguanidine XIII can be prepared using diphenyl N-cyanocarboimidate and various substituted amines (Scheme 4).
Scheme 4.
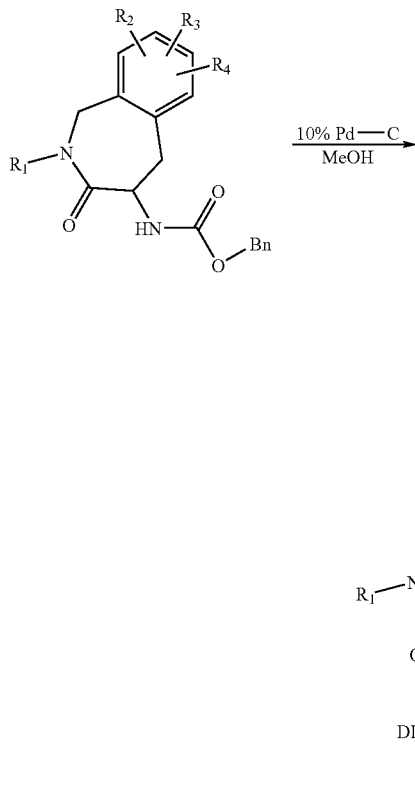
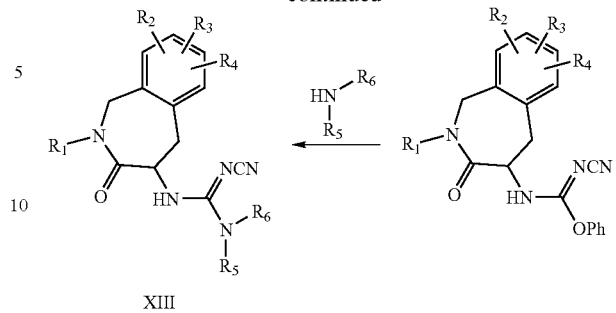
XIII
Scheme 5.
Conditions:
(a) NaH (60%), THF, 0° C., and then TIPS-Cl.
(b) sec-BuLi, THF, -78° C., and then (MeO)3O, -78° C.,
(c) HCl (4M in 1,4-dioxane), THF, 0° C. -> rt.
Scheme 6.
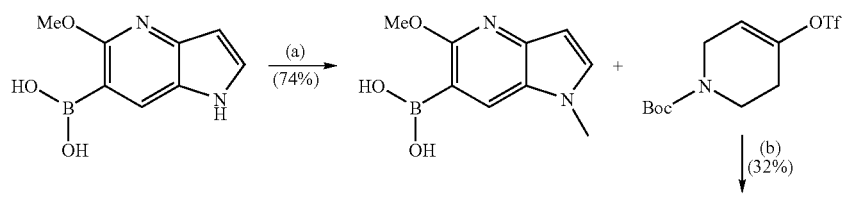
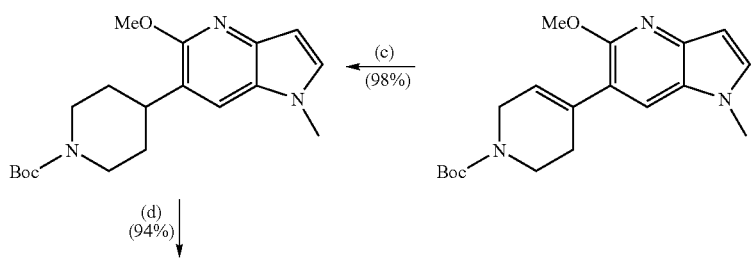

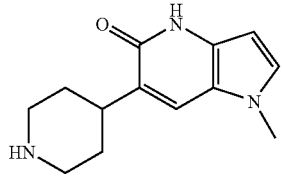
Conditions:
(a) NaH (60%), THF, 0° C., and then I-Me.
(b) Na₂CO₃, LiCl, ((PPh₃)₄Pd(0), 1,4-dioaxne/H₂O, 80° C.
(c) Pd(0)/C, H₂ (60 psi), MeOH, rt. (d) TMS-I, CH₂Cl₂, 60° C.
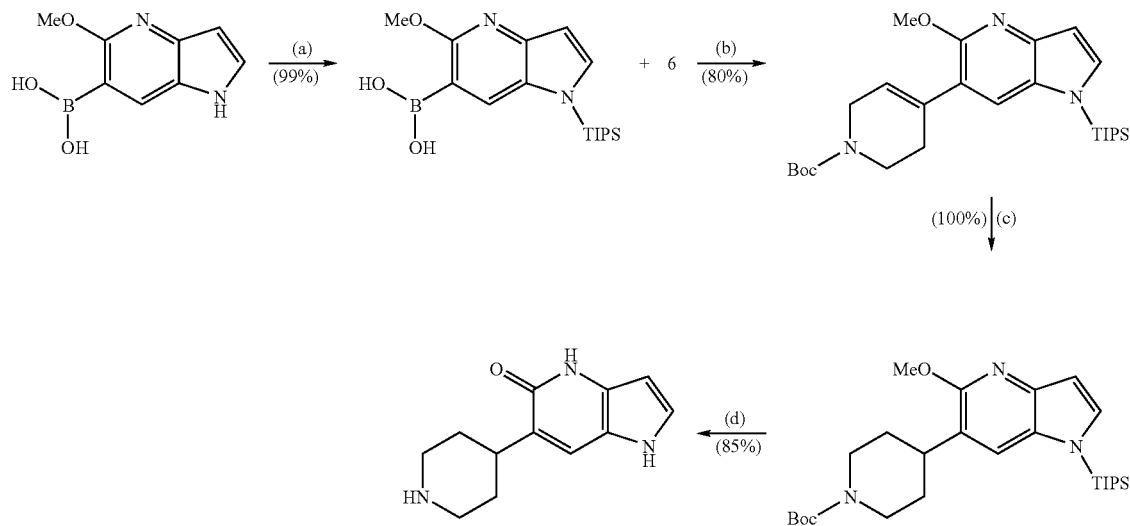
Conditions:
(a) NaH (60%), TIPS-Cl. THF, 0° C.
(b) Na₂CO₃, LiCl, ((PPh₃)₄Pd(0), 1,4-dioaxne/H₂O, 80° C.
(c) Pd(0)/C, H₂ (60 psi), MeOH, rt.
(d) TMS-I, CH₂Cl₂, 60° C.
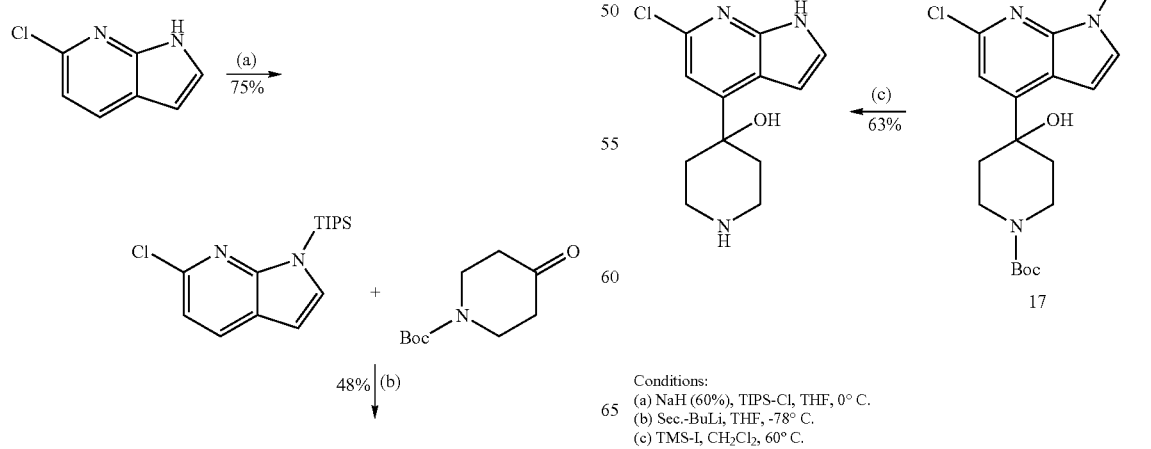
Conditions:
(a) NaH (60%), TIPS-Cl, THF, 0° C.
(b) Sec.-BuLi, THF, -78° C.
(c) TMS-I, CH₂Cl₂, 60° C.

Scheme 9.

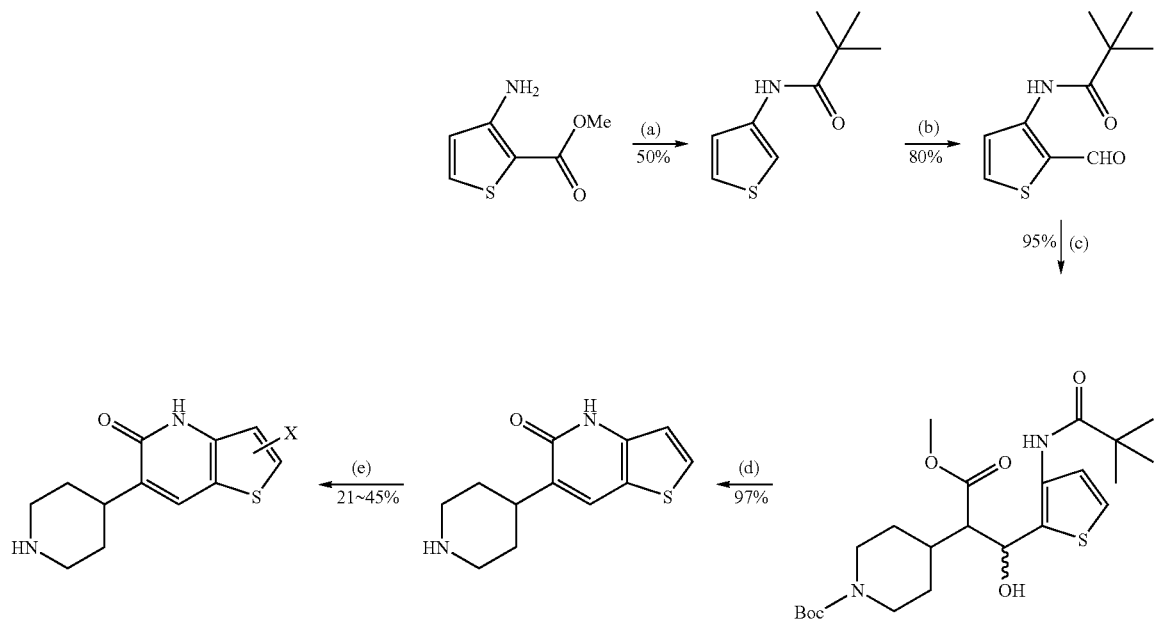

Conditions:
(a) pyvaloyl chloride, py, reflux.
(b) n-BuLi, THF, -78° C. and then DMF, -78° C. -> rt.
(c) DIEA, n-BuLi, -78° C., THF; NaH(60%), THF, 0° C.
(d) conc. HCl, H$_2$O, MeOH, reflux.
(e) MeOH, silica gel, NBS or NCS, rt or 60° C.

Biological Methods

CGRP Binding Assay. Tissue Culture. SK-N-MC cells were grown at 37° C. in 5% CO$_2$ as a monolayer in medium consisting of MEM with Earle's salts and L-glutamine (Gibco) supplemented with 10% fetal bovine serum (Gibco). Cell Pellets. The cells were rinsed twice with phosphate-buffered saline (155 mM NaCl, 3.3 mM Na$_2$HPO$_4$, 1.1 mM KH2PO4, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was then aliquoted and stored at −80° C. until needed.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM MgCl$_2$, 0.005% Triton X-100) and transferred (volume 50 µl) into 96 well assay plates. [$^{125}$I]-CGRP (Amersham Biosciences) was diluted to 60 pM in assay buffer and a volume of 50 µ was added to each well. SK-N-MC pellets were thawed, diluted in assay buffer with fresh 0.1% mammalian protease inhibitor cocktail (Sigma), and homogenized again. SK-N-MC homogenate (5 µg/well) was added in a volume of 100 µl. The assay plates were then incubated at room temperature for 2 h. Assays were stopped by addition of excess cold wash buffer (20 mM Tris-Cl pH 7.5, 0.1% BSA) immediately followed by filtration over glass fiber filters (Whatman GF/B) previously soaked in 0.5% PEI. Non-specific binding was defined with 1 µM beta-CGRP. Protein bound radioactivity was determined using a gamma or scintillation counter. The IC$_{50}$ was defined as the concentration of a compound of invention required to displace 50% of radioligand binding.

Cyclic AMP Functional Antagonism Assay. Antagonism of the compounds of invention was determined by measuring the formation of cyclic AMP (adenosine 3'5'-cyclic monophosphate) in SK-N-MC cells that endogenously express the human CGRP receptor. CGRP receptor complex is coupled with Gs protein and CGRP binding to this complex leads to the cyclic AMP production via Gs-dependent activation of an adenylate cyclase (Juaneda C. et al., TiPS, 2000; 21:432-438). Consequently, CGRP receptor antagonists inhibit CGRP—induced cyclic AMP formation in SK-N-MC cells (Doods H, et al., Br J Pharmacol, 2000; 129(3):420-423). For cyclic AMP measurements SK—N-MC cells were incubated with 0.3 nM CGRP alone or in the presence of various concentrations of the compounds of invention for 30 min at room temperature. Compounds of invention were pre-incubated with SK—N-MC cells for 15 min before the addition of CGRP to allow receptor occupancy (Edvinsson et al., Eur J Pharmacol, 2001, 415:39-44). Cyclic AMP was extracted using the lysis reagent and its concentration was determined by radioimmunoassay using RPA559 cAMP SPA Direct Screening Assay Kit (Amersham Pharmacia Biotech). IC$_{50}$ values were calculated using Excel fit. The tested compounds of invention were determined to be antagonists as they exhibited a dose—dependent inhibition of the CGRP—induced cyclic AMP production.

TABLE 1
CGRP Binding.
| Compound | CGRP binding IC$_{50}$ (nM) |
| --- | --- |
| 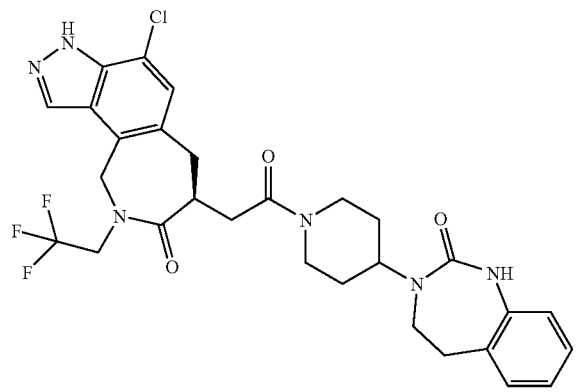 | A |
| 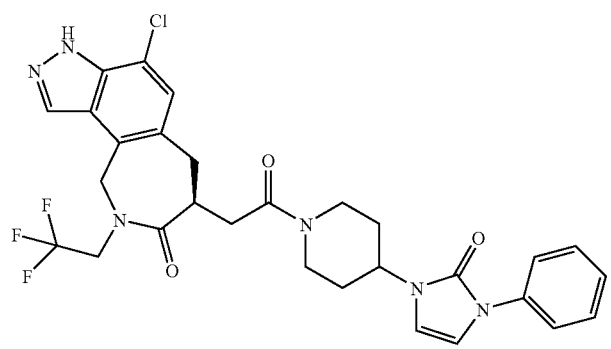 | C |
| 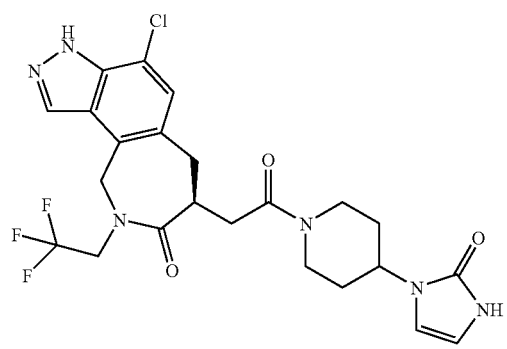 | A |
| 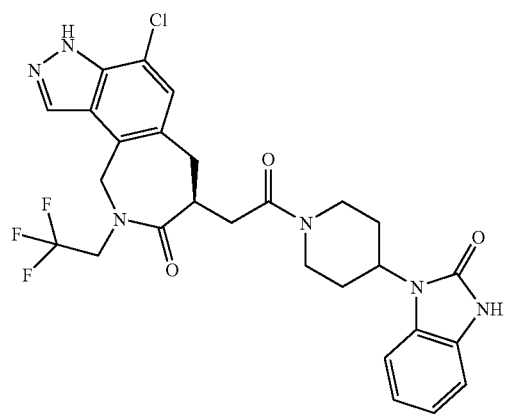 | A |

TABLE 1-continued

CGRP Binding.

| Compound | CGRP binding IC$_{50}$ (nM) |
|---|---|
| [structure] | B |
| [structure] | D |
| [structure] | D |
| [structure] | A |

TABLE 1-continued
CGRP Binding.
| Compound | CGRP binding IC$_{50}$ (nM) |
|---|---|
| 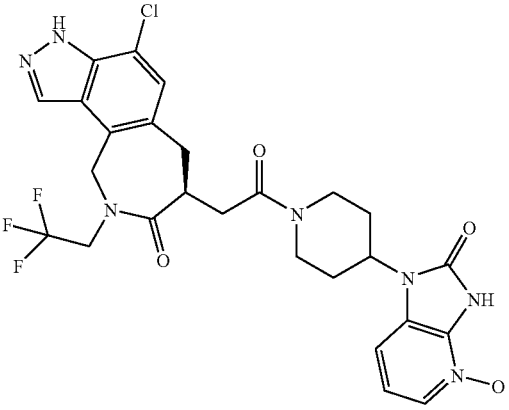 | B |
| 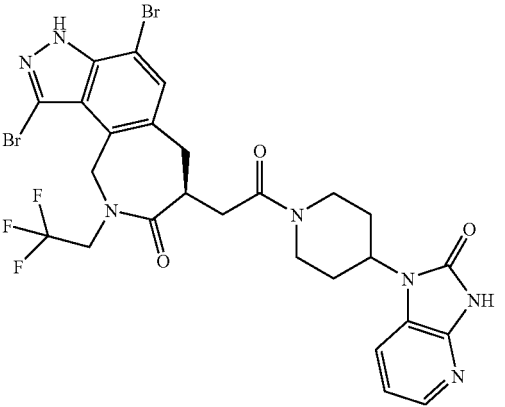 | A |
| 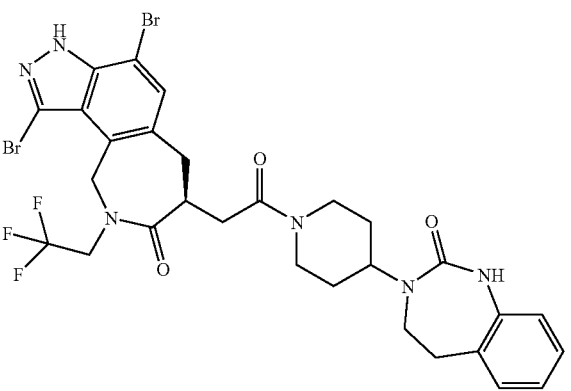 | A |

TABLE 1-continued
CGRP Binding.
| Compound | CGRP binding IC$_{50}$ (nM) |
| --- | --- |
| 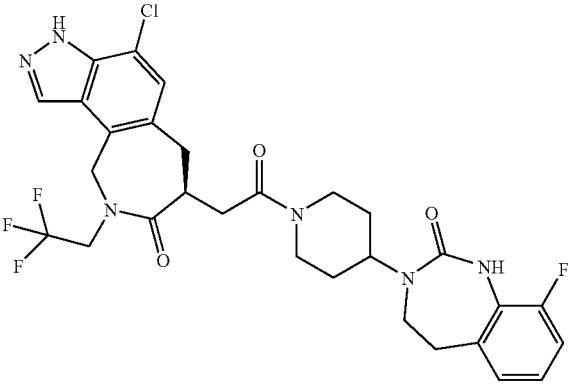 | B |
| 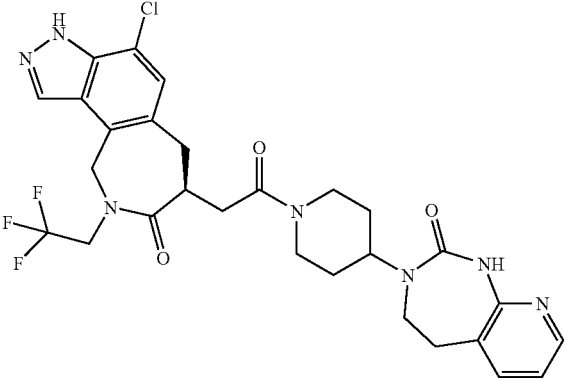 | A |
| 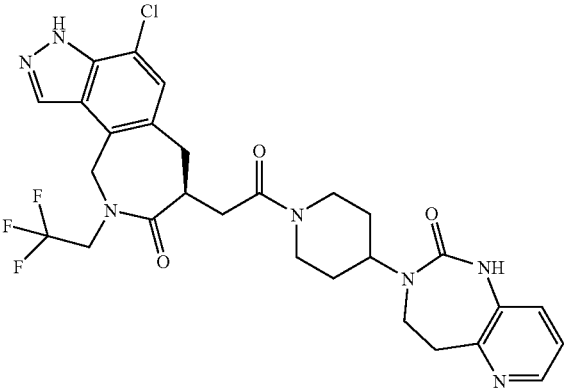 | A |

TABLE 1-continued

CGRP Binding.

| Compound | CGRP binding IC$_{50}$ (nM) |
|---|---|
| [structure] | A |
| [structure] | A |
| [structure] | A |

TABLE 1-continued

CGRP Binding.

| Compound | CGRP binding IC$_{50}$ (nM) |
|---|---|
| (structure) | A |
| (structure) | A |
| (structure) | A |

TABLE 1-continued

CGRP Binding.

| Compound | CGRP binding IC$_{50}$ (nM) |
|---|---|
| | A |
| | A |
| | A |

TABLE 1-continued

CGRP Binding.

| Compound | CGRP binding IC$_{50}$ (nM) |
|---|---|
| [structure] | A |
| [structure] | |
| [structure] mixture | A |
| [structure] mixture | |

TABLE 1-continued
CGRP Binding.
| Compound | CGRP binding IC$_{50}$ (nM) |
|---|---|
| 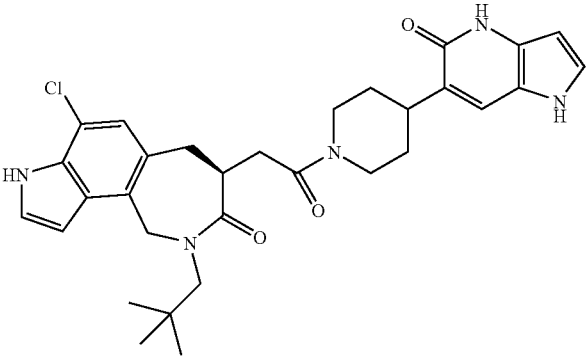 | A |
| 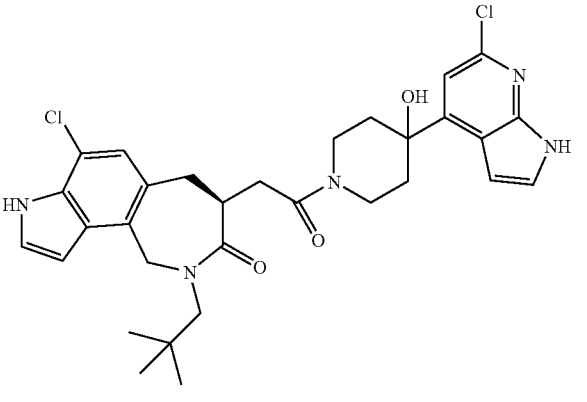 | C |
| 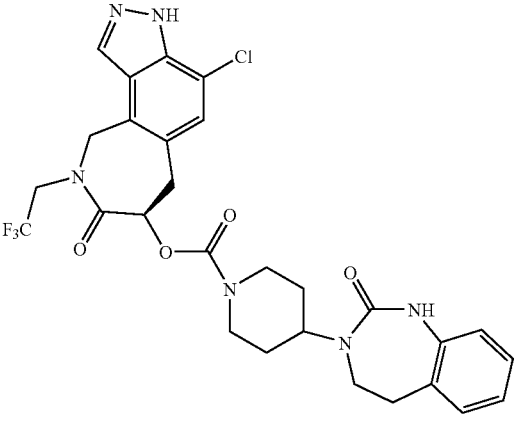 | A |
| 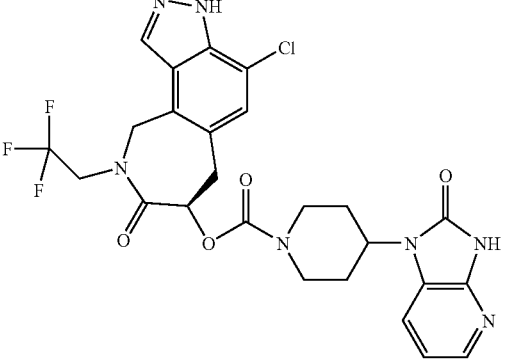 | A |

TABLE 1-continued

CGRP Binding.

| Compound | CGRP binding IC$_{50}$ (nM) |
|---|---|
| (structure) | A |
| (structure) | C |
| (structure) | B |
| (structure) | B |

TABLE 1-continued

CGRP Binding.

| Compound | CGRP binding IC$_{50}$ (nM) |
| --- | --- |
| [structure] | A |
| [structure] | B |
| [structure] | B |
| [structure] | A |

TABLE 1-continued
CGRP Binding.
| Compound | CGRP binding IC$_{50}$ (nM) |
|---|---|
| 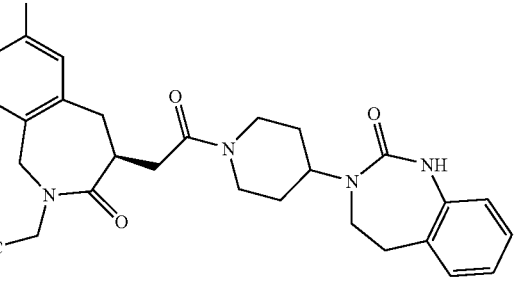 | B |
| 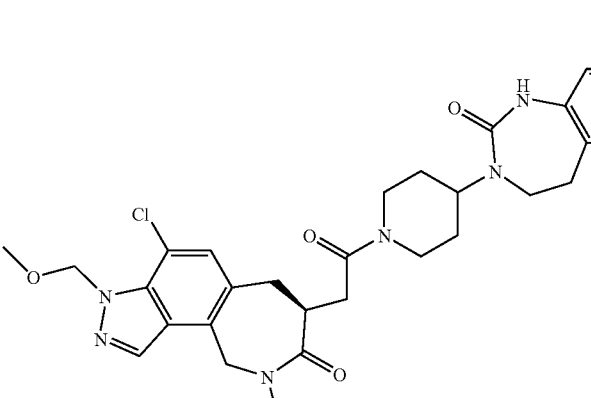 | B |
| 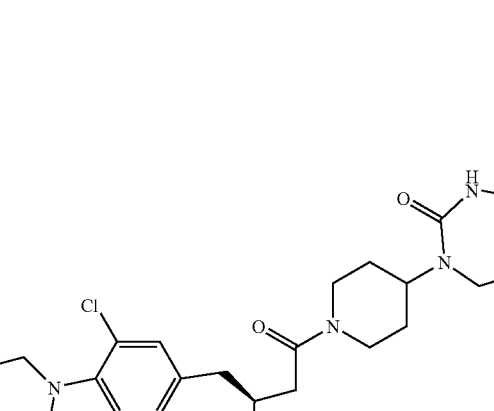 | A |
A 0.01-10 nM;
B = 10-100 nM;
C = 100-1000 nM;
D > 1000 nM.

Table 2 discloses some compounds which have been shown to inhibit CGRP. Results for Table 2 are denoted as follows: A 0.01-10 nM; B=10-100 nM; C=100-1000 nM; D>1000 nM.

TABLE 2

CGRP Binding and cAMP Functional Data

| Compound | CGRP binding IC$_{50}$ (nM) | cAMP Function IC$_{50}$ (nM) |
| --- | --- | --- |
|  | B | B |
|  | C | * |
|  | C | * |

TABLE 2-continued

CGRP Binding and cAMP Functional Data

| Compound | CGRP binding IC$_{50}$ (nM) | cAMP Function IC$_{50}$ (nM) |
|---|---|---|
| | C | * |
| | C | * |
| | B | B |

TABLE 2-continued
CGRP Binding and cAMP Functional Data
| Compound | CGRP binding IC$_{50}$ (nM) | cAMP Function IC$_{50}$ (nM) |
|---|---|---|
| 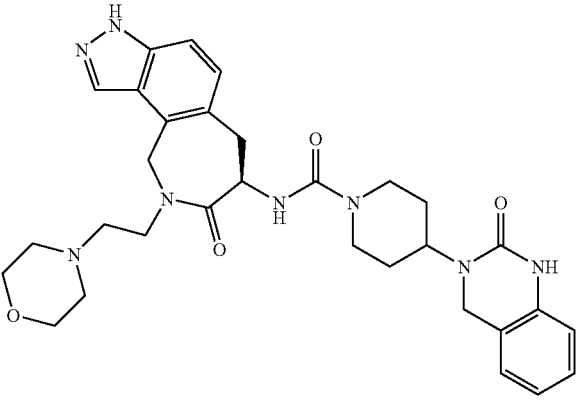 | B | * |
| 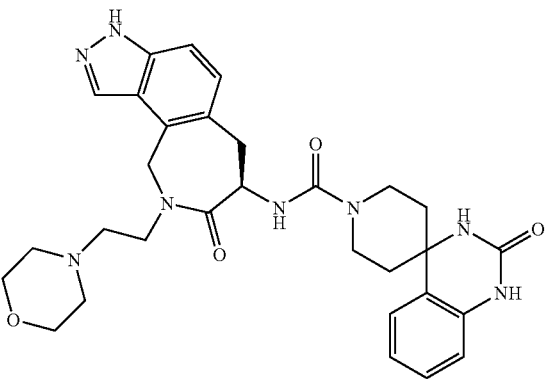 | D | * |
| 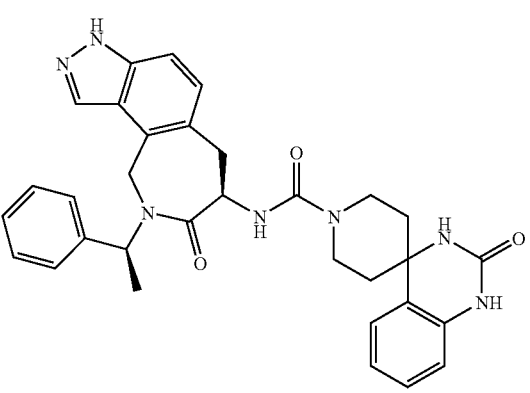 | C | * |

TABLE 2-continued

CGRP Binding and cAMP Functional Data

| Compound | CGRP binding IC$_{50}$ (nM) | cAMP Function IC$_{50}$ (nM) |
|---|---|---|
| | B | B |
| | B | B |
| | A | A |

TABLE 2-continued
CGRP Binding and cAMP Functional Data
| Compound | CGRP binding IC$_{50}$ (nM) | cAMP Function IC$_{50}$ (nM) |
|---|---|---|
| 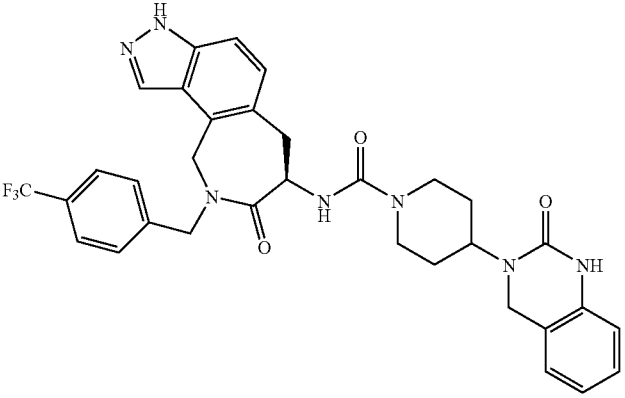 | B | * |
| 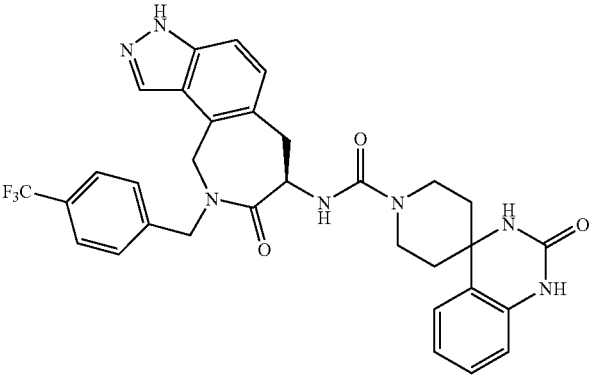 | C | * |
| 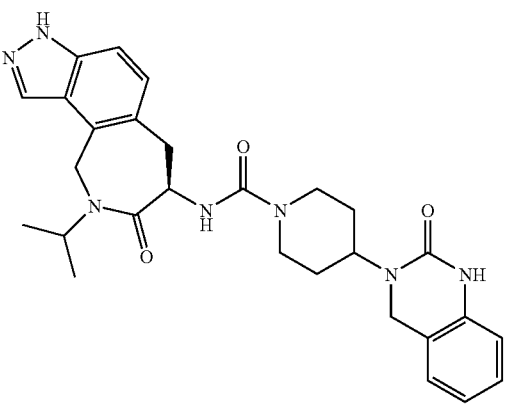 | B | * |

TABLE 2-continued

CGRP Binding and cAMP Functional Data

| Compound | CGRP binding IC$_{50}$ (nM) | cAMP Function IC$_{50}$ (nM) |
|---|---|---|
| | A | A |
| | B | * |
| | C | * |

TABLE 2-continued
CGRP Binding and cAMP Functional Data
| Compound | CGRP binding IC$_{50}$ (nM) | cAMP Function IC$_{50}$ (nM) |
|---|---|---|
| 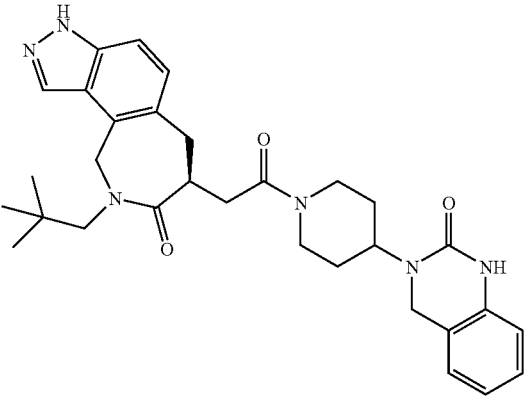 | B | A |
| 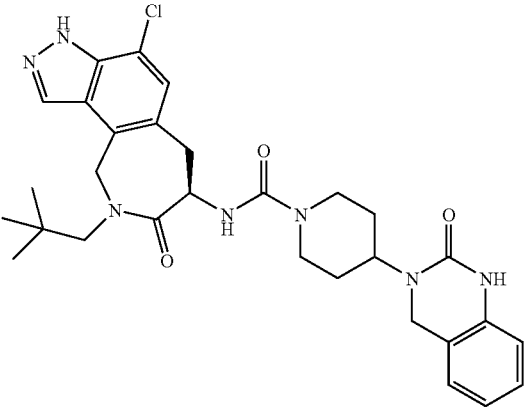 | A | A |
| 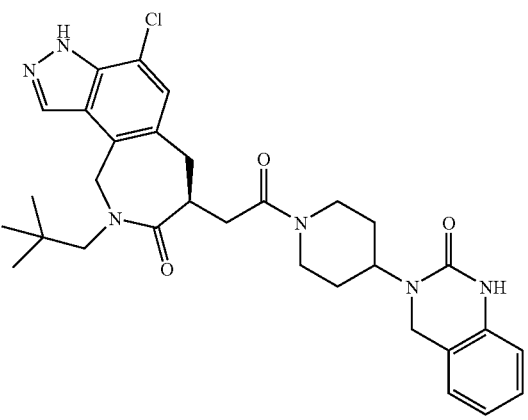 | A | A |

TABLE 2-continued

CGRP Binding and cAMP Functional Data

| Compound | CGRP binding IC$_{50}$ (nM) | cAMP Function IC$_{50}$ (nM) |
|---|---|---|
| [structure] | A | A |
| [structure] | B | * |
| [structure] | B | B |

TABLE 2-continued
CGRP Binding and cAMP Functional Data
| Compound | CGRP binding IC$_{50}$ (nM) | cAMP Function IC$_{50}$ (nM) |
|---|---|---|
| 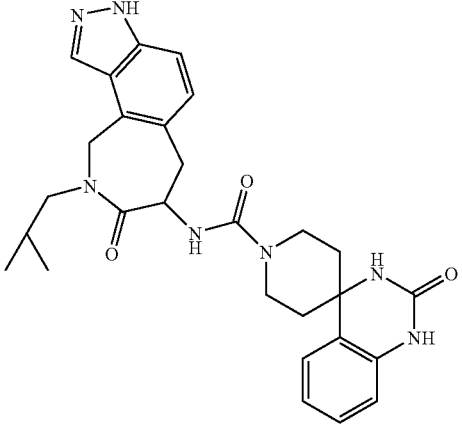 | C | * |
| 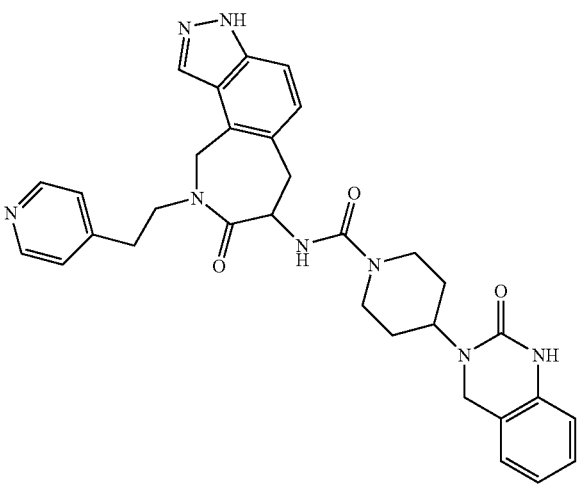 | A | A |
| 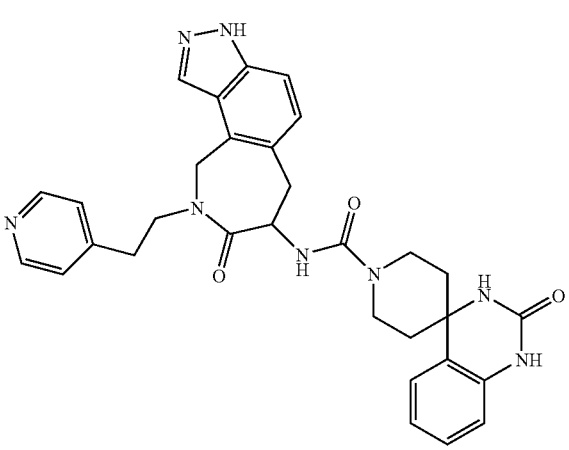 | C | * |

TABLE 2-continued

CGRP Binding and cAMP Functional Data

| Compound | CGRP binding IC$_{50}$ (nM) | cAMP Function IC$_{50}$ (nM) |
|---|---|---|
| *(structure)* | B | B |
| *(structure)* | C | * |
| *(structure)* | B | B |

TABLE 2-continued

CGRP Binding and cAMP Functional Data

| Compound | CGRP binding IC$_{50}$ (nM) | cAMP Function IC$_{50}$ (nM) |
|---|---|---|
| (structure) | D | * |
| (structure) | C | * |
| (structure) | D | * |

TABLE 2-continued

CGRP Binding and cAMP Functional Data

| Compound | CGRP binding IC$_{50}$ (nM) | cAMP Function IC$_{50}$ (nM) |
|---|---|---|
| | C | * |
| | B | * |
| | B | B |

TABLE 2-continued

CGRP Binding and cAMP Functional Data

| Compound | CGRP binding IC$_{50}$ (nM) | cAMP Function IC$_{50}$ (nM) |
|---|---|---|
| (structure) | A | B |
| (structure) | C | * |
| (structure) | B | B |

TABLE 2-continued

CGRP Binding and cAMP Functional Data

| Compound | CGRP binding IC$_{50}$ (nM) | cAMP Function IC$_{50}$ (nM) |
|---|---|---|
| | A | A |
| | A | A |
| | B | B |

TABLE 2-continued

CGRP Binding and cAMP Functional Data

| Compound | CGRP binding IC$_{50}$ (nM) | cAMP Function IC$_{50}$ (nM) |
|---|---|---|
| (structure) | A | A |
| (structure) | A | A |
| (structure) | A | A |

TABLE 2-continued
CGRP Binding and cAMP Functional Data
| Compound | CGRP binding IC$_{50}$ (nM) | cAMP Function IC$_{50}$ (nM) |
|---|---|---|
| 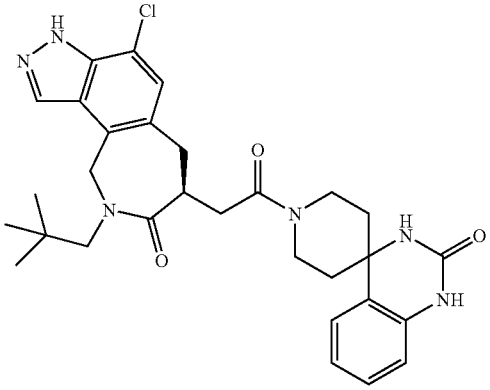 | A | A |
| 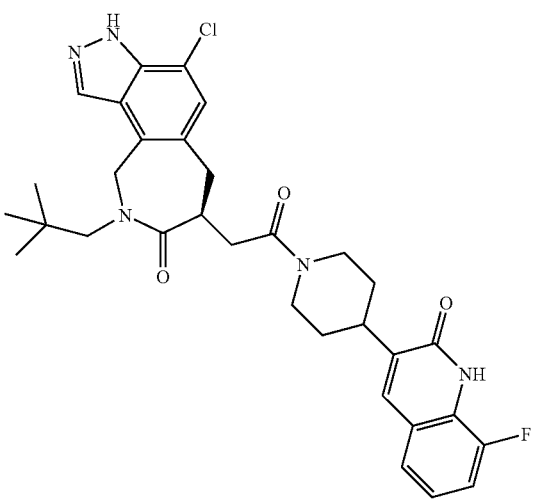 | B | B |
| 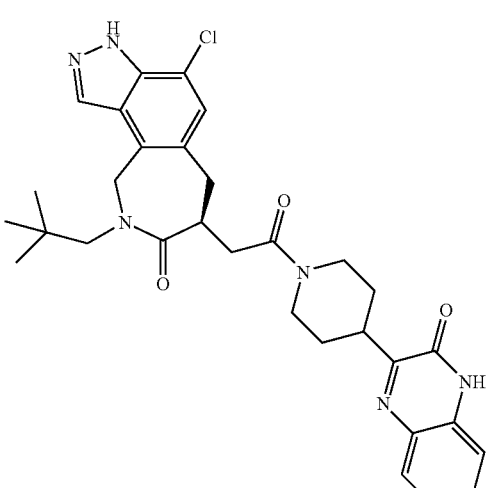 | B | * |

TABLE 2-continued

CGRP Binding and cAMP Functional Data

| Compound | CGRP binding IC$_{50}$ (nM) | cAMP Function IC$_{50}$ (nM) |
|---|---|---|
| (structure) | A | A |
| (structure) | A | A |
| (structure) | A | * |

TABLE 2-continued

CGRP Binding and cAMP Functional Data

| Compound | CGRP binding IC$_{50}$ (nM) | cAMP Function IC$_{50}$ (nM) |
|---|---|---|
| *[structure]* | A | A |
| *[structure]* | A | A |
| *[structure]* | A | A |

TABLE 2-continued
CGRP Binding and cAMP Functional Data
| Compound | CGRP binding IC$_{50}$ (nM) | cAMP Function IC$_{50}$ (nM) |
|---|---|---|
| 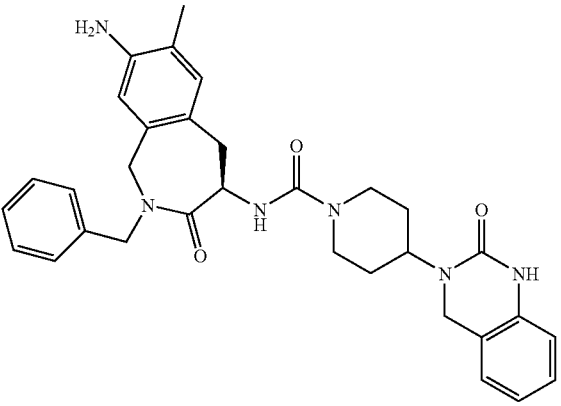 | C | * |
| 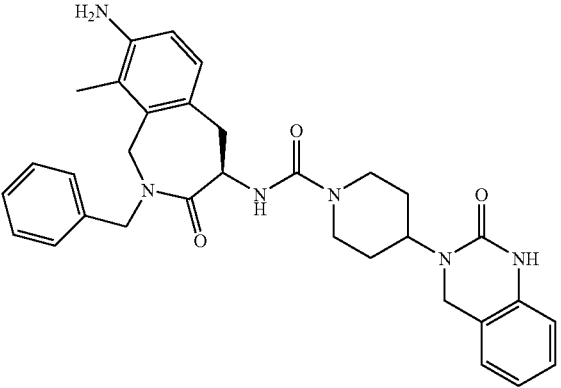 | C | * |
| 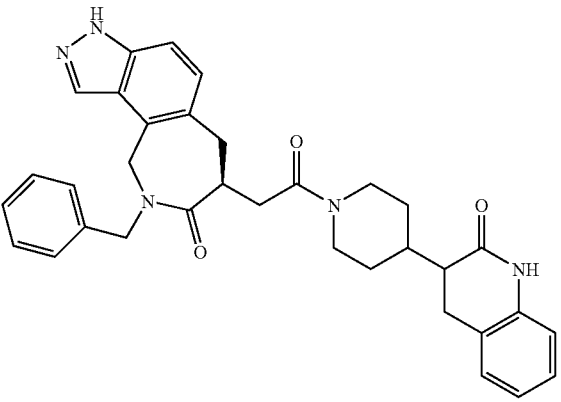 | C | * |

TABLE 2-continued

CGRP Binding and cAMP Functional Data

| Compound | CGRP binding IC$_{50}$ (nM) | cAMP Function IC$_{50}$ (nM) |
|---|---|---|
| | C | * |
| | C | * |
| | D | * |

TABLE 2-continued
CGRP Binding and cAMP Functional Data
| Compound | CGRP binding IC$_{50}$ (nM) | cAMP Function IC$_{50}$ (nM) |
|---|---|---|
| 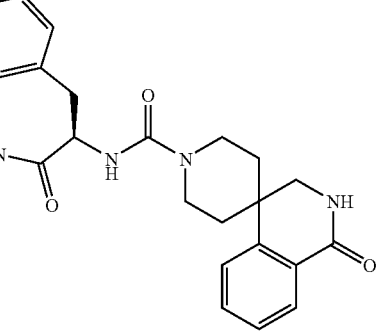 | D | * |
| 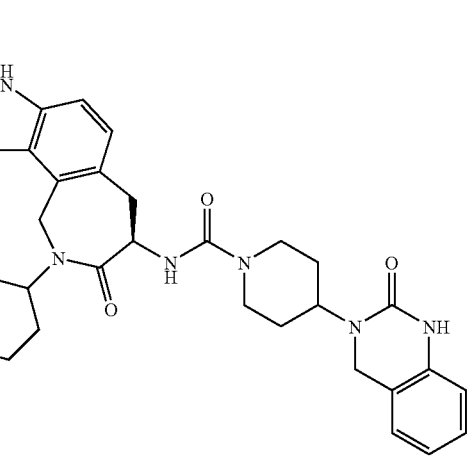 | B | * |
| 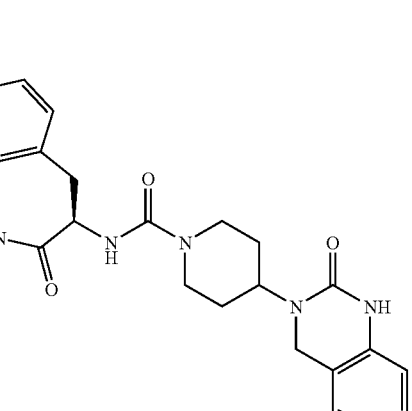 | C | * |

TABLE 2-continued

CGRP Binding and cAMP Functional Data

| Compound | CGRP binding IC$_{50}$ (nM) | cAMP Function IC$_{50}$ (nM) |
|---|---|---|
| *[chemical structure]* | D | * |
| *[chemical structure]* | D | * |
| *[chemical structure]* | B | * |

TABLE 2-continued

CGRP Binding and cAMP Functional Data

| Compound | CGRP binding IC$_{50}$ (nM) | cAMP Function IC$_{50}$ (nM) |
|---|---|---|
| (structure) | B | * |
| (structure) | C | * |
| (structure) | B | * |

TABLE 2-continued
CGRP Binding and cAMP Functional Data
| Compound | CGRP binding IC$_{50}$ (nM) | cAMP Function IC$_{50}$ (nM) |
|---|---|---|
| 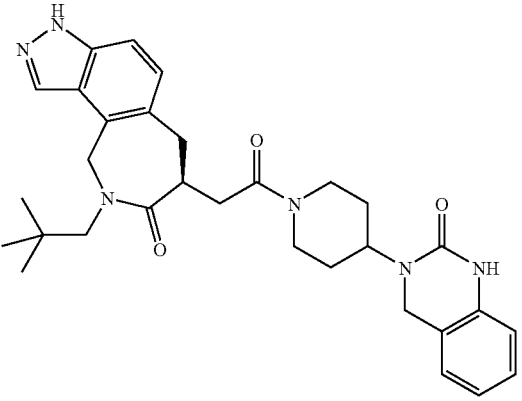 | C | * |
| 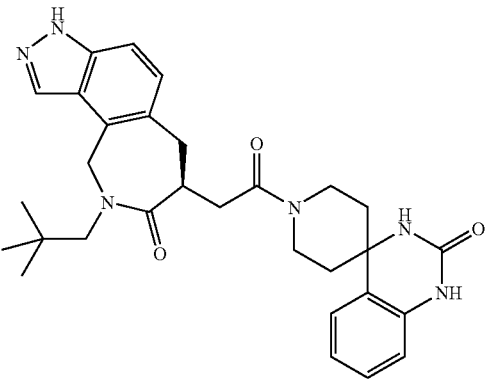 | C | * |
| 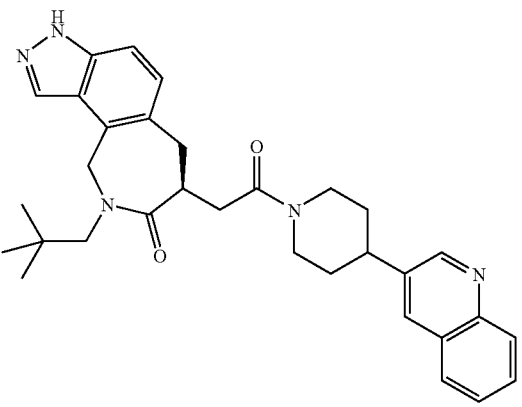 | D | * |

TABLE 2-continued

CGRP Binding and cAMP Functional Data

| Compound | CGRP binding IC$_{50}$ (nM) | cAMP Function IC$_{50}$ (nM) |
|---|---|---|
| (structure) | D | * |
| (structure) | D | * |
| (structure) | A | * |

TABLE 2-continued
CGRP Binding and cAMP Functional Data
| Compound | CGRP binding IC$_{50}$ (nM) | cAMP Function IC$_{50}$ (nM) |
|---|---|---|
| 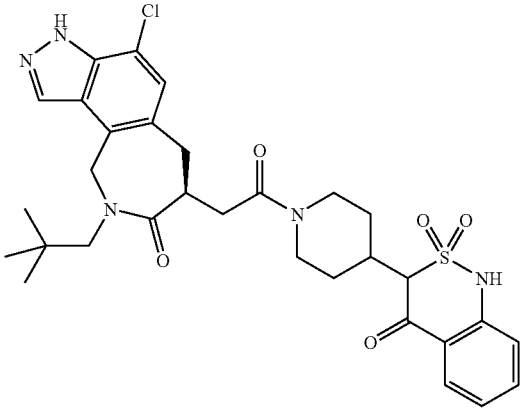 | B | * |
| 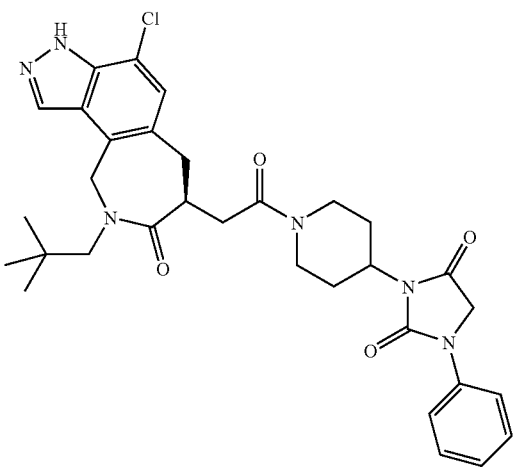 | B | * |
| 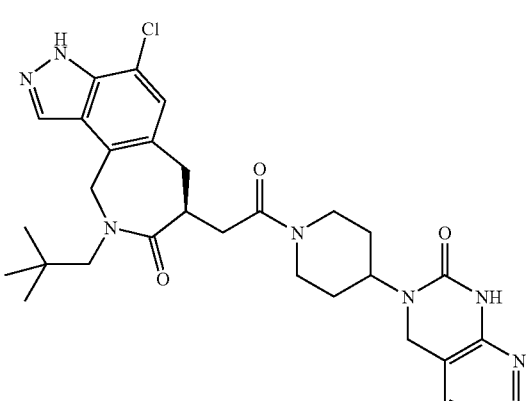 | A | * |

TABLE 2-continued
CGRP Binding and cAMP Functional Data
| Compound | CGRP binding IC$_{50}$ (nM) | cAMP Function IC$_{50}$ (nM) |
|---|---|---|
| 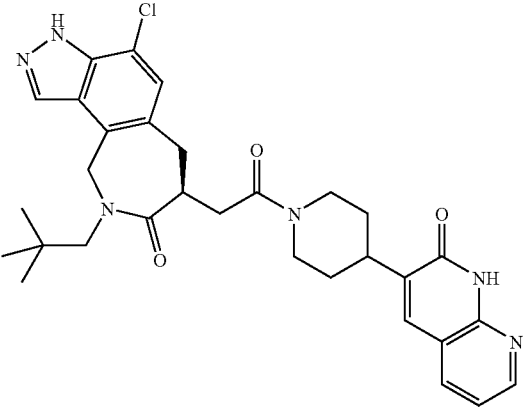 | A | * |
| 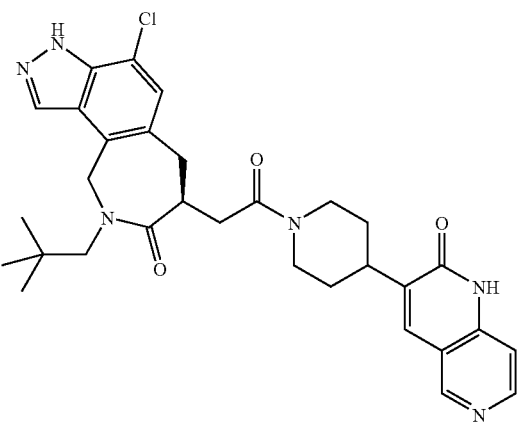 | B | B |
| 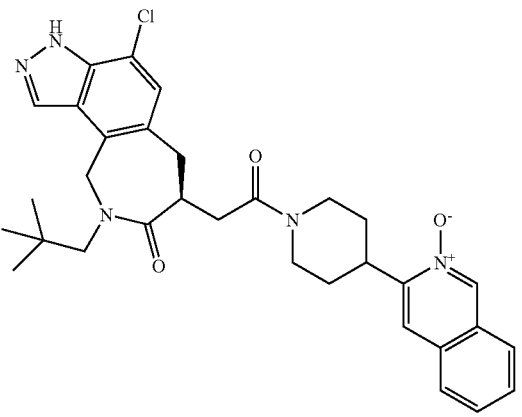 | B | * |

TABLE 2-continued
CGRP Binding and cAMP Functional Data
| Compound | CGRP binding IC$_{50}$ (nM) | cAMP Function IC$_{50}$ (nM) |
|---|---|---|
| 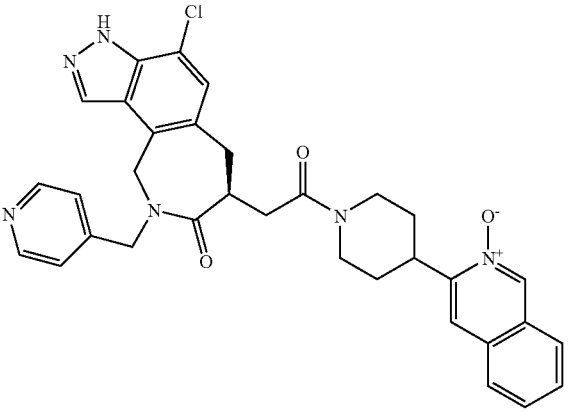 | A | * |
| 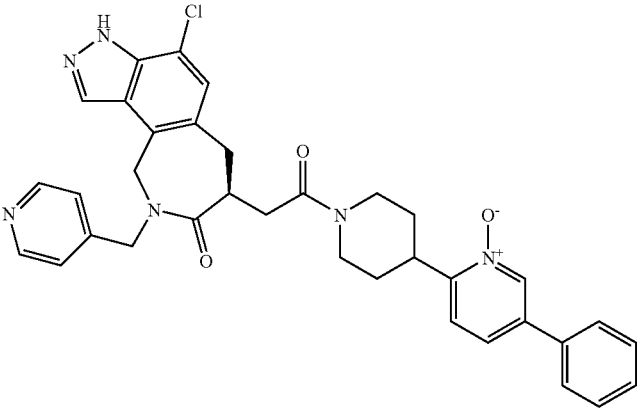 | C | * |
| 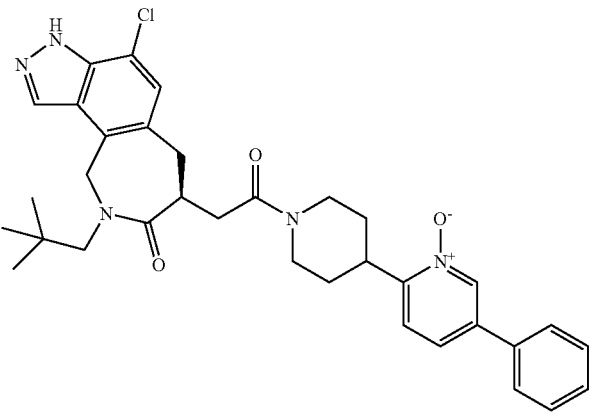 | C | * |

TABLE 2-continued

CGRP Binding and cAMP Functional Data

| Compound | CGRP binding IC$_{50}$ (nM) | cAMP Function IC$_{50}$ (nM) |
|---|---|---|
| *(structure)* | B | B |
| *(structure)* | A | * |
| *(structure)* | B | * |
| *(structure)* | A | * |

TABLE 2-continued
CGRP Binding and cAMP Functional Data
| Compound | CGRP binding IC$_{50}$ (nM) | cAMP Function IC$_{50}$ (nM) |
|---|---|---|
| 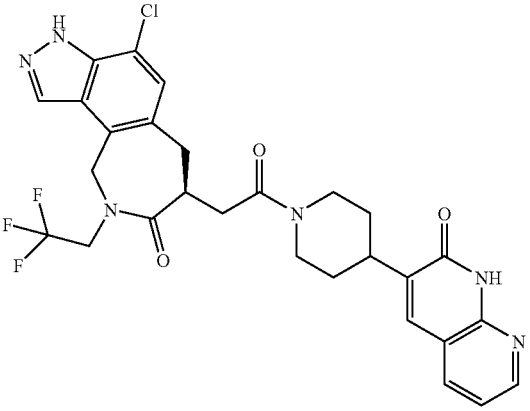 | A | * |
| 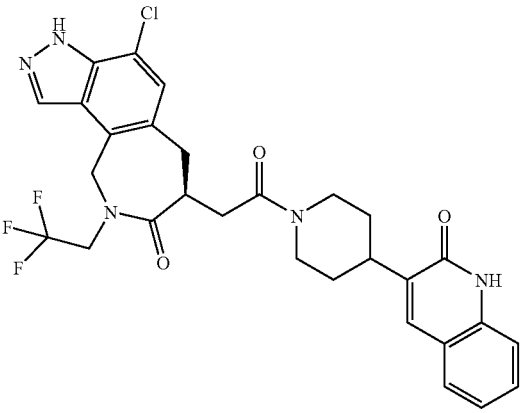 | A | * |
| 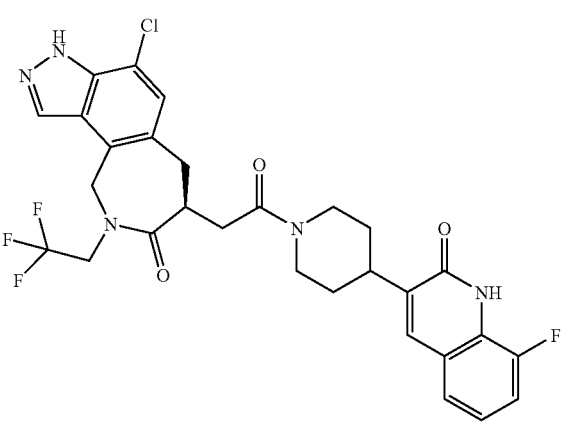 | A | * |

TABLE 2-continued

CGRP Binding and cAMP Functional Data

| Compound | CGRP binding IC$_{50}$ (nM) | cAMP Function IC$_{50}$ (nM) |
|---|---|---|
| | B | * |
| | C | * |
| | A | * |

TABLE 2-continued
CGRP Binding and cAMP Functional Data
| Compound | CGRP binding IC$_{50}$ (nM) | cAMP Function IC$_{50}$ (nM) |
|---|---|---|
| 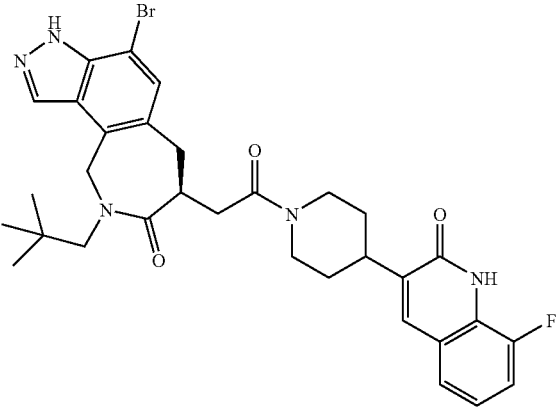 | B | * |
| 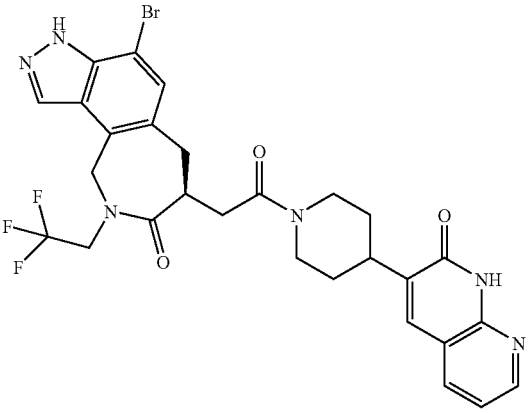 | A | * |
| 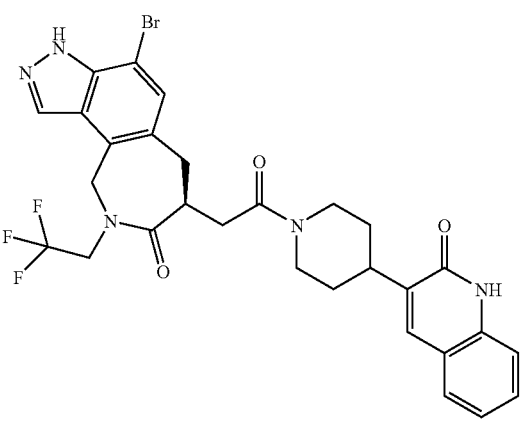 | A | * |

TABLE 2-continued
CGRP Binding and cAMP Functional Data
| Compound | CGRP binding IC$_{50}$ (nM) | cAMP Function IC$_{50}$ (nM) |
|---|---|---|
| 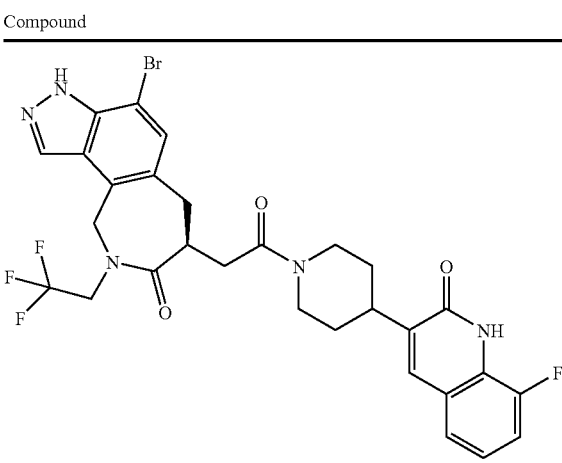 | B | * |
| 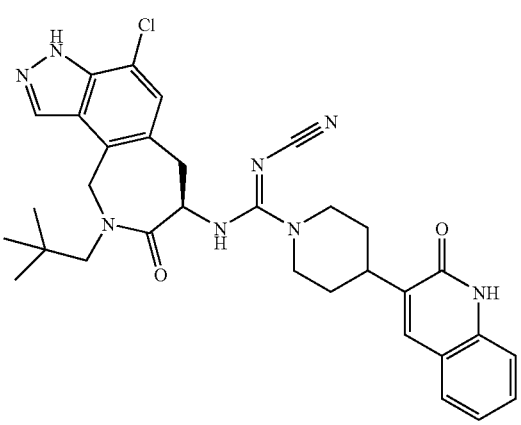 | A | * |
| 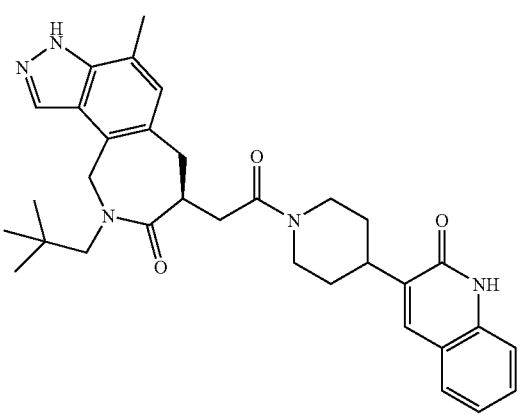 | A | * |

TABLE 2-continued

CGRP Binding and cAMP Functional Data

| Compound | CGRP binding IC$_{50}$ (nM) | cAMP Function IC$_{50}$ (nM) |
|---|---|---|
| | B | * |
| | A | * |
| | B | * |

TABLE 2-continued
CGRP Binding and cAMP Functional Data
| Compound | CGRP binding IC$_{50}$ (nM) | cAMP Function IC$_{50}$ (nM) |
|---|---|---|
| 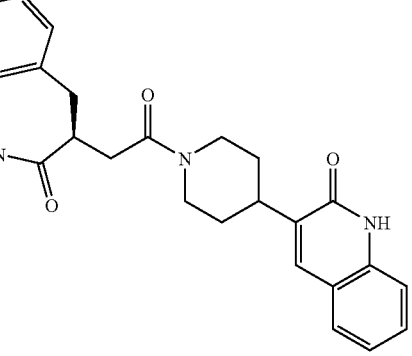 | B | * |
| 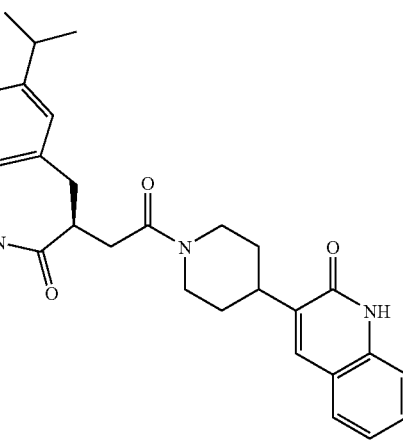 | B | * |
| 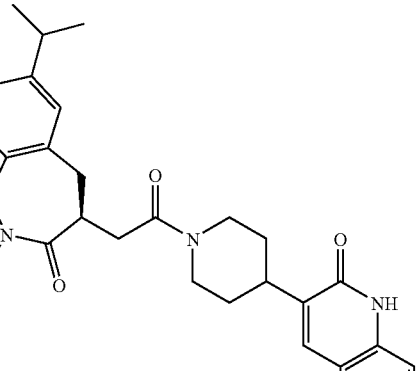 | B | * |

TABLE 2-continued
CGRP Binding and cAMP Functional Data
| Compound | CGRP binding IC$_{50}$ (nM) | cAMP Function IC$_{50}$ (nM) |
|---|---|---|
| 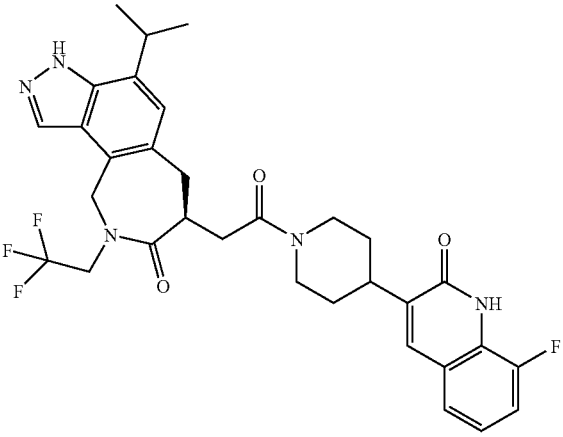 | C | * |
| 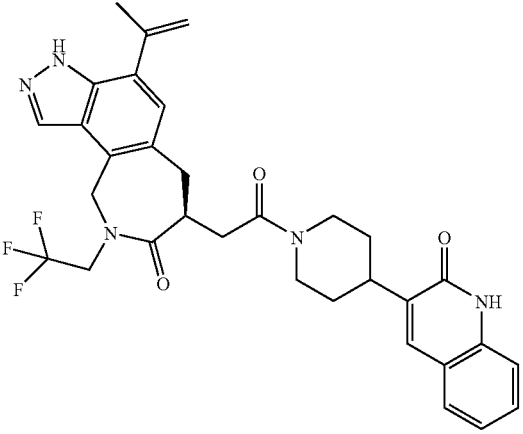 | B | * |
| 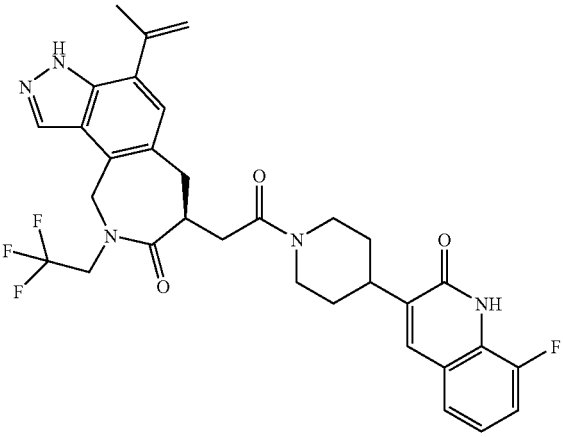 | C | * |

TABLE 2-continued
CGRP Binding and cAMP Functional Data
| Compound | CGRP binding IC$_{50}$ (nM) | cAMP Function IC$_{50}$ (nM) |
|---|---|---|
| 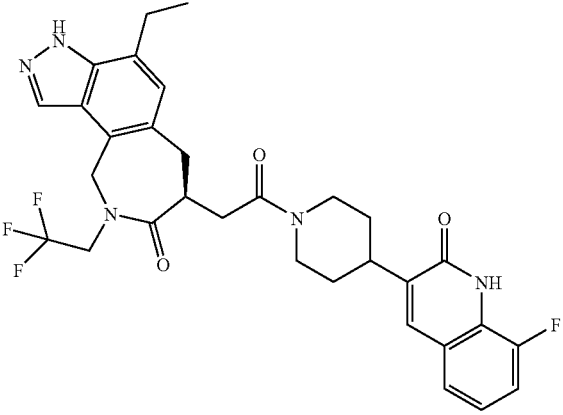 | B | * |
| 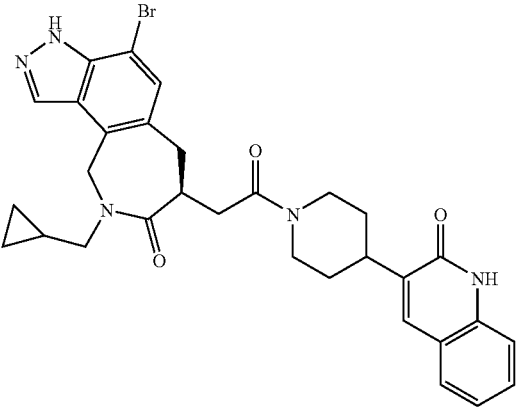 | A | * |
| 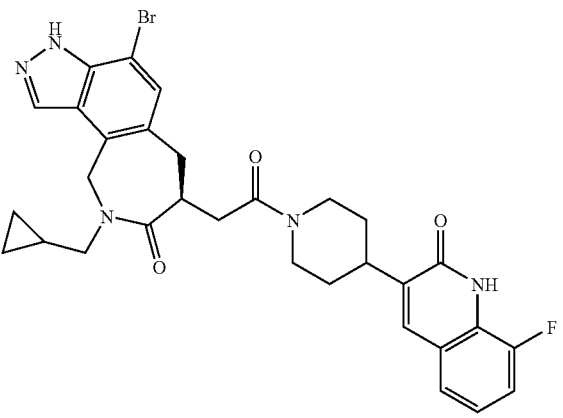 | B | * |

TABLE 2-continued
CGRP Binding and cAMP Functional Data
| Compound | CGRP binding IC$_{50}$ (nM) | cAMP Function IC$_{50}$ (nM) |
|---|---|---|
| 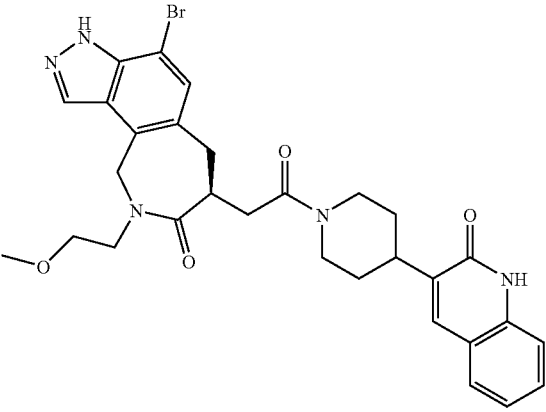 | A | * |
| 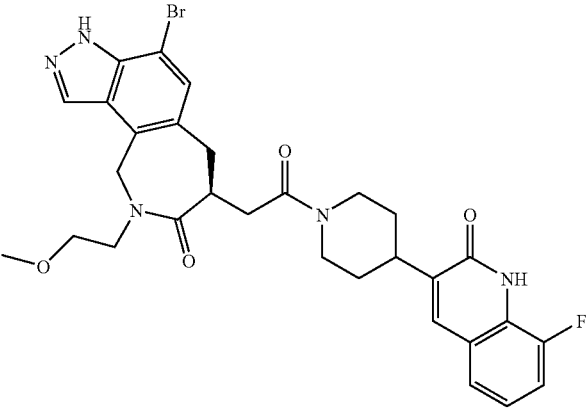 | B | * |
| 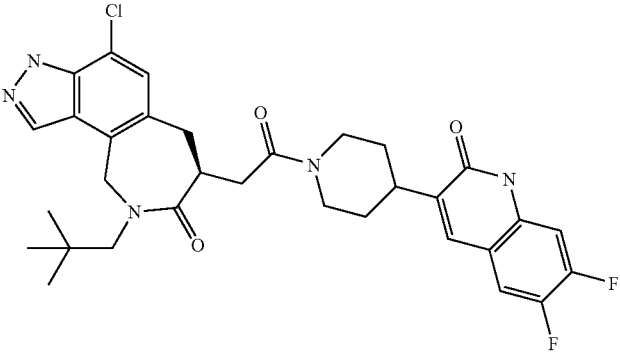 | B | * |
| 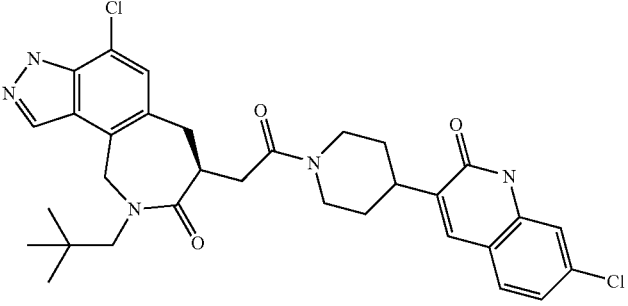 | A | * |

TABLE 2-continued

CGRP Binding and cAMP Functional Data

| Compound | CGRP binding IC$_{50}$ (nM) | cAMP Function IC$_{50}$ (nM) |
|---|---|---|
| | C | * |
| | B | * |
| | D | * |
| | A | * |

A 0.01-10 nM;
B = 10-100 nM;
C = 100-1000 nM;
D > 1000 nM.

Pharmaceutical Compositions and Methods of Treatment

The compounds of Formula I inhibit the CGRP receptor. As such, they are useful for treating disorders associated with aberrant CGRP levels or where modulating CGRP levels may have therapeutic benefit.

Accordingly, another aspect of the invention is a pharmaceutical composition comprising a compound of Formula I with a pharmaceutically acceptable adjuvant, carrier, or diluent.

Compounds are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regime, however, should be determined by a physician using sound medical judgement.

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001, 15(10), 745-53; Williamson, D. J. Microsc. Res. Tech. 2001, 53, 167-178; Grant, A. D. Brit. J. Pharmacol. 2002, 135, 356-362.). Serum levels of CGRP are elevated during migraine (Goadsby P. J. et al. Ann. Neurol. 1990, 28, 183-7) and treatment with anti-migraine drugs returns CGRP levels to normal coincident with alleviation of headache (Gallai V. et al. Cephalalgia 1995, 15, 384-90). Migraineurs exhibit elevated basal CGRP levels compared to controls (Ashina M. et al., Pain 2000, 86(1-2), 133-8). Intravenous CGRP infusion produces lasting headache in migraineurs (Lassen L. H. et al. Cephalalgia. 2002, 22(1), 54-61). Preclinical studies in dog and rat report that systemic CGRP blockade with the peptide antagonist CGRP(8-37) does not alter resting systemic hemodynamics nor regional blood flow (Shen, Y-T. et al. J. Pharmacol. Exp. Ther. 2001, 298, 551-8). Thus, CGRP-receptor antagonists may present a novel treatment for migraine that avoids the cardiovascular liabilities of active vasoconstriction associated with non-selective 5-HT1B/1D agonists, "triptans" (e.g., sumatriptan).

Another aspect of the invention is a method of treating migraine or headache.

"Migraine," "headache," and related terms are as understood by medical practitioners. Migraine encompasses all classes of migraine including common, classic, cluster, fulgurating, hemiplegic, opthalmoplegic, and opthomalmic.

"Therapeutically effective" means there is a meaningful patient benefit as understood by medical practitioners.

"Patient" means a person who may benefit from treatment as determined by medical practitioners.

Another aspect of the invention relates to a method of treating inflammation (particularly neurogenic inflammation), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

Another aspect of the invention relates to methods selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin1 receptors by rat spinal neurons. Seybold V S, McCarson K E, Mermelstein P G, Groth R D, Abrahams L G. J. Neurosci. 2003 23 (5): 1816-1824. department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5, Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef, Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218 all incorporated by reference herein.

Another aspect of this invention relates to a method of treatment using combinations of Formula I compounds with one or more agents selected from the group consisting of COX-2 inhibitors, NSAIDS, aspirin, acetaminophen, triptans, ergotamine and caffeine for the treatment of migraine.

DESCRIPTION OF SPECIFIC EMBODIMENTS

Proton magnetic resonance (1H NMR) spectra were recorded on a Bruker AC 300 or AC 500. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak. Low resolution mass spectra (MS) and the apparent molecular (MH+) or (M-H)+ was determined on a Micromass platform. The elemental analysis are reported as percent by weight. The products were purified by Prep HPLC using the column YMC S5 ODS (30×100 mm) at a flow rate of 40.0 mL/min and gradient time of 8.0 min. starting from solvent composition of 40% MeOH—60% $H_2O$—0.1% TFA and ending with solvent composition 95% MeOH—5% $H_2O$—0.1% TFA. The products were analyzed by a HPLC instrument using an XTERA column (3.0×50 mm S7) starting from solvent A (10% MeOH—90% water—0.1% trifluoroacetic acid (TFA)) and reaching solvent B (10% water—90% methanol—0.1% TFA) over a gradient time of 2 min. The flow rate is 5 mL/min. and retention time (Rf) of product was measured at 220 nm wavelength.

Intermediate 1

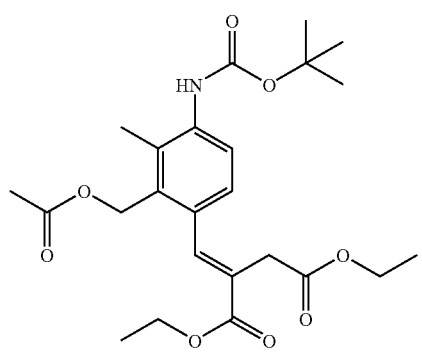

2-(Acetoxymethyl-4-tert-butoxycarbonylamino-3-methyl-benzylidene)-succinic acid diethyl ester. Nitrogen gas was bubbled through a solution of acetic acid 3-tert-butoxycarbonylamino-6-iodo-2-methyl-benzyl ester (3.85 g, 9.5 mmol), itaconic acid diethyl ester (2.2 mL, 12 mmol), tetrabutylammonium chloride (3.4 g, 12 mmol), and triethylamine (4.0 mL, 29 mmol) in N,N-dimethylformamide (25 mL) for 5 minutes. Palladium (II) acetate (0.32 g, 1.4 mmol) was added. Mixture was heated at 100° C. for 45 minutes. Mixture was cooled to room temperature then diluted with diethyl ether (100 ml). Mixture was washed successively with water (3×50 mL), and brine (25 mL). Organic was dried ($MgSO_4$), filtered and concentrated in vacuo. Silica gel purification yielded the desired product in 99% yield as an amber oil. $^1$H NMR (300 MHz, $CDCl_3$): δ=8.0 (s, 1H), 7.78 (d, J=8.4, 1H), 7.08 (d, J=8.4, 1H), 6.32 (s, 1H), 5.11 (s, 2H), 4.27 (q, J=7.3, 2H), 4.11 (q, J=7.1, 2H), 3.30 (s, 2H), 2.24 (s, 3H), 2.04 (s, 3H), 1.55 (s, 3H), 1.51 (s, 9H), 1.32 (t, J=7.1, 3H), 1.23 (t, J=7.3, 3H). MS m/e (M-H)$^-$=462.0.

Intermediate 2

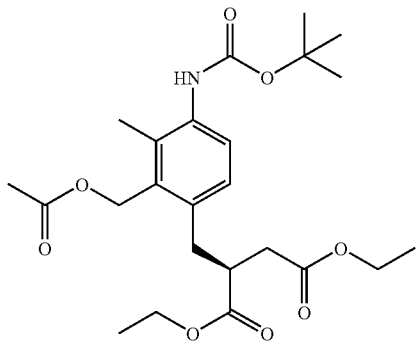

2-(S)-(Acetoxymethyl-4-tert-butoxycarbonylamino-3-methyl-benzyl)-succinic acid diethyl ester. 2-(S)-(Acetoxymethyl-4-tert-butoxycarbonylamino-3-methyl-benzylidene)-succinic acid diethyl ester (4.4 g, 9.5 mmol) and (-)-1,2-bis((2R,5R)-diethylphospholano)benzene(cyclooctadiene)rhodium (I) trifluoromethane sulfonate (100 mg) was dissolved in ethanol (80 mL). Mixture was placed on a Parr hydrogenation apparatus. Reaction vessel was charged with 60 psi of hydrogen gas. Reaction mixture was allowed to shake at room temperature for 18 hours. Reaction mixture was concentrated in vacuo. Residue was passed through a plug of silica gel eluting 80% ethyl acetate-hexanes (250 mL). Filtrate was concentrated in vacuo to afford the desired product in 97% yield as an amber oil. $^1$H NMR (300 MHz, $CDCl_3$): δ=7.62 (d, J=8.1, 1H), 7.01 (d, J=8.4, 1H) , 6.20 (s, 1H), 5.20 (m, 2H), 4.09 (m, 4H), 3.14 (m, 1H), 2.69 (m, 2H), 2.38 (dd, J1=16.8, J2=4.8, 1H), 2.23 (s, 3H), 2.07 (s, 3H), 1.56 (3, 3H), 1.50 (s, 9H), 1.22 (m, 6H). MS m/e (M-H)$^-$=464.0.

Intermediate 3

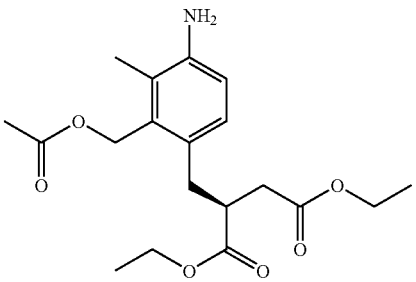

2-(S)-(2-Acetoxymethyl-4-amino-3-methyl-benzyl)-succinic acid diethyl ester. Trifluoroacetic acid (10 mL) was added to a solution of 2-(S)-(acetoxymethyl-4-tert-butoxycarbonylamino-3-methyl-benzyl)-succinic acid diethyl ester (4.6 g, 9.9 mmol) in dichloromethane (40 mL). Reaction mixture was stirred at room temperature for 1.5 hours. Mixture was concentrated in vacuo. Residue was dissolved in dichloromethane (75 mL) and washed successively with saturated aqueous sodium bicarbonate (2×50 mL) and brine (30 mL). Organic was dried (magnesium sulfate), filtered and concentrated in vacuo to yield the desired product in 99% yield as an amber oil. $^1$H NMR (300 MHz, CDCl$_3$): δ=6.85 (d, J=8.1, 1H), 6.67 (d, J=8.4, 1H), 5.18 (m, 2H), 4.09 (m, 4H), 3.09 (dd, J1=6.2, J2=13.9, 1H), 2.96 (m, 1H), 2.66 (m, 2H), 2.37 (dd, J1=4.6, J2=16.7, 1H), 2.15 (s, 3H), 2.06 (s, 3H), 1.20 (m, 6H). MS m/e (M−C$_2$H$_4$O$_2$+H)$^+$=306.2.

removed from the mixture in vacuo. Remaining aqueous was basified with sodium bicarbonate. Mixture was extracted with ethyl acetate (2×40 mL). Combined organic layers were washed successively with water (30 mL) and brine (30 mL). Organic was dried (magnesium sulfate), filtered then concentrated in vacuo. Desired product was obtained in 92% yield as an amber oil. $^1$H NMR (300 MHz, CDCl$_3$): δ=8.21 ((s, 1H), 7.34 (d, J=9.2, 1H), 7.17 (d, J=8.8, 1H), 5.02 (dd, J1=12.4, J2=17.9, 1H)3.63 (s, 6H), 3.23 (m, 1H), 2.98 (m, 1H), 2.77 (dd, J1=7.7, J2=16.8, 1H), 2.53 (dd, J1=6.4, J2=16.7, 1H). MS m/e (M+H)$^-$=307.0.

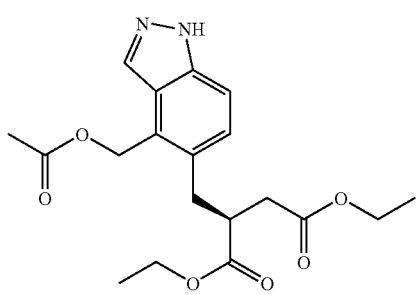

Intermediate 4

2-(S)-(4-Acetoxymethyl-1H-indazol-5-ylmethyl)-succinic acid diethyl ester. Isoamyl nitrite (1.6 mL, 12 mmol) was added dropwise to a cooled (water ice bath) sollution of 2-(S)-(2-acetoxymethyl-4-amino-3-methyl-benzyl)-succinic acid diethyl ester in carbontetrachloride (80 mL) and acetic acid (4 mL). Mixture was stirred at 0° C. for 2 hours. Mixture was warmed and stirred at ambient temperature for 14 hours. Mixture was concentrated in vacuo. Residue was dissolved in dichloromethane (75 mL) then washed successively with saturated aqueous sodium bicarbonate (2×50 mL), and brine (30 mL). Organic was dried (magnesium sulfate), filtered and concentrated in vacuo. Silica gel chromatography (ethyl acetate-hexanes) afforded the product in 55% yield as an amber oil. $^1$H NMR (300 MHz, CDCl$_3$): δ=8.19 (s, 1H), 7.44 (d, J=8.8, 1H), 7.24 (d, J=8.8, 1H), 5.49 (s, 2H), 4.06 (m, 4H), 3.25 , (m, 1H), 3.11 (m, 1H), 2.97 (m, 1H), 2.72 (dd, J1=8.8, J2=16.5, 1H) 2.43 (dd, J1=5.1 , J2=16.5), 2.09 (s, 3H), 1.19 (m, 6H). MS m/e (M+H) $^+$=377.1.

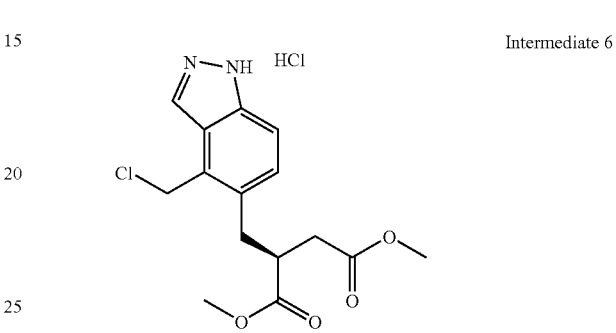

Intermediate 6

2-(S)-(4-Chloromethyl-1H-indazol-5-ylmethyl)-succinic acid dimethyl ester hydrochoride. Thionyl chloride (5.0 mL) was added to a solution of 2-(S)-(4-hydroxymethyl-1H-indazol-5-ylmethyl)-succinic acid dimethyl ester (1.53 g, 5.0 mmol) in dichloromethane (30 mL). Reaction mixture was stirred at ambient temperature for 2 hours. Mixture was concentrated in vacuo. Residue was triturated in toluene (30 mL), then concentrated in vacuo. Residue was treated with dichloromethane (30 mL) then concentrated in vacuo. Desired product was obtained in 96% yield as an orange solid. $^1$H NMR (300 MHz, CDCl$_3$): δ=8.22 (s, 1H), 7.49 (d, J=8.8, 1H), 7.15 (d, J=8.8, 1H), 5.12 (s, 2H), 3.56 (s, 3H), 3.52 (s, 3H), 3.05 (m, 3H), 2.69 (dd, J1=8.1, J2=16.5), 2.54 (m, 1H). MS m/e (M+H)$^+$=325.2.

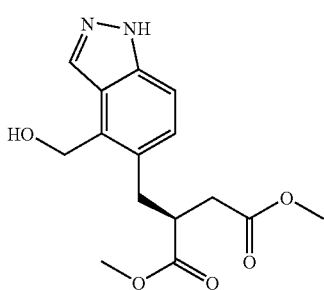

Intermediate 5

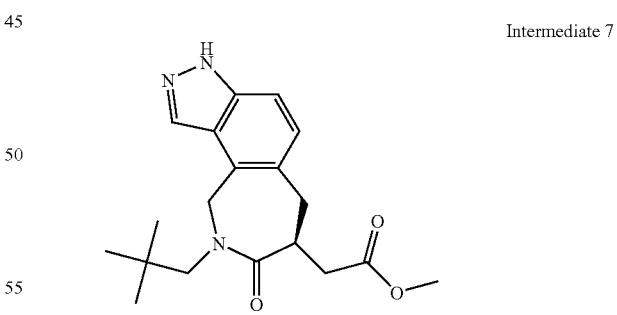

Intermediate 7

2-(S)-(4-Hydroxymethyl-1H-indazol-5-ylmethyl)-succinic acid dimethyl ester. Potassium carbonate (1.6 g, 11.6 mmol) was added to a solution of 2-(S)-(4-acetoxymethyl-1H-indazol-5-ylmethyl)-succinic acid diethyl ester (2.0 g, 5.5 mmol) in methanol (60 mL). Mixture was stirred at room temperature for 1.5 hours. Reaction was quenched with the addition of 1N hydrochloric acid (30 mL). Methanol was

[9-(2,2-Dimethyl-propyl)-8-oxo-3,6,7,8,9,10-hexahydro-2,3,9-triaza-(S)-cyclohepta[e]inden-7-yl]-acetic acid methyl ester. Neopentylamine (2.0 mL, 17 mmol) was added to a mixture of potassium carbonate (1.2 g, 8.7 mmol) and 2-(S)-(4-chloromethyl-1H-indazol-5-ylmethyl)-succinic acid dimethyl ester hydrochloride (1.56 g, 4.3 mmol) in acetonitrile (30 mL). Reaction mixture was heated at reflux until starting material was deemed to be consumed by HPLC (1.5 hours).

Mixture was cooled to room temperature then filtered. Filtrate was concentrated in vacuo. Residue was dissolved in a mixture of toluene (40 mL) and acetic acid (2 mL). Reaction mixture was heated at reflux until judged complete by HPLC (44 hours). Mixture was concentrated in vacuo. Residue was dissolved in ethyl acetate (50 mL) and washed with saturated aqueous sodium bicarbonate (2×25 mL). Organic was dried (magnesium sulfate), filtered and concentrated in vacuo. Silica gel chromatography (ethyl acetate-hexanes) yielded the desired product in 90% yield as a yellow foam. $^1$H NMR (300 MHz, CDCl$_3$): δ=8.01 (s, 1H), 7.35 (d, J=8.4, 1H), 7.13 (d, J=8.4, 1H), 5.41 (d, J=16.8, 1H), 4.50 (d, J=16.8, 1H), 3.90 (m, 1H), 3.70 (s, 3H), 3.62 (m, 1H), 3.50 (d, J=13.9, 1H), 3.18 (d, J=13.5, 1H), 3.05 (m, 2H), 2.43 (dd, J1=16.7, J2=5.3, 1H), 0.83 (s, 9H). MS m/e (M−H)$^−$=342.0.

(9-Benzyl-8-oxo-3,6,7,8,9,10-hexahydro-2,3,9-triaza-(S)-cyclohepta[e]inden-7-yl)-acetic acid methyl ester. Benzylamine (250 μL, 2.3 mmol) and 2-(S)-(4-Chloromethyl-1H-indazol-5-ylmethyl)-succinic acid dimethyl ester hydrochloride were converted following a procedure analogous to the preparation of [9-(2,2-Dimethyl-propyl)-8-oxo-3,6,7,8,9,10-hexahydro-2,3,9-triaza-(S)-cyclohepta[e]inden-7-yl]-acetic acid methyl ester. Silica gel chromatography (ethyl acetate-hexanes) afforded the desired product in 62% yield as an amber oil. $^1$H NMR (300 MHz, CDCl$_3$): δ=7.77 (s, 1H), 7.28 (m, 6H), 7.09 (d, J=8.4, 1H), 5.18 (d, J=16.8, 1H), 4.99 (d, J=15.0, 1H), 4.43 (d, J=5.9, 1H), 4.39 (d, J=1.8, 1H), 4.34 (d, J=4.0, 1H), 3.74 (s, 3H), 3.13 (m, 2H), 2.51 (dd, J1=5.5, J2=16.8, 1H). MS m/e (M+H)$^+$=364.0.

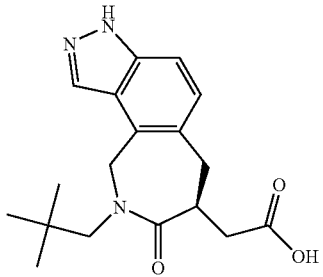

Intermediate 8

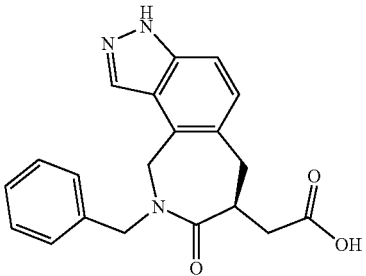

Intermediate 10

[9-(2,2-Dimethyl-propyl)-8-oxo-3,6,7,8,9,10-hexahydro-2,3,9-triaza-(S)-cyclohepta[e]inden-7-yl]-acetic acid. Lithium hydroxide monohydrate (335 mg, 8.0 mmol) was added to a solution of [9-(2,2-dimethyl-propyl)-8-oxo-3,6,7,8,9,10-hexahydro-2,3,9-triaza-(S)-cyclohepta[e]inden-7-yl]-acetic acid methyl ester (1.32 g, 3.8 mmol) in methanol (15 mL), tetrahydrofuran (15 mL) and water (15 mL). Reaction mixture was heated at 50° C. for 1 hour. The organic solvents were removed from the mixture in vacuo. Remaining aqueous was diluted with water (25 mL). Mixture was neutralized with 1 N hydrochloric acid (8.0 mL). Mixture was extracted with ethyl acetate (2×30 mL). Combined organic layers were washed with brine (20 mL) then dried (magnesium sulfate), filtered and concentrated in vacuo. Desired product was obtained in 88% yield as a light yellow solid. $^1$H NMR (300 MHz, CDCl$_3$): δ=7.98 (s, 1H), 7.36 (d, J=8.8, 1H), 7.10 (d, J=8.8, 1H), 5.38 (d, J=16.8, 1H), 4.48 (d, J=16.8, 1H), 3.85 (m, 1H), 3.49 (d, J=13.5, 1H), 3.18 (d, J=13.9, 1H), 3.08 (s, 2H), 2.92 (dd, J1=8.2, J2=16.3, 1H), 2.55 (dd, J1=16.5, J=2=4.8, 1H) 0.81 (s, 9H). MS m/e (M−H)$^−$=328.0.

(9-Benzyl-8-oxo-3,6,7,8,9,10-hexahydro-2,3,9-triaza-(S)-cyclohepta[e]inden-7-yl)-acetic acid. Lithium hydroxide (32 mg, 0.76 mmol) and (9-benzyl-8-oxo-3,6,7,8,9,10-hexahydro-2,3,9-triaza-(S)-cyclohepta[e]inden-7-yl)-acetic acid methyl ester were reacted in a manner analogous to the preparation of [9-(2,2-dimethyl-propyl)-8-oxo-3,6,7,8,9,10-hexahydro-2,3,9-triaza-(S)-cyclohepta[e]inden-7-yl]-acetic acid. Desired product was obtained as a yellow oil in 99% yield. $^1$H NMR (300 MHz, DMSO, D$_6$): δ=7.72 (s, 1H), 7.28 (m, 4H), 7.16 (m, 2H), 7.06 (d, J=8.8, 1H), 5.15 (d, J=16.8, 1H), 4.95 (d, J=15.0, 1H), 4.37 (m,4H), 3.09 (m,2H), 2.59 (dd, J1=5.1, J2=16.5, 1H). MS m/e (M+H)$^+$=350.0.

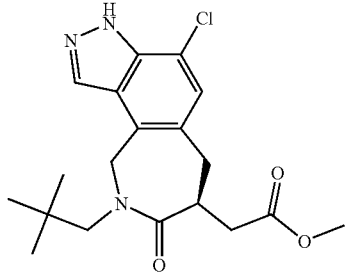

Intermediate 11

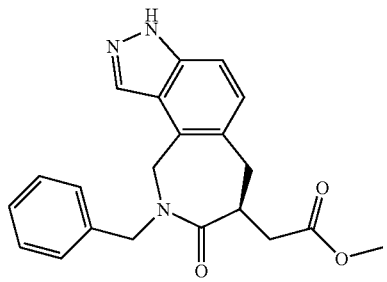

Intermediate 9

[4-Chloro-9-(2,2-dimethyl-propyl)-8-oxo-3,6,7,8,9,10-hexahydro-2,3,9-triaza-(S)-cyclohepta[e]inden-7-yl]-acetic acid methyl ester. Potassium carbonate (190 mg, 1.4 mmol) was added to a solution of 2-(S)-(4-acetoxymethyl-7-chloro-1H-indazol-5-ylmethyl)-succinic acid diethyl ester (240 mg, 0.58 mmol) in methanol (10 mL) and ethanol (5 mL). Mixture was stirred at room temperature for 1.5 hours. Reaction was quenched with the addition of 1 N hydrochloric acid (10 mL). Organic solvents were removed from the mixture in vacuo. Remaining aqueous was basified with sodium bicarbonate. Mixture was extracted 2× ethyl acetate (15 mL). Combined organic layers were dried (magnesium sulfate), filtered and concentrated. Residue was dissolved in dichloromethane (6 mL). Thionyl chloride (2 mL) was added to the mixture. Reaction was stirred at room temperature for 1.5 hours. Mixture was concentrated in vacuo. Residue was treated with dichloromethane (25 mL) then concentrated in vacuo. Residue was suspended in acetonitrile (5 mL). Potassium carbonate (200 mg, 1.4 mmol) was added to the mixture followed by neopentylamine (150 μL, 1.3 mmol). Reaction mixture was heated at reflux for 1 hour. Mixture was cooled to room temperature then filtered through a 0.45 μm PTFE membrane. Filtrate was concentrated. Residue was dissolved in a mixture of toluene (5 mL) and acetic acid (250 μL). Reaction mixture was heated at 100° C. for 15 hours then warmed to reflux for 7 hours. Mixture was cooled to room temperature then diluted with ethyl acetate (15 mL). Mixture was washed successively 2× saturated aqueous sodium bicarbonate (20 mL), water (15 mL) and brine (10 mL). Organic was dried (magnesium sulfate), filtered and concentrated in vacuo. Silica gel chromatography (ethyl acetate-hexanes) afforded the desired product in 48% yield as a yellow oil. $^1$H NMR (300 MHz, CDCl$_3$): δ=8.02 (s, 1H), 7.13 (s, 1H), 5.37 (m, 1H), 4.42 (d, J=17.2, 1H), 3.88 (m, 1H), 3.70 (s, 3H), 3.53 (d, J=13.9, 1H), 3.12 (d, J=13.9, 1H), 3.03 (m, 3H), 2.44 (dd, J1=5.9, J2=16.9, 1H), 0.81 (s, 9HMS m/e (M+H)$^+$=378.1.

Intermediate 12

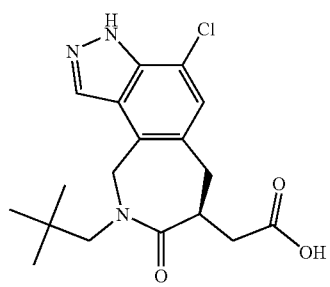

[4-Chloro-9-(2,2-dimethyl-propyl)-8-oxo-3,6,7,8,9,10-hexahydro-2,3,9-triaza-(S)-cyclohepta[e]inden-7-yl]-acetic acid. Lithium hydroxide monohydrate (30 mg, 0.71 mmol) was added to a solution of [4-chloro-9-(2,2-dimethyl-propyl)-8-oxo-3,6,7,8,9,10-hexahydro-2,3,9-triaza-(S)-cyclohepta[e]iden-7-yl]-acetic acid methyl ester (100 mg, 0.26 mmol) in methanol (2 mL), tetrahydrofuran (2 mL) and water (2 mL). Reaction mixture was stirred at ambient temperature for two hours followed by heating at 50° C. for 40 minutes. Organic solvents were removed from the mixture in vacuo. Remaining aqueous was neutralized with 1N hydrochloric acid (750 μL). Mixture was extracted 2× ethyl acetate (10 mL). Combined organic layers were washed with brine (10 mL) then dried (magnesium sulfate), filtered and concentrated in vacuo. Desired product was obtained in 93% yield as an orange solid. $^1$H NMR (300 MHz, CDCl$_3$): δ=7.98 (s, 1H), 7.09 (s, 1H), 5.35 (d, J=17.2, 1H), 4.41 (d, J=17.2, 1H), 3.82 (m, 1H), 3.48 (d, J=13.9, 1H), 3.12 (d, J=13.9, 1H), 3.02 (m, 2H), 2.92 (dd, J1=8.4, J2=16.8, 1H), 2.45 (dd, J1=5.1, J2=16.8, 1H), 0.78 (s, 9H). MS m/e (M−H)$^-$=362.0.

Intermediate 13

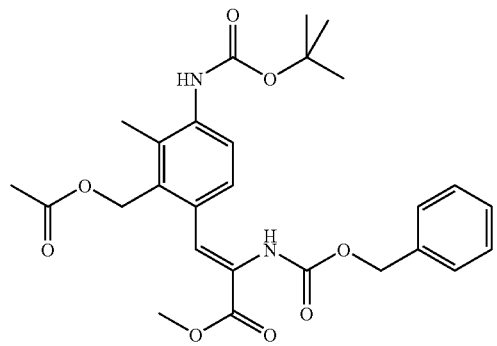

3-(2-Acetoxymethyl-4-tert-butoxycarbonylamino-3-methyl-phenyl)-2-benzyloxycarbonylamino-acrylic acid methyl ester. Palladium (II) acetate (105 mg, 0.43 mmol) was added to a mixture of acetic acid 3-tert-butoxycarbonylamino-6-iodo-2-methyl-benzyl ester (2.89 g, 7.1 mmol), Z-dehydroalanine methyl ester (2.20 g, 9.4 mmol), tetrabutylammonium chloride hydrate (2.70 g, 9.7 mmol), and sodium bicarbonate (1.80 g, 21.4 mmol) in THF (100 mL). Reaction was heated at reflux for 3.75 hours. Mixture was cooled to room temperature then filtered through a plug of silica gel eluting 70% ethyl acetate-hexanes (500 mL). Filtrate was concentrated in vacuo. Silica gel chromatography afforded the title compound as a yellow solid in 69% yield. $^1$H NMR (300 MHz, CDCl$_3$): δ=7.79 (d, J=8.4, 1H), 7.42 (s, 1H), 7.27 (m, 6H), 6.30 (s, 1H), 5.11 (s, 2H), 5.02 (s, 2H), 3.81 (s, 3H), 2.21 (s, 3H), 2.02 (s, 3H), 1.51 (s, 9H). MS m/e (M−H)$^-$=511.0.

Intermediate 14

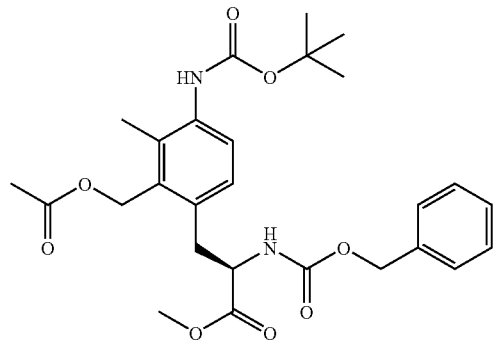

3-(2-Acetoxymethyl-4-tert-butoxycarbonylamino-3-methyl-phenyl)-2-(R)-benzyloxycarbonylamino-propionic acid methyl ester. A solution of 3-(2-acetoxymethyl-4-tert-butoxycarbonylamino-3-methyl-phenyl)-2-benzyloxycarbonylamino-acrylic acid methyl ester (2.51 g, 4.9 mmol) in methanol (50 mL) and ethyl acetate (15 mL) was reacted in a manner similar to the preparation of 2-(S)-(acetoxymethyl-4-tert-butoxycarbonylamino-3-methyl-benzyl)-succinic acid diethyl ester. Title compound was obtained as an off-white solid in 97% yield. $^1$H NMR (300 MHz, CDCl$_3$): δ=7.66 (d, J=7.9, 1H), 7.31 (m, 5H), 6.99 (d, J=8.5, 1H), 6.21 (s, 1H), 5.31 (d, J=7.6, 1H), 5.17 (d, J=3.7, 2H), 5.04 (d, J=5.80, 2H), 4.56 (m, 1H), 3.71 (s, 3H), 3.23 (dd, J1=5.80, J2=14.7, 1H), 3.07 (dd, J1=7.8, J=14.2, 1H), 2.21 (s, 3H), 2.00 (s, 3H), 1.50 (s, 9H). MS m/e (M−H)$^-$=513.0.

Intermediate 15

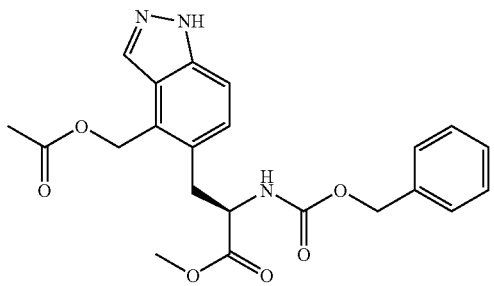

3-(4-Acetoxymethyl-1H-indazol-5-yl)-2-(R)-benzyloxycarbonylamino-propionic acid methyl ester. Trifluoroacetic acid (2.5 mL) was added to a solution of 3-(2-acetoxymethyl-4-tert-butoxycarbonylamino-3-methyl-phenyl)-2-(R)-benzyloxycarbonylamino-propionic acid methyl ester (770 mg, 1.5 mmol) in dichloromethane (10 mL). Reaction mixture was stirred at room temperature for 1.5 hours. Mixture was concentrated in vacuo. Residue was treated with chloroform (40 mL) then concentrated in vacuo. Residue was dissolved in 5% acetic acid in chloroform (10 mL). Isoamyl nitrite (240 µL, 1.8 mmol) was added to the mixture. Reaction mixture was stirred at ambient temperature for 20 minutes. Potassium acetate (690 mg, 7.0 mmol) was added to the mixture. Reaction mixture was stirred at ambient temperature for 45 minutes. Mixture was washed successively with water (10 mL), and 2× saturated aqueous sodium bicarbonate (15 mL). Organic was dried (magnesium sulfate), filtered and concentrated. Crude product was obtained in 81% yield as an amber oil and was used without further purification. $^1$H NMR (300 MHz, CDCl$_3$): δ=8.17 (s, 1H), 7.41 (d, J=8.4, 1H), 7.25 (m, 6H), 5.54 (d, J=8.1, 1H), 5.44 (s, 2H), 5.03 (s, 2H), 4.67 (m, 1H), 3.78 (s, 3H), 3.37 (dd, J1=5.9, J2=14.3, 1H), 3.22 (dd, J1=8.1, J2=14.3, 1H), 1.98 (s, 3H). MS m/e (M+H)$^+$=426.0.

Intermediate 16

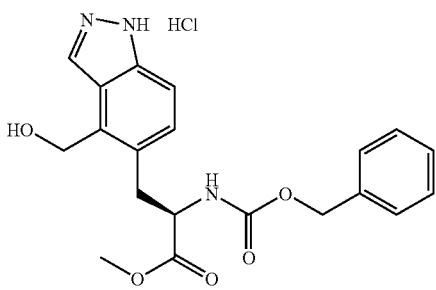

2-(R)-Benzyloxycarbonylamino-3-(4-tert-butoxycarbonylamino-2-hydroxymethyl-3-methyl-phenyl)-propionic acid methyl ester hydrochloride. Potassium carbonate (1.65 g, 12 mmol) was added to a solution of 3-(4-acetoxymethyl-1H-indazol-5-yl)-2-benzyloxycarbonylamino-propionic acid methyl ester (2.30 g, 5.4 mmol) in methanol (70 mL). Reaction mixture was stirred at room temperature for 2 hours. Reaction was quenched with 1N hydrochloric acid (50 mL). Methanol was removed from the mixture in vacuo. Remaining aqueous was basified with sodium bicarbonate. Aqueous was extracted with ethyl acetate (2×50 mL). Combined extracts were washed with water (30 mL) and brine (20 mL). Organic was dried (magnesium sulfate), filtered and concentrated. Residue was dissolved in 1:1 ethyl acetate:hexanes (50 mL). 1N hydrochloric acid in 1,4 dioxane (1.4 mL), was added to the mixture dropwise causing a precipitate to form. Mixture was stirred at room temperature for 1 hour. Solids were filtered, washed with 1:1 ethyl acetate:hexanes, then dried in vacuo. Product was obtained in 61% yield as a tan solid. $^1$H NMR (300 MHz, DMSO-D$_6$): δ=8.67 (s, 1H), 7.49 (s, 2H), 7.22 (m, 5H), 4.99 (m, 4H), 4.50 (m, 1H), 3.73 (s, 3H), 3.41 (m, 1H), 3.13 (dd, J1=9.9, J2=13.9, 1H). MS m/e (M+H)$^+$=384.0.

Intermediate 17

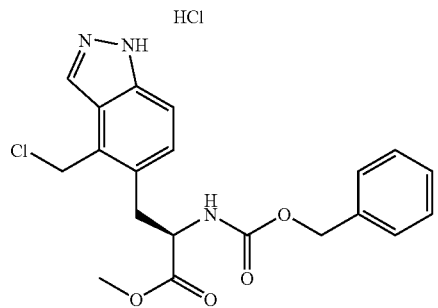

2-(R)-Benzyloxycarbonylamino-3-(4-chloromethyl-1H-indazol-5-yl)-propionic acid methyl ester hydrochloride. 2-(R)-Benzyloxycarbonylamino-3-(4-tert-butoxycarbonylamino-2-hydroxymethyl-3-methyl-phenyl)-propionic acid methyl ester hydrochloride was reacted in a manner analogous to the preparation of 2-(S)-(4-chloromethyl-1H-indazol-5-ylmethyl)-succinic acid dimethyl ester hydrochloride. Title compound was obtained as an orange solid in 99% yield. $^1$H NMR (300 MHz, CD$_3$OD): δ=8.43 (s, 1H), 7.50 (d, J=8.8, 1H), 7.38 (d, J=8.4, 1H), 7.24 (m, 5H), 5.06 (d, J=11.0, 1H), 4.98 (d, J=4.8, 2H), 4.56 (dd, J1=5.7, J2=9.3, 1H), 3.71 (s, 3H), 3.42 (dd, J1=5.5, J2=14.3, 1H), 3.17 (dd, J1=9.3, J2=14.1, 1H). MS m/e (M+H)$^+$=402.0.

Intermediate 18

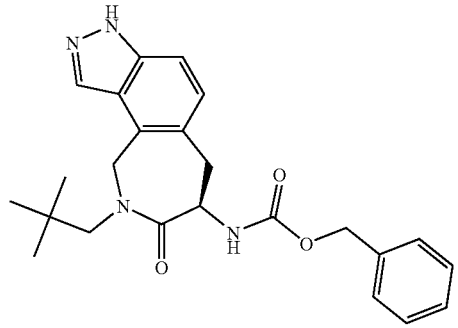

[9-(2,2-Dimethyl-propyl)-8-oxo-3,6,7,8,9,10-hexahydro-2,3,9-triaza-(R)-cyclohepta[e]inden-7-yl]-carbamic acid benzyl ester. Neopentylamine (600 µL, 4.5 mmol) and 2-(R)-benzyloxycarbonylamino-3-(4-chloromethyl-1H-indazol-5-yl)-propionic acid methyl ester hydrochloride were reacted in a manner analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Silica gel chromatography afforded the title compound as a lightly colored oil in 88% yield. $^1$H NMR (300 MHz, CDCl$_3$): δ=7.97 (d, J=2.9, 1H), 7.38 (d, J=4.0, 3H), 7.31 (m, 3H), 7.06 (dd, J1=3.7, J2=8.8, 6.32 (d, J=6.3, 1H), 5.24 (m, 2H), 5.15 (s, 2H), 4.42 (dd, J1=5.5, J2=17.2, 1H), 3.56 (d, J=13.9, 1H), 3.45 (d, J=16.5, 1H), 3.07 (m, 2H), 0.82 (s, 9H). (M+H)$^+$= 421.0.

Intermediate 19

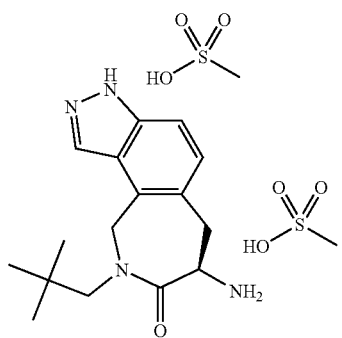

7-(R)-Amino-9-(2,2-dimethyl-propyl)-6,7,9,10-tetrahydro-3H-2,3,9-triaza-cyclohepta[e]inden-8-one bismethanesulfonate. Methanesulfonic acid (1 mL) was added to a solution of [9-(2,2-dimethyl-propyl)-8-oxo-3,6,7,8,9,10-hexahydro-2,3,9-triaza-(R)-cyclohepta[e]inden-7-yl]-carbamic acid benzyl ester (145 mg, 0.34 mmol) and anisole (100 μL, 0.92 mmol) in dichloromethane (4 mL). Reaction mixture was stirred at room temperature for 2.5 hours. Mixture was diluted with diethyl ether (25 mL). Mixture was allowed to stand at room temperature for 30 minutes. Solvents were decanted off. Remaining residue was washed with diethyl ether (25 mL) then dried in vacuo. Crude product was obtained as an orange oil in quantitative yield, and was used without further purification. $^1$H NMR (300 MHz, CD$_3$OD): δ=8.50 (s, 1H), 7.56 (d, J=8.8, 1H), 7.39 (s, J=8.8, 1H), 5.42 (d, J=17.9, 1H), 5.10 (dd, J1=4.4, J2=12.4, 1H), 4.75 (d, J=17.6, 1H), 3.84 (d, J=13.5, 1H), 3.42 (m, 3H), 3.10 (d, J=13.9, 1H), 2.71 (s, 6H), 0.82 (s, 9H). (M+H)$^+$=287.1.

Intermediate 20

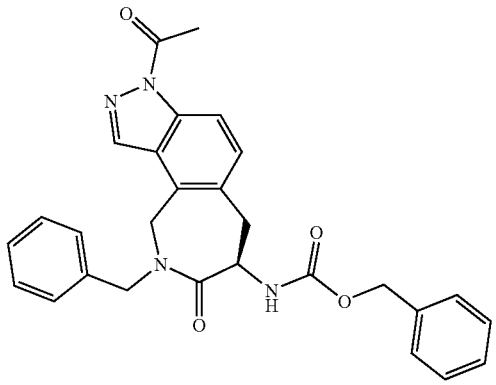

(3-Acetyl-9-benzyl-8-oxo-3,6,7,8,9,10-hexahydro-2,3,9-triaza-(R)-cyclohepta[e]inden-7-yl)-carbamic acid benzyl ester. Benzylamine (53 μL, 0.49 mmol) was added to a mixture of 2-(R)-benzyloxycarbonylamino-3-(4-chloromethyl-1H-indazol-5-yl)-propionic acid methyl ester (125 mg, 0.31 mmol) and potassium carbonate (50 mg, 0.36 mmol) in acetonitrile (5 mL). Reaction was heated at reflux for 1 hour. Mixture was cooled to room temperature then filtered. Filtrate was concentrated. Residue was dissolved in a mixture of toluene (5 mL) and acetic acid (50 μL). Mixture was heated at reflux for 2 hours. Mixture was cooled to room temperature. Acetic anhydride (500 μL) was added to the mixture. Reaction was stirred at room temperature for 2 hours. Mixture was diluted with ethyl acetate (20 mL). Mixture was washed successively with water (15 mL), 1N hydrochloric acid (2×10 mL), and brine (10 mL). Organic was dried (magnesium sulfate), filtered and concentrated. Silica gel chromatography (ethyl acetate-hexanes) yielded the title compound in 43% yield as an amber oil. $^1$H NMR (300 MHz, CDCl$_3$): δ=8.33 (s, 1H), 7.47 (d, J=8.8, 1H), 7.33 (m, 5H), 7.17 (m, 5H), 7.02 (d, J=9.2, 1H), 6.28 (d, J=6.6, 1H), 5.34 (m, 1H), 5.16 (s, 2H), 5.00 (m, 1H), 4.84 (m, 1H), 5.43 (t, J=14.5, 1H), 4.43 (d, J=5.9, 1H), 4.32 (d, J=16.8, 1h), 4.11 (m, 1H), 2.02 (s, 3H). MS m/e (M+H)$^+$=483.2.

Intermediate 21

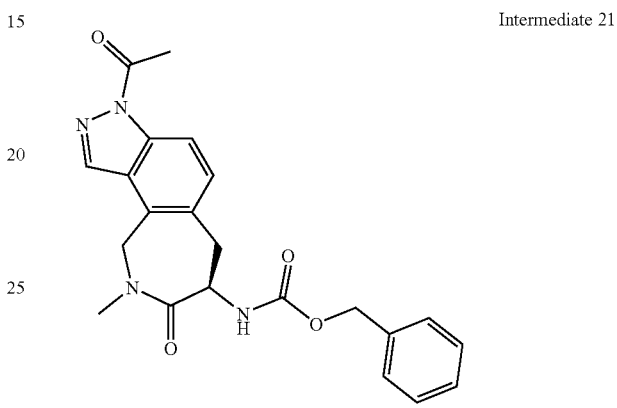

(3-Acetyl-9-methyl-8-oxo-3,6,7,8,9,10-hexahydro-2,3,9-triaza-(R)-cyclohepta[e]inden-7-yl)-carbamic acid benzyl ester. Methylamine solution in methanol (2M, 2 mL, 4 mmol) was added to a mixture of potassium carbonate (130 mg, 0.94 mmol) and 2-(R)-benzyloxycarbonylamino-3-(4-chloromethyl-1H-indazol-5-yl)-propionic acid methyl ester (165 mg, 0.41 mmol) in acetonitrile (5 mL). Mixture was heated at 40° C. for 1 hour. Mixture was cooled to room temperature. Mixture was filtered. Filtrate was concentrated. Residue was treated with a mixture of toluene (5 mL) and acetic acid (200 μL). Mixture was heated at reflux for 45 minutes. Mixture was cooled to room temperature then acetic anhydride was added (2 mL). Reaction was stirred at room temperature for 16 hours. Mixture was diluted with ethyl acetate (10 mL) then washed successively with water (10 mL), saturated aqueous sodium bicarbonate (2×15 mL) and brine (10 mL). Organic was dried (magnesium sulfate), filtered and concentrated. Silica gel chromatography (ethyl acetate-hexanes) yielded the desired product as a yellow solid in 18% yield. $^1$H NMR (300 MHz, CDCl$_3$): δ=8.70 (s, 1H), 7.51 (d, J=9.2, 1H), 7.34 (m, 5H), 7.05 (d, J=9.2, 1H), 6.19 (m, 1H), 5.23 (s, 2H), 5.13 (s, 2H), 4.18 (d, J=17.2, 1H), 3.46 (d, J=17.2, 1H), 3.11 (s, 3H), 2.95 (m, 1H), 2.89 (s, 3H). MS m/e (M+H)$^-$=407.2.

Intermediate 22

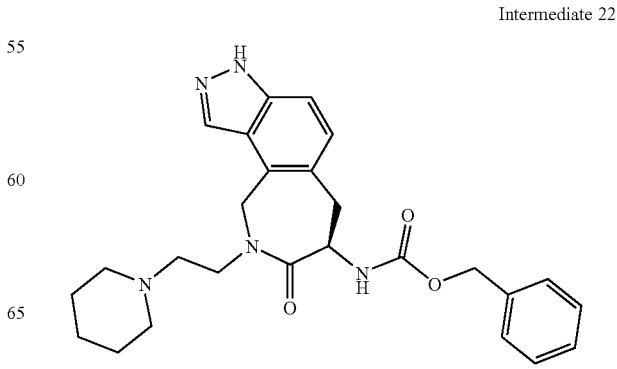

[8-Oxo-9-(2-piperidin-1-yl-ethyl)-3,6,7,8,9,10-hexahydro-2,3,9-triaza-(R)-cyclohepta[e]inden-7-yl]-carbamic acid benzyl ester. 1-(2-Aminoethyl)piperidine (150 μL, 1.1 mmol) was added to a mixture of potassium carbonate (150 mg, 1.1 mmol) and 2-(R)-benzyloxycarbonylamino-3-(4-chloromethyl-1H-indazol-5-yl)-propionic acid methyl ester hydrochloride (220 mg, 0.50 mmol) in acetonitrile (5 mL). Reaction was heated at reflux for 1 hour. Mixture was cooled to room temperature then concentrated. Residue was dissolved in a mixture of dichloromethane (10 mL) and acetic acid (200 μL). Mixture was heated at 40° C. for 32 hours and heated at reflux for 8 hours. Mixture was cooled to room temperature then washed successively with saturated aqueous sodium bicarbonate (2×10 mL), water (10 mL) and brine (10 mL). Organic was dried (magnesium sulfate), filtered and concentrated. Crude product was obtained as a maroon solid in 86% yield. Material was carried forward without further purification. MS m/e (M+H)$^+$=462.4. HPLC rf=1.19 min.

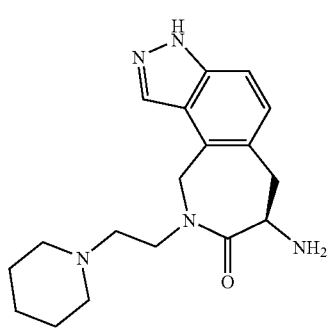

Intermediate 23

7-(R)-Amino-9-(2-piperidin-1-yl-ethyl)-6,7,9,10-tetrahydro-3H-2,3,9-triaza-cyclohepta[e]inden-8-one. Methanesulfonic acid (1 mL) was added to a mixture of anisole (100 μL, 0.92 mmol) and [8-oxo-9-(2-piperidin-1-yl-ethyl)-3,6,7,8,9,10-hexahydro-2,3,9-triaza-(R)-cyclohepta[e]inden-7-yl]-carbamic acid benzyl ester (200 mg, 0.43 mmol) in dichloromethane (4 mL). Reaction was stirred at ambient temperature for 1 hour. Mixture was diluted with diethyl ether (30 mL). Mixture was allowed to stand at room temperature for 15 minutes. Solvents were decanted off. Remaining residue was dissolved in water (5 mL). Mixture was washed with diethyl ether (2×10 mL). Aqueous was basified with 1N sodium hydroxide (2 mL). Mixture was extracted with ethyl acetate (2×15 mL). Combined extracts were washed with brine (5 mL). Organic was dried (magnesium sulfate), filtered and concentrated. Title compound was obtained as an amber oil in 42% yield. Material was carried forward without further purification. $^1$H NMR (300 MHz, CDCl$_3$): δ=8.06 (S, 1H), 7.35 (d, J=8.4, 1H), 7.11 (d, J=8.4, 1H), 5.16 (d, J=16.8, 1H), 4.57 (d, J=16.8, 1H), 4.40 (dd, J1=12.8, J2=4.4, 1H), 3.77 (m, 1H), 3.54 (m, 1H), 3.29 (m, 1H), 3.03 (m, 1H), 2.36 (m, 6H), 2.14 (m, 2H), 1.38 (m, 4H). MS m/e (M+H)$^+$=328.3.

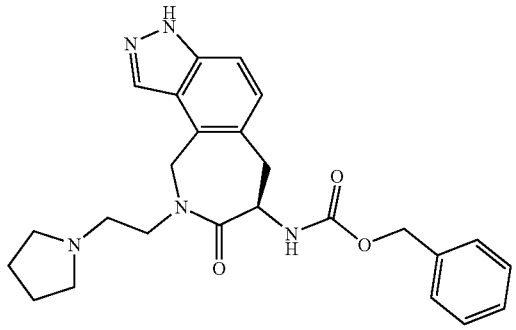

Intermediate 24

[8-Oxo-9-(2-pyrrolidin-1-yl-ethyl)-3,6,7,8,9,10-hexahydro-2,3,9-triaza-(R)-cyclohepta[e]inden-7-yl]-carbamic acid benzyl ester. 1-(2-Aminoethyl)pyrrolidine (90 μL, 0.71 mmol) was added to a mixture of 2-(R)-benzyloxycarbonylamino-3-(4-chloromethyl-1H-indazol-5-yl)-propionic acid methyl ester (100 mg, 0.23 mmol) and potassium carbonate (120 mg, 0.87 mmol) in acetonitrile (5 mL). Reaction was heated at reflux until HPLC suggested the starting material had been consumed (2 hours). Mixture was cooled to room temperature then filtered. Acetic acid (200 μL) was added to the filtrate. Reaction was heated at reflux until judged complete by HPLC (1 hour). Mixture was diluted with ethyl acetate (20 mL) then washed successively with saturated aqueous sodium bicarbonate (15 mL), water (10 mL) and brine (10 mL). Organic was dried (magnesium sulfate), filtered and concentrated. Crude product was obtained in 69% yield as a yellow oil. Material was carried forward without further purification. $^1$H NMR (300 MHz, CDCl$_3$): δ=8.04 (s, 1), 7.38 (m, 5H), 7.28 (d, J=8.4, 1H), 7.02 (d, J=8.8, 1H), 6.25 (d, J=6.2, 1H), 5.25 (m, 1H), 5.15 (s, 2H), 4.56 (d, J=16.8, 1H), 3.70 (m, 2H), 3.47 (dd, J1=3.5, J2=16.7, 1H), 3.01 (m, 1H), 2.62 (m, 2H), 2.48 (m, 3H), 1.74 (m, 4H). MS m/e (M+H)$^+$=448.4.

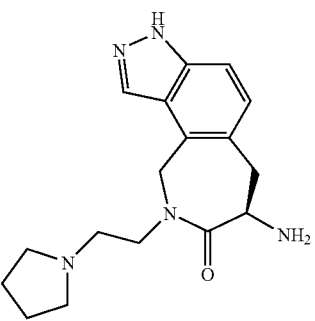

Intermediate 25

7-(R)-Amino-9-(2-pyrrolidin-1-yl-ethyl)-6,7,9,10-tetrahydro-3H-2,3,9-triaza-cyclohepta[e]inden-8-one. Title compound was obtained from [8-oxo-9-(2-pyrrolidin-1-yl-ethyl)-3,6,7,8,9,10-hexahydro-2,3,9-triaza-(R)-cyclohepta[e]inden-7-yl]-carbamic acid benzyl ester following a procedure analogous to the preparation of 7-(R)-amino-9-(2-piperidin-1-yl-ethyl)-6,7,9,10-tetrahydro-3H-2,3,9-triaza-cyclohepta[e]inden-8-one. Material was obtained as an amber oil in 52% yield and used without further purification. $^1$H NMR (300 MHz, DMSO-D$_6$): δ=8.06 (s, 1H), 7.33 (d, J=8.8, 1H), 7.10 (d, J=8.8, 1H), 5.16 (d, J=16.8, 1H), 5.48 (d, J=16.8, 1H), 4.40 (dd, J1=13.0, J2=4.2, 1H), 3.67 (m, 2H), 3.29 (dd, J1=3.11, J2=17.0, 1H), 3.01 (dd, J1=16.8, J2=12.8, 1H), 2.58 (m, 2H)m 1.87 (m, 4H), 1.67 (m, 4H). MS m/e (M+H)$^+$=422.4.

J1=4.8, J2=12.8, 1H), 3.62 (m, 2H), 3.30 (m, 1H), 3.01 (dd, J1=13.0, J2=16.7, 1H), 2.37 (m, 2H), 2.15 (s, 6H). MS m/e (M+H)$^+$=288.3.

Intermediate 26

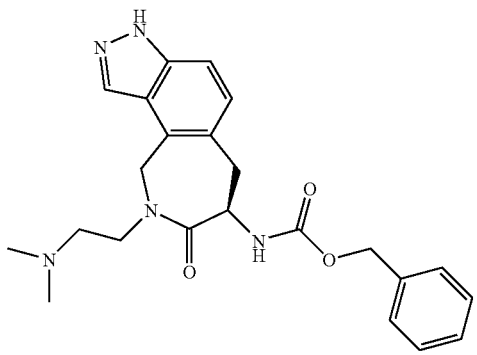

[9-(2-Dimethylamino-ethyl)-8-oxo-3,6,7,8,9,10-hexahydro-2,3,9-triaza-(R)-cyclohepta[e]inden-7-yl]-carbamic acid benzyl ester. N,N-Ethylenediamine (70 µL, 0.66 mmol) and 2-(R)-benzyloxycarbonylamino-3-(4-chloromethyl-1H-indazol-5-yl)-propionic acid methyl ester (100 mg, 0.23 mmol) were converted to the title compound following a procedure analogous to the preparation of [8-oxo-9-(2-pyrrolidin-1-yl-ethyl)-3,6,7,8,9,10-hexahydro-2,3,9-triaza-(R)-cyclohepta[e]inden-7-yl]-carbamic acid benzyl ester. Crude product was obtained as an amber oil in 52% yield. Material was carried forward without further purification. $^1$H NMR (300 MHz, CDCl$_3$): δ=7.99 (s, 1H), 7.36 (m, 6H), 6.27 (d, J=6.2, 1H), 5.25 (m, 1H), 5.16 (s, 2H), 5.13 (m, 1H), 5.06 (d, J=18.7, 1H), 4.52 (d, J=17.2, 1H), 3.61 (t, J=6.8, 2H), 3.45 (dd, J1=2.4, J2=16.7, 1H), 3.01 (m, 1H), 2.38 (m, 2H), 2.11 (s, 6H). MS m/e (M+H)$^+$=422.4.

Intermediate 28

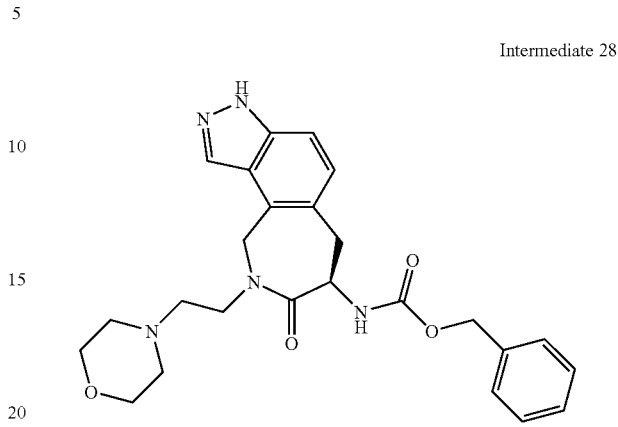

[9-(2-Morpholin-4-yl-ethyl)-8-oxo-3,6,7,8,9,10-hexahydro-2,3,9-triaza-(R)-cyclohepta[e]inden-7-yl]-carbamic acid benzyl ester. 4-(2-Aminoethyl)morpholine (90 µL, 0.69 mmol) and 2-(R)-benzyloxycarbonylamino-3-(4-chloromethyl-1H-indazol-5-yl)-propionic acid methyl ester (100 mg, 0.23 mmol) were converted into the title compound following a procedure analogous to the preparation of [8-oxo-9-(2-piperidin-1-yl-ethyl)-3,6,7,8,9,10-hexahydro-2,3,9-triaza-(R)-cyclohepta[e]inden-7-yl]-carbamic acid benzyl ester. Crude material was obtained as an amber oil in 92% yield. Product was carried forward without further purification. MS m/e (M+H)$^+$=464.4. HPLC rf=1.15 min.

Intermediate 27

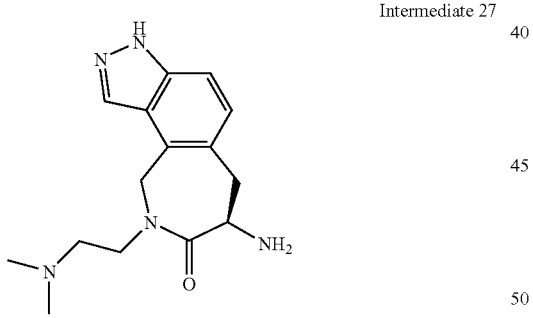

Intermediate 29

7-(R)-Amino-9-(2-dimethylamino-ethyl)-6,7,9,10-tetrahydro-3H-2,3,9-triaza-cyclohepta[e]inden-8-one. [9-(2-Dimethylamino-ethyl)-8-oxo-3,6,7,8,9,10-hexahydro-2,3,9-triaza-(R)-cyclohepta[e]inden-7-yl]-carbamic acid benzyl ester (65 mg, 0.15 mmol) was converted to the desired product in a manner analogous to the preparation of 7-(R)-amino-9-(2-pyrrolidin-1-yl-ethyl)-6,7,9,10-tetrahydro-3H-2,3,9-triaza-cyclohepta [e]inden-8-one. Crude material was obtained as a yellow oil in 25% yield. Material was carried forward without further purification. $^1$H NMR (300 MHz, CDCl$_3$): δ=8.07 (s, 1H), 7.35 (d, J=8.4, 1H), 7.12 (d, J=8.4, 1H), 5.15 (d, J=16.8, 1H), 4.58 (d, J=16.8, 1H), 4.42 (dd, 7-(R)-Amino-9-(2-morpholin-4-yl-ethyl)-6,7,9,10-tetrahydro-3H-2,3,9-triaza-cyclohepta[e]inden-8-one. [9-(2-Morpholin-4-yl-ethyl)-8-oxo-3,6,7,8,9,10-hexahydro-2,3,9-triaza-(R)-cyclohepta[e]inden-7-yl]-carbamic acid benzyl ester (95 mg, 0.20 mmol) was converted into the title compound following a procedure analogous to the preparation of 7-(R)-amino-9-(2-piperidin-1-yl-ethyl)-6,7,9,10-tetrahydro-3H-2,3,9-triaza-cyclohepta[e]inden-8-one. Crude product was obtained as an amber oil in 62% yield. Material was carried forward without further purification. $^1$H NMR (300 MHz, CDCl$_3$): δ=8.06 (s, 1H), 7.34 (d, J=8.4, 1H), 7.15 (d, J=8.8, 1H), 5.22 (d, J=16.8, 1H), 4.51 (d, J=17.2, 2H), 4.44

(m, 1H), 4.02 (m, 1H), 3.40 (t, J=4.8, 4H), 3.31 (m, 3H), 3.07 (m, 1H), 2.32 (m, 4H), 1.95 (m, 2H). MS m/e (M+H)⁺=330.3.

Intermediate 30

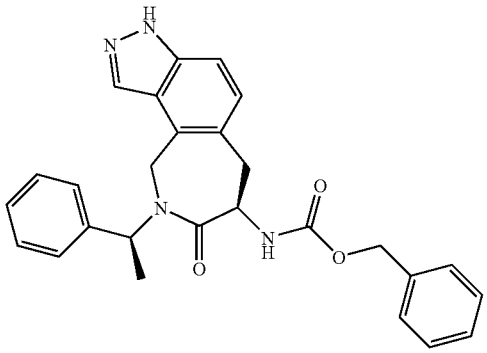

[8-Oxo-9-(1-(S)-phenyl-ethyl)-3,6,7,8,9,10-hexahydro-2,3,9-triaza-(R)-cyclohepta[e]inden-7-yl]-carbamic acid benzyl ester. (S)-(−)-α-Methylbenzylamine (85 µL, 0.67 mmol) and 2-(R)-benzyloxycarbonylamino-3-(4-chloromethyl-1H-indazol-5-yl)-propionic acid methyl ester (100 mg, 0.23 mmol) were converted into the desired product following a procedure analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude product was obtained as a dark oil in quantitative yield. Material was carried forward without further purification. MS m/e (M+H)⁺=455.3. HPLC rf=1.68 min.

Intermediate 31

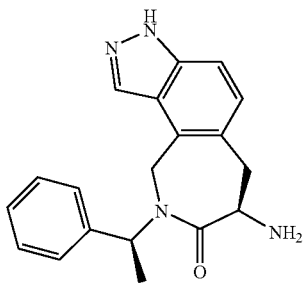

7-Amino-9-(1-(S)-phenyl-ethyl)-6,7,9,10-tetrahydro-3H-2,3,9-triaza-(R)-cyclohepta[e]inden-8-one. [8-Oxo-9-(1-(S)-phenyl-ethyl)-3,6,7,8,9,10-hexahydro-2,3,9-triaza-(R)-cyclohepta[e]inden-7-yl]-carbamic acid benzyl ester (105 mg, 0.23 mmol) was reacted in a manner analogous to the preparation of 7-(R)-amino-9-(2-piperidin-1-yl-ethyl)-6,7,9,10-tetrahydro-3H-2,3,9-triaza-cyclohepta[e]inden-8-one. Crude product was obtained as a dark oil in 82% yield. Material was carried forward without further purification. MS m/e (M−H)⁻= 319.3. HPLC rf=1.49 min.

Intermediate 32

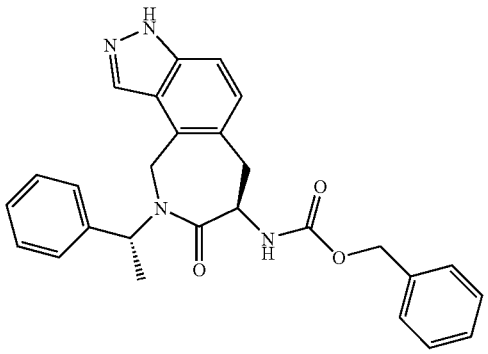

[8-Oxo-9-(1-(R)-phenyl-ethyl)-3,6,7,8,9,10-hexahydro-2,3,9-triaza-(R)-cyclohepta[e]inden-7-yl]-carbamic acid benzyl ester. (R)-(+)-α-Methylbenzylamine (85 µL, 0.67 mmol) and 2-(R)-benzyloxycarbonylamino-3-(4-chloromethyl-1H-indazol-5-yl)-propionic acid methyl ester (100 mg, 0.23 mmol) were converted into the title compound in a manner similar to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude material was obtained as a dark foam in quantitative yield. Material was carried forward without further purification. MS m/e (M−H)⁻=453.4. HPLC rf=1.98 min.

Intermediate 33

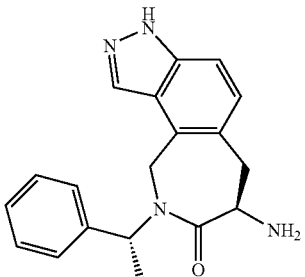

7-Amino-9-(1-(R)-phenyl-ethyl)-6,7,9,10-tetrahydro-3H-2,3,9-triaza-(R)-cyclohepta[e]inden-8-one. [8-Oxo-9-(1-(R)-phenyl-ethyl)-3,6,7,8,9,10-hexahydro-2,3,9-triaza-(R)-cyclohepta[e]inden-7-yl]-carbamic acid benzyl ester (105 mg, 0.23 mmol) was reacted in a manner analogous to the preparation of 7-(R)-amino-9-(2-piperidin-1-yl-ethyl)-6,7,9,10-tetrahydro-3H-2,3,9-triaza-cyclohepta[e]inden-8-one. Crude product was obtained as a maroon solid in 78% yield. Material was carried forward without further purification. ¹H NMR (300 MHz, CDCl₃): δ=7.88 (s, 1H), 7.40 (m,6H), 7.14 (d, J=8.8, 1H), 6.85 (m, 1H), 6.09 (m, 1H), 4.67 (d, J=16.8, 1H), 4.47 (dd, J1=4.6, J2=12.6, 1H), 4.25 (d, J=17.2, 1H), 1.48 (d, J=7.0, 3H). MS m/e (M−H)⁻=319.3.

Intermediate 34

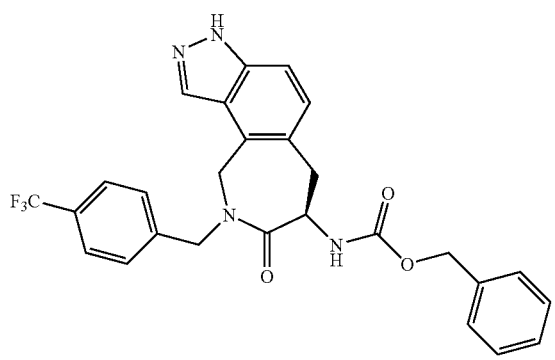

[8-Oxo-9-(4-trifluoromethyl-benzyl)-3,6,7,8,9,10-hexahydro-2,3,9-triaza-(R)-cyclohepta[e]inden-7-yl]-carbamic acid benzyl ester. 4-Trifluoromethylbenzylamine (72 µL, 0.51 mmol) and 2-(R)-benzyloxycarbonylamino-3-(4-chloromethyl-1H-indazol-5-yl)-propionic acid methyl ester (100 mg, 0.23 mmol) were converted into the title compound in a manner similar to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude material was obtained as a dark brown solid in quantitative yield. Material was carried forward without further purification. MS m/e (M+H)⁺=509.4. HPLC rf=1.67 min.

Intermediate 35

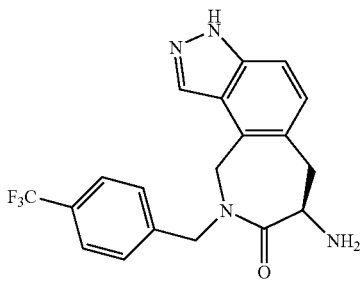

7-Amino-9-(4-trifluoromethyl-benzyl)-6,7,9,10-tetrahydro-3H-2,3,9-triaza-(R)-cyclohepta[e]inden-8-one bismethanesulfonate. [8-Oxo-9-(4-trifluoromethyl-benzyl)-3,6,7,8,9,10-hexahydro-2,3,9-triaza-(R)-cyclohepta[e]inden-7-yl]-carbamic acid benzyl ester was converted into the title compound in a manner analogous to the preparation of 7-(R)-amino-9-(2,2-dimethyl-propyl)-6,7,9,10-tetrahydro-3H-2,3,9-triaza-cyclohepta[e]inden-8-one bismethaneslufonate. Crude material was obtained as a dark foam in quantitative yield. Material was carried forward without further purification. MS m/e (M+H)$^+$=375.2. HPLC rf=1.00 min.

Intermediate 36

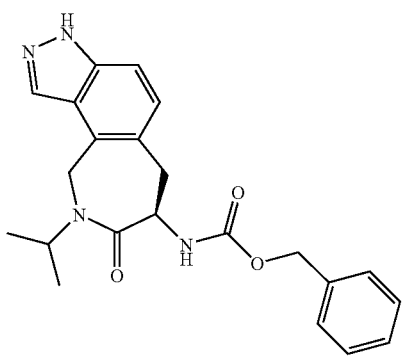

(9-Isopropyl-8-oxo-3,6,7,8,9,10-hexahydro-2,3,9-triaza-(R)-cyclohepta[e]inden-7-yl)-carbamic acid benzyl ester. Isopropylamine (300 μL, 3.5 mmol) and 2-(R)-benzyloxycarbonylamino-3-(4-chloromethyl-1H-indazol-5-yl)-propionic acid methyl ester were converted into the title compound following a procedure analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude product was obtained as a dark oil in quantitative yield. Material was carried forward without further purification. $^1$H NMR (500 MHz, CDCl$_3$): δ=8.09 (s, 1H), 7.39 (m, 3H), 7.23 (m, 2H), 7.17 (m, 1H), 6.32 (d, J=5.8, 1H), 5.25 (m, 1H), 5.15 (m, 2H), 4.90 (m, 1H), 4.82 (d, J=17.4, 1H), 4.51 (m, 1H), 3.51 (m, 1H), 3.05 (t, J=13.6, 1H), 1.56 (s, 6H). MS m/e (M+H)$^+$=393.4.

Intermediate 37

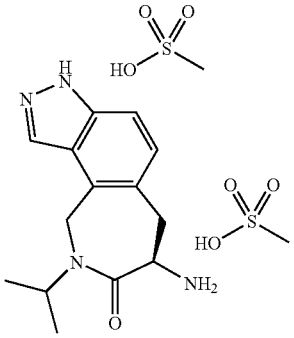

7-(R)-Amino-9-isopropyl-6,7,9,10-tetrahydro-3H-2,3,9-triaza-cyclohepta[e]inden-8-one bismethanesulfonate. (9-Isopropyl-8-oxo-3,6,7,8,9,10-hexahydro-2,3,9-triaza-(R)-cyclohepta[e]inden-7-yl)-carbamic acid benzyl ester (90 mg, 0.23 mmol) was converted into the title comound following a procedure analogous to the synthesis of 7-(R)-amino-9-(2,2-dimethyl-propyl)-6,7,9,10-tetrahydro-3H-2,3,9-triaza-cyclohepta[e]inden-8-one bismethaneslufonate. Crude product was obtained as a dark oil in quantitative yield. Crude material was carried forward without further purification. MS m/e (M+H)$^+$=259.2. HPLC rf=0.60 min.

Intermediate 38

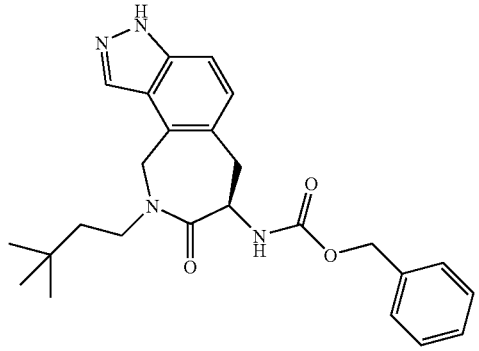

[9-(3,3-Dimethyl-butyl)-8-oxo-3,6,7,8,9,10-hexahydro-2,3,9-triaza-(R)-cyclohepta[e]inden-7-yl]-carbamic acid benzyl ester. 3,3-Dimethylbutylamine (100 μL, 0.74 mmol) and 2-(R)-benzyloxycarbonylamino-3-(4-chloromethyl-1H-indazol-5-yl)-propionic acid methyl ester were converted into the title compound following a procedure analogous to the preparation of [8-oxo-9-(2-piperidin-1-yl-ethyl)-3,6,7,8,9,10-hexahydro-2,3,9-triaza-(R)-cyclohepta[e]inden-7-yl]-carbamic acid benzyl ester. Crude material was obtained as a dark oil in quantitative yield. Material was carried forward without further purification. $^1$H NMR (300 MHz, CDCl$_3$): δ=8.03 (m, 1H), 4.38 (m, 4H), 7.31 (m, 2H), 7.06 (d, J=8.4, 1H), 6.26 (d, J=6.2, 1H), 5.23 (m, 1H), 5.14 (s, 2H), 5.08 (m, 1H), 4.35 (dd, J1=8.8, J2=17.2, 1H), 3.50 (m, 2H), 1.33 (dd, J=6.2, J2=11.0, 2H), 0.91 (m, 2H), 0.85 (s, 9H). MS m/e (M+H)$^+$=435.1.

Intermediate 39

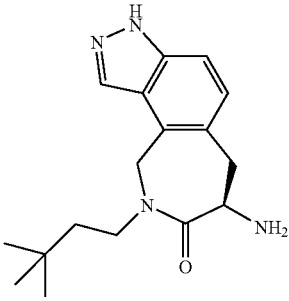

7-(R)-Amino-9-(3,3-dimethyl-butyl)-6,7,9,10-tetrahydro-3H-2,3,9-triaza-cyclohepta[e]inden-8-one bismethanesulfonate. [9-(3,3-dimethyl-butyl)-8-oxo-3,6,7,8,9,10-hexahydro-2,3,9-triaza-(R)-cyclohepta[e]inden-7-yl]-carbamic acid benzyl ester (100 mg, 0.23 mmol) was converted into the title compound following a procedure analogous to the preparation of 7-(R)-amino-9-(2,2-dimethyl-propyl)-6,7,9,10-tetrahydro-3H-2,3,9-triaza-cyclohepta[e]inden-8-one bismethaneslufonate. Crude material was obtained as a dark oil in quantitative yield. Material was carried forward without further purification. MS m/e (M+H)+= 301.2. HPLC rf=1.11 min.

Intermediate 40

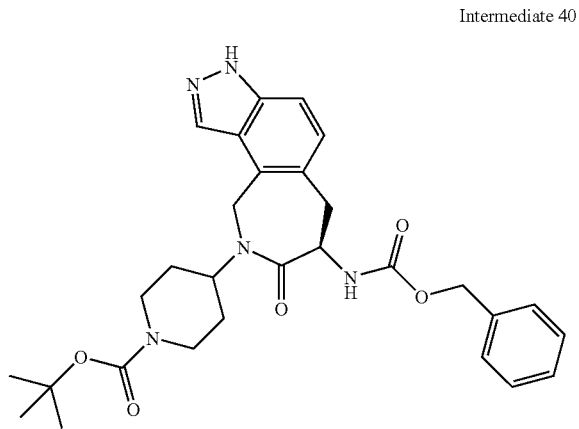

4-(7-(R)-Benzyloxycarbonylamino-8-oxo-6,7,8,10-tetrahydro-3H-2,3,9-triaza-cyclohepta[e]inden-9-yl)-piperidine-1-carboxylic acid tert-butyl ester. 4-Amino-1-N-Boc-piperidine (110 mg, 0.55 mmol) and 2-(R)-benzyloxycarbonylamino-3-(4-chloromethyl-1H-indazol-5-yl)-propionic acid methyl ester (150 mg, 0.34 mmol) was converted into the title compound in a manner analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude product was obtained as a dark foam in quantitative yield. Material was carried forward without further purification. $^1$H NMR (300 MHz, CDCl$_3$): δ=8.05 (m, 1H), 7.35 (m,6H), 7.15 (m, 1H), 6.27 (m, 1H), 5.28 (m, 1H), 5.15 (s, 2H), 4.87 (d, J=16.5, 1H), 4.63 (m, 1H), 4.47 (m, 1H), 4,24 (m, 1H), 3.99 (m, 1H), 3.49 (m, 1H), 3.04 (m, 1H), 2.83 (m, 2H), 2.63 (m, 1H), 1.90 (m, 1H), 1.74 (m, 2H), 1.58 (s, 9H). MS m/e (M−H)−=532.1.

Intermediate 41

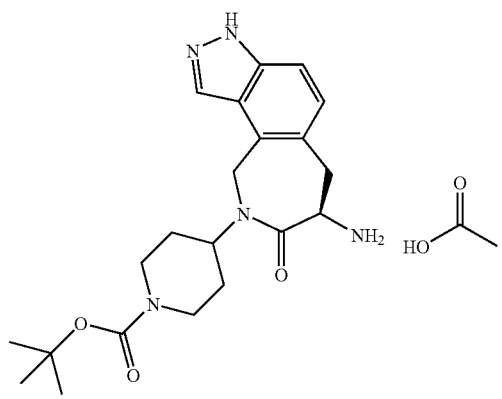

4-(7-(R)-Amino-8-oxo-6,7,8,10-tetrahydro-3H-2,3,9-triaza-cyclohepta[e]inden-9-yl)-piperidine-1-carboxylic acid tert-butyl ester acetate. A catalytic amount of 10% palladium on carbon was added to a solution of 4-(7-R)-Benzyloxycarbonylamino-8-oxo-6,7,8,10-tetrahydro-3H-2,3,9-triaza-cyclohepta[e]inden-9-yl)-piperidine-1-carboxylic acid tert-butyl ester (200 mg, 0.37 mmol) and acetic acid (100 μL, 1.7 mmol) in methanol (10 mL). Reaction vessel was placed on a Parr apparatus and charged with 30 psi of hydrogen gas. Mixture was allowed to shake at room temperature for 3 hours. Mixture was filtered. Filtrate was concentrated in vacuo. Crude compound was obtained as a dark oil in quantitative yield. Material was carried forward without further purification. $^1$H NMR (300 MHz, CDCl$_3$): δ=8.06 (s, 1H), 7.36 (d, J=8.8, 1H), 7.12 (d, J=8.8, 1H), 4.92 (d, J=17.6, 1 H), 4.67 (m, 1H), 4.49 (d, J=17.2, 1H), 4.26 (m, 1H), 3.98 (m, 2H), 3.05 (m, 1H), 2.83 (m, 2H), 2.64 (m, 1H), 1.89 (m, 1H), 1.73 (m, 1H), 1.45 (d, J=2.9, 9H), 1.25 (m, 2H). MS m/e (M−C$_4$H$_8$+H)+=344.2.

Intermediate 42

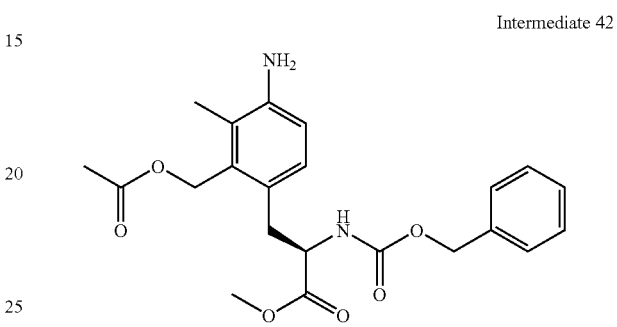

3-(2-Acetoxymethyl-4-amino-3-methyl-phenyl)-2-(R)-benzyloxycarbonylamino-propionic acid methyl ester. 3-(2-Acetoxymethyl-4-tert-butoxycarbonylamino-3-methyl-phenyl)-2-(R)-benzyloxycarbonylamino-propionic acid methyl ester was converted into 3-(2-Acetoxymethyl-4-amino-3-methyl-phenyl)-2-benzyloxycarbonylamino-(R)-propionic acid methyl ester following an analogous procedure to the synthesis of 2-(2-Acetoxymethyl-4-amino-3-methyl-benzyl)-(S)-succinic acid diethyl ester. Desired product was obtained as an yellow oil in 95% yield. $^1$H NMR (300 MHz, CDCl$_3$): δ=7.31 (m, 5H); 6.81 (d, J=8.1, 1H); 6.65 (d, J=8.4, 1H); 5.35 (d, J=8.1, 1H); 5.15 (s, 2H); 5.04 (s, 2H); 4.53 (m, 1H); 3.71 (s, 3H); 3.16 (m, 1H); 3.01 (m, 1H); 2.12 (s, 3H); 1.99 (s, 3H). MS m/e (M+H)+=415.2.

Intermediate 43

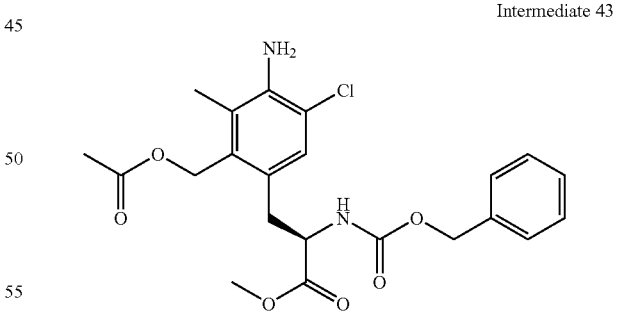

3-(2-Acetoxymethyl-4-amino-5-chloro-3-methyl-phenyl)-2-(R)-benzyloxycarbonylamino-propionic acid methyl ester. Desired product was obtained from 3-(2-Acetoxymethyl-4-amino-3-methyl-phenyl)-2-(R)-benzyloxycarbonylamino-propionic acid methyl ester in a manner analogous to the preparation of 2-(2-Acetoxymethyl-4-amino-5-chloro-3-methyl-benzyl)-(S)-succinic acid diethyl ester. Silica gel chromatography (ethyl acetate-hexanes) afforded the product as an yellow oil in 40% yield. $^1$H NMR (300 MHz, CDCl$_3$): δ=7.31 (m, 5H); 6.96 (s, 1H); 5.36 (d, J=8.4, 1H); 5.12 (s, 2H); 5.05 (s, 2H), 4.53 (m, 1H); 3.72 (s, 3H); 3.15 (m, 1H), 2.99 (m, 1H); 2.15 (s, 3H); 1.99 (s, 3H). MS m/e (M−C$_2$H$_4$O$_2$+H)$^-$=398.3.

Intermediate 44

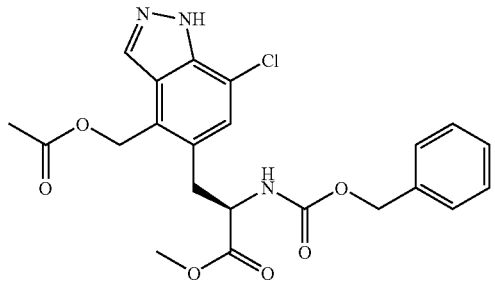

3-(4-Acetoxymethyl-7-chloro-1H-indazol-5-yl)-2-(R)-benzyloxycarbonylamino-propionic acid methyl ester. Trifluoroacetic acid (70 µL, 0.91 mmol) was added to a solution of 3-(2-acetoxymethyl-4-amino-5-chloro-3-methyl-phenyl)-2-(R)-benzyloxycarbonylamino-propionic acid methyl ester (345 mg, 0.77 mmol) in 5% acetic acid in chloroform (5.2 mL). Isoamyl nitrite (120 µL, 0.89 mmol) was added to the mixture drop-wise. Reaction mixture was stirred at room temperature for 40 minutes. Potassium acetate (300 mg, 3.1 mmol) was added to the mixture. Reaction mixture was stirred at room temperature for 45 minutes. Mixture was diluted with dichloromethane (10 mL) then washed successively with water (2×10 mL), and saturated aqueous sodium bicarbonate (2×10 mL). Organic was dried (magnesium sulfate), filtered and concentrated in vacuo. Crude product was obtained as an orange solid in 83% yield. Material was carried forward without further purification. $^1$H NMR (300 MHz, CDCl$_3$): δ=8.20 (s, 1H); 7.29 (m, 5H); 7.21 (s, 1H); 5.53 (d, J=7.7, 1H); 5.40 (s, 2H); 5.04 (s, 2H); 4.67 (m, 1H); 3.74 (s, 3H); 3.34 (m, 1H); 3.21 (m, 1H); 2.02 (s, 3H). MS m/e (M+H)$^+$=460.1.

Intermediate 45

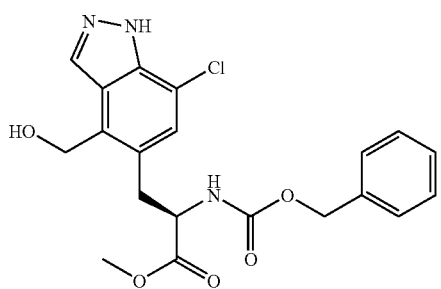

2-(R)-Benzyloxycarbonylamino-3-(7-chloro-4-hydroxymethyl-1H-indazol-5-yl)-propionic acid methyl ester. 3-(4-Acetoxymethyl-7-chloro-1H-indazol-5-yl)-2-(R)-benzyloxycarbonylamino-propionic acid methyl ester (290 mg, 0.63 mmol) was converted into the desired product in a manner analogous to the preparation of 2-(R)-benzyloxycarbonylamino-3-(4-tert-butoxycarbonylamino-2-hydroxymethyl-3-methyl-phenyl)-propionic acid methyl ester. Crude product was obtained as an orange solid in 95% yield. Material was carried forward without further purification. $^1$H NMR (300 MHz, CDCl$_3$): δ=8.15 (s, 1H); 7.27 (m, 5H); 7.14 (s, 1H); 6.10 (m, 1H); 5.01 (d, J=4.8, 2H); 4.95 (s, 2H); 4.75 (m, 1H); 3.79 (s, 3H); 3.34 (m, 1H); 3.09 (m, 1H). MS m/e (M+H)$^+$=418.0.

Intermediate 46

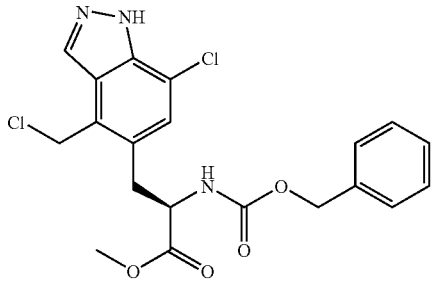

2-(R)-Benzyloxycarbonylamino-3-(7-chloro-4-chloromethyl-1H-indazol-5-yl)-propionic acid methyl ester. Thionyl chloride (2 mL) was added to a solution of 2-(R)-benzyloxycarbonylamino-3-(7-chloro-4-hydroxymethyl-1H-indazol-5-yl)-propionic acid methyl ester (245 mg, 0.59 mmol) in dichloromethane (3 mL). Mixture was stirred at room temperature for 1.5 hours. Mixture was concentrated. Residue was dissolved in dichloromethane (15 mL) then washed with saturated aqueous sodium bicarbonate (2×10 mL). Organic was dried (magnesium sulfate), filtered and concentrated. Title compound was obtained as an orange solid in 86% yield. Material was carried forward without further purification. $^1$H NMR (300 MHz, CDCl$_3$): δ=8.19 (s, 1H), 7.32 (m, 5H), 7.16 (s, 1H), 5.49 (d, J=7.3, 2H), 5.07 (d, J=4.4, 2H), 4.85 (s, 2H), 4.68 (d, J=7.0, 1H), 3.72 (s, 3H), 3.27 (m, 2H). MS m/e (M+H)$^+$=436.1.

Intermediate 47

[4-Chloro-9-(2,2-dimethyl-propyl)-8-oxo-3,6,7,8,9,10-hexahydro-2,3,9-triaza-(R)-cyclohepta[e]inden-7-yl]-carbamic acid benzyl ester. Neopentylamine (200 µL, 1.7 mmol) was added to a mixture of 2-(R)-benzyloxycarbonylamino-3-(7-chloro-4-chloromethyl-1H-indazol-5-yl)-propionic acid methyl ester (180 mg, 0.41 mmol) and potassium carbonate (160 mg, 1.2 mmol) in acetonitrile (5 mL). Reaction was heated at reflux for 1 hour. Mixture was cooled to room temperature then filtered through a 0.45 µm PTFE syringeless filter system. Filtrate was concentrated. Residue was dissolved in a mixture of toluene (5 mL) and acetic acid (200 µL). Mixture was heated at 110° C. overnight. Mixture was diluted with ethyl acetate (15 mL) then washed successively with water (15 mL), saturated aqueous sodium bicarbonate (2×15 mL) and brine (10 mL). Organic was dried (magnesium sulfate), filtered and concentrated. Silica gel chromatography afforded the title compound in 52% yield as a yellow solid. $^1$H NMR (300 MHz, CDCl$_3$): δ=7.89 (d, J=10.6, 1H), 7.38 (m, 5H), 6.96 (d, J=10.3, 1H), 6.35 (d, J=5.9, 1H), 5.25 (m, 1H), 5.19 m, 2H), 4.28 (m, 1H), 3.66 (m, 1H), 3.40 (m, 1H), 2.96 (dd, J1=13.9, J2=5.5, 2H), 0.76 (d, J=2.6, 9H). MS m/e (M+H)$^+$=455.2.

Intermediate 48

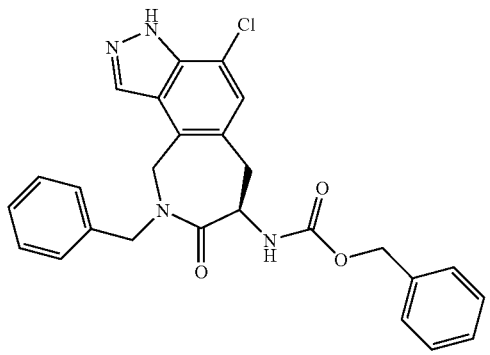

(9-Benzyl-4-chloro-8-oxo-3,6,7,8,9,10-hexahydro-2,3,9-triaza-(R)-cyclohepta[e]inden-7-yl)-carbamic acid benzyl ester. Title compound was obtained from benzylamine (100 μL, 0.92 mmol) and 2-(R)-Benzyloxycarbonylamino-3-(7-chloro-4-chloromethyl-1H-indazol-5-yl)-propionic acid methyl ester (210 mg, 0.48 mmol) following a procedure analogous to the preparation of [4-Chloro-9-(2,2-dimethyl-propyl)-8-oxo-3,6,7,8,9,10-hexahydro-2,3,9-triaza-(R)-cyclohepta[e]inden-7-yl]-carbamic acid benzyl ester. Silica gel chromatography (ethyl acetate-hexanes) afforded the desired product as a yellow solid in 52% yield. $^1$H NMR (300 MHz, CDCl$_3$): δ=7.64 (s, 1H), 7.38 (m, 5H), 7.19 (m, 3H), 7.12 (m, 2H), 7.00 (s, 1H), 6.36 (d, J=6.2 1H), 5.28 (m, 1H), 5.21 (s, 2H), 5.19 (m, 1H), 4.88 (m, 1H), 4.75 (d, J=16.8, 1H), 4.34 (d, J=14.6, 1H), 3.49 (m, 1H), 3.03 (m, 1H). MS m/e (M+H)$^+$=475.0.

Intermediate 49

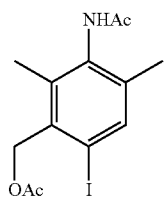

Acetic acid 3-acetylamino-6-iodo-2,4-dimethyl-benzyl ester. To a well stirred solution of (3-amino-2,4-dimethyl-phenyl)-methanol (1.5 g) in methanol (70 mL) and solid sodium hydrogen carbonate (4.0 eq) was added a 1.0 M solution of iodine monochloride dropwise over a period of 5 min at 0° C. The cooling bath was removed after the addition of iodine monochloride. The reaction mixture was brought to room temperature and stirring continued for another 1 h. The reaction mixture was concentrated to remove most of methanol, diluted with dichloromethane (50 mL) and washed with 10% solution of sodium thiosulfate and dried (Na2SO4). The desired compound was purified by trituration with dichloromethane and hexane to give in 1.9 g of iodide. The iodide was then treated with dichloromethane (100 mL) followed by acetic anhydride (4 eq) and catalytic amount of dimethylaminopyridine and stirred for a period of 12 h at room temperature. The reaction mixture was then washed with aqueous sodium hydrogen carbonate, 1.0 M hydrochloric acid and dried (Na2SO4). The desired compound was triturated with dichloromethane and hexane to give acetic acid 3-acetylamino-6-iodo-2,4-dimethyl-benzyl ester in 95% yield. $^1$H NMR (300 MHz, CDCl$_3$): in δ 7.68 (s, 1 H), 6.68 (s, 1 H), 2.28 (s, 3 H), 2.25 (s, 3 H), 2.18 (s, 3 H), 2.07(s, 3 H); MS (ESI) 384 (M+Na); R$_f$=1.12.

Intermediate 50

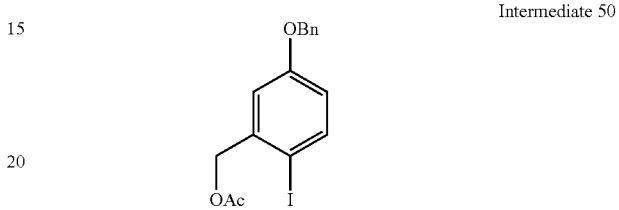

Acetic acid 5-benzyloxy-2-iodo-benzyl ester. To a well stirred solution of 3-benzyloxybenzyl alcohol (5.5 g, 25.7 mmol) in methanol (100 mL) and sodium hydrogencarbonate (8.4 g, 100 mmol) was added a 1.0 M solution of iodine monochloride in dichloromathane (30 mL) at 0° C. The reaction mixture was brought to room temperature and stirring continued for additional 1 h. The reaction mixture was concentrated and then diluted with dicholomethane (150 mL), washed with 10% aqueous sodium thiosulfate and dried (Na$_2$SO$_4$). The desired compound was purified by flash chromatography (silica) using 20% ethyl acetate in hexane to give 5-benzyloxy-2-iodobenzyl alcohol (6.2 g, 71% yield). The alcohol (4.2 g, 12.4 mmol) was dissolved in dichloromethane (100 mL) added acetic anhydride (2.52 g, 24.7 mmol) and catalytic amount of 4-dimethylaminopyridine. The reaction mixture was then stirred for 12 h, washed with aqueous sodium hydrogencarbonate and then dried (Na$_2$SO$_4$) to give acetic acid 5-benzyloxy-2-iodo-benzyl ester in quantitative yield. MS (ESI) 405 (M+Na); R$_f$=2.27.

Intermediate 51

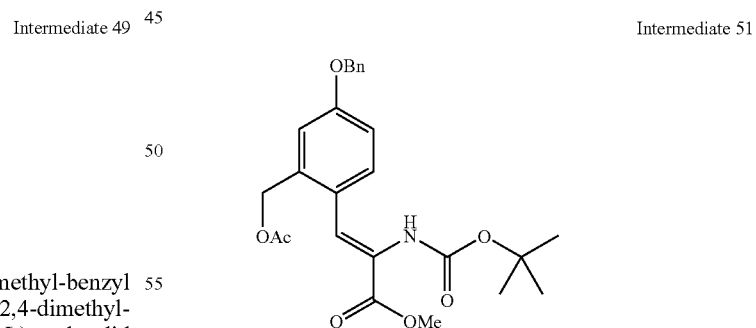

3-(2-Acetoxymethyl-4-benzyloxy-phenyl)-2-tert-butoxy-carbonylamino-acrylic acid methyl ester. In a manner similar to 2-(acetoxymethyl-4-tert-butoxycarbonylamino-3-methyl-benzylidene)-succinic acid diethyl ester, 3-(2-acetoxymethyl-4-benzyloxy-phenyl)-2-tert-butoxycarbonylamino-acrylic acid methyl ester was prepared by reacting acetic acid 5-benzyloxy-2-iodo-benzyl ester with 2-tert-butoxycarbony-lamino-acrylic acid methyl ester in 74% yield. MS (ESI) 456 (M+H); R$_f$=1.87.

Intermediate 52

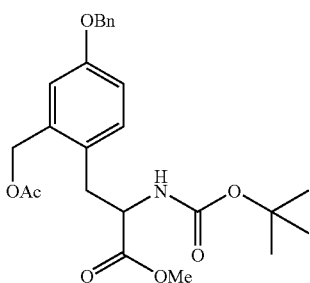

3-(2-Acetoxymethyl-4-benzyloxy-phenyl)-2-tert-butoxycarbonylamino-propionic acid methyl ester. To a solution of 3-(2-acetoxymethyl-4-benzyloxy-phenyl)-2-tert-butoxycarbonylamino-acrylic acid methyl ester (1.9 g, 4.2 mmol) in anhydrous methanol under nitrogen atmosphere was added 1,2-bis((2R,5R)-2,5-diethylphospholano)benzene(cyclooctadiene)rhodium (I) trifluoromethanesulfonate (50 mg) and stirred on a Parr shaker at 50 psi of hydrogen atmosphere for 18 h. The solvent was evaporated and the desired product was crystallized from ethyl acetate-hexane in 90% yield. MS (ESI) 458 (M+H); $R_f$=1.81.

Intermediate 53

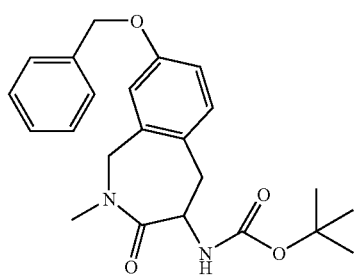

(8-Benzyloxy-2-methyl-3-oxo-2,3,4,5-tetrahydro-1H-benzo[c]azepin-4-yl)-carbamic acid tert-butyl ester. To a solution of 3-(2-acetoxymethyl-4-benzyloxy-phenyl)-2-tert-butoxycarbonylamino-propionic acid methyl ester (1.85 g, 4.0 mmol) in methanol (40 mL) was added potassium carbonate (560 mg, 4.0 mmol) at room temperature and stirred for 1 h. The reaction mixture was diluted with dichloromethane (150 mL), washed with 1.0 M aqueous hydrogen chloride and dried ($Na_2SO_4$) to give the pure 3-(4-benzyloxy-2-hydroxymethyl-phenyl)-2-tert-butoxycarbonylamino-propionic acid methyl ester in almost quantitative yield. To the alcohol (800 mg, 1.93 mmol) in dichloromethane (50 mL) was added methanesulfonyl chloride (0.18 mL, 2.3 mmol) followed by triethylamine (0.38 mL, 2.70 mmol) at 0° C. and then brought to room temperature. After 1 h, the reaction mixture was washed with aqueous sodium hydrogencarbonate, dried ($Na_2SO_4$). The solvent was removed, dissolved the crude product in anhydrous THF (20 mL) followed by addition of 2.0 M solution of methylamine in THF (10 mL) in a sealed tube. The sealed tube was heated at 80° C. for a period of 12 h and then removed the solvent. The crude product was purified by flash chromatography using 30% ethyl acetate in hexane to give (8-benzyloxy-2-methyl-3-oxo-2,3,4,5-tetrahydro-1H-benzo[c]azepin-4-yl)-carbamic acid tert-butyl ester in 39% overall yield. $^1$H NMR (500 MHz, CDCl$_3$): in δ 7.40-7.31(m, 5 H), 7.01-7.00(m, 1 H), 6.83-6.82(m, 1 H), 6.66 (s, 1 H), 5.91-5.90(m, 1 H), 5.13-5.01(m, 4 H), 3.50-3.46 (m, 1 H), 3.03 (s, 3 H), 2.85-2.78 (m, 1 H), 1.45 (s, 9 H).

Intermediate 54

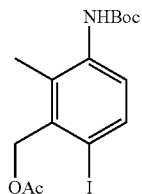

Acetic acid 3-tert-butoxycarbonylamino-6-iodo-2-methyl-benzyl ester. To a well stirred solution of 3-amino-2-methylbenzyl alcohol (10 g, 72.9 mmol) in methanol (250 mL) was added a 1.0 M solution of iodine monochloride in dichloromethame (76.6 mL) dropwise over a period of 5 min at 0° C. The reaction mixture was then brought to room temperature and stirring continued for additional 2 h. The reaction mixture was then concentrated, diluted with dichloromethane (250 mL), washed with 10% aqueous sodium thiosulphate and dried (Na2SO4). The solvent was evaporated and the crude product was dissolved in THF (200 mL). Di-tert-butyl dicarbonate (15.9 g, 72.9 mmol) was added and the reaction mixture was refluxed for 48 h. The reaction mixture was then diluted with ether (400 mL) washed with 1 M HCl (2×100 mL) followed by brine and dried (Na2SO4). The solvent was removed and the desired product was crystallized from 20% ethyl acetate in hexane to give (3-hydroxymethyl-4-iodo-2-methyl-phenyl)-carbamic acid tert-butyl ester (12.5 g). The filtrate was then concentrated and the desired product was purified by flash chromatography (silica) using 30% ethyl acetate to give additional 2.5 g of (3-hydroxymethyl-4-iodo-2-methyl-phenyl)-carbamic acid tert-butyl ester. To a stirred solution of 3-hydroxymethyl-4-iodo-2-methyl-phenyl)-carbamic acid tert-butyl ester (14.5 g, 40 mmol) in dichloromethane (150 mL) was added acetic anhydride (7.5 mL, 80 mmol) and catalytic amount of 4-dimethylaminopyridine and stirred for 12 h at room temperature. The reaction mixture was then quenched with aqueous sodium hydrogencarbonate, brine and dried ($Na_2SO_4$). The solvent was removed and the crude product was purified by crystallization from dichloromethane and hexane to give acetic acid 3-tert-butoxycarbonylamino-6-iodo-2-methyl-benzyl ester (15.5 g, 94%). $^1$H NMR (500 MHz, CDCl$_3$): in δ 7.71 (d, J=8.5 Hz, 1 H), 7.25 (d, J=8.5 Hz, 1 H), 5.30 (s, 2 H), 2.28 (s, 3 H), 2.08 (s, 3 H), 1.50 (s, 9 H); MS (ESI) 428 (M+Na); $R_f$=1.59.

Intermediate 55

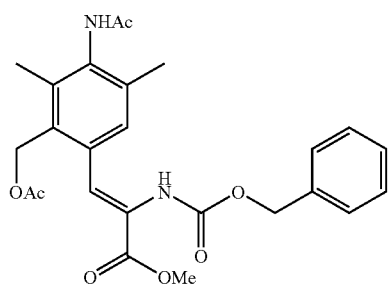

3-(2-Acetoxymethyl-4-acetylamino-3,5-dimethyl-phenyl)-2-benzyloxycarbonylamino-acrylic acid methyl ester. In a manner similar to 2-(acetoxymethyl-4-tert-butoxycarbonylamino-3-methyl-benzylidene)-succinic acid diethyl ester, 3-(2-acetoxymethyl-4-acetylamino-3,5-dimethyl-phenyl)-2-benzyloxycarbonylamino-acrylic acid methyl ester was prepared by reacting acetic acid 3-acetylamino-6-iodo-2,4-dimethyl-benzyl ester with 2-benzyloxycarbonylamino-acrylic acid methyl ester in 74% yield. MS (ESI) 491 (M+H); $R_f$=1.87.

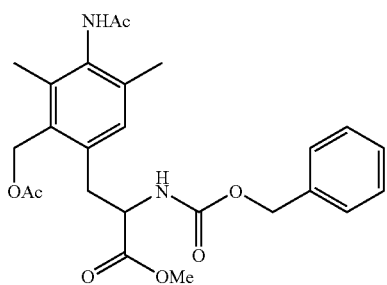

Intermediate 56

3-(2-Acetoxymethyl-4-acetylamino-3,5-dimethyl-phenyl)-2-benzyloxycarbonylamino-propionic acid methyl ester. In a manner similar to 3-(2-acetoxymethyl-4-benzyloxy-phenyl)-2-tert-butoxycarbonylamino-acrylic acid methyl ester, 3-(2-acetoxymethyl-4-acetylamino-3,5-dimethyl-phenyl)-2-benzyloxycarbonylamino-propionic acid methyl ester was prepared from 3-(2-acetoxymethyl-4-acetylamino-3,5-dimethyl-phenyl)-2-benzyloxycarbonylamino-acrylic acid methyl ester (1.5 g) using 1,2-bis((2R,5R)-2,5-diethylphospholano)benzene(cyclootadiene)rhodium, (I) trifluoromethanesulfonate (25 mg) in 98% yield. MS (ESI) 491 (M+H); $R_f$=1.87.

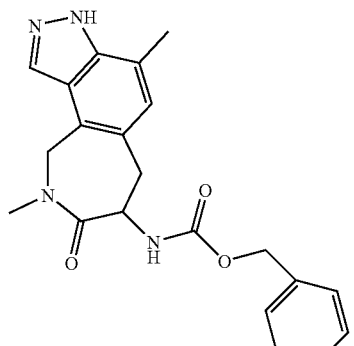

Intermediate 57

(8-Acetylamino-2,7,9-trimethyl-3-oxo-2,3,4,5-tetrahydro-1H-benzo[c]azepin-4-yl)-carbamic acid benzyl ester. In a manner similar to 2-(R)-benzyloxycarbonylamino-3-(4-tert-butoxycarbonylamino-2-hydroxymethyl-3-methyl-phenyl)-propionic acid methyl ester hydrochloride, the title compound was prepared by hydrolyzing 3-(2-acetoxymethyl-4-acetylamino-3,5-dimethyl-phenyl)-2-benzyloxycarbonylamino-propionic acid methyl ester (1.84 g, 3.78 mmol) with potassium carbonate (525 mg, 3.8 mmol) in MeOH (40 mL). The alcohol was dissolved in dichloromethane (100 mL) and then treated with methanesulfonyl chloride (0.35 mL, 4.5 mmol) and triethylamine (0.68 mL, 4.9 mmol). The reaction mixture was stirred for 12 h, washed with aqueous sodium hydrogencarbonate, 1.0 M aqueous hydrogen chloride and dried (Na$_2$SO$_4$). The solvent was removed to give pure 3-(4-acetylamino-2-chloromethyl-3,5-dimethyl-phenyl)-2-benzyloxycarbonylamino-propionic acid methyl ester in almost quantitative yield. The chloride (480 mg, 1.08 mmol) was treated with 1.0 M methylamine solution in THF in a sealed tube for 3 h at 90° C. The solvent was removed and the crude product was dissolved in toluene and acetic acid (0.5 mL) and refluxed for 2 h to give (8-acetylamino-2,7,9-trimethyl-3-oxo-2,3,4,5-tetrahydro-1H-benzo[c]azepin-4-yl)-carbamic acid benzyl ester in 68% yield. To the acetate in chloroform (20 mL) was added acetic acid (0.5 mL) followed by isoamylnitrite (1.0 mL) and 18-crown-6(50 mg). The reaction mixture was refluxed for 12 h and removed the solvent. The crude product was purified by flash chromatography using ethyl acetate as eluent to give (4,9-dimethyl-8-oxo-3,6,7,8,9,10-hexahydro-2,3,9-triaza-cyclohepta[e]inden-7-yl)-carbamic acid benzyl ester as a major product in 37% overall yield. $^1$H NMR (500 MHz, CDCl$_3$): in δ 7.96 (s, 1 H), 7.35-7.24 (m, 5 H), 6.7 (s, 1 H), 6.43-6.41 (m, 1 H), 5.25-5.05 (m, 3 H), 4.18-4.10 (m, 2 H), 3.07-3.05 (m, 2 H), 3.00)s, 3 H), 2.40 (s, 3 H).

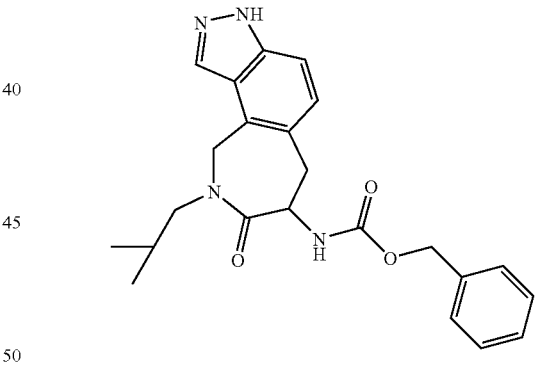

Intermediate 58

(9-Isobutyl-8-oxo-3,6,7,8,9,10-hexahydro-2,3,9-triaza-cyclohepta[e]inden-7-yl)-carbamic acid benzyl ester. In a manner similar to [9-(2,2-dimethyl-propyl)-8-oxo-3,6,7,8,9,10-hexahydro-2,3,9-triaza-(R)-cyclohepta[e]inden-7-yl]-carbamic acid benzyl ester, the title compound was prepared by treating 2-benzyloxycarbonylamino-3-(4-chloromethyl-1H-indazol-5-yl)-propionic acid methyl ester, hydrochloride with isobutylamine followed by treatment with acetic acid in refluxing toluene to give (9-Isobutyl-8-oxo-3,6,7,8,9,10-hexahydro-2,3,9-triaza-cyclohepta[e]inden-7-yl)-carbamic acid benzyl ester in 91% yield. MS (ESI) 407 (M+H); $R_f$=1.58.

Intermediate 59

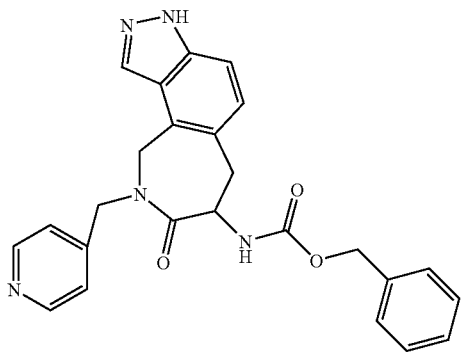

(8-Oxo-9-pyridin-4-ylmethyl-3,6,7,8,9,10-hexahydro-2,3,9-triaza-cyclohepta[e]inden-7-yl)-carbamic acid benzyl ester. In a manner similar to [9-(2,2-dimethyl-propyl)-8-oxo-3,6,7,8,9,10-hexahydro-2,3,9-triaza-(R)-cyclohepta[e]inden-7-yl]-carbamic acid benzyl ester, the title compound was prepared by treating 2-benzyloxycarbonylamino-3-(4-chloromethyl-1H-indazol-5-yl)-propionic acid methyl ester, hydrochloride with 4-(aminomethyl)pyridine followed by treatment with acetic acid in refluxing toluene to give (8-oxo-9-pyridin-4-ylmethyl-3,6,7,8,9,10-hexahydro-2,3,9-triaza-cyclohepta[e]inden-7-yl)-carbamic acid benzyl ester in 65% yield. MS (ESI) 442 (M+H); $R_f$=1.10.

Intermediate 60

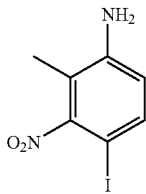

4-Iodo-2-methyl-3-nitrobenzenamine. To a well stirred solution of 2-methyl-3-nitroaniline (10 g, 66 mmol) in methanol (150 mL) was added sodium hydrogencarbonate (264 mmol) followed by 1.0 M solution of iodine monochloride (72 mmol) at room temperature. After stirring for 1 h, the solvent was removed, diluted with ether, washed with 10% aqueous sodium thiosulfate solution. The solvent was removed and the crude iodide was in the next step.

Intermediate 61

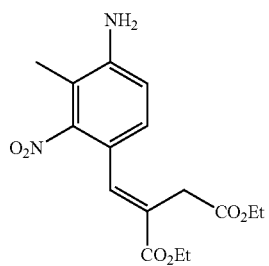

(E)-Diethyl 2-(4-amino-3-methyl-2-nitrobenzylidene) succinate. To a solution of 4-iodo-2-methyl-3-nitrobenzenamine (59 mmol) in dimethylformamide (100 mL) was added diethyl itaconate (13.2 g, 71 mmol), tetrabutylammonium chloride (16.4 g, 59 mmol), triethylamine (236 mmol) and palladium acetate (675 mg, 3 mmol) under nitrogen. The reaction mixture was heated to 80° C. for 2 h. The crude reaction mixture was then filtered, diluted with ether (250 mL), washed with water (2×300 mL). The crude product was purified by flash chromatography using 20% ethyl acetate in hexane to give 8.5 g of the title compound. $^1$H NMR (500 MHz, CDCl$_3$): in δ 7.58 (s, 1 H), 7.10 (d, J=8.5 Hz, 1H), 6.73 (d, J=8.5 Hz, 1 H), 4.24-4.15 (m, 4 H), 3.40 (s, 2 H), 2.06 (s, 3 H), 1.30-1.23 (m, 6 H).

Intermediate 62

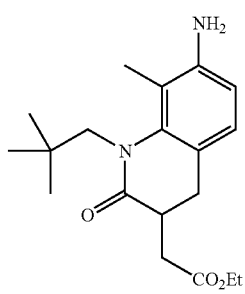

Ethyl 2-(7-amino-8-methyl-1-neopentyl-2-oxo-1,2,3,4-tetrahydroquinolin-3-yl)acetate. To a solution of (E)-diethyl 2-(4-amino-3-methyl-2-nitrobenzylidene)succinate (4.5 g, 13.4 mmol) in THF (100 mL) was added (Boc)$_2$O (16 mmol) followed by catalytic amount of dimethylaminopyridine (10 mg). The reaction mixture was heated in a sealed tube for 3 h at 100° C. The reaction mixture was cooled, removed solvent, diluted with ether and then washed with aqueous sodium hydrogencarbonate (50 mL). The crude product was found to contain both mono- and di-Boc protected compounds. The crude product was dissolved in methanol (200 mL) and was added water (150 ml) followed by ammonium chloride (14.3 g, 268 mmol) and iron powder (8.9 g, 160 mmol). The reaction mixture was heated at 50° C. for 1 h, cooled and then filtered over a pad of celite. The solvent was removed, extracted with ethyl acetate and then washed with brine and dried (Na$_2$SO$_4$). The crude product was purified by flash chromatography using 30% ethyl acetate in hexane as eluent to give the amine. The amine (4.1 g, 10 mmol) was dissolved in dichloroethane (100 mL) followed by addition of acetic acid (10 mL), trimethylacetaldehyde (11 mmol) and magnesium sulfate (5.0 g). The reaction mixture was stirred for 2 h and then filtered. To the filtered reaction mixture was added sodium triacetoxyborohydride (2.33 g, 11 mmol) and stirring continued for additional 2 h. The reaction mixture was diluted with hexane (150 mL), washed with water (2×100 mL), aqueous NaHCO$_3$ solution and dried (Na$_2$SO$_4$). The solvent was removed and the crude product was dissolved in methanol (100 mL) followed by addition of acetic acid (5 mL) and hydrogenated in a parr bottle at a pressure of 50 psi hydrogen. The catalyst was removed by filtration and the solvent was removed. The crude product was dissolved in toluene (100 mL) followed by addition of tosic acid (100 mg) and sodium cyanide (50 mg). The reaction mixture was refluxed for 12 h and the crude product was purified by flash chromatography using 50% ethyl acetate in hexane to give ethyl 2-(7-amino-8-methyl-1-neopentyl-2-oxo-1,2,3,4-tetrahydroquinolin-3-yl)acetate. MS (ESI) 333 (M+H); $R_f$=1.29.

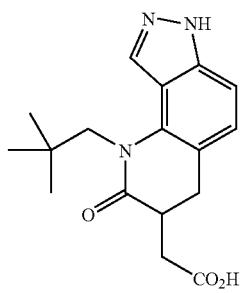

Intermediate 63

2-(1-Neopentyl-2-oxo-2,3,4,7-tetrahydro-1H-pyrazolo[3,4-h]quinolin-3-yl)acetic acid. To a solution of ethyl 2-(7-amino-8-methyl-1-neopentyl-2-oxo-1,2,3,4-tetrahydro-quinolin-3-yl)acetate (170 mg, 0.51 mmol) in carbon tetrachloride (4.5 mL) was added acetic acid (0.5 mL) followed by isoamylnitrite (0.04 mL) and the reaction mixture was stirred for 2 h at room temperature. The reaction mixture was diluted with dichloromethane (40 mL), washed with aqueous NaHCO$_3$ and dried. The solvent was removed and the crude product was dissolved in THF (15 mL) followed by addition of lithium hydroxide (43 mg, 1 mmol) and water (5 mL). After stirring for 12 h, the solvent was removed, acidified with 6 M HCl and extracted with ethyl acetate to give 2-(1-neopentyl-2-oxo-2,3,4,7-tetrahydro-1H-pyrazolo[3,4-h]quinolin-3-yl)acetic acid. MS (ESI) 316 (M+H); $R_f$=1.31.

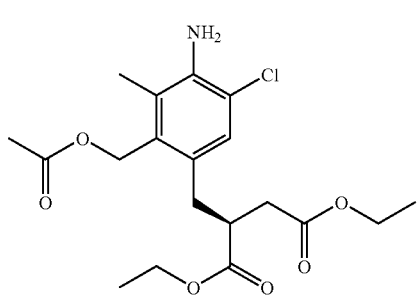

Intermediate 64

2-(S)-(2-Acetoxymethyl-4-amino-5-chloro-3-methyl-benzyl)-succinic acid diethyl ester. 2-(S)-(2-Acetoxymethyl-4-amino-3-methyl-benzyl)-succinic acid diethyl ester (3.0 g, 8.2 mmol) was dissolved in acetonitrile (40 mL). Mixture was warmed to 60° C. N-Chlorosuccinimide (1.29 g, 9.7 mmol) was added to the warm solution. Reaction mixture was heated at reflux for 10 minutes. Mixture was cooled to room temperature then diluted with ethyl acetate (20 mL). Mixture was washed successively with saturated aqueous sodium bicarbonate (40 mL), and brine (20 mL). Organic was dried (magnesium sulfate), filtered and concentrated in vacuo. Silica gel chromatography (ethyl acetate-hexanes) afforded the desired product in 59% yield as an amber oil. $^1$H NMR (300 MHz, CDCl$_3$): δ=6.98 (s, 1H), 5.15 (d, J=3.3, 2H), 4.09 (m, 4H), 2.99 (m, 2H), 2.69 (m, 2H), 2.39 (dd, J1=4.8, J2=16.5, 1H), 2.17 (s, 3H), 2.06 (s, 3H), 1.20 (m, 6H). MS m/e (M–C$_2$H$_4$O$_2$+H)$^+$=340.0.

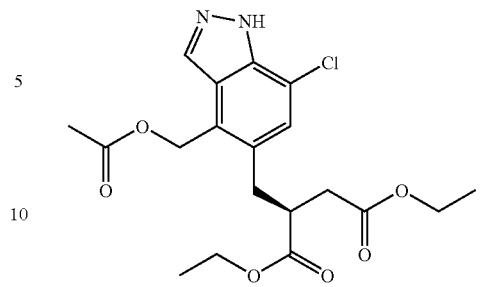

Intermediate 65

2-(S)-(4-Acetoxymethyl-7-chloro-1H-indazol-5-ylmethyl)-succinic acid diethyl ester. Isoamyl nitrite (700 µL, 5.2 mmol), was added dropwise to an ice cold solution of 2-(S)-(2-Acetoxymethyl-4-amino-5-chloro-3-methyl-benzyl)-succinic acid diethyl ester (1.91 g, 4.8 mmol) in 5% acetic acid in tolune (81.2 mL). Mixture stirred at 0° C. for 45 minutes. Potassium acetate (1.50 g, 15.3 mmol) was added to the mixture. Reaction was stirred at room temperature for 14 hours. Mixture was quenched with water. Mixture was extracted with ethyl acetate (30 mL). Mixture was washed 2× saturated aqueous sodium bicarbonate. Organic was dried (magnesium sulfate) filtered and concentrated. Silica gel chromatography (ethyl acetate-hexanes) afforded the desired product in 80% yield as an amber oil. $^1$H NMR (300 MHz, CDCl$_3$): δ=8.23 (s, 1H), 7.26 (s, 1H), 5.45 (s, 2H), 4.09 (q, J=7.0, 4H). 3.20 (dd, J1=7.32, J2=13.2, 1H), 3.10 (m, 1H), 2.97 (dd, J1=7.0, J2=13.3, 1H), 2.73 (dd, J1=8.4, J2=16.8, 1H), 2.44 (dd, J1=5.5, J2=16.8, 1H), 2.08 (s, 3H), 1.18 (m, 6H). MS m/e (M+H)$^+$=411.0.

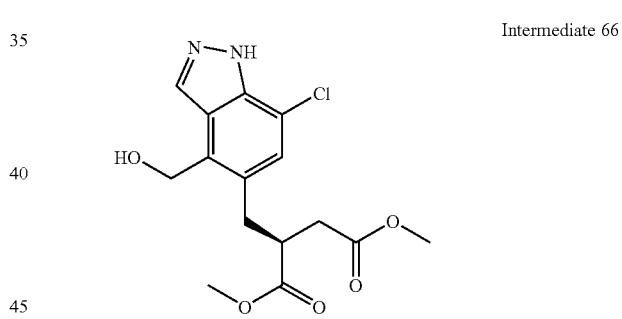

Intermediate 66

(S)-Dimethyl 2-((7-chloro-4-(hydroxymethyl)-1H-indazol-5-yl)methyl)succinate. 2-(S)-(2-Acetoxymethyl-4-amino-5-chloro-3-methyl-benzyl)-succinic acid diethyl ester (2.21 g, 5.4 mmol) was converted to the title compound in a manner analogous to the preparation of 2-(S)-(4-Hydroxymethyl-1H-indazol-5-ylmethyl)-succinic acid dimethyl ester. Material was obtained as amber solid in 99% yield. MS m/e (M+H)$^+$=241.2.

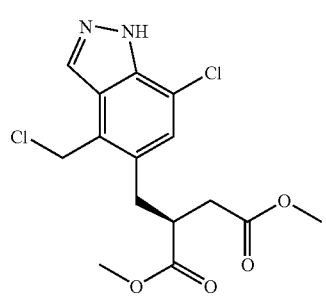

Intermediate 67

(S)-Dimethyl 2-((7-chloro-4-(chloromethyl)-1H-indazol-5-yl)methyl)succinate. (S)-Dimethyl 2-((7-chloro-4-(hydroxymethyl)-1H-indazol-5-yl)methyl)succinate (2.0 g, 5.9 mmol) was dissolved in dichloromethane (35 mL). Thionyl chloride (5.0 mL) was added to the mixture. Reaction stirred at room temperature for 1.5 hours. Mixture was concentrated. Residue was dissolved in ethyl acetate. Mixture was washed twice with aqueous sodium bicarbonate and once with brine. Organic was dried (magnesium sulfate), filtered and concentrated in vacuo. Title compound was obtained as amber solid in 89% yield. MS m/e (M+H)$^+$=359.1.

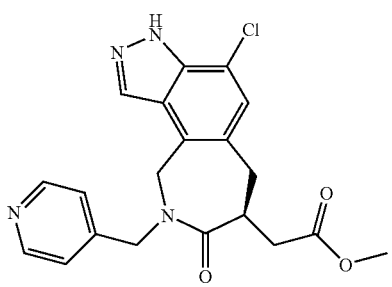

Intermediate 68

(S)-Methyl 2-(4-chloro-8-oxo-9-(pyridin-4-ylmethyl)-3,6,7,8,9,10-hexahydroazepino[3,4-e]indazol-7-yl)acetate. (S)-Dimethyl 2-((7-chloro-4-(chloromethyl)-1H-indazol-5-yl)methyl)succinate (120 mg, 0.33 mmol) was dissolved in DMF (1.0 mL). 4-Aminomethylpyridine (100 μL, 1.0 mmol) was added to the mixture. Reaction stirred at room temperature for 24 hours. Mixture was diluted with ethyl acetate. Mixture was washed twice with water and once with brine. Organic was dried (magnesium sulfate), filtered and concentrated in vacuo. Residue was dissolved in toluene (4 mL). Acetic acid (1 mL) was added to the mixture. Reaction was heated at reflux for 3.5 hours. Mixture was cooled to room temperature then diluted with ethyl acetate. Material was washed once with water and twice with aqueous sodium bicarbonate. Aqueous was made basic with sodium bicarbonate. Back extracted from the aqueous twice with ethyl acetate. Combined organics were dried (magnesium sulfate), filtered and concentrated in vacuo. Residue was purified with silica gel chromatography eluting dichloromethane and 2N ammonia in methanol. Title compound was obtained as yellow solid in 48% yield. MS m/e (M+H)$^+$=399.2.

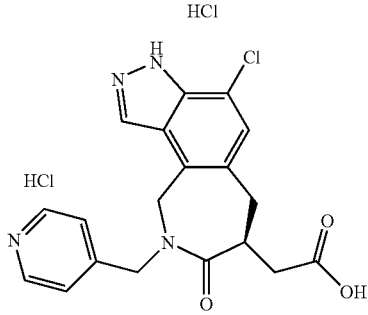

Intermediate 69

(S)-2-(4-Chloro-8-oxo-9-(pyridin-4-ylmethyl)-3,6,7,8,9,10-hexahydroazepino[3,4-e]indazol-7-yl)acetic acid dihydrochloride. (S)-Methyl 2-(4-chloro-8-oxo-9-(pyridin-4-ylmethyl)-3,6,7,8,9,10-hexahydroazepino[3,4-e]indazol-7-yl)acetate (21 mg, 0.05 mmol) was dissolved in 1N hydrochloric acid (1.0 mL). Reaction was heated at 50° C. for 5 hours. Another 1 mL of 1N hydrochloric acid was added to the mixture. Reaction was heated at 50° C. for 17 hours. Mixture was concentrated in vacuo. Residue was treated with acetonitrile and then the material was concentrated. Title compound was obtained as dark yellow solid in 83% yield. MS m/e (M+H)$^+$=385.2.

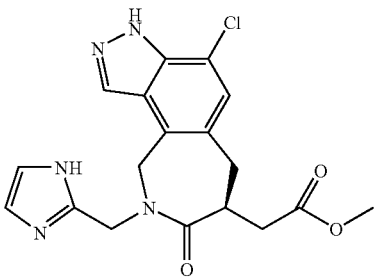

Intermediate 70

(S)-Methyl 2-(9-((1H-imidazol-2-yl)methyl)-4-chloro-8-oxo-3,6,7,8,9,10-hexahydroazepino[3,4-e]indazol-7-yl)acetate. (S)-Dimethyl 2-((7-chloro-4-(chloromethyl)-1H-indazol-5-yl)methyl)succinate (250 mg, 0.63 mmol) and (1H-imidazol-2-yl)methanamine dihydrochloride (170 mg, 1.0 mmol) were combined and suspended in acetonitrile (10 mL). Triethylamine (800 μL, 5.7 mmol) was added to the mixture. Reaction was warmed to reflux for 3 hours. Acetic acid (1.5 mL) was added to the mixture. Reaction was heated at reflux for 20 hours. Mixture was cooled to room temperature then diluted with dichloromethane. Mixture was extracted twice with water. Aqueous layer was concentrated in vacuo. Residue was purified by preparatory HPLC. Water was lyophilized off. Remaining residue was passed through a column of Dowex 1×4-200 ion exchange resin eluting methanol. Title compound was recovered as amber residue in 24% yield. MS m/e (M+H)$^+$=388.1.

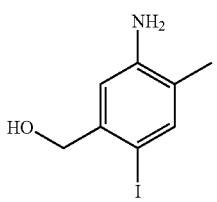

Intermediate 71

5-Amino-2-iodo-4-methybenzyl alcohol. To an ice cooled solution of 3-amino-4-methylbenzyl alcohol (10.0 g, 72.9 mmol) in methanol (200 mL) 1M iodinemonochloride in dichloromethane (80.0 mL, 80.0 mmoles) was added dropwise over 30 minutes. Ice bath was removed. Reaction was stirred at ambient temperature for 40 minutes. Mixture was concentrated in vacuo. Residue was treated with dichloromethane (250 mL). Solids were filtered off and washed with dichloromethane. Solids were partitioned between ethyl acetate and 1N aqueous sodium hydroxide. Layers were partitioned. Organic layer was washed with 1N aqueous sodium hydroxide. The combined aqueous layers were back extracted two times with ethyl acetate. Combined organic layers were washed with brine. Combined extracts were dried (magnesium sulfate), filtered and concentrated in vacuo. Desired product was obtained as tan solid in 81% yield. MS m/e (M+H)⁻=264.

Intermediate 72

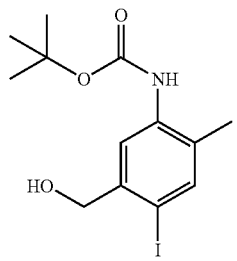

tert-Butyl 5-(hydroxymethyl)-4-iodo-2-methylphenylcarbamate. 5-Amino-2-iodo-4-methybenzyl alcohol (4.60 g, 17.5 mmoles) was dissolved in tetrahydrofuran (80 mL). Di-tert-butyl dicarbonate (5.30 g, 24.3 mmoles) was added to the mixture. Reaction was heated at 60° C. for 20 hours. Mixture was concentrated. Residue was purified by silica gel chromatography eluting ethyl acetate-hexanes. Title compound was obtained as off-white solid. MS m/e (M–C$_4$H$_8$O+H)⁺=290.

Intermediate 73

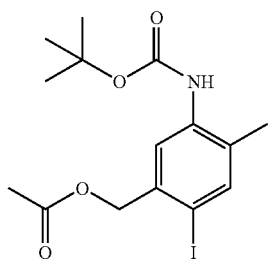

5-(tert-Butoxycarbonyl)-2-iodo-4-methylbenzyl acetate. tert-Butyl 5-(hydroxymethyl)-4-iodo-2-methylphenylcarbamate (4.32 g, 11.9 mmol) was dissolved in dichloromethane (60 mL). Acetic anhydride (2.6 mL, 27.6 mmol) was added to the mixture followed by potassium acetate (2.0 g, 20.4 mmol). Reaction was stirred at room temperature over 15 hours. Mixture was warmed to 50° C. and held for 1 hour. Mixture was cooled to room temperature then diluted with dichloromethane. Mixture was washed twice with water, and once with saturated aqueous sodium bicarbonate. Organic layer was dried (magnesium sulfate), filtered and concentrated in vacuo. Residue was treated with 10% ethyl acetate-hexanes (100 mL). Material was concentrated in vacuo. Desired compound was obtained as white solid in 98% yield. ¹H NMR (300 MHz, CD$_3$OD): δ=7.64 (s, 1H), 7.54 (s, 1H), 4.51 (s, 2H), 2.19 (s, 3H), 1.51 (s, 9H).

Intermediate 74

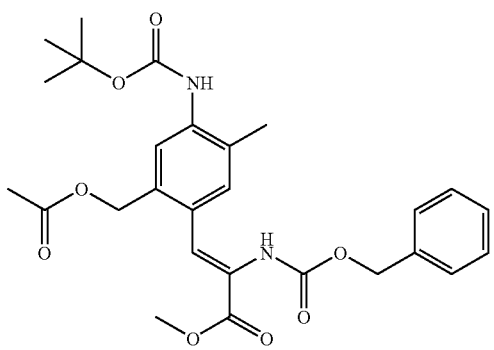

3-(2-Acetoxymethyl-4-tert-butoxycarbonylamino-5-methyl-phenyl)-2-benzyloxycarbonylamino-acrylic acid methyl ester. Title compound was prepared in a manner analogous to the preparation of 3-(2-Acetoxymethyl-4-tert-butoxycarbonylamino-3-methyl-phenyl)-2-benzyloxycarbonylamino-acrylic acid methyl ester. Material was obtained as a white solid in 65% yield. MS m/e (M+H)⁺=513.

Intermediate 75

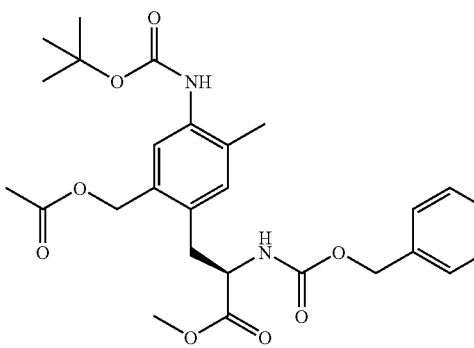

3-(2-Acetoxymethyl-4-tert-butoxycarbonylamino-5-methyl-phenyl)-2-(R)-benzyloxycarbonylamino-propionic acid methyl ester. Title compound was prepared in a manner analogous to the preparation of 2-(S)-(acetoxymethyl-4-tert-butoxycarbonylamino-3-methyl-benzyl)-succinic acid diethyl ester. Material was obtained as clear colorless oil in 99% yield. MS m/e (M–H)⁻=513.

Intermediate 76

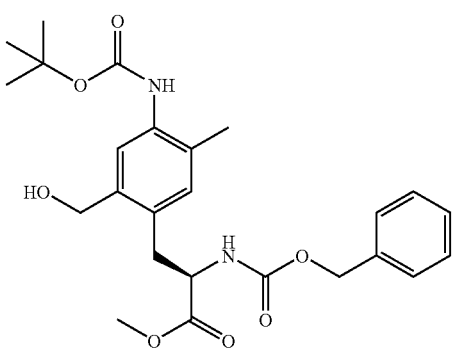

3-(2-Hydroxymethyl-4-tert-butoxycarbonylamino-5-methyl-phenyl)-2-(R)-benzyloxycarbonylamino-propionic acid methyl ester. Title compound was obtained in a manner analogous to the preparation of 2-(R)-Benzyloxycarbonylamino-3-(4-tert-butoxycarbonylamino-2-hydroxymethyl-3-methyl-phenyl)-propionic acid methyl ester. Material was obtained as white solid in 94% yield.

Intermediate 77

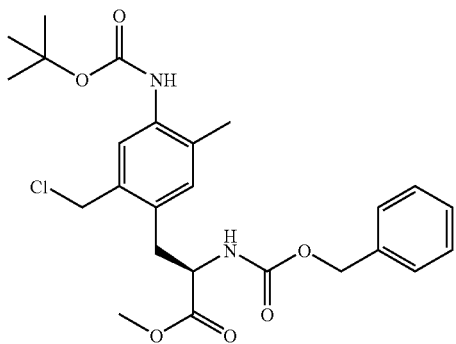

3-(2-Chloromethyl-4-tert-butoxycarbonylamino-5-methyl-phenyl)-2-(R)-benzyloxycarbonylamino-propionic acid methyl ester. 3-(2-Hydroxymethyl-4-tert-butoxycarbonylamino-5-methyl-phenyl)-2-(R)-benzyloxycarbonylamino-propionic acid methyl ester (510 mg, 1.1 mmol) was dissolved in dichoromethane (5 mL). Triethylamine (250 μL, 1.8 mmol) was added to the mixture followed by methanesulfonyl chloride (100 μL, 1.3 mmol). Mixture was stirred at room temperature for 1.5 hours. Mixture was diluted with dichloromethane then washed once with water, twice with 1N hydrochloric acid, and once with brine. Organics were dried (magnesium sulfate), filtered and concentrated in vacuo. Title compound was obtained as white solid in 91% yield. MS m/e (M+H)+=491.

Intermediate 78

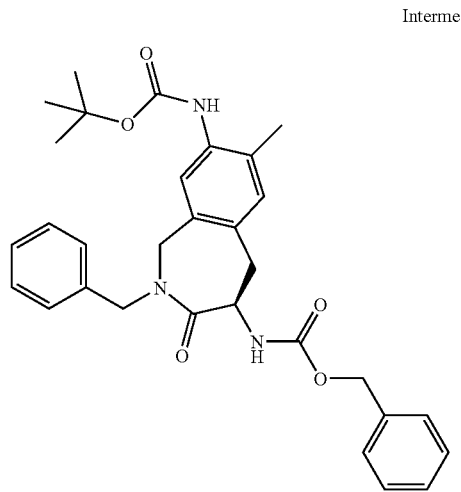

(R)-Benzyl 8-tert-butoxycarbonylamido-2-benzyl-7-methyl-3-oxo-2,3,4,5-tetrahydro-1H-benzo[c]azepin-4-ylcarbamate. 3-(2-Chloromethyl-4-tert-butoxycarbonylamino-5-methyl-phenyl)-2-(R)-benzyloxycarbonylamino-propionic acid methyl ester (335 mg, 0.72 mmol) was dissolved in acetonitrile (10 mL). Potassium carbonate (220 mg, 1.6 mmol) was added to the mixture followed by benzylamine (150 μL, 1.4 mmol). Reaction was heated to reflux for 4.5 hours. Mixture was cooled to room temperature. Mixture was filtered over celite. Filtrate was concentrated. Residue was dissolved in toluene (15 mL). Acetic acid (100 μL) was added to the mixture. Reaction was heated at reflux for 3 hours. Mixture was cooled to room temperature. Mixture was concentrated. Residue was purified by silica gel chromatography eluting ethyl acetate-hexanes. Title compound was obtained as clear colorless oil in 81% yield. MS m/e (M+H)+=530.

Intermediate 79

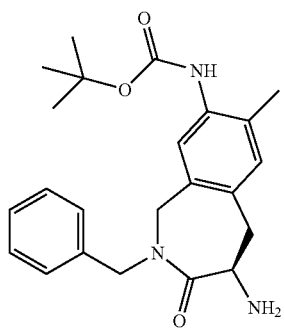

(R)-tert-Butyl 4-amino-2-benzyl-7-methyl-3-oxo-2,3,4,5-tetrahydro-1H-benzo[c]azepin-8-ylcarbamate. (R)-Benzyl 8-tert-butoxycarbonylamido-2-benzyl-7-methyl-3-oxo-2,3,4,5-tetrahydro-1H-benzo[c]azepin-4-ylcarbamate (305 mg, 0.58 mmol) was dissolved in methanol. A catalytic amount of 10% palladium on carbon was added to the mixture. Reaction was placed on a Parr apparatus under 50 psi of hydrogen gas. Reaction shook at room temperature for 1 hour. Reaction was removed from the apparatus. Catalyst was filtered off. Filtrate was concentrated in vacuo. Title compound was obtained as clear colorless oil in 97% yield. MS m/e (M+H)+=396.

Intermediate 80

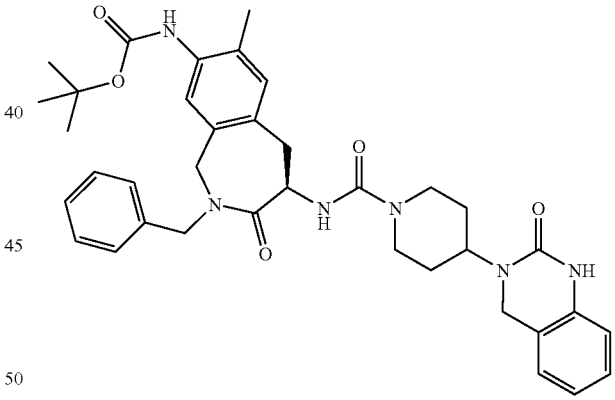

(R)-tert-Butyl 2-benzyl-7-methyl-3-oxo-4-(4-(2-oxo-1,2-dihydroquinazolin-3(4H)-yl)piperidine-1-carboxamido)-2,3,4,5-tetrahydro-1H-benzo[c]azepin-8-ylcarbamate. (R)-tert-Butyl 4-amino-2-benzyl-7-methyl-3-oxo-2,3,4,5-tetrahydro-1H-benzo[c]azepin-8-ylcarbamate (155 mg, 0.39 mmol) was dissolved in dichloromethane (10 mL). Aqueous sodium bicarbonate (10 mL) was added to the mixture. A solution of 20% phosgene in toluene (230 μL, 0.43 mmol) was added to the mixture with vigorous stirring. Reaction stirred at room temperature for 20 minutes. 4-(2-oxo-1,4-dihydro-2H-quinazolin-3-yl) piperidine acetate (140 mg, 0.48 mmol) was added to the mixture. Reaction stirred at room temperature for 1 hour. Reaction layers were partitioned. Organic layer was washed successively with 1N hydrochloric acid and brine. Organic was dried (magnesium sulfate), filtered and concentrated in vacuo. Title compound was obtained as off-white solid in 94% yield. MS m/e (M+H)⁺=653.

Intermediate 81

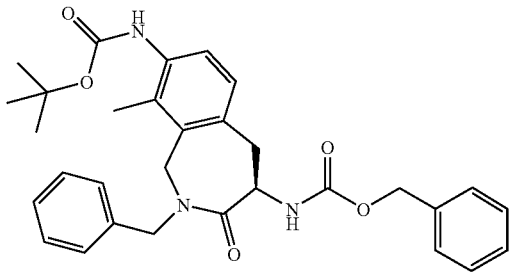

(R)-Benzyl 8-tert-butoxycarbonylamido-2-benzyl-9-methyl-3-oxo-2,3,4,5-tetrahydro-1H-benzo[c]azepin-4-ylcarbamate. 3-(2-Chloromethyl-4-tert-butoxycarbonylamino-3-methyl-phenyl)-2-(R)-benzyloxycarbonylamino-propionic acid methyl ester was reacted in a manner analogous to the preparation of (R)-benzyl 8-tert-butoxycarbonylamido-2-benzyl-7-methyl-3-oxo-2,3,4,5-tetrahydro-1H-benzo[c]azepin-4-ylcarbamate. Title compound was obtained as white solid in 78% yield. MS m/e (M+H)⁺=530.

Intermediate 82

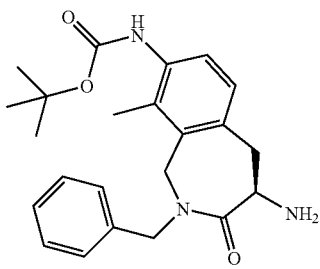

(R)-tert-Butyl 4-amino-2-benzyl-9-methyl-3-oxo-2,3,4,5-tetrahydro-1H-benzo[c]azepin-8-ylcarbamate. (R)-Benzyl 8-tert-butoxycarbonylamido-2-benzyl-9-methyl-3-oxo-2,3,4,5-tetrahydro-1H-benzo[c]azepin-4-ylcarbamate was reacted in a manner analogous to the preparation of (R)-tert-butyl 4-amino-2-benzyl-7-methyl-3-oxo-2,3,4,5-tetrahydro-1H-benzo[c]azepin-8-ylcarbamate. Title compound was obtained as clear colorless oil in 99% yield. MS m/e (M+H)⁺= 340.

Intermediate 83

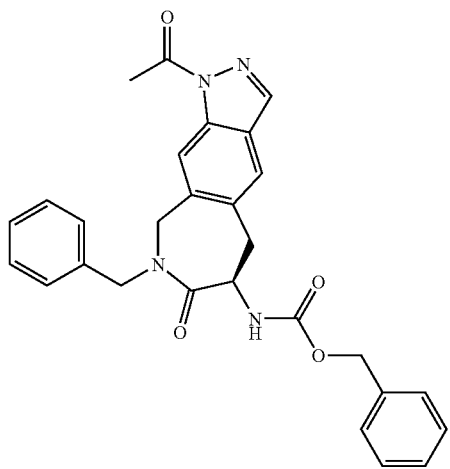

(R)-Benzyl 1-acetyl-8-benzyl-7-oxo-1,5,6,7,8,9-hexahydroazepino[4,3-f]indazol-6-ylcarbamate. 3-(2-Chloromethyl-4-tert-butoxycarbonylamino-5-methyl-phenyl)-2-(R)-benzyloxycarbonylamino-propionic acid methyl ester (160 mg, 0.33 mmol) was dissolved in dichloromethane (3 mL). Trifluoroacetic acid (1 mL) was added to the mixture. Reaction was stirred at room temperature for 45 minutes. Mixture was concentrated to a yellow oil. Residue was dissolved in chloroform (3 mL). Acetic acid (100 µL) was added to the mixture followed by isoamyl nitrite (50 µL, 0.37 mmol) then potassium acetate (65 mg, 0.66 mmol). Reaction was heated at reflux for 30 minutes. Mixture was cooled to room temperature then diluted with dichloromethane. Mixture was washed once with water, and twice with aqueous sodium bicarbonate. Organics were dried (magnesium sulfate), filtered and concentrated in vacuo. Reside was dissolved in acetonitrile (3 mL). Benzylamine (100 µL, 0.92 mmol) was added to the mixture followed by potassium carbonate (50 mg, 0.36 mmol). Reaction was heated at reflux for 1 hour. Mixture was cooled to room temperature. Solids were filtered. Filtrate was concentrated in vacuo. Residue was treated with toluene (3 mL) and acetic acid (100 µL). Reaction was heated at reflux for 1 hour. Mixture was cooled to room temperature. Acetic anhydride (1 mL) was added to the mixture. Reaction was stirred at room temperature for 1 hour. Mixture was concentrated. Residue was purified by silica gel chromatography eluting ethyl acetate-hexanes. Title compound was obtained as amber oil in 27% yield. MS m/e (M+H)⁺=483.

Intermediate 84

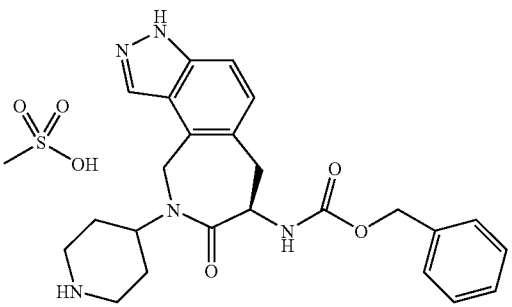

(R)-benzyl 8-oxo-9-(piperidin-4-yl)-3,6,7,8,9,10-hexahydroazepino[3,4-e]indazol-7-ylcarbamate methanesulfonate. 4-(7-(R)-Benzyloxycarbonylamino-8-oxo-6,7,8,10-tetrahydro-3H-2,3,9-triaza-cyclohepta[e]inden-9-yl)-piperidine-1-carboxylic acid tert-butyl ester (100 mg, 0.19 mmol) was dissolved in dichloromethane (2 mL). Anisole (100 µL, 0.92 mmol) was added to the mixture followed by methanesulfonic acid (200 µL). Reaction stirred at room temperature for 30 minutes. Mixture was diluted with diethyl ether, and the mixture stirred at room temperature for 30 minutes. Solvents were decanted off. Residue was dried in vacuo. Title compound was obtained as dark oil in quantitative yield. MS m/e (M+H)⁺=434.

Intermediate 85

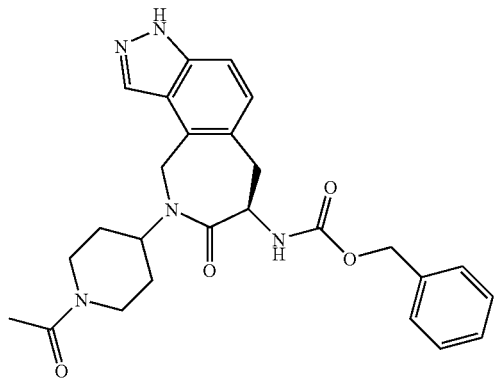

(R)-benzyl 9-(1-acetylpiperidin-4-yl)-8-oxo-3,6,7,8,9,10-hexahydroazepino[3,4-e]indazol-7-ylcarbamate. (R)-benzyl 8-oxo-9-(piperidin-4-yl)-3,6,7,8,9,10-hexahydroazepino[3,4-e]indazol-7-ylcarbamate methanesulfonate (100 mg, 0.19 mmol) was dissolved in a mixture of dichloromethane (4 mL) and triethylamine (500 µL, 3.6 mmol). Acetic anhydride (500 µL, 5.3 mmol) was added to the mixture. Reaction stirred at room temperature overnight. Reaction mixture was washed successively 1× water, 2× 1N hydrochloric acid, 2× 1N sodium hydroxide, and 1× brine. Organic was dried (magnesium sulfate), and filtered. Filtrate was concentrated in vacuo. Residue was treated with methanol (3 mL). Potassium carbonate (40 mg, 0.29 mmol) was added to the mixture. Reaction stirred at room temperature for 2 hours. Reaction was quenched with 1N hydrochloric acid (6 mL). Methanol was removed from the mixture in vacuo. Remaining aqueous mixture was made basic with sodium bicarbonate. Mixture was extracted with ethyl acetate. Organic layer was dried (magnesium sulfate), filtered and concentrated. Title compound was obtained as yellow solid in 43% yield. MS m/e (M+H)$^+$=476.

Intermediate 86

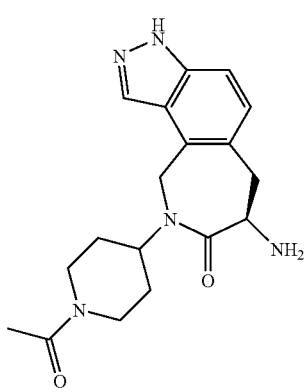

(R)-9-(1-acetylpiperidin-4-yl)-7-amino-6,7,9,10-tetrahydroazepino[3,4-e]indazol-8(3H)-one methanesulfonate. (R)-benzyl 9-(1-acetylpiperidin-4-yl)-8-oxo-3,6,7,8,9,10-hexahydroazepino[3,4-e]indazol-7-ylcarbamate (38 mg, 0.08 mmol) was dissolved in dichloromethane (1 mL). Anisole (30 µL, 0.27 mmol) was added to the mixture followed by methanesulfonic acid (250 µL). Reaction stirred at room temperature for 2 hours. Mixture was diluted with diethyl ether. Mixture sat at room temperature for 30 minutes. Solvents were decanted off. Remaining residue was dried in vacuo. Title compound was obtained as dark oil in quantitative yield. MS m/e (M+H)$^+$=342.

Intermediate 87

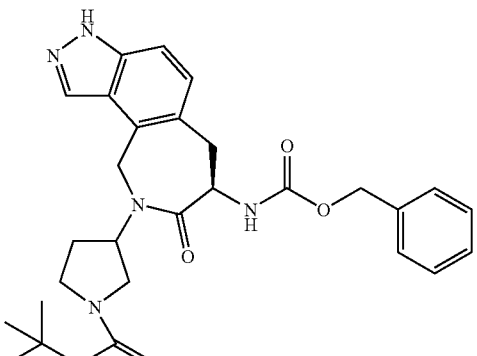

tert-butyl 3-((R)-7-(benzyloxycarbonyl)-8-oxo-7,8-dihydroazepino[3,4-e]indazol-9(3H,6H,10H)-yl)pyrrolidine-1-carboxylate. 2-(R)-Benzyloxycarbonylamino-3-(4-chloromethyl-1H-indazol-5-yl)-propionic acid methyl ester hydrochloride (150 mg, 0.31 mmol) and R,S-3-amino-1-N-Boc-pyrrolidine (90 µL, 0.48 mmol) were reacted in a manner analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Title compound was obtained without purification as dark foam in 96% yield. MS m/e (M+H)$^+$=342.

Intermediate 88

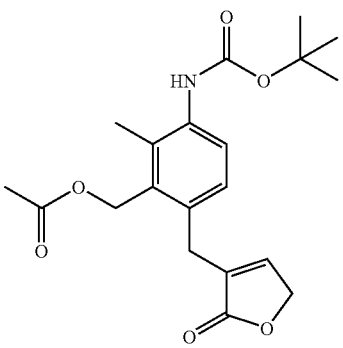

3-(tert-butoxycarbonyl)-2-methyl-6-((2-oxo-2,5-dihydrofuran-3-yl)methyl)benzyl acetate. Acetic acid 3-tert-butoxycarbonylamino-6-iodo-2-methyl-benzyl ester (575 mg, 1.4 mmol) was dissolved in N,N-dimethylformamide (2.5 mL). α-Methylene-γ-butyrolactone (190 µL, 2.2 mmol) was added to the mixture followed by potassium acetate (420 mg, 4.3 mmol), and then palladium(II) acetate (16 mg, 0.07 mmol). Reaction mixture was heated at 80° C. for 26 hours. Mixture was cooled to room temperature and partitioned between ethyl acetate and aqueous sodium bicarbonate. Layers were separated. Organic layer was dried (magnesium sulfate), filtered and concentrated in vacuo. Silica gel chromatography afforded the title compound as off-white solid in 54% yield. MS m/e (M−H)$^−$=374.

Intermediate 89

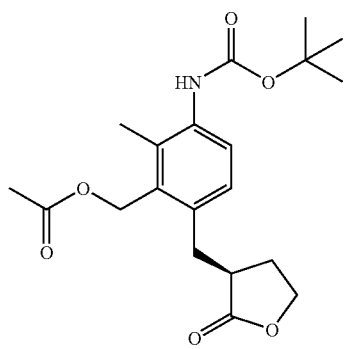

(S)-3-(tert-butoxycarbonyl)-2-methyl-6-((2-oxo-tetrahydrofuran-3-yl)methyl)benzyl acetate. 3-(tert-butoxycarbonyl)-2-methyl-6-((2-oxo-2,5-dihydrofuran-3-yl)methyl)benzyl acetate (280 mg, 0.75 mmol) was dissolved in a mixture of ethyl acetate (10 mL) and methanol (10 mL). A catalytic amount of (−)-1,2-bis((2R,5R)-diethylphospholano)benzene (cyclooctadiene)rhodium (I) tetrafluoroborate was added to the mixture. Reaction vessel was placed on a Parr apparatus and charged with 50 psi of hydrogen gas. Reaction shook at room temperature for 16 hours. A fresh portion of (−)-1,2-bis ((2R,5R)-diethylphospholano)benzene(cyclooctadiene) rhodium (I) tetrafluoroborate was added to the mixture. Reaction vessel was charged with 50 psi of hydrogen gas. Reaction shook at room temperature for 24 hours. Reaction mixture was concentrated in vacuo. Residue was passed through a plug of silica gel eluting 80% ethyl acetate-hexanes. Filtrate was concentrated in vacuo. Title compound was obtained as clear colorless oil in 69% yield. MS m/e (M−H)⁻=376.

Intermediate 90

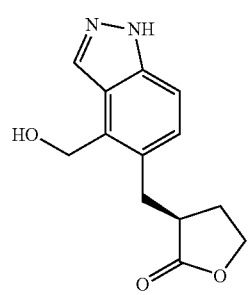

(S)-3-((4-(hydroxymethyl)-1H-indazol-5-yl) methyl)-dihydrofuran-2(3H)-one. (S)-3-(tert-butoxycarbonyl)-2-methyl-6-((2-oxo-tetrahydrofuran-3-yl)methyl)benzyl acetate (190 mg, 0.50 mmol) was dissolved in dichloromethane (4 mL). Trifluoroacetic acid (1 mL) was added to the mixture. Reaction stirred at room temperature for 30 minutes. Mixture was diluted with dichloromethane and then concentrated in vacuo. Residue was dissolved in chloroform (5 mL). Acetic acid (250 μL) was added to the mixture followed by isoamyl nitrite (80 μL, 0.60 mmol). Reaction stirred at room temperature for 20 minutes. Potassium acetate (400 mg, 4.1 mmol) was added to the mixture. Reaction stirred at room temperature for 1 hour. Mixture was diluted with dichloromethane. Mixture was washed successively 1× water, 2× aqueous sodium bicarbonate. Organic layer was dried (magnesium sulfate), filtered and concentrated in vacuo. Residue was dissolved in methanol (5 mL). Potassium carbonate (120 mg, 0.87 mmol) was added to the mixture. Reaction stirred at room temperature for 1 hour. Reaction was quenched with 1N hydrochloric acid. Methanol was removed from the mixture in vacuo. Remaining aqueous was extracted 2× diethyl ether, made basic with sodium bicarbonate, and then extracted again 2× diethyl ether. Combined extracts were dried (magnesium sulfate), filtered, and concentrated in vacuo. Title compound was obtained as amber oil in 73% yield. MS m/e (M+H)⁺=247.

Intermediate 91

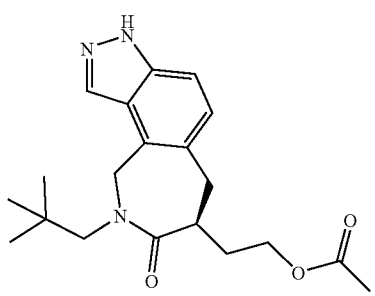

(S)-2-(9-neopentyl-8-oxo-3,6,7,8,9,10-hexahydroazepino [3,4-e]indazol-7-yl)ethyl acetate. (S)-3-((4-(hydroxymethyl)-1H-indazol-5-yl)methyl)-dihydrofuran-2(3H)-one (70 mg, 0.28 mmol), was dissolved in dichloromethane (1.5 mL). Thionyl chloride (500 μL) was added to the mixture. Reaction stirred at room temperature for 45 minutes. Mixture was concentrated. Residue was treated with dichloromethane and re-concentrated. Residue was dissolved in acetonitrile (3 mL). Potassium carbonate (150 mg, 1.1 mmol) was added to the mixture followed by neopentylamine (100 μL, 0.85 mmol). Mixture was heated at reflux for 45 minutes. Mixture was cooled to room temperature and filtered. Filtrate was concentrated in vacuo. Residue was dissolved in toluene (5 mL). Acetic acid (200 μL) was added to the mixture. Reaction was heated at reflux for 5.5 hours. Mixture was concentrated in vacuo. Preparatory HPLC purification gave the title compound as yellow solid in 19% yield. MS m/e (M−H)⁻=356.

Intermediate 92

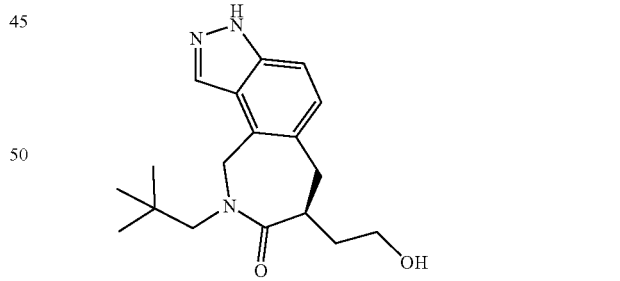

(S)-7-(2-hydroxyethyl)-9-neopentyl-6,7,9,10-tetrahydroazepino[3,4-e]indazol-8(3H)-one. (S)-2-(9-neopentyl-8-oxo-3,6,7,8,9,10-hexahydroazepino[3,4-e]indazol-7-yl) ethyl acetate (18 mg, 0.05 mmol) was dissolved in methanol (1 mL). Potassium carbonate (20 mg, 0.14 mmol) was added to the mixture. Reaction stirred at room temperature for 1 hour. Amberlite IRC-50 ion exchange resin was added to the mixture. Reaction stirred at room temperature for 15 minutes. Mixture was filtered. Filtrate was concentrated in vacuo. The title compound was obtained as yellow residue in 94% yield. MS m/e (M+H)⁺=316.

Intermediate 93

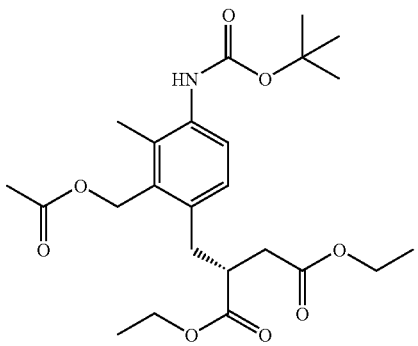

2-(R)-(Acetoxymethyl-4-tert-butoxycarbonylamino-3-methyl-benzyl)-succinic acid diethyl ester. 2-(S)-(Acetoxymethyl-4-tert-butoxycarbonylamino-3-methyl-benzylidene)-succinic acid diethyl ester (700 mg, 1.5 mmol) was hydrogenated in a manner analogous to the preparation of 2-(S)-(acetoxymethyl-4-tert-butoxycarbonylamino-3-methyl-benzyl)-succinic acid diethyl ester using (+)-1,2-bis((2S,5S)-diethylphospholano)benzene(cyclooctadiene)rhodium (I) trifluoromethane sulfonate as the catalyst. Silica gel chromatography afforded the title compound as lightly colored oil in 75% yield. MS m/e (M−H)⁻=464.0.

Intermediate 94

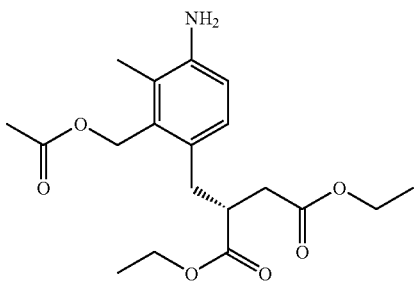

2-(R)-(2-Acetoxymethyl-4-amino-3-methyl-benzyl)-succinic acid diethyl ester. Trifluoroacetic acid (2.5 mL) was added to a solution of 2-(R)-(acetoxymethyl-4-tert-butoxycarbonylamino-3-methyl-benzyl)-succinic acid diethyl ester (525 mg, 1.1 mmol) in dichloromethane (10 mL). Reaction mixture was stirred at room temperature for 1 hour. Mixture was concentrated in vacuo. Residue was treated with aqueous sodium bicarbonate and extracted with ethyl acetate (2× 20 mL). Combined organic layers were dried (magnesium sulfate), filtered and concentrated in vacuo. The title compound was obtained as amber oil in 99% yield. MS m/e (M−C₂H₄O₂+H)⁻=306.1.

Intermediate 95

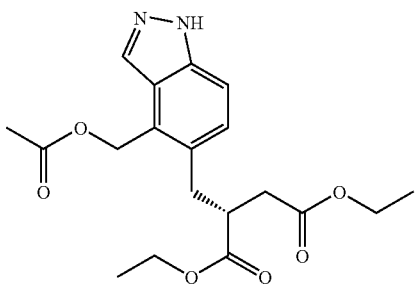

2-(R)-(4-Acetoxymethyl-1H-indazol-5-ylmethyl)-succinic acid diethyl ester. Isoamyl nitrite (170 μL, 1.3 mmol) was added dropwise to a cooled (water ice bath) solution of 2-(R)-(2-acetoxymethyl-4-amino-3-methyl-benzyl)-succinic acid diethyl ester in 5% acetic acid-chloroform (5 mL). Mixture was stirred at 0° C. for 1.5 hours. Mixture was diluted with dichloromethane (20 mL) and then washed with saturated aqueous sodium bicarbonate (2×20 mL). Organic was dried (magnesium sulfate), filtered and concentrated in vacuo. Title compound was obtained as amber oil in 99% yield. MS m/e (M+H)⁺=377.1.

Intermediate 96

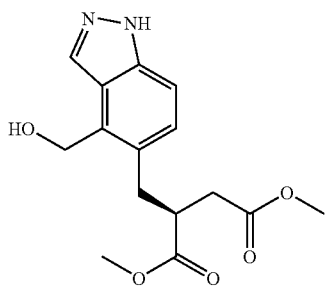

2-(R)-(4-Hydroxymethyl-1H-indazol-5-ylmethyl)-succinic acid dimethyl ester. Potassium carbonate (380 mg, 2.7 mmol) was added to a solution of 2-(R)-(4-acetoxymethyl-1H-indazol-5-ylmethyl)-succinic acid diethyl ester (420 mg, 1.1 mmol) in methanol (10 mL). Mixture was stirred at room temperature for 2 hours. Reaction was quenched with 1N hydrochloric acid. Methanol was removed from the mixture in vacuo. Remaining aqueous made basic with sodium bicarbonate. Mixture was extracted with ethyl acetate (2×20 mL). Combined organic layers were washed successively with water (20 mL) and brine (20 mL). Organic was dried (magnesium sulfate), filtered and concentrated in vacuo. Title compound was obtained as amber oil in 92% yield. MS m/e (M+H)⁺=307.1.

Intermediate 97

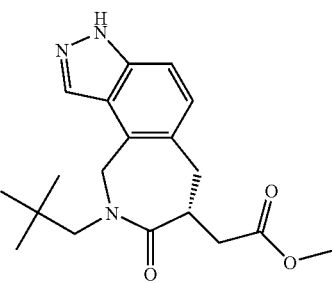

[9-(2,2-Dimethyl-propyl)-8-oxo-3,6,7,8,9,10-hexahydro-2,3,9-triaza-(R)-cyclohepta[e]inden-7-yl]-acetic acid methyl ester. Thionyl chloride (2 mL) was added to a solution of 2-(R)-(4-hydroxymethyl-1H-indazol-5-ylmethyl)-succinic acid dimethyl ester (280 mg, 0.91 mmol) in dichloromethane (4 mL). Reaction was stirred at room temperature for 1 hour. Mixture was diluted with dichloromethane and then concentrated in vacuo. Residue was suspended in acetonitrile (5 mL). Potassium carbonate (300 mg, 2.2 mmol) was added to the mixture followed by neopentylamine (250 μL, 2.1 mmol). Reaction was heated at reflux for 30 minutes. Neopentylamine (150 μL, 1.3 mmol) was added to the mixture. Reaction was heated at reflux for 20 minutes. Mixture was cooled to room temperature and filtered. Filtrate was concentrated in vacuo. Residue was dissolved in toluene (5 mL). Acetic acid (300 μL) was added to the mixture. Reaction was heated at reflux for 16 hours. Mixture was cooled to room temperature and diluted with ethyl acetate. Mixture was washed successively with aqueous sodium bicarbonate (2×), water, and brine. Organic layer was dried (magnesium sulfate), filtered and concentrated in vacuo. Silica gel chromatography afforded the title compound as amber oil in 29% yield. MS m/e (M–H)⁻=342.1.

Intermediate 98

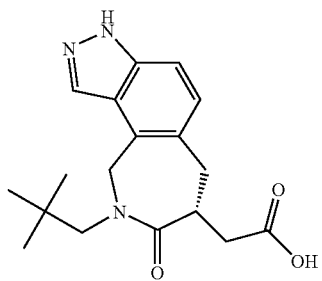

[9-(2,2-Dimethyl-propyl)-8-oxo-3,6,7,8,9,10-hexahydro-2,3,9-triaza-(R)-cyclohepta[e]inden-7-yl]-acetic acid. Lithium hydroxide monohydrate (31 mg, 0.74 mmol) was added to a solution of [9-(2,2-dimethyl-propyl)-8-oxo-3,6,7,8,9,10-hexahydro-2,3,9-triaza-(R)-cyclohepta[e]inden-7-yl]-acetic acid methyl ester (90 mg, 0.26 mmol) in methanol (2.5 mL), tetrahydrofuran (2 mL) and water (2.5 mL). Reaction mixture was heated at 50° C. for 1.5 hours. The organic solvents were removed from the mixture in vacuo. Remaining aqueous was neutralized with 1 N hydrochloric acid (730 μL). Mixture was extracted with ethyl acetate (2×20 mL). Combined organic layers were washed with brine (20 mL) and then dried (magnesium sulfate), filtered and concentrated in vacuo. Title compound was obtained as amber solid in 88% yield. MS m/e (M–H)⁻=328.1.

Intermediate 99

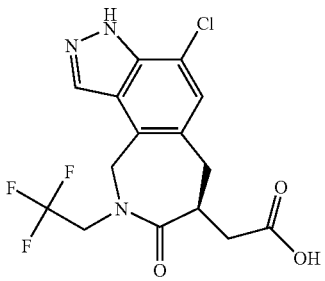

[4-Chloro-3,6,7,8,9,10-hexahydro-8-oxo-9-(2,2,2-trifluoroethyl)-2,3,9-triaza-(S)-cyclohepta[e]inden-7-yl]acetic acid. 2-(S)-(4-acetoxymethyl-7-chloro-1H-indazol-5-ylmethyl)-succinic acid diethyl ester (530 mg, 1.48 mmol) and 2,2,2-trifluoroethylamine (1 mL, 12.5 mmol) was reacted following reaction scheme and procedures analogous to the preparation of [4-Chloro-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 20% yield. MS m/e (M–H)⁻=374.0.

Intermediate 100

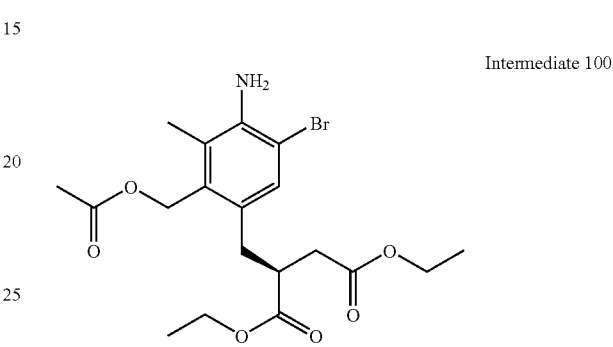

2-(S)-(2-Acetoxymethyl-4-amino-5-bromo-3-methyl-benzyl)-succinic acid diethyl ester. 2-(S)-(2-Acetoxymethyl-4-amino-3-methyl-benzyl)-succinic acid diethyl ester (7.6 g, 21 mmol) was dissolved in acetic acid (100 mL). Sodium acetate (4.2 g, 51 mmol) was added to the solution. Reaction vessel was placed in a cool water bath to control reaction exotherm. Bromine (1.1 mL, 22 mmol) was added to the mixture in one portion. Reaction stirred at ambient temperature for 10 minutes. Mixture was poured into 1N aqueous sodium thiosulfate solution (400 mL). Material was extracted twice with ethyl acetate. Organic phase was washed successively with water and brine. Organic was dried (magnesium sulfate), filtered and concentrated in vacuo. Silica gel chromatography (ethyl acetate-hexanes) afforded the desired product in 77% yield as an amber oil. MS m/e (M–H)⁻= 440.0, 442.0.

Intermediate 101

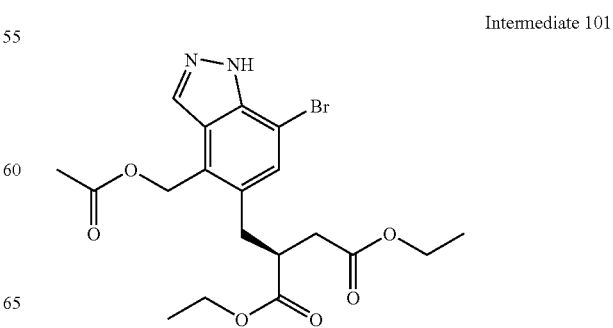

2-(S)-(4-Acetoxymethyl-7-bromo-1H-indazol-5-ylmethyl)-succinic acid diethyl ester. Isoamyl nitrite (2.3 mL, 17 mmol), was added drop-wise to an ice cold solution of 2-(S)-(2-Acetoxymethyl-4-amino-5-bromo-3-methyl-benzyl)-succinic acid diethyl ester (7.14 g, 16 mmol) in 5% acetic acid in toluene (280 mL). Mixture stirred at 0° C. for 40 minutes. Potassium acetate (4.00 g, 41 mmol) was added to the mixture. Mixture was slowly warmed to room temperature. Reaction was stirred at room temperature for 14 hours. Mixture was washed twice with water and once with brine. Organic was dried (magnesium sulfate) filtered and concentrated. Silica gel chromatography (ethyl acetate-hexanes) afforded the desired product in 77% yield as an amber oil. MS m/e (M+H)$^+$=455.0, 457.0.

Intermediate 102

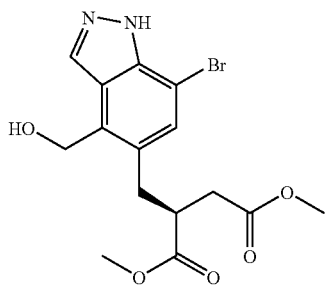

(S)-dimethyl 2-((7-bromo-4-(hydroxymethyl)-1H-indazol-5-yl)methyl)succinate. 2-(S)-(2-Acetoxymethyl-4-amino-5-bromo-3-methyl-benzyl)-succinic acid diethyl ester (2.78 g, 6.1 mmol) was converted to the title compound in a manner analogous to the preparation of 2-(S)-(4-Hydroxymethyl-1H-indazol-5-ylmethyl)-succinic acid dimethyl ester. Material was obtained as amber solid in 96% yield. MS m/e (M–H)$^-$=383.0, 385.0.

Intermediate 103

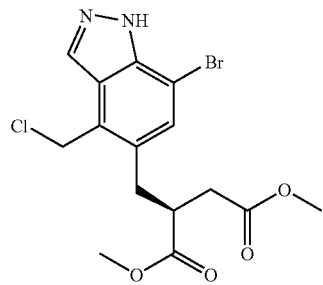

(S)-dimethyl 2-((7-bromo-4-(chloromethyl)-1H-indazol-5-yl)methyl)succinate. (S)-dimethyl 2-((7-bromo-4-(hydroxymethyl)-1H-indazol-5-yl)methyl)succinate (2.25 g, 5.8 mmol) was dissolved in 2M thionyl chloride in dichloromethane (42 mL, 84 mmol). Reaction stirred at room temperature for 2.0 hours. Mixture was concentrated. Residue was treated with toluene and then concentrated by roto-vap. Residue was dissolved in ethyl acetate. Mixture was washed twice with aqueous sodium bicarbonate. Organic was dried (magnesium sulfate), filtered and concentrated in vacuo. Title compound was obtained as amber solid in 99% yield. MS m/e (M+H)$^+$=404.9, 403.0, 406.9.

Intermediate 104

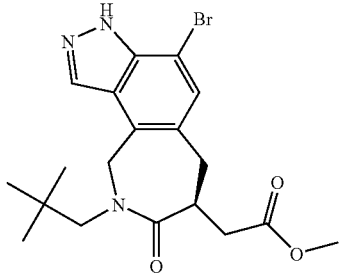

[4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester. (S)-dimethyl 2-((7-bromo-4-(chloromethyl)-1H-indazol-5-yl)methyl)succinate (860 mg, 2.1 mmol) was dissolved in acetonitrile (50 mL). Potassium carbonate (625 mg, 4.5 mmol) was added to the mixture followed by neopentylamine (800 µL, 6.78 mmol). Mixture was heated to reflux and held with stirring for 1.5 hours. Mixture was cooled to room temperature. Mixture was filtered over celite. Filtrate was concentrated by roto-vap. Residue was dissolved in a mixture of toluene (50 mL) and acetic acid (3 mL). Mixture was heated to reflux and held with stirring for 37 hours. Mixture concentrated by roto-vap. Silica gel chromatography (ethyl acetate-hexanes) afforded the title compound as tan solid in 75% yield. MS m/e (M–H)$^-$=420.0, 422.0.

Intermediate 105

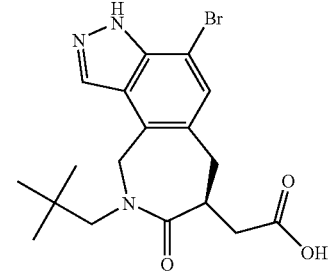

[4-Bromo-9-(2,2-dimethyl-propyl)-8-oxo-3,6,7,8,9,10-hexahydro-2,3,9-triaza-(S)-cyclohepta[e]inden-7-yl]-acetic acid. [4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester (160 mg, 0.38 mmol) was dissolved in a mixture of tetrahydrofuran (5.0 mL) and methanol (5.0 mL). Water (5.0 mL) was added to the mixture followed by lithium hydroxide monohydrate (41 mg, 0.98 mmol). Mixture was heated to 50° C. and held with stirring for 5 hours. Mixture was cooled to room temperature. Organic solvents were removed from the mixture in vacuo. Remaining aqueous was diluted with water and then made neutral with 1 mL of 1N hydrochloric acid. Material was extracted twice with ethyl acetate. Organic phase was dried (magnesium sulfate), filtered and concentrated to dryness. Title compound was obtained as tan solid in quantitative yield. $^1$H NMR (300 MHz, CDCl$_3$) δ=0.77 (s, 9 H) 2.31-2.60 (m, 3 H) 2.91 (dd, J=16.47, 8.42 Hz, 1 H) 2.98-3.05 (m, 1 H) 3.09 (d, J=13.54 Hz, 1 H) 3.47 (d, J=13.91 Hz, 1 H) 3.71-3.89 (m, 1 H) 4.39 (d, J=17.20 Hz, 1 H) 5.30 (d, J=17.20 Hz, 1 H) 7.25 (s, 1 H) 8.00 (s, 1 H).

Intermediate 106

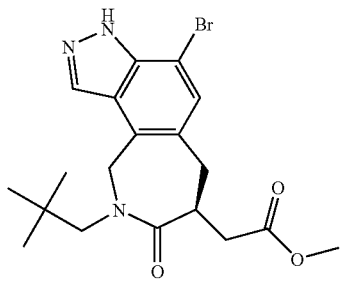

[4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester. (S)-dimethyl 2-((7-bromo-4-(chloromethyl)-1H-indazol-5-yl)methyl)succinate (860 mg, 2.1 mmol) was dissolved in acetonitrile (50 mL). Potassium carbonate (625 mg, 4.5 mmol) was added to the mixture followed by neopentylamine (800 μL, 6.78 mmol). Mixture was heated to reflux and held with stirring for 1.5 hours. Mixture was cooled to room temperature. Mixture was filtered over celite. Filtrate was concentrated by roto-vap. Residue was dissolved in a mixture of toluene (50 mL) and acetic acid (3 mL). Mixture was heated to reflux and held with stirring for 37 hours. Mixture concentrated by roto-vap. Silica gel chromatography (ethyl acetate-hexanes) afforded the title compound as tan solid in 75% yield. MS m/e (M−H)⁻=420.0, 422.0.

Intermediate 107

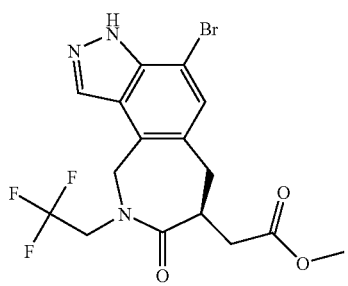

[4-Bromo-3,6,7,8,9,10-hexahydro-8-oxo-9-(2, 2, 2-trifluoroethyl)-2,3,9-triaza-(S)-cyclohepta[e]inden-7-yl]acetic acid methyl ester. 2-(S)-(4-chloromethyl-7-bromo-1H-indazol-5-ylmethyl)-succinic acid diethyl ester (325 mg, 0.81 mmol) was dissolved in acetonitrile (10 mL). Potassium carbonate (310 mg, 2.2 mmol) was added to the mixture with 2,2,2-trifluoroethylamine (1.2 mL, 15 mmol). Mixture was heated at 60° C. and held with stirring for 15 hours. Mixture was cooled to room temperature. Mixture was filtered over celite. Filtrate was concentrated by roto-vap. Residue was dissolved in a mixture of toluene (10 mL) and acetic acid (600 μL). Mixture was heated to reflux and held with stirring for 22 hours. Mixture was concentrated by roto-vap. Residue was dissolved in ethyl acetate. Material was washed successively with water and aqueous sodium bicarbonate. Organic phase was dried (magnesium sulfate), filtered and concentrated to dryness. Title compound was obtained as amber residue in 74% yield. MS m/e (M−H)⁻=431.9, 433.9.

Intermediate 108

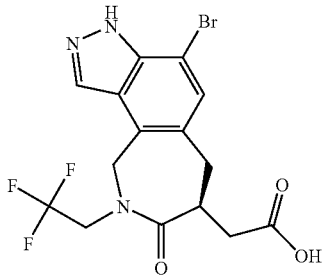

[4-Bromo-3,6,7,8,9,10-hexahydro-8-oxo-9-(2,2,2-trifluoroethyl)-2,3,9-triaza-(S)-cyclohepta[e]inden-7-yl]acetic acid. [4-Bromo-3,6,7,8,9,10-hexahydro-8-oxo-9-(2,2,2-trifluoroethyl)-2,3,9-triaza-(S)-cyclohepta[e]inden-7-yl]acetic acid methyl ester (250 mg, 0.58 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as light yellow solid in quantitative yield. MS m/e (M−H)⁻=417.9, 419.9.

Intermediate 109

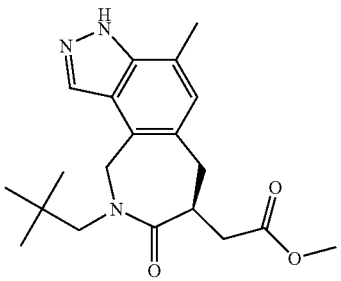

[4-Methyl-9-(2,2-dimethyl-propyl)-8-oxo-3,6,7,8,9,10-hexahydro-2,3,9-triaza-(S)-cyclohepta[e]inden-7-yl]-acetic acid methyl ester. [4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester (110 mg, 0.26 mmol) was dissolved in N,N-dimethylformamide (1.0 mL). Nitrogen gas was bubbled through the mixture for 5 minutes. Tetrakis(triphenylphosphine)palladium(0) (6.0 mg, 0.01 mmol) was added to the mixture followed by tetramethyltin (100 μL, 0.72 mmol). Reaction vessel was flushed with nitrogen gas and then sealed. Reaction was subjected to microwave heating at 175° C. for 35 minutes. Mixture was diluted with ethyl acetate. Material was washed successively with water and brine. Silica gel chromatography (ethyl acetate-hexanes) afforded the title compound as white solid in 83% yield. MS m/e (M+H)⁺=358.2.

Intermediate 110

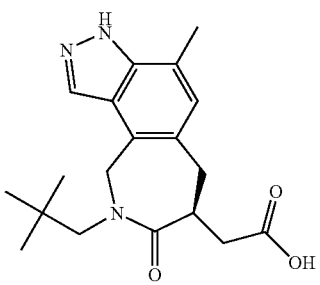

[4-Methyl-9-(2,2-dimethyl-propyl)-8-oxo-3,6,7,8,9,10-hexahydro-2,3,9-triaza-(S)-cyclohepta[e]inden-7-yl]-acetic acid. [4-Methyl-9-(2,2-dimethyl-propyl)-8-oxo-3,6,7,8,9,10-hexahydro-2,3,9-triaza-(S)-cyclohepta[e]inden-7-yl]-acetic acid methyl ester (70 mg, 196 µmol) was dissolved in tetrahydrofuran (2.0 mL). Methanol (2.0 mL) was added to the mixture followed by water (2.0 mL) and then lithium hydroxide hydrate (20 mg, 477 µmol). Reaction was warmed to 50° C. and held with stirring for 1.5 hours. Mixture was cooled to room temperature. Organic solvents were removed from the mixture by roto-vap. Remaining aqueous was diluted with water and then neutralized with 1N hydrochloric acid (500 µL). Mixture was extracted twice with ethyl acetate. Organics were dried MgSO4, filtered and then concentrated to dryness. Title compound was obtained as white solid in 95% yield. MS m/e (M−H)⁻=342.2.

Intermediate 111

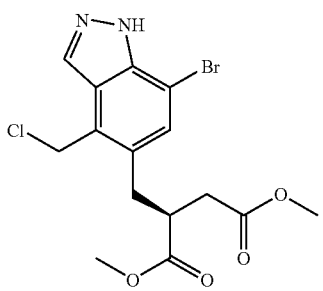

2-(S)-(4-Acetoxymethyl-7-methyl-1H-indazol-5-ylmethyl)-succinic acid diethyl ester. 2-(S)-(4-Acetoxymethyl-7-bromo-1H-indazol-5-ylmethyl)-succinic acid diethyl ester (350 mg, 0.77 mmol) and tetramethyltin (150 µL, 1.1 mmol) were reacted in a manner analogous to the preparation of [4-Methyl-9-(2,2-dimethyl-propyl)-8-oxo-3,6,7,8,9,10-hexahydro-2,3,9-triaza-(S)-cyclohepta[e]inden-7-yl]-acetic acid methyl ester. Title compound was obtained as pale yellow solid in 68% yield. MS m/e (M−H)⁻=389.1.

Intermediate 112

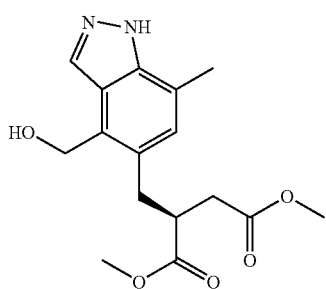

(S)-dimethyl 2-((7-methyl-4-(hydroxymethyl)-1H-indazol-5-yl)methyl)succinate. 2-(S)-(2-Acetoxymethyl-4-amino-5-methyl-3-methyl-benzyl)-succinic acid diethyl ester (230 mg, 0.59 mmol) was converted to the title compound in a manner analogous to the preparation of 2-(S)-(4-Hydroxymethyl-1H-indazol-5-ylmethyl)-succinic acid dimethyl ester. Material was obtained as off-white solid in 98% yield. MS m/e (M−H)⁻=319.2.

Intermediate 113

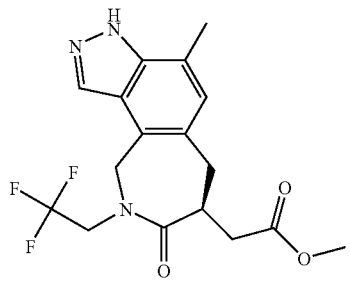

(S)-dimethyl 2-((7-methyl-4-(chloromethyl)-1H-indazol-5-yl)methyl)succinate. (S)-dimethyl 2-((7-methyl-4-(hydroxymethyl)-1H-indazol-5-yl)methyl)succinate (180 mg, 0.56 mmol) was dissolved in dichloromethane (4.0 mL). 2M Thionyl chloride in dichloromethane (4.0 mL, 8.0 mmol) was added to the mixture. Reaction stirred at room temperature for 2.5 hours. Mixture was concentrated. Residue was treated with toluene and then concentrated by roto-vap. Residue was dissolved in dichloromethane and then concentrated to dryness Title compound was obtained as amber solid in 99% yield. MS m/e (M+H)⁺=339.1.

Intermediate 114

[4-Methyl-3,6,7,8,9,10-hexahydro-8-oxo-9-(2,2,2-trifluoroethyl)-2,3,9-triaza-(S)-cyclohepta[e]inden-7-yl]acetic acid methyl ester. 2-(S)-(4-chloromethyl-7-methyl-1H-indazol-5-ylmethyl)-succinic acid diethyl ester (190 mg, 0.56 mmol) and 2,2,2-trifluoroethylamine (45 µL, 0.56 mmol) were reacted in a manner analogous to the preparation of [4-bromo-3,6,7,8,9,10-hexahydro-8-oxo-9-(2,2,2-trifluoroethyl)-2,3,9-triaza-(S)-cyclohepta[e]inden-7-yl]acetic acid methyl ester. Title compound was obtained as amber residue in 76% yield. MS m/e (M+H)⁻=370.1.

Intermediate 115

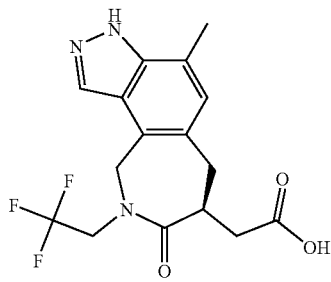

[4-Methyl-3,6,7,8,9,10-hexahydro-8-oxo-9-(2,2,2-trifluoroethyl)-2,3,9-triaza-(S)-cyclohepta[e]inden-7-yl]acetic acid. [4-Methyl-3,6,7,8,9,10-hexahydro-8-oxo-9-(2,2,2-trifluoroethyl)-2,3,9-triaza-(S)-cyclohepta[e]inden-7-yl]acetic acid methyl ester (250 mg, 0.58 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 97% yield. MS m/e (M–H)⁻=354.2.

Intermediate 116

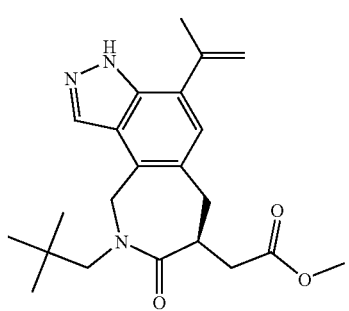

[(S)-9-(2,2-Dimethyl-propyl)-4-isopropenyl-8-oxo-3,6,7,8,9,10-hexahydro-2,3,9-triaza-cyclohept[e]inden-7-yl]-acetic acid methyl ester. [4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester (100 mg, 0.24 mmol) was dissolved in 2-propanol (1.0 mL). Nitrogen gas was bubbled through the mixture for 5 minutes. Triethylamine (60 µL, 0.43 mmol) was added to the mixture followed by [1,1'-bis(diphenylphosphino)ferrocene]palladium(II) chloride (19 mg, 0.02 mmol) and potassium 2-propenyltrifluoroborate (41 mg, 0.28 mmol). Reaction vessel was flushed with nitrogen gas and then sealed. Reaction was subjected to microwave heating at 150° C. for 30 minutes. Silica gel chromatography (ethyl acetate-hexanes) afforded the title compound as amber solid in 73% yield. MS m/e (M+H)⁺=384.4.

Intermediate 117

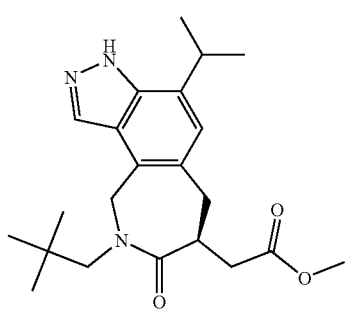

[(S)-9-(2,2-Dimethyl-propyl)-4-isopropyl-8-oxo-3,6,7,8,9,10-hexahydro-2,3,9-triaza-cyclohept[e]inden-7-yl]-acetic acid methyl ester. [(S)-9-(2,2-Dimethyl-propyl)-4-isopropenyl-8-oxo-3,6,7,8,9,10-hexahydro-2,3,9-triaza-cyclohept[e]inden-7-yl]-acetic acid methyl ester (100 mg, 0.26 mmol) was dissolved in a mixture of ethyl acetate (5.0 mL) and methanol (5.0 mL). A catalytic amount of 10% palladium on carbon was added to the mixture. Reaction vessel was placed on a Parr apparatus and charged with 50 psi of hydrogen gas. Reaction shook at room temperature for 1 hour. Mixture was filtered and the filtrate was concentrated to dryness. Title compound was obtained as brown residue in 90% yield. MS m/e (M+H)⁺=386.3.

Intermediate 118

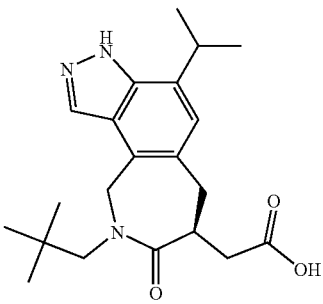

[(S)-9-(2,2-Dimethyl-propyl)-4-isopropyl-8-oxo-3,6,7,8,9,10-hexahydro-2,3,9-triaza-cyclohept[e]inden-7-yl]acetic acid. [(S)-9-(2,2-Dimethyl-propyl)-4-isopropyl-8-oxo-3,6,7,8,9,10-hexahydro-2,3,9-triaza-cyclohept[e]inden-7-yl]-acetic acid methyl ester (90 mg, 0.23 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 92% yield. MS m/e (M–H)⁻=370.3.

Intermediate 119

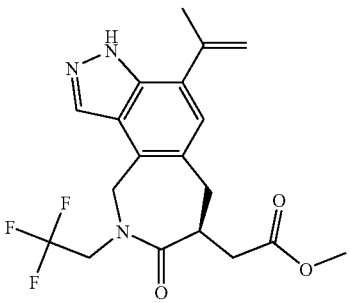

[4-Isopropenyl-3,6,7,8,9,10-hexahydro-8-oxo-9-(2,2,2-trifluoroethyl)-2,3,9-triaza-(S)-cyclohepta[e]inden-7-yl] acetic acid methyl ester. [4-Bromo-3,6,7,8,9,10-hexahydro-8-oxo-9-(2,2,2-trifluoroethyl)-2,3,9-triaza-(S)-cyclohepta[e]inden-7-yl]acetic acid methyl ester (400 mg, 0.92 mmol) and potassium 2-propenyltrifluoroborate (165 mg, 1.1 mmol) were reacted in a manner analogous to the preparation of [(S)-9-(2,2-Dimethyl-propyl)-4-isopropenyl-8-oxo-3,6,7,8,9,10-hexahydro-2,3,9-triaza-cyclohept[e]inden-7-yl]-acetic acid methyl ester. Title compound was obtained as amber oil in 71% yield. MS m/e (M–H)⁻=394.1.

Intermediate 120

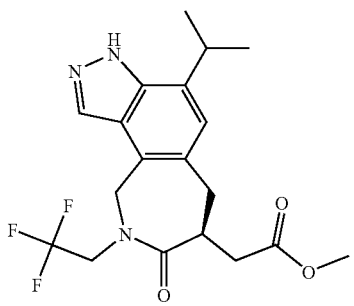

[4-Isopropyl-3,6,7,8,9,10-hexahydro-8-oxo-9-(2,2,2-trifluoroethyl)-2,3,9-triaza-(S)-cyclohepta[e]inden-7-yl]acetic acid methyl ester. [4-Isopropenyl-3,6,7,8,9,10-hexahydro-8-oxo-9-(2,2,2-trifluoroethyl)-2,3,9-triaza-(S)-cyclohepta[e]inden-7-yl]acetic acid methyl ester (150 mg, 0.38 mmol) was reacted in a manner analogous to the preparation of [(S)-9-(2,2-Dimethyl-propyl)-4-isopropyl-8-oxo-3,6,7,8,9,10-hexahydro-2,3,9-triaza-cyclohept[e]inden-7-yl]-acetic acid methyl ester. Title compound was obtained as white solid in 73% yield. MS m/e (M+H)⁺=398.2.

Intermediate 121

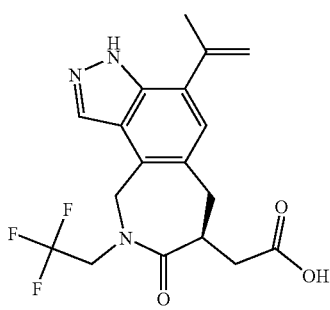

[4-Isopropenyl-3,6,7,8,9,10-hexahydro-8-oxo-9-(2,2,2-trifluoroethyl)-2,3,9-triaza-(S)-cyclohepta[e]inden-7-yl] acetic acid. [4-Isopropenyl-3,6,7,8,9,10-hexahydro-8-oxo-9-(2,2,2-trifluoroethyl)-2,3,9-triaza-(S)-cyclohepta[e]inden-7-yl]acetic acid methyl ester (100 mg, 0.25 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as off-white solid in 98% yield. MS m/e (M−H)⁻=380.2.

Intermediate 122

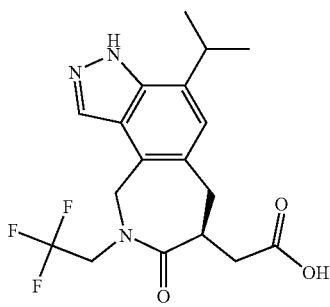

[4-Isopropyl-3,6,7,8,9,10-hexahydro-8-oxo-9-(2,2,2-trifluoroethyl)-2,3,9-triaza-(S)-cyclohepta[e]inden-7-yl]acetic acid. [4-Isopropyl-3,6,7,8,9,10-hexahydro-8-oxo-9-(2,2,2-trifluoroethyl)-2,3,9-triaza-(S)-cyclohepta[e]inden-7-yl] acetic acid methyl ester (105 mg, 0.26 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 99% yield. MS m/e (M−H)⁻=382.2.

Intermediate 123

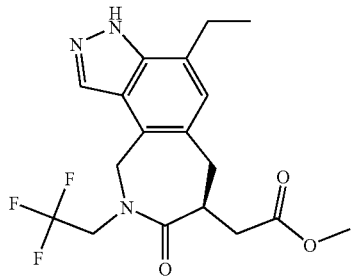

[4-Ethyl-3,6,7,8,9,10-hexahydro-8-oxo-9-(2,2,2-trifluoroethyl)-2,3,9-triaza-(S)-cyclohepta[e]inden-7-yl]acetic acid methyl ester. [4-Bromo-3,6,7,8,9,10-hexahydro-8-oxo-9-(2,2,2-trifluoroethyl)-2,3,9-triaza-(S)-cyclohepta[e]inden-7-yl]acetic acid methyl ester (150 mg, 0.35 mmol) and tetraethyltin (200 µL, 1.0 mmol) were reacted in a manner analogous to the preparation of [(S)-9-(2,2-Dimethyl-propyl)-4-methyl-8-oxo-3,6,7,8,9,10-hexahydro-2,3,9-triaza-cyclohept[e]inden-7-yl]-acetic acid methyl ester. Title compound was obtained as clear colorless oil in 28% yield. MS m/e (M+H)⁺=384.2.

Intermediate 124

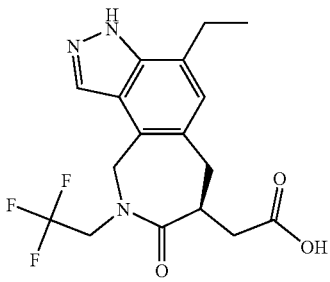

[4-Ethyl-3,6,7,8,9,10-hexahydro-8-oxo-9-(2,2,2-trifluoroethyl)-2,3,9-triaza-(S)-cyclohepta[e]inden-7-yl]acetic acid. [4-Ethyl-3,6,7,8,9,10-hexahydro-8-oxo-9-(2,2,2-trifluoroethyl)-2,3,9-triaza-(S)-cyclohepta[e]inden-7-yl]acetic acid methyl ester (105 mg, 0.26 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 73% yield. MS m/e (M−H)⁻=368.3.

Intermediate 125

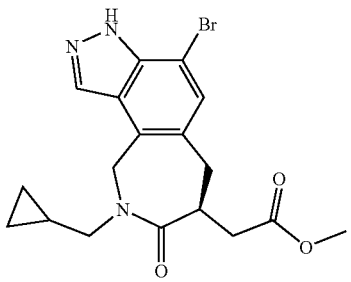

((S)-4-Bromo-9-cyclopropylmethyl-8-oxo-3,6,7,8,9,10-hexahydro-2,3,9-triaza-cyclohept[e]inden-7-yl)-acetic acid methyl ester. (S)-dimethyl 2-((7-bromo-4-(chloromethyl)-1H-indazol-5-yl)methyl)succinate (630 mg, 1.6 mmol) was dissolved in acetonitrile (5 mL). Potassium carbonate (560 mg, 4.1 mmol) was added to the mixture followed by (aminomethyl)cyclopropane (700 µL, 8.1 mmol). Mixture was heated to reflux and held with stirring for 1.5 hours. Mixture was cooled to room temperature. Mixture was filtered. Filtrate was concentrated by roto-vap. Residue was dissolved in a mixture of toluene (10 mL) and acetic acid (1 mL). Mixture was heated to reflux and held with stirring for 18 hours. Mixture was concentrated by roto-vap. Silica gel chromatography (ethyl acetate-hexanes) afforded the title compound as tan solid in 64% yield. MS m/e (M+H)⁺=406.0, 408.0.

Intermediate 126

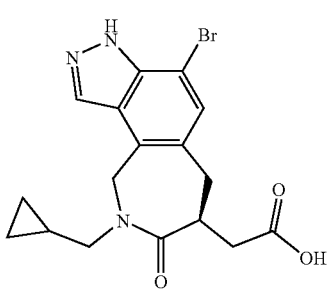

((S)-4-Bromo-9-cyclopropylmethyl-8-oxo-3,6,7,8,9,10-hexahydro-2,3,9-triaza-cyclohept[e]inden-7-yl)-acetic acid. ((S)-4-Bromo-9-cyclopropylmethyl-8-oxo-3,6,7,8,9,10-hexahydro-2,3,9-triaza-cyclohept[e]inden-7-yl)-acetic acid methyl ester (290 mg, 0.71 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as yellow solid in 96% yield. MS m/e (M−H)⁻=390.0, 392.0.

Intermediate 127

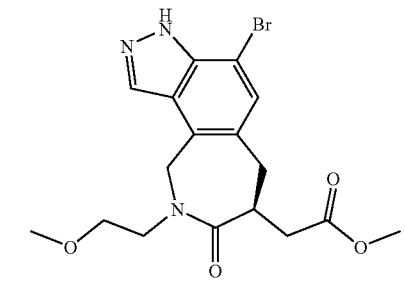

[(S)-4-Bromo-9-(2-methoxy-ethyl)-8-oxo-3,6,7,8,9,10-hexahydro-2,3,9-triaza-cyclohept[e]inden-7-yl]-acetic acid methyl ester. (S)-dimethyl 2-((7-bromo-4-(chloromethyl)-1H-indazol-5-yl)methyl)succinate (400 mg, 0.99 mmol) and 2-methoxyethylamine were reacted in a manner analogous to the preparation of ((S)-4-Bromo-9-cyclopropylmethyl-8-oxo-3,6,7,8,9,10-hexahydro-2,3,9-triaza-cyclohept[e]inden-7-yl)-acetic acid methyl ester. Title compound was obtained as tan solid in 66% yield. MS m/e (M−H)⁻=408.1, 410.0.

Intermediate 128

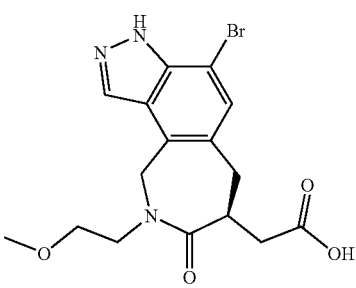

[(S)-4-Bromo-9-(2-methoxy-ethyl)-8-oxo-3,6,7,8,9,10-hexahydro-2,3,9-triaza-cyclohept[e]inden-7-yl]-acetic acid. [(S)-4-Bromo-9-(2-methoxy-ethyl)-8-oxo-3,6,7,8,9,10-hexahydro-2,3,9-triaza-cyclohept[e]inden-7-yl]-acetic acid methyl ester (265 mg, 0.65 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as tan solid in 89% yield. MS m/e (M−H)⁻=394.1, 396.0.

Intermediate 129

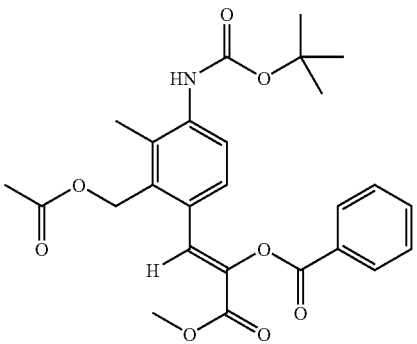

(Z)-1-(2-(acetoxymethyl)-4-(tert-butoxycarbonylamino)-3-methylphenyl)-3-methoxy-3-oxoprop-1-en-2-yl benzoate. 3-(tert-butoxycarbonylamino)-6-iodo-2-methylbenzyl acetate (18.0 g, 44.4 mmol) in tetrahydrofuran (180.00 ml, 2197 mmol) was added triethylamine (24.76 ml, 178 mmol) followed by tetrabutylammonium chloride, hydrate (13.15 g, 44.4 mmol) and 3-methoxy-3-oxoprop-1-en-2-yl benzoate (11.91 g, 57.7 mmol). After introducing nitrogen atmosphere, palladium(II) acetate (0.898 g, 4.0 mmol) was added. The reaction mixture was refluxed for 3 h. The crude product was cooled and most of the solvent was removed. The crude product was diluted with ether (300 mL) and solids were removed by filtration. The solvent was evaporated and the crude product was purified by flash chromatography using 30% EtOAc in hexane to 50% EtOAc in hexane. The product was crystallized from a mixture of EtOAc-hexane to give a white powder of (Z)-1-(2-(acetoxymethyl)-4-(tert-butoxycarbonylamino)-3-methylphenyl)-3-methoxy-3-oxoprop-1-en-2-yl benzoate (20.5 g, 42.4 mmol, 95% yield). $^1$H NMR (500 MHz, CDCl$_3$): in δ 8.08-8.06 (m, 2H), 7.75-7.74 (m, 2H), 7.60-7.58 (m, 1H), 7.49-7.44 (m, 3H), 5.25 (s, 2H), 3.85 (m, 3H), 2.24 (s, 3H), 2.07 (s, 3H), 1.52 (s, 9H); MS (ESI) 506 (M+H); R$_f$=2.61.

Intermediate 130

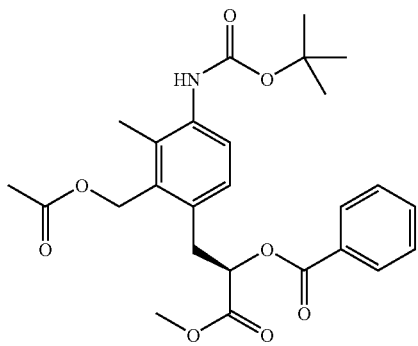

(R)-3-(2-(acetoxymethyl)-4-(tert-butoxycarbonylamino)-3-methylphenyl)-1-methoxy-1-oxopropan-2-yl benzoate. (Z)-1-(2-(acetoxymethyl)-4-(tert-butoxycarbonylamino)-3-methylphenyl)-3-methoxy-3-oxoprop-1-en-2-yl benzoate (20.00 g, 41.4 mmol) in dichloromethane (120.00 ml) was added (−)-1,2-bis((2R,5R)-2,5-diethylphospholano)benzene (cyclooctadiene)rhodium (I) tetrafluoroborate (280.00 mg, 0.424 mmol) under nitrogen atmosphere. The reaction mixture was hydrogenated at 60 psi pressure of hydrogen for 12 h. The solvent was removed and crude product was carried to the next step as such. MS (ESI) 508 (M+H); R$_f$=2.53.

Intermediate 131

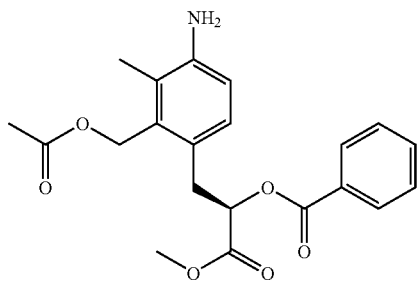

(R)-3-(2-(acetoxymethyl)-4-amino-3-methylphenyl)-1-methoxy-1-oxopropan-2-yl benzoate. (R)-3-(2-(acetoxymethyl)-4-(tert-butoxycarbonylamino)-3-methylphenyl)-1-methoxy-1-oxopropan-2-yl benzoate (19.5 g, 40.2 mmol) in dichloromethane (100.00 ml, 1554 mmol) was added trifluoroacetic acid (30.00 ml, 389 mmol). The reaction mixture was stirred at RT. After 4 h, LC-MS suggested complete removal of protecting group. The solvent was removed and the crude product was dissolved in dichloromethane (300 mL) and washed with aqueous NaHCO$_3$. The solvent was removed to give (R)-3-(2-(acetoxymethyl)-4-amino-3-methylphenyl)-1-methoxy-1-oxopropan-2-yl benzoate (15.0 g, 38.9 mmol, 97% yield). MS (ESI) 408 (M+H); R$_f$=1.69.

Intermediate 132

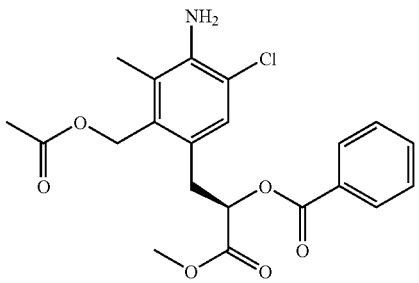

(R)-3-(2-(acetoxymethyl)-4-amino-5-chloro-3-methylphenyl)-1-methoxy-1-oxopropan-2-yl benzoate. (R)-3-(2-(acetoxymethyl)-4-amino-3-methylphenyl)-1-methoxy-1-oxopropan-2-yl benzoate (15.00 g, 38.9 mmol) in acetonitrile (200. ml, 3829 mmol) was added N-chlorosuccinimide (5.72 g, 42.8 mmol). The reaction mixture was then heated to reflux for 2 min. The solvent was removed and the crude product was washed with aqueous NaHCO$_3$. The crude product was purified by flash chromatography using 30% EtOAc in hexane to give (R)-3-(2-(acetoxymethyl)-4-amino-5-chloro-3-methylphenyl)-1-methoxy-1-oxopropan-2-yl benzoate in 57% yield. MS (ESI) 442 (M+H); R$_f$=2.42.

Intermediate 133

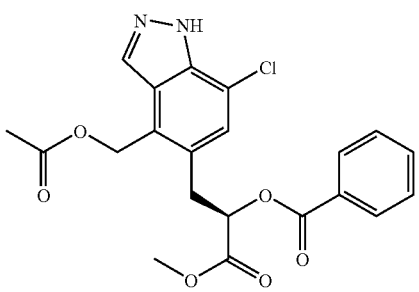

(R)-3-(4-(acetoxymethyl)-7-chloro-1H-indazol-5-yl)-1-methoxy-1-oxopropan-2-yl benzoate. (R)-3-(2-(acetoxymethyl)-4-amino-5-chloro-3-methylphenyl)-1-methoxy-1-oxopropan-2-yl benzoate (16.33 g, 38.9 mmol) in toluene (100.0 ml, 939 mmol) was added acetic acid (5.0 ml, 87 mmol) followed by isoamyl nitrite (5.76 ml, 42.8 mmol) at 0° C. After 15 min, potassium acetate (7.64 g, 78 mmol) was added and the reaction mixture was stirred for 12 h. The solvent was removed and the crude product was dissolved in dichloromethane (250 mL) and washed with aqueous NaHCO$_3$. The solvent was dried (Na$_2$SO$_4$), evaporated and the crude product was purified by flash chromatography using 40% EtOAc in hexane to give (R)-3-(4-(acetoxymethyl)-7-chloro-1H-indazol-5-yl)-1-methoxy-1-oxopropan-2-yl benzoate in 88% yield. MS (ESI) 453 (M+Na); $R_f$=2.46.

Intermediate 134

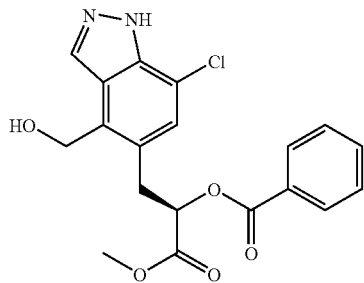

(R)-3-(7-chloro-4-(hydroxymethyl)-1H-indazol-5-yl)-1-methoxy-1-oxopropan-2-yl benzoate. (R)-3-(4-(acetoxymethyl)-7-chloro-1H-indazol-5-yl)-1-methoxy-1-oxopropan-2-yl benzoate (8.5 g, 19.73 mmol) in a mixture of chloroform (80.0 ml, 992 mmol) and methanol (60.0 ml, 1483 mmol) was added magnesium methoxide (4.18 ml, 39.5 mmol). After 3 h, quenched with 1.0 M HCl and extracted with dichloromethane (300 mL). The crude product was purified by flash chromatography using 70% EtOAc in hexane to give (R)-3-(7-chloro-4-(hydroxymethyl)-1H-indazol-5-yl)-1-methoxy-1-oxopropan-2-yl benzoate in 67% yield. $^1$H NMR (500 MHz, CDCl$_3$): in δ 8.09 (s, 1H), 7.93 (d, J=7.5 Hz, 1H), 7.47 (m, 1H), 7.32 (t, J=8 Hz, 2H), 7.22 (s, 1H), 5.49 (m, 1H), 4.99 (m, 2H), 3.45-3.41 (m, 1H), 3.68 (s, 3 H), 3.36-3.31 (m, 1H); MS (ESI) 389 (M+H); $R_f$=2.07.

Intermediate 135

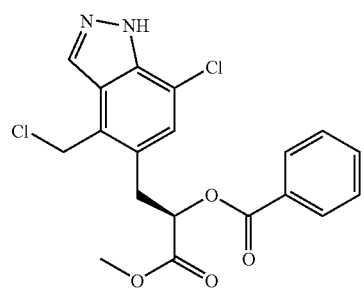

(R)-3-(7-chloro-4-(chloromethyl)-1H-indazol-5-yl)-1-methoxy-1-oxopropan-2-yl benzoate. (R)-3-(7-chloro-4-(hydroxymethyl)-1H-indazol-5-yl)-1-methoxy-1-oxopropan-2-yl benzoate (6.5 g, 16.72 mmol) in dichloromethane (100.0 ml, 1554 mmol) was added Diisopropylethyl amine (2.59 g, 20.06 mmol) followed by methanesulfonyl chloride (1.433 ml, 18.39 mmol). After 2 h, the reaction mixture was quenched with aqueous NaHCO$_3$, dried (Na$_2$SO$_4$) and the solvent was removed. MS (ESI) 407 (M+H); $R_f$=1.69.

Intermediate 136

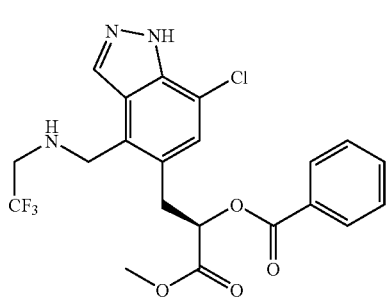

(R)-3-(7-chloro-4-((2,2,2-trifluoroethylamino)methyl)-1H-indazol-5-yl)-1-methoxy-1-oxopropan-2-yl benzoate. (R)-3-(7-chloro-4-(chloromethyl)-1H-indazol-5-yl)-1-methoxy-1-oxopropan-2-yl benzoate (6.80 g, 16.7 mmol) in acetonitrile (70.0 ml, 1340 mmol) was added 2,2,2-trifluoroethylamine (8.27 g, 84 mmol). After 20 min, potassium carbonate (2.308 g, 16.70 mmol) was added and the reaction mixture was refluxed for 2 h. The solvent was evaporated and the crude product was dissolved in a mixture of dichloromethane and chloroform. A thick emulsion formed and addition of methanol provided a clear organic phase. The organic layer was dried (Na$_2$SO$_4$), the solvent was removed and the crude product was used as such for the next step. MS (ESI) 470 (M+H); $R_f$=1.56.

Intermediate 137

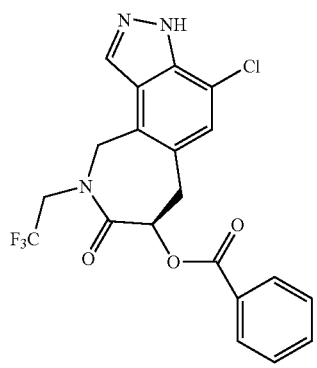

(R)-4-chloro-8-oxo-9-(2,2,2-trifluoroethyl)-3,6,7,8,9,10-hexahydroazepino[3,4-e]indazol-7-yl benzoate. (R)-3-(7-chloro-4-((2,2,2-trifluoroethylamino)methyl)-1H-indazol-5-yl)-1-methoxy-1-oxopropan-2-yl benzoate (7.75 g, 16.5 mmol) in toluene (70.00 ml, 657 mmol) was added acetic acid (1.2 ml, 20.96 mmol) and refluxed for 12 h. The solvent was evaporated and the crude product was dissolved in EtOAc, washed with aqueous NaHCO$_3$. The solvent was removed and the crude product was purified by flash chromatography using 50% EtOAc in hexane to give (R)-4-chloro-8-oxo-9-(2,2,2-trifluoroethyl)-3,6,7,8,9,10-hexahydroazepino[3,4-e]indazol-7-yl benzoate in 74% yield. MS (ESI) 438 (M+H); $R_f$=2.60.

Intermediate 138

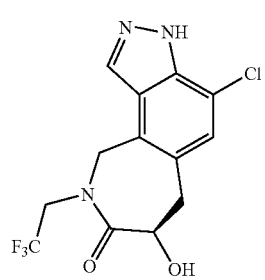

(R)-4-chloro-7-hydroxy-9-(2,2,2-trifluoroethyl)-6,7,9,10-tetrahydroazepino[3,4-e]indazol-8(3H)-one. (R)-4-chloro-8-oxo-9-(2,2,2-trifluoroethyl)-3,6,7,8,9,10-hexahydroazepino [3,4-e]indazol-7-yl benzoate (7.00 g, 16.0 mmol) in THF (60.00 ml, 732 mmol) was added lithium hydroxide (0.766 g, 32.0 mmol) followed by water (6.0 ml, 333 mmol). After 3 h, the solvent was removed and the crude product was diluted with dichloromethane and neutralized with 1.0 M HCl. The organic phase was dried and the crude product was purified by flash chromatography using 70% EtOAc in hexane to give (R)-4-chloro-7-hydroxy-9-(2,2,2-trifluoroethyl)-6,7,9,10-tetrahydroazepino[3,4-e]indazol-8(3 H)-one in 53% yield. $^1$HNMR (500 MHz, CDCl$_3$): in δ 8.12 (s, 1H), 7.16 (s, 1H), 5.18-5.14 (m, 2H), 4.55 (d, J=17 Hz, 1H), 4.30-4.28 (m, 1H), 4.27-4.24 (m, 1H), 3.86 (m, 1H), 3.46 (dd, J=5 Hz, J=1.5 Hz, 1H), 3.09 (dd, J=5 Hz, J=1.5 Hz, 1H), 1.52 (s, 9H), MS (ESI) 334 (M+H); R$_f$=1.49.

Intermediate 139

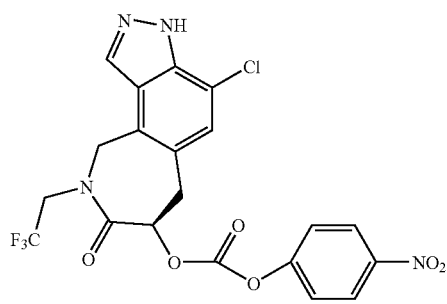

(R)-4-chloro-8-oxo-9-(2,2,2-trifluoroethyl)-3,6,7,8,9,10-hexahydroazepino[3,4-e]indazol-7-yl 4-nitrophenyl carbonate. (R)-4-chloro-7-hydroxy-9-(2,2,2-trifluoroethyl)-6,7,9,10-tetrahydroazepino [3,4-e]indazol-8(3H)-one (1.2 g, 3.60 mmol) in dichloromethane (100.0 ml, 1554 mmol) was added diisopropylethyl amine (0.651 g, 5.03 mmol) followed by 4-nitrophenyl carbonochloridate (0.942 g, 4.67 mmol). After 48 h, the reaction mixture was washed with 1.0 M HCl and the crude product was purified by flash chromatography using 75% EtOAc in hexane to give (R)-4-chloro-8-oxo-9-(2,2,2-trifluoroethyl)-3,6,7,8,9,10-hexahydroazepino[3,4-e]indazol-7-yl 4-nitrophenyl carbonate (1.0 g, 2.005 mmol, 56% yield). MS (ESI) 499 (M+H); R$_f$=1.64.

Intermediate 140

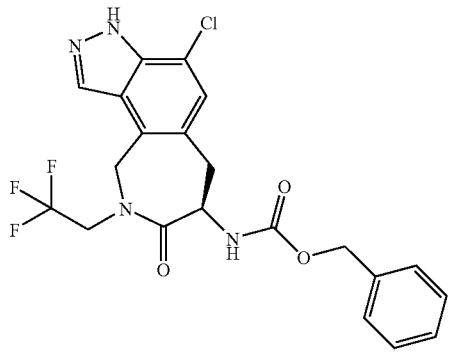

(R)-benzyl 4-chloro-8-oxo-9-(2,2,2-trifluoroethyl)-3,6,7,8,9,10-hexahydroazepino[3,4-e]indazol-7-ylcarbamate. (R)-Methyl 2-(benzyloxycarbonyl)-3-(7-chloro-4-(chloromethyl)-1H-indazol-5-yl)propanoate (630 mg, 1444 µmol) was dissolved in acetonitrile (15 ml). Potassium carbonate (240 mg, 1737 µmol) was added to the mixture followed by 2,2,2-Trifluoroethylamine (400 µl, 5028 µmol). Mixture was warmed to reflux and held with stirring for 1 hour. Another 1 mL of 2,2,2-trifluoroethylamine was added to the mixture followed by another 320 mg of potassium carbonate. Mixture was heated at reflux for 45 minutes. Mixture was cooled to room temperature and then filtered over celite. Filtrate was concentrated by roto-vap. Residue was dissolved in toluene (15 ml). Acetic acid (0.50 ml, 8734 µmol) was added to the mixture. Reaction was warmed to reflux and held for 16 hours. Mixture was concentrated by roto-vap. Silica gel chromatography eluting ethyl acetate-hexanes afforded the desired product as tan solid in 67% yield. MS (M+H)$^+$=466.8.

Intermediate 141

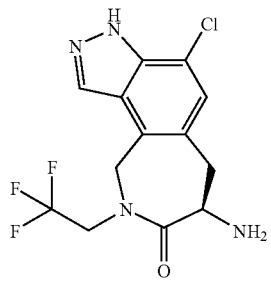

(R)-7-amino-4-chloro-9-(2,2,2-trifluoroethyl)-6,7,9,10-tetrahydroazepino[3,4-e]indazol-8(3H)-one. (R)-Benzyl 4-chloro-8-oxo-9-(2,2,2-trifluoroethyl)-3,6,7,8,9,10-hexahydroazepino[3,4-e]indazol-7-ylcarbamate (450 mg, 964 µmol) was dissolved in dichloromethane (20 ml). Anisole (250 µl, 2300 µmol) was added to the mixture followed by methanesulfonic acid (5.0 ml, 77051 µmol). Reaction stirred at room temperature for 1.5 hours. 100 mL of diethyl ether was added to the mixture. Reaction stirred at room temperature for 45 minutes. Liquids were decanted off. Remaining solid was washed with diethyl ether and the liquids decanted. Solids were dissolved in water. Mixture was made basic with aqueous sodium bicarbonate. Mixture was extracted twice with ethyl acetate and the aqueous phase was discarded. Material was washed successively with aqueous sodium bicarbonate, water and brine and the aqueous phases were discarded. Organics were dried MgSO$_4$, filtered and then concentrated to dryness. Title compound was obtained as light yellow solid in 78% yield. MS (M+H)$^-$=321.2.

Intermediate 142

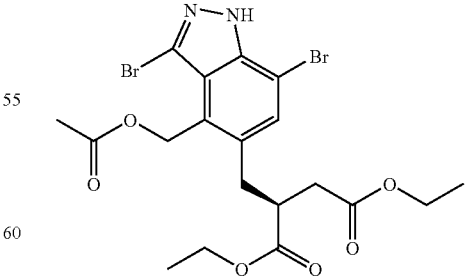

(S)-diethyl 2-((4-(acetoxymethyl)-3,7-dibromo-1H-indazol-5-yl)methyl)succinate. (S)-Diethyl 2-((4-(acetoxymethyl)-7-bromo-1H-indazol-5-yl)methyl)succinate (555 mg, 1.219 mmol) was dissolved in dichloromethane (20 mL).

N-Bromosuccinimide (250 mg, 1.405 mmol) was added to the mixture followed by a small amount of silica gel. Reaction stirred at room temperature for 1 hour. Mixture was concentrated some by roto-vap. Silica gel chromatography eluting ethyl acetate-hexanes afforded the title compound as clear colorless oil in 84% yield. MS (M–H)⁻=533.1, 531.2, 535.1.

Intermediate 143

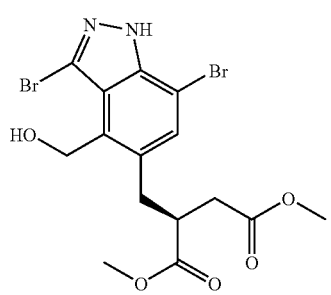

(S)-dimethyl 2-((3,7-dibromo-4-(hydroxymethyl)-1H-indazol-5-yl)methyl)succinate. (S)-Diethyl 2-((4-(acetoxymethyl)-3,7-dibromo-1H-indazol-5-yl)methyl)succinate(540 mg, 1.011 mmol) was dissolved in methanol (12 mL). 6-10% Magnesium methoxide solution in methanol (2.7 mL, 2.041 mmol) was added to the mixture. Reaction stirred at room temperature for 18 hours. Reaction was quenched with 5 mL 1N hydrochloric acid. Mixture stirred at room temperature for 30 minutes. Methanol was removed from the mixture by roto-vap. Residue was dissolved in water and then made basic with aqueous sodium bicarbonate. Material was extracted twice with ethyl acetate and the aqueous phase was discarded. Organics were dried MgSO₄, filtered and then concentrated to dryness. Title compound was obtained as white foam in 99% yield. 1H NMR, MS (M–H)⁻=463.1, 461.1, 465.1.

Intermediate 144

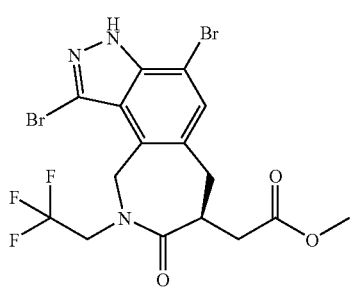

(S)-methyl 2-(1,4-dibromo-8-oxo-9-(2,2,2-triluoroethyl)-3,6,7,8,9,10-hexahydroazepino[3,4-e]indazol-7-yl)acetate. (S)-Dimethyl 2-((3,7-dibromo-4-(hydroxymethyl)-1H-indazol-5-yl)methyl)succinate (460 mg, 0.991 mmol) was dissolved in thionyl chloride (2.0 M in dichloromethane) (496 µl, 0.992 mmol). Reaction stirred at room temperature for 4 hours. Mixture was concentrated by roto-vap. Residue was dissolved in ethyl acetate. Material was washed twice with aqueous sodium bicarbonate and the aqueous phase was discarded. Organics were dried MgSO₄, filtered and then concentrated to dryness. Residue (415 mg, 0.860 mmol) was dissolved in acetonitrile (15 mL). Potassium carbonate (165 mg, 1.194 mmol) was added to the mixture followed by 2,2,2-trifluoroethylamine (350 µl, 4.40 mmol). Mixture was warmed to reflux and held with stirring for 30 minutes. Mixture was cooled to room temperature. Mixture was filtered over celite. Filtrate was concentrated by roto-vap. Residue was dissolved in toluene (17 mL). Acetic acid (200 µl, 3.49 mmol) was added to the mixture. Reaction was warmed to reflux and held with stirring for 16 hours. Mixture was cooled to room temperature and then diluted with ethyl acetate. Mixture was washed with aqueous sodium bicarbonate and the aqueous phase was discarded. Organics were dried MgSO₄, filtered and then concentrated to dryness. Silica gel chromatography eluting ethyl acetate-hexanes afforded the title compound as white solid in 45% yield. MS (M–H)⁻=512.1, 510.1, 514.1.

Intermediate 145

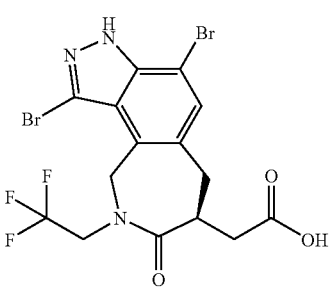

(S)-2-(1,4-dibromo-8-oxo-9-(2,2,2-trifluoroethyl)-3,6,7,8,9,10-hexahydroazepino[3,4-e]indazol-7-yl)acetic acid. (S)-Methyl 2-(1,4-dibromo-8-oxo-9-(2,2,2-trifluoroethyl)-3,6,7,8,9,10-hexahydroazepino[3,4-e]indazol-7-yl)acetate (220 mg, 0.429 mmol) was dissolved in a mixture of methanol (5.0 mL) and tetrahydrofuran (5.0 mL). Water (5.0 mL) was added to the mixture followed by lithium hydroxide hydrate (66.0 mg, 1.573 mmol). Reaction was warmed to 60° C. and held with stirring for 1.25 hours. Mixture was cooled to room temperature and then neutralized with 1.6 mL 1N hydrochloric acid. Mixture was concentrated by roto-vap. Residue was partitioned between ethyl acetate and water. Layers were separated and the aqueous phase was discarded. Material was washed with brine and the aqueous phase was discarded. Organics were dried MgSO₄, filtered and then concentrated to dryness. Title compound was obtained as white solid in 96% yield. MS (M–H)⁻=498.1, 496.1, 500.1.

Intermediate 146

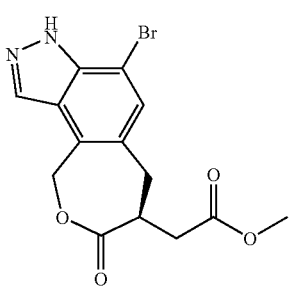

(S)-methyl 2-(4-bromo-8-oxo-6,7,8,10-tetrahydro-3H-oxepino[3,4-e]indazol-7-yl)acetate. (S)-Dimethyl 2-((3,7-dibromo-4-(hydroxymethyl)-1H-indazol-5-yl)methyl)succinate (440 mg, 1.065 mmol) was dissolved in toluene (30 mL). p-Toluenesulfonic acid monohydrate (28 mg, 0.147 mmol) was added to the mixture. Reaction was warmed to reflux and held for 18 hours with stirring. Mixture was cooled to room temperature and then diluted with ethyl acetate. Material was washed with aqueous sodium bicarbonate and the aqueous phase was discarded. Organics were dried MgSO₄, filtered and then concentrated to dryness. Silica gel chromatography eluting ethyl acetate-hexanes afforded the title compound as amber oil in 42% yield. MS (M+H)⁺=367.2, 369.2.

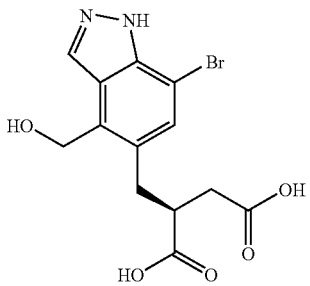

Intermediate 147

(S)-2-((7-bromo-4-(hydroxymethyl)-1H-indazol-5-yl) methyl)succinic acid. (S)-Methyl 2-(4-bromo-8-oxo-6,7,8, 10-tetrahydro-3H-oxepino[3,4-e]indazol-7-yl)acetate (135 mg, 0.368 mmol) was dissolved in a mixture of tetrahydrofuran (4.0 mL) and methanol (4.0 mL). Water (4.0 mL) was added to the mixture followed by lithium hydroxide hydrate (31.5 mg, 0.751 mmol). Reaction stirred at room temperature for 5 hours. Another 30 mg of lithium hydroxide hydrate was added to the mixture. Reaction stirred at room temperature for 18 hours. Reaction was quenched with 1.6 mL 1N hydrochloric acid. Organic solvents were removed from the mixture by roto-vap. Material was extracted from the remaining aqueous twice with ethyl acetate and the aqueous phase was discarded. Organics were dried MgSO₄, filtered and then concentrated to dryness. Title compound was obtained as white solid in 73% yield. MS (M−H)⁻=355.2, 357.1.

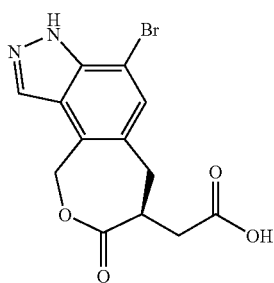

Intermediate 148

(S)-2-(4-bromo-8-oxo-6,7,8,10-tetrahydro-3H-oxepino [3,4-e]indazol-7-yl)acetic acid. (S)-2-((7-Bromo-4-(hydroxymethyl)-1H-indazol-5-yl)methyl)succinic acid (95 mg, 0.266 mmol) was suspended in toluene (15 mL). p-Toluenesulfonic acid monohydrate (3.5 mg, 0.018 mmol) was added to the mixture. Reaction was warmed to reflux and held with stirring for 18 hours. Mixture was concentrated to dryness. Title compound was obtained as tan solid in 99% yield. LCMS (M−H)⁻=339.0, 337.0.

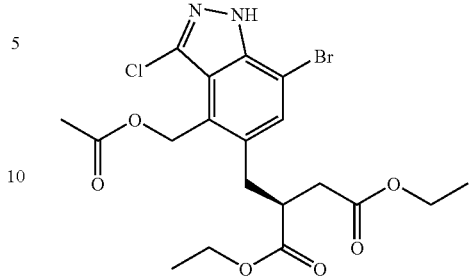

Intermediate 149

(S)-diethyl 2-((4-(acetoxymethyl)-7-bromo-3-chloro-1H-indazol-5-yl)methyl)succinate. (S)-Diethyl 2-((4-(acetoxymethyl)-7-bromo-1H-indazol-5-yl)methyl)succinate (400 mg, 0.879 mmol) was dissolved in N,N-dimethylformamide (5.0 ml). N-Chlorosuccinimide (130 mg, 0.974 mmol) was added to the solution. Mixture was warmed to 150° C. and held with stirring for 1.5 hours. Mixture was cooled to room temperature and then diluted with ethyl acetate. Material was washed twice with water and the aqueous phase was discarded. Material was washed with brine and the aqueous phase was discarded. Organics were dried MgSO4, filtered and then concentrated to dryness. Silica gel chromatography eluting ethyl acetate-hexanes afforded the title compound as clear colorless oil in 88% yield. MS (M+H)⁺=491.0.

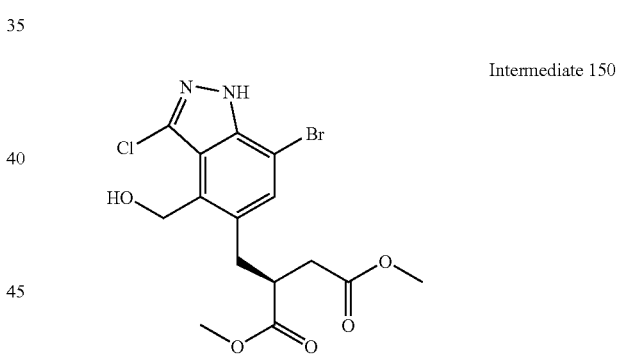

Intermediate 150

(S)-dimethyl 2-((7-bromo-3-chloro-4-(hydroxymethyl)-1H-indazol-5-yl)methyl)succinate. (S)-Diethyl 2-((4-(acetoxymethyl)-7-bromo-3-chloro-1H-indazol-5-yl)methyl) succinate (550 mg, 1.123 mmol) was dissolved in methanol (15 mL, 370 mmol). 6-10% Magnesium methoxide in methanol (3.4 mL, 2.57 mmol) was added to the mixture. Reaction stirred at room temperature for 18 hours. Reaction was quenched with 6 mL of 1N hydrochloric acid. Mixture stirred at room temperature for 10 minutes. Mixture was concentrated by roto-vap. Residue was suspended in water. Mixture was made basic with aqueous sodium bicarbonate. Material was extracted twice and the aqueous phase was discarded. Organics were dried MgSO₄, filtered and then concentrated to dryness. Title compound was obtained as white solid in 96% yield. MS (M−H)⁻=419.0.

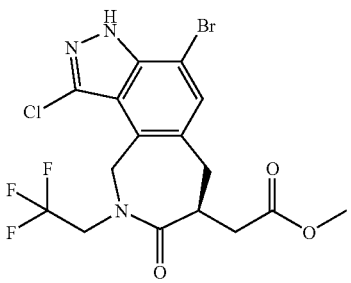

Intermediate 151

(S)-methyl 2-(4-bromo-1-chloro-8-oxo-9-(2,2,2-trifluoroethyl)-3,6,7,8,9,10-hexahydroazepino[3,4-e]indazol-7-yl)acetate. (S)-Dimethyl 2-((7-bromo-3-chloro-4-(hydroxymethyl)-1H-indazol-5-yl)methyl)succinate (450 mg, 1.072 mmol) was dissolved in thionyl chloride (2.0 M in dichloromethane) (5.0 mL, 10.00 mmol). Reaction stirred at room temperature for 2.5 hours. Mixture was concentrated by roto-vap. Residue was dissolved in ethyl acetate. Material was washed twice with aqueous sodium bicarbonate and the aqueous phase was discarded. Organics were dried MgSO$_4$, filtered and then concentrated to dryness. Residue (430 mg, 0.982 mmol) was dissolved in acetonitrile (15 mL). 2,2,2-Trifluoroethylamine (400 µl, 5.03 mmol) was added to the mixture followed by potassium carbonate (195 mg, 1.411 mmol). Mixture was warmed to reflux and held with stirring for 30 minutes. Mixture was cooled to room temperature. Mixture was filtered over celite. Filtrate was concentrated by roto-vap. Residue was dissolved in toluene (15 mL). Acetic acid (500 µl, 8.73 mmol) was added to the mixture. Reaction was warmed to reflux and held with stirring for 14 hours. Mixture was cooled to room temperature. Mixture was diluted with ethyl acetate. Material was washed twice with aqueous sodium bicarbonate and the aqueous phase was discarded. Organics were dried MgSO$_4$, filtered and then concentrated to dryness. Silica gel chromatography eluting ethyl acetate-hexanes afforded the title compound as white solid in 46% yield. MS (M–H)$^-$=467.9.

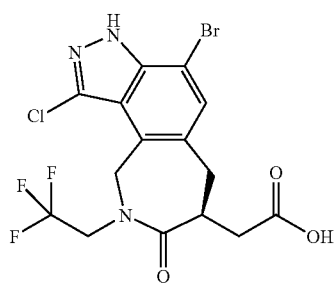

Intermediate 152

(S)-2-(4-bromo-1-chloro-8-oxo-9-(2,2,2-trifluoroethyl)-3,6,7,8,9,10-hexahydroazepino[3,4-e]indazol-7-yl)acetic acid. (S)-Methyl 2-(4-bromo-1-chloro-8-oxo-9-(2,2,2-trifluoroethyl)-3,6,7,8,9,10-hexahydroazepino[3,4-e]indazol-7-yl)acetate (210 mg, 0.448 mmol) was dissolved in a mixture of tetrahydrofuran (3.0 ml) and methanol (3.0 ml). Water (3.00 ml) was added to the mixture followed by lithium hydroxide hydrate (30 mg, 0.715 mmol). Reaction was warmed to 50° C. and held with stirring for 5 hours. Mixture was cooled to room temperature and allowed to stand for 64 hours. More lithium hydroxide hydrate (24.9 mg, 0.593 mmol) was added to the mixture. Reaction was warned to 50° C. and held for 3 hours. Mixture was cooled to room temperature. Organic solvents were removed from the mixture by roto-vap. Residue was diluted with water. Mixture was neutralized with 1.4 mL 1N hydrochloric acid. Material was extracted twice with ethyl acetate and the aqueous phase was discarded. Organics were dried MgSO$_4$, filtered and then concentrated to dryness. Title compound was obtained as off-white solid in quantitative yield. LCMS (M–H)$^-$=453.9.

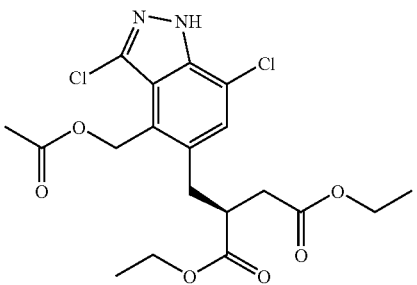

Intermediate 153

(S)-diethyl 2-((4-(acetoxymethyl)-3,7-dichloro-1H-indazol-5-yl)methyl)succinate. (S)-Diethyl 2-((4-(acetoxymethyl)-7-chloro-1H-indazol-5-yl)methyl)succinate (1.12 g, 2.73 mmol) was dissolved in N,N-dimethylformamide (30 ml). Mixture was warmed to 70° C. N-Chlorosuccinimide (400 mg, 3.00 mmol) was added to the solution. Mixture was warmed to 150° C. and held with stirring for 30 minutes. Mixture was cooled to room temperature and then diluted with ethyl acetate. Material was washed twice with 1N sodium thiosulfate and the aqueous phase was discarded. Material was washed successively with water and brine and the aqueous phases were discarded. Organics were dried MgSO$_4$, filtered and then concentrated to dryness. Title compound was obtained as dark amber oil in quantitative yield. MS (M–H)$^-$=443.0.

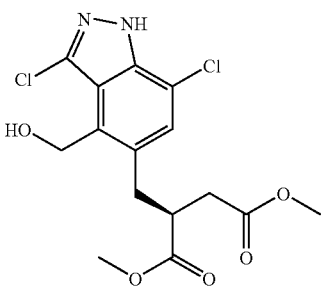

Intermediate 154

(S)-dimethyl 2-((3,7-dichloro-4-(hydroxymethyl)-1H-indazol-5-yl)methyl)succinate. (S)-Diethyl 2-((4-(acetoxymethyl)-3,7-dichloro-1H-indazol-5-yl)methyl)succinate (1.30 g, 2.92 mmol) was dissolved in methanol (45 mL). 6-10% Magnesium methoxide in methanol (8.4 mL, 6.35 mmol) was added to the mixture. Reaction stirred at room temperature for 16 hours. Reaction was quenched with 14 mL 1N hydrochloric acid. Methanol was removed from the mixture by roto-vap. Residue was treated with aqueous sodium bicarbonate. Material was extracted twice with ethyl acetate and the aqueous phase was discarded. The combined organic phases were washed with water and the aqueous phase was discarded.

Organics were dried MgSO₄, filtered and then concentrated to dryness. Title compound was obtained as dark amber oil in 91% yield. MS (M−H)⁻=373.0, 375.0.

Intermediate 155

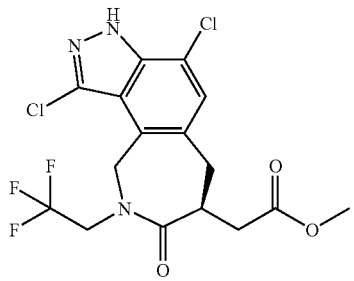

(S)-methyl 2-(1,4-dichloro-8-oxo-9-(2,2,2-trifluoroethyl)-3,6,7,8,9,10-hexahydroazepino[3,4-e]indazol-7-yl)acetate. (S)-Dimethyl 2-((3,7-dichloro-4-(hydroxymethyl)-1H-indazol-5-yl)methyl)succinate (990 mg, 2.64 mmol) was dissolved in thionyl chloride (2.0 M in dichloromethane) (20 mL, 40.0 mmol). Mixture stirred at room temperature for 3 hours. Mixture was concentrated by roto-vap. Residue was dissolved in ethyl acetate. Mixture was washed twice with aqueous sodium bicarbonate. Organics were dried MgSO₄, filtered and then concentrated to dryness. A portion of the residue (535 mg, 1.359 mmol) was dissolved in acetonitrile (15 mL). 2,2,2-Trifluoroethylamine (600 μl, 7.57 mmol) was added to the mixture followed by potassium carbonate (225 mg, 1.628 mmol). Mixture was warmed to reflux and held with stirring for 1 hour. Mixture was cooled to room temperature and then filtered over celite. Filtrate was concentrated by roto-vap. Residue was dissolved in toluene (15 mL). Acetic acid (500 μl, 8.73 mmol) was added to the mixture. Reaction was warmed to reflux and held with stirring for 14 hours. Mixture was cooled to room temperature and then diluted with ethyl acetate. Material was washed twice with aqueous sodium bicarbonate and the aqueous phase was discarded. Organics were dried MgSO₄, filtered and then concentrated to dryness. Silica gel chromatography eluting ethyl acetate-hexanes afforded the title compound as off-white solid in 42% yield. MS (M+H)⁺=423.9, 425.9.

Intermediate 156

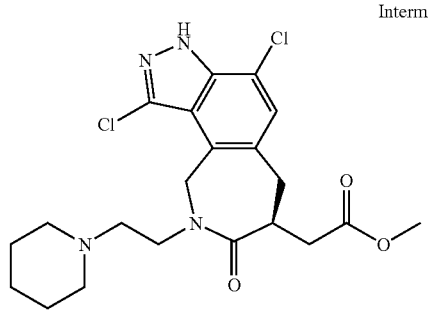

(S)-methyl 2-(1,4-dichloro-8-oxo-9-(2-(piperidin-1-yl)ethyl)-3,6,7,8,9,10-hexahydroazepino[3,4-e]indazol-7-yl)acetate. (S)-Dimethyl 2-((3,7-dichloro-4-(hydroxymethyl)-1H-indazol-5-yl)methyl)succinate (990 mg, 2.64 mmol) was dissolved in thionyl chloride (2.0 M in dichloromethane) (20 mL, 40.0 mmol). Mixture stirred at room temperature for 3 hours. Mixture was concentrated by roto-vap. Residue was dissolved in ethyl acetate. Mixture was washed twice with aqueous sodium bicarbonate. Organics were dried MgSO₄, filtered and then concentrated to dryness. A portion of the residue (460 mg, 1.169 mmol) was dissolved in acetonitrile (15 mL). 1-(2-Aminoethyl)-piperidine (600 μl, 4.21 mmol) was added to the mixture followed by potassium carbonate (200 mg, 1.447 mmol). Mixture was warmed to reflux and held with stirring for 1 hour. Mixture was cooled to room temperature and then filtered over celite. Filtrate was concentrated by roto-vap. Residue was dissolved in toluene (15 mL). Acetic acid (1.0 mL, 17.47 mmol) was added to the mixture. Reaction was warmed to reflux and held with stirring for 16 hours. Mixture was cooled to room temperature and then concentrated by roto-vap. Residue was suspended in ethyl acetate. Mixture was washed twice with aqueous sodium bicarbonate and the aqueous phase was discarded. Organics were dried MgSO₄, filtered and then concentrated to dryness. Silica gel chromatography eluting 2M ammonia in methanol-dichloromethane afforded the title compound as amber oil in 51% yield. (M+H)⁺=453.0, 455.0.

Intermediate 157

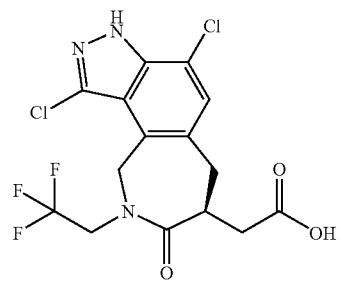

(S)-2-(1,4-dichloro-8-oxo-9-(2,2,2-trifluoroethyl)-3,6,7,8,9,10-hexahydroazepino[3,4-e]indazol-7-yl)acetic acid. (S)-Methyl 2-(1,4-dichloro-8-oxo-9-(2,2,2-trifluoroethyl)-3,6,7,8,9,10-hexahydroazepino[3,4-e]indazol-7-yl)acetate (230 mg, 0.542 mmol) was dissolved in a mixture of tetrahydrofuran (5.0 mL) and methanol (5.0 mL). Water (5.0 mL) was added to the mixture followed by lithium hydroxide hydrate (66 mg, 1.573 mmol). Reaction was warmed to 50° C. and held with stirring for 4.5 hours. Mixture was cooled to room temperature. Organic solvents were removed from the mixture by roto-vap. Residue was neutralized with 1.6 mL 1N hydrochloric acid. Material was extracted twice with ethyl acetate and the aqueous phase was discarded. Organics were dried MgSO₄, filtered and then concentrated to dryness. Title compound was obtained as white solid in 94% yield. MS (M−H)⁻=407.9, 409.9.

Intermediate 158

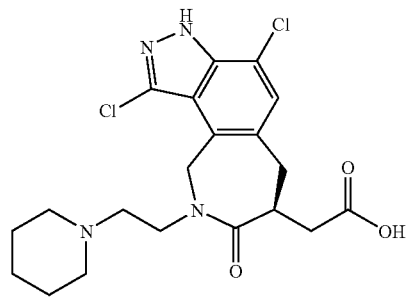

(S)-2-(1,4-dichloro-8-oxo-9-(2-(piperidin-1-yl)ethyl)-3,6,7,8,9,10-hexahydroazepino[3,4-e]indazol-7-yl)acetic acid.

(S)-Methyl 2-(1,4-dichloro-8-oxo-9-(2-(piperidin-1-yl)ethyl)-3,6,7,8,9,10-hexahydroazepino[3,4-e]indazol-7-yl)acetate (260 mg, 0.573 mmol) was dissolved in a mixture of tetrahydrofuran (5.0 mL, 61.6 mmol) and methanol (5.0 mL, 123 mmol). Water (5.0 mL, 278 mmol) was added to the mixture followed by lithium hydroxide hydrate (65 mg, 1.549 mmol). Mixture was warmed to 50° C. and held with stirring for 4.5 hours. Mixture was cooled to room temperature. Organic solvents were removed from the mixture by roto-vap. Residue was neutralized with 1.6 mL 1N hydrochloric acid and treated with ethyl acetate. Mixture sat at room temperature for 20 minutes allowing solids to form. Solids were filtered off and washed with water. Solids were dried in vacuo. Title compound was obtained as white solid in 50% yield. MS (M−H)⁻=437.1, 439.2

Intermediate 159

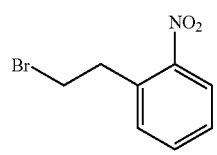

1-(2-bromoethyl)-2-nitrobenzene. Triphenylphosphine (6.60 g, 25.2 mmol) was dissolved in dichloromethane (75 ml). Mixture was cooled to 0° C. 2-Nitrophenethyl alcohol (3.0 ml, 21.36 mmol) was added to the mixture drop-wise. A solution of carbon tetrabromide (8.50 g, 25.6 mmol) in 5 mL dichloromethane was added to the reaction mixture drop-wise. Reaction stirred at 0° C. for 45 minutes. Mixture was concentrated by roto-vap. Residue was treated with 100 mL diethyl ether. Solids were filtered off, washed with diethyl ether and discarded. Filtrate was concentrated. Silica gel chromatography on the residue eluting ethyl acetate-hexanes afforded the title compound as yellow oil in 81% yield. 1H NMR (300 MHz, CHLOROFORM-D) δ ppm 7.97 (d, J=8.05 Hz, 1 H) 7.49-7.68 (m, 1 H) 7.41 (t, J=7.68 Hz, 2 H) 3.66 (t, J=6.77 Hz, 2 H) 3.43 (t, J=7.14 Hz, 2 H).

Intermediate 160

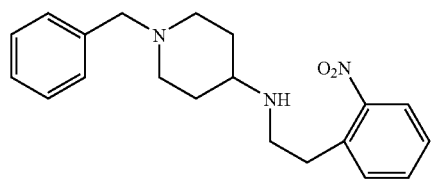

N-(2-nitrophenethyl)-1-benzylpiperidin-4-amine. 1-(2-Bromoethyl)-2-nitrobenzene (1.5 g, 6.52 mmol) and 4-amino-1-benzylpiperidine (3.0 ml, 14.71 mmol) were combined. Mixture was heated neat at 100° C. and held with stirring for 17 hours. Mixture was cooled to room temperature. Residue was triturated in 30 mL diethyl ether. Solids were filtered off, washed with diethyl ether and discarded. Filtrate was concentrated. Silica gel chromatography on the residue eluting 2M ammonia in methanol-dichloromethane afforded the title compound as brown oil in 81% yield. MS (M+H)⁺=340.4.

Intermediate 161

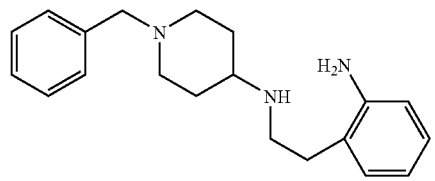

N-(2-aminophenethyl)-1-benzylpiperidin-4-amine. N-(2-Nitrophenethyl)-1-benzylpiperidin-4-amine (1.98 g, 5.83 mmol) was dissolved in methanol (60 mL). Platinum(IV) oxide (55 mg, 0.242 mmol) was added to the mixture. Reaction vessel was placed on a Parr apparatus and charged with 50 psi of hydrogen gas. Reaction shook at room temperature for 75 minutes. Mixture was removed from the apparatus and then filtered over celite. Filtrate was concentrated to dryness. Title compound was obtained as brown oil in quantitative yield. MS (M+H)⁺=310.4.

Intermediate 162

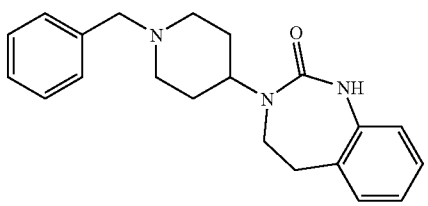

3-(1-benzylpiperidin-4-yl)-4,5-dihydro-1H-benzo[d][1,3]diazepin-2(3H)-one. N-(2-Aminophenethyl)-1-benzylpiperidin-4-amine (1.90 g, 6.14 mmol) was dissolved in acetonitrile (200 ml). N,N'-Carbonyldiimidazole (1.08 g, 6.66 mmol) was added to the mixture. Reaction stirred at room temperature for 1.5 hours. Solids were filtered off and washed with acetonitrile. Solids were dried in vacuo. Title compound was obtained as white solid in 63% yield. MS (M+H)⁺=336.3.

Intermediate 163

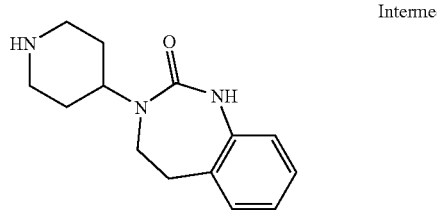

3-(piperidin-4-yl)-4,5-dihydro-1H-benzo[d][1,3]diazepin-2(3H)-one. 3-(1-Benzylpiperidin-4-yl)-4,5-dihydro-1H-benzo[d][1,3]diazepin-2(3H)-one (1.30 g, 3.88 mmol) was dissolved in methanol (50 ml). 10% Palladium on carbon (650 mg) was added to the mixture. Reaction vessel was placed on a Parr apparatus and charged with 60 psi of hydrogen gas. Reaction shook at room temperature for 15 hours. Reaction was removed from the apparatus. Mixture was filtered through a 0.45 μm PVDF membrane. Filtrate was concentrated to dryness. Title compound was obtained as white solid in 82% yield. MS (M+H)⁺=246.4.

Intermediate 164

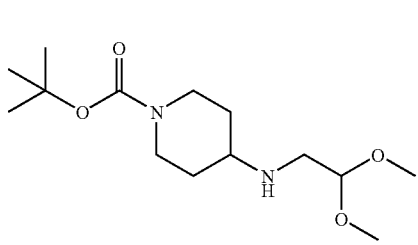

tert-butyl 4-(2,2-dimethoxyethylamino)piperidine-1-carboxylate. tert-Butyl 4-oxopiperidine-1-carboxylate (10.56 g, 53.0 mmol) was dissolved in 1,2-dichloroethane (100 ml). 4 Å Molecular sieves were added to the mixture followed by aminoacetaldehyde dimethyl acetal (8.0 ml, 73.4 mmol). Mixture was heated to reflux and held with stirring for 2 hours. Mixture was cooled to room temperature. Sodium triacetoxyborohydride (12.05 g, 56.9 mmol) was added to the mixture. Reaction stirred at room temperature for 3 hours. Another 3.22 g of sodium triacetoxyborohydride was added to the mixture. Reaction stirred at room temperature for 17 hours. Mixture was filtered over celite. Solids were washed with 50 mL dichloromethane. Material was extracted from the filtrate 3 times with 1N hydrochloric acid and the organic phase was discarded. Aqueous phase was made basic with sodium carbonate. Material was extracted three times with dichloromethane and the aqueous phase was discarded. Organics were dried MgSO$_4$, filtered and then concentrated to dryness. Title compound was obtained as amber oil in 74% yield. MS (M+H)$^+$=289.1.

Intermediate 165

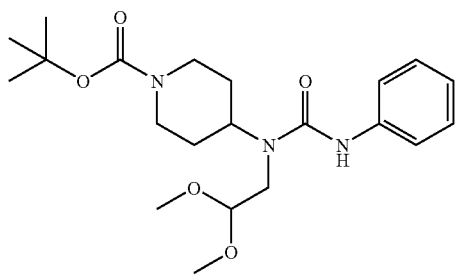

tert-butyl 4-(1-(2,2-dimethoxyethyl)-3-phenylureido)piperidine-1-carboxylate. tert-Butyl 4-(2,2-dimethoxyethylamino)piperidine-1-carboxylate (1.10 g, 3.81 mmol) was dissolved in dichloromethane (15 ml). N,N'-Carbonyldiimidazole (650 mg, 4.01 mmol) was added to the mixture. Reaction stirred at room temperature for 1 hour. Aniline (400 µl, 4.38 mmol) was added to the mixture. Reaction stirred at room temperature for 2 hours. Mixture was washed twice with 1N hydrochloric acid and the aqueous phase was discarded. Mixture was washed with brine and the aqueous phase was discarded. Organics were dried MgSO$_4$, filtered and then concentrated to dryness. Title compound was obtained as white solid in 83% yield. 1H NMR (300 MHz, CHLOROFORM-D) δ ppm 8.36 (s, 1 H) 7.14-7.40 (m, 4 H) 6.96 (t, J=7.14 Hz, 1 H) 4.25-4.45 (m, 2 H) 4.18 (d, J=12.81 Hz, 2 H) 3.46-3.55 (m, 6 H) 3.32 (d, J=5.12 Hz, 2 H) 2.46-2.97 (m, 2 H) 1.61-1.83 (m, 2 H) 1.47-1.64 (m, 2 H), 1.37-1.47 (m, 9 H).

Intermediate 166

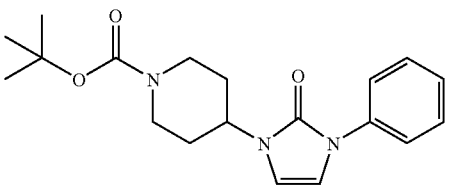

tert-butyl 4-(2-oxo-3-phenyl-2,3-dihydroimidazol-1-yl)piperidine-1-carboxylate. tert-Butyl 4-(1-(2,2-dimethoxyethyl)-3-phenylureido)piperidine-1-carboxylate (1.29 g, 3.17 mmol) was dissolved in a mixture of water (5 ml) and methanesulfonic acid (5 ml, 77 mmol). Reaction was heated to 100° C. and held with stirring for 20 minutes. Mixture was cooled to room temperature. Sodium carbonate (3.75 g, 35.4 mmol) was slowly added to the mixture. Mixture was made basic with aqueous sodium bicarbonate. 1,4-Dioxane (20 ml) was added to the mixture followed by di-tert-butyl dicarbonate (1.0 g, 4.58 mmol). Mixture stirred at room temperature for 18 hours. Reaction was quenched with aqueous ammonium chloride. Material was extracted twice with ethyl acetate and the aqueous phase was discarded. Organics were dried MgSO$_4$, filtered and then concentrated to dryness. Silica gel chromatography eluting ethyl acetate-hexanes afforded the title compound as white solid in 59% yield. MS (M−C$_5$H$_8$O$_2$+H)$^+$=244.2.

Intermediate 167

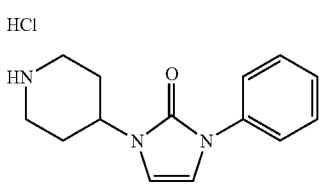

3-phenyl-1-(piperidin-4-yl)-1H-imidazol-2(3H)-one hydrochloride. tert-Butyl 4-(2-oxo-3-phenyl-2,3-dihydroimidazol-1-yl)piperidine-1-carboxylate (290 mg, 844 µmol) was dissolved in ethyl acetate (3.0 mL). 4M Hydrogen chloride in 1,4-dioxane (3.0 mL, 12 mmol) was added to the mixture. Reaction was allowed to stir at room temperature for 18 hours. Material was concentrated by roto-vap. Residue was triturated in diethyl ether. Solids were filtered and washed with diethyl ether. Air was pulled through the filter cake to dry. Title compound was obtained as tan solid in 91% yield. MS (M+H)$^+$=244.1.

Intermediate 168

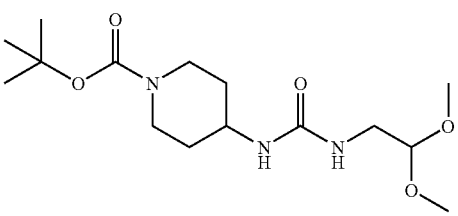

tert-butyl 4-(3-(2,2-dimethoxyethyl)ureido)piperidine-1-carboxylate. 4-Amino-1-Boc-piperidine (1.02 g, 5.09 mmol)

was dissolved in dichloromethane (25 mL). Aqueous sodium bicarbonate solution was added to the mixture followed by 20% phosgene in toluene (3.2 mL, 6.08 mmol). Mixture stirred vigorously at room temperature for 45 minutes. Aminoacetaldehyde dimethyl acetal (760 µl, 6.98 mmol) was added to the mixture. Reaction stirred vigorously at room temperature for 30 minutes. Reaction layers were partitioned. Aqueous layer was back extracted with dichloromethane and the aqueous phase was discarded. Organic phases were combined. Mixture was dried MgSO$_4$, filtered and then concentrated to dryness. Title compound was obtained as pale yellow oil in 96% yield. MS (M−H)$^-$=330.2.

Intermediate 169

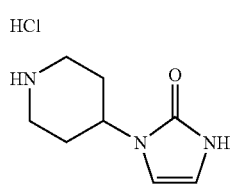

1-(piperidin-4-yl)-1H-imidazol-2(3H)-one hydrochloride. tert-Butyl 4-(3-(2,2-dimethoxyethyl)ureido)piperidine-1-carboxylate (1.62 g, 4.89 mmol) was suspended in water (15 ml). Concentrated hydrochloric acid (15 ml, 183 mmol) was added to the mixture. Reaction was held at room temperature for 20 minutes. Mixture was concentrated by roto-vap. Residue was treated with ethanol and the mixture was then concentrated by roto-vap. Residue was treated with ethyl acetate and then concentrated to dryness. Resulting yellow oil was triturated in 80% acetone-diethyl ether. After 10 minutes a consistent solid was formed. Solids were filtered off and washed with acetone. Solids were dried in vacuo. Title compound was obtained as off-white solid in 99% yield. MS (M+H)$^+$=168.1.

Intermediate 170

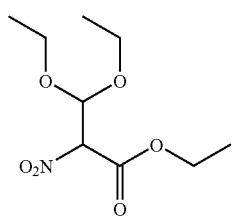

ethyl 3,3-diethoxy-2-nitropropanoate. Ethyl nitroacetate (1.70 ml, 15.31 mmol) was dissolved in dichloromethane (50 ml). Mixture was cooled to −10° C. Titanium(IV) chloride (1.90 ml, 17.23 mmol) was added to the mixture drop-wise. Mixture was held at −10° C. with stirring for 15 minutes. A solution of N,N-diisopropylethylamine (3.0 ml, 17.22 mmol) in 10 mL dichloromethane was added to the mixture drop-wise over 25 minutes. Mixture was held at −10° C. with stirring for 1.25 hours. Triethyl orthoformate (6.4 ml, 38.5 mmol) was added to the mixture drop-wise. Reaction was held at −10° C. with stirring for 2 hours. Reaction mixture was poured into a mixture of 40 mL ethanol and 100 mL aqueous sodium bicarbonate to quench. Mixture was stirred vigorously for 10 minutes. Organic solvents were removed from the mixture by roto-vap. Residue was treated with ethyl acetate and celite. Slurry was filtered over celite. Filtrate layers were separated. Aqueous phase was back extracted twice with ethyl acetate. Organic phases were combined. Material was dried MgSO$_4$, filtered and then concentrated to dryness. Title compound was obtained as yellow oil in 68% yield. 1H NMR (300 MHz, CHLOROFORM-D) δ ppm 5.19-5.26 (m, 1 H) 5.10-5.17 (m, 1 H) 4.26 (q, J=6.95 Hz, 2 H) 3.68-3.85 (m, 2 H) 3.52-3.68 (m, 2 H) 1.28 (t, J=7.14 Hz, 3 H) 1.12-1.21 (m, 6 H).

Intermediate 171

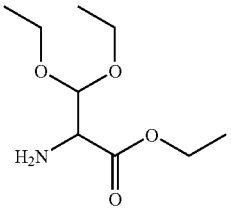

ethyl 2-amino-3,3-diethoxypropanoate. Ethyl 3,3-diethoxy-2-nitropropanoate (2.45 g, 10.42 mmol) was dissolved in Ethanol (70 mL, 1240 mmol). Nitrogen gas was bubbled through the mixture for 5 minutes. Raney® nickel was added to the mixture. Reaction vessel was placed on a Parr apparatus and charged with 13 psi of hydrogen gas. Reaction shook at room temperature for 1 hour. Mixture was removed from the apparatus and filtered over celite. Filter cake was washed with 150 mL ethanol followed by 250 mL hot ethanol. Filtrate was concentrated to dryness. Title compound was obtained as red oil in 92% yield. 1H NMR (300 MHz, CHLOROFORM-D) δ ppm 4.59 (d, J=4.39 Hz, 1 H) 4.05-4.30 (m, 2 H) 3.65-3.81 (m, 2 H) 3.38-3.63 (m, 3 H) 1.87 (s, 2 H) 1.20-1.29 (m, 3 H) 1.12-1.20 (m, 6 H).

Intermediate 172

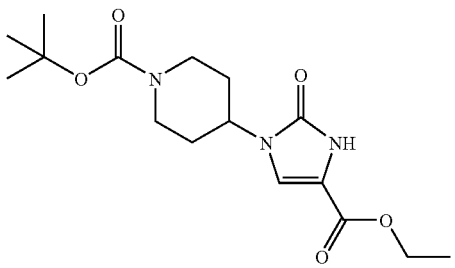

tert-butyl 4-(4-(ethoxycarbonyl)-2-oxo-2,3-dihydroimidazol-1-yl)piperidine-1-carboxylate. 4-Amino-1-Boc-piperidine (1.60 g, 7.99 mmol) was dissolved in a mixture of dichloromethane (30 mL) and aqueous sodium bicarbonate (15 mL). 20% Phosgene in toluene (4.8 mL, 9.12 mmol) was added to the mixture in one portion with vigorous stirring. Reaction stirred vigorously at room temperature for 15 minutes. A solution of ethyl 2-amino-3,3-diethoxypropanoate (1.95 g, 9.50 mmol) in 20 mL dichloromethane was added to the mixture. Reaction stirred vigorously at room temperature for 30 minutes. Reaction layers were partitioned and the aqueous phase was back extracted with dichloromethane. Organic layers were combined. Material was washed twice with 1N hydrochloric acid and the aqueous phase was discarded. Material was washed with brine and the aqueous phase was discarded. Organics were dried MgSO$_4$, filtered and then concentrated to dryness. 2.70 g (6.26 mmol) of the residue was suspended in water (25 ml). Concentrated hydrochloric acid (25 ml, 304 mmol) was added to the mixture.

Reaction was warmed to 80° C. and held with stirring for 5 minutes. Mixture was cooled to room temperature. Reaction mixture was carefully poured into a stirred solution of sodium carbonate (16.19 g, 153 mmol) in 50 mL water. 1,4-Dioxane (50 ml) was added to the mixture followed by di-tert-butyl dicarbonate (1.60 g, 7.33 mmol). Reaction stirred at room temperature for 2 hours. Mixture was extracted twice with ethyl acetate and the aqueous phase was discarded. Organics were dried MgSO$_4$, filtered and then concentrated to dryness. Silica gel chromatography eluting ethyl acetate-hexanes afforded the title compound as tan foam in 19% yield. MS (M−H)$^-$=338.2.

Intermediate 173

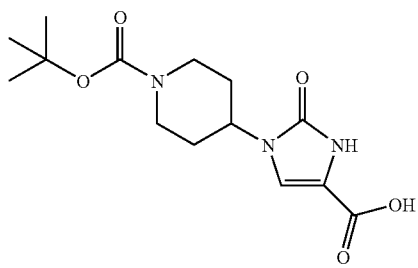

1-(1-(tert-butoxycarbonyl)piperidin-4-yl)-2-oxo-2,3-dihydro-1H-imidazole-4-carboxylicacid. tert-Butyl 4-(4-(ethoxycarbonyl)-2-oxo-2,3-dihydroimidazol-1-yl)piperidine-1-carboxylate (400 mg, 1.179 mmol) was dissolved in tetrahydrofuran (10 mL). Water (10 mL) was added to the mixture followed by lithium hydroxide hydrate (180 mg, 4.29 mmol). Mixture was warmed to 70° C. and held with stirring for 16 hours. Mixture was cooled to room temperature. Reaction was quenched with 4.5 mL 1N hydrochloric acid. Material was extracted twice with ethyl acetate. Organics were dried MgSO$_4$, filtered and then concentrated to dryness. Title compound was obtained as white solid in 98% yield. MS (M−H)$^-$=310.2.

Intermediate 174

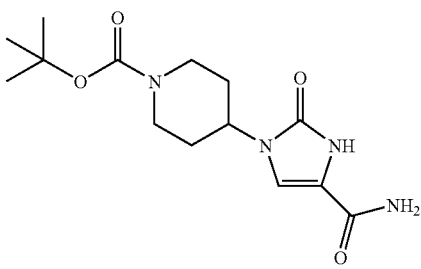

tert-butyl 4-(4-carbamoyl-2-oxo-2,3-dihydroimidazol-1-yl)piperidine-1-carboxylate. 1-(1-(tert-Butoxycarbonyl)piperidin-4-yl)-2-oxo-2,3-dihydro-1H-imidazole-4-carboxylic acid (355 mg, 1.140 mmol) was dissolved in a mixture of tetrahydrofuran (20 mL,) and N,N-dimethylformamide (15 μL, 0.194 mmol). Mixture was cooled to −10° C. Oxalyl chloride (150 μL, 1.714 mmol) was added to the mixture drop-wise. Reaction mixture was warmed to room temperature and held with stirring for 1 hour. Another 60 μL of oxalyl chloride was added to the mixture. Reaction stirred at room temperature for 30 minutes. Mixture was cooled to −10° C. Ammonia gas was bubbled through the mixture for 5 minutes. Reaction was held at −10° C. with stirring for 30 minutes. Mixture was warmed to room temperature and then diluted with water. Material was extracted three times with ethyl acetate and the aqueous phase was discarded. Material was washed with brine and the aqueous phase was discarded. Organics were dried MgSO$_4$, filtered and then concentrated to dryness. Title compound was obtained as off-white solid in 79% yield. MS (M−H)$^-$=309.2.

Intermediate 175

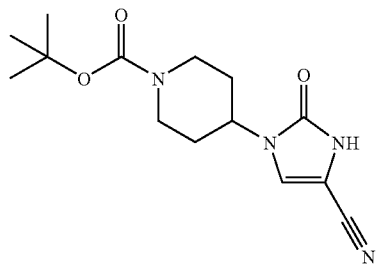

tert-butyl 4-(4-cyano-2-oxo-2,3-dihydroimidazol-1-yl)piperidine-1-carboxylate. tert-Butyl 4-(4-carbamoyl-2-oxo-2,3-dihydroimidazol-1-yl)piperidine-1-carboxylate (175 mg, 0.564 mmol) was suspended in pyridine (3.0 mL). Phosphorus oxychloride (53 μL, 0.569 mmol) was added to the mixture drop-wise. Mixture stirred at ambient temperature for 30 minutes. Reaction was quenched with the drop-wise addition of water. Material was extracted twice with ethyl acetate and the aqueous phase was discarded. Material was washed successively with 1N hydrochloric acid brine and the aqueous phases were discarded. Organics were dried MgSO$_4$, filtered and then concentrated to dryness. Silica gel chromatography eluting ethyl acetate-hexanes afforded the title compound as white solid in 29% yield. MS (M−H)$^-$=291.1.

Intermediate 176

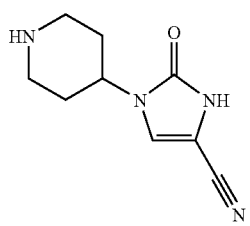

2-oxo-1-(piperidin-4-yl)-2,3-dihydro-1H-imidazole-4-carbonitrile hydrochloride. tert-Butyl 4-(4-cyano-2-oxo-2,3-dihydroimidazol-1-yl)piperidine-1-carboxylate (45 mg, 0.154 mmol) was dissolved in ethyl acetate (5.0 mL). 4M Hydrogen chloride in 1,4-dioxane (10 mL, 40 mmol) was added to the mixture. Reaction was stirred at room temperature for 18 hours. Liquids were decanted off. Remaining solids were dissolved in methanol and then transferred to a smaller flask. Material was concentrated by roto-vap. Residue was treated with dichloromethane and then concentrated to dryness. Title compound was obtained as yellow solid in quantitative yield. MS (M+H)$^+$=193.0.

Intermediate 177

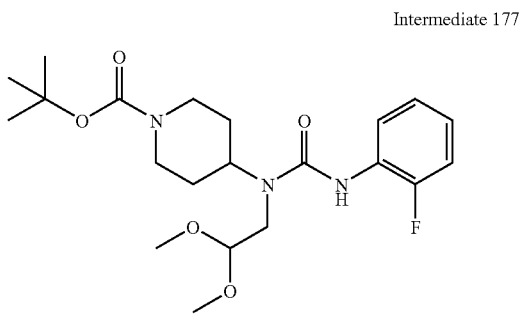

tert-butyl 4-(1-(2,2-dimethoxyethyl)-3-(2-fluorophenyl)ureido)piperidine-1-carboxylate. 20% Phosgene in toluene (4.0 ml, 7.6 mmol) was diluted with ethyl acetate (20 ml, 205 mmol). 2-Fluoroaniline (0.600 ml, 6.2 mmol) was added to the mixture in one portion causing a white precipitate. Mixture was heated to reflux and held with stirring for 1 hour. Mixture was concentrated by roto-vap. Residue was dissolved in a small amount of dichloromethane. Resulting solution was added to a mixture of tert-butyl 4-(2,2-dimethoxyethylamino)piperidine-1-carboxylate (1.99 g, 6.9 mmol), dichloromethane (30 mL) and aqueous sodium bicarbonate (15 mL) while stirring vigorously. Reaction stirred at room temperature for 2 hours. Layers were separated and the aqueous phase was discarded. Material was washed twice with 1N hydrochloric acid and the aqueous phase was discarded. Organics were dried MgSO$_4$, filtered and then concentrated to dryness. Title compound was obtained as yellow oil in 53% yield. MS (M–H)$^-$=424.1.

Intermediate 178

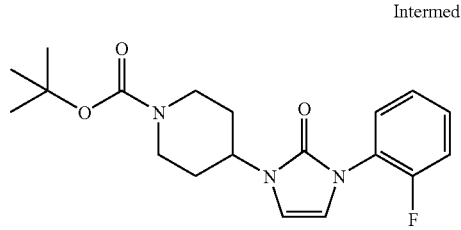

tert-butyl 4-(3-(2-fluorophenyl)-2-oxo-2,3-dihydroimidazol-1-yl)piperidine-1-carboxylate. tert-Butyl 4-(1-(2,2-dimethoxyethyl)-3-(2-fluorophenyl)ureido)piperidine-1-carboxylate (1.39 g, 3267 μmol) was dissolved in a mixture of water (8.0 ml) and methanesulfonic acid (8.0 ml, 123281 μmol). Mixture was heated to 100° C. and held for 15 minutes. Mixture was cooled to room temperature. Reaction was neutralized with sodium carbonate (6.15 g, 58025 μmol). Mixture was diluted with aqueous sodium bicarbonate. 1,4-Dioxane (10 ml) was added to the mixture followed by di-tert-butyl dicarbonate (880 mg, 4032 μmol). Reaction stirred vigorously at room temperature for 3 hours. Reaction was quenched with aqueous ammonium chloride. Material was extracted twice with ethyl acetate and the aqueous phase was discarded. Organics were dried MgSO$_4$, filtered and then concentrated to dryness. Silica gel chromatography eluting ethyl acetate-hexanes afforded the title compound as clear colorless oil in 64% yield. MS (M–C$_4$H$_{10}$O+H)$^-$=288.1.

Intermediate 179

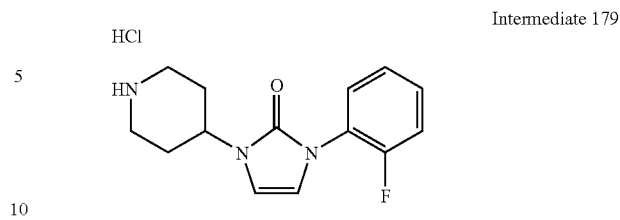

3-(2-fluorophenyl)-1-(piperidin-4-yl)-1H-imidazol-2(3H)-one hydrochloride. tert-Butyl 4-(3-(2-fluorophenyl)-2-oxo-2,3-dihydroimidazol-1-yl)piperidine-1-carboxylate (215 mg, 594.9 μmol) was dissolved in ethyl acetate (4.0 mL). 4N Hydrogen chloride in 1,4-dioxane (5.0 mL, 20.0 mmol) was added to the mixture. Reaction stirred at room temperature for 18 hours. The material was concentrated by roto-vap. Residue was triturated in diethyl ether. Solids were filtered off and washed with diethyl ether. Solids were collected and dried in vacuo. Title compound was obtained as tan solid in 46% yield. MS (M+H)$^+$=262.0.

Intermediate 180

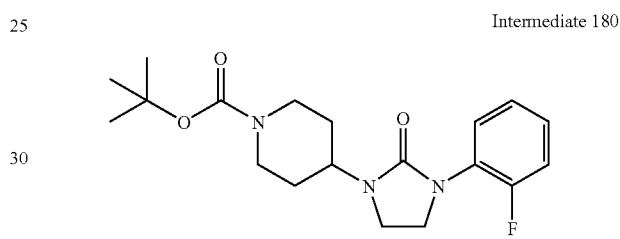

tert-butyl 4-(3-(2-fluorophenyl)-2-oxoimidazolidin-1-yl)piperidine-1-carboxylate. tert-Butyl 4-(3-(2-fluorophenyl)-2-oxo-2,3-dihydroimidazol-1-yl)piperidine-1-carboxylate (530 mg, 1.5 mmol) was dissolved in methanol (25 mL). Platinum(IV) oxide (28 mg, 123.3 Emoles) was added to the mixture. Reaction vessel was placed on a Parr apparatus and charged with 60 psi of hydrogen gas. Reaction shook at room temperature for 4 hours. More platinum(IV) oxide (28 mg, 123.3 μmol) was added to the mixture. Reaction vessel was placed on a Parr apparatus and charged with 60 psi of hydrogen gas. Reaction shook at room temperature for 18 hours. Mixture was removed from the apparatus and then filtered over celite. The filtrate was concentrated by roto-vap. Silica gel chromatography eluting ethyl acetate-hexanes afforded the title compound as clear colorless oil in 45% yield. MS (M–C$_4$H$_{10}$O+H)$^+$=290.0.

Intermediate 181

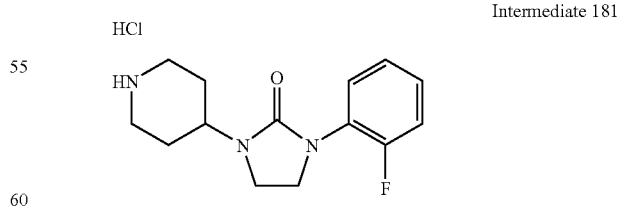

1-(2-fluorophenyl)-3-(piperidin-4-yl)imidazolidin-2-one hydrochloride. tert-Butyl 4-(3-(2-fluorophenyl)-2-oxoimidazolidin-1-yl)piperidine-1-carboxylate (235 mg, 0.647 mmol) was dissolved in ethyl acetate (3.0 mL). 2N Hydrogen chloride in diethyl ether (5.0 mL, 10.00 mmol) was added to the mixture. Reaction stirred at room temperature for 22 hours.

Solids were filtered off, washed with diethyl ether and then dried in vacuo. Title compound was obtained as white solid in 52% yield. MS (M+H)$^+$=264.1.

Intermediate 182

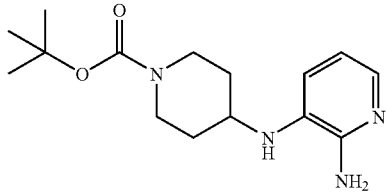

tert-butyl 4-(2-aminopyridin-3-ylamino)piperidine-1-carboxylate. tert-Butyl 4-oxopiperidine-1-carboxylate (9.59 g, 48.1 mmol) and pyridine-2,3-diamine (5.0 g, 45.8 mmol) were combined and dissolved in 1,2-dichloroethane (75 ml). Sodium triacetoxyborohydride (14.5 g, 68.4 mmol) was added to the mixture. Reaction stirred at room temperature for 7 hours. Additional sodium triacetoxyborohydride (3.60 g, 16.99 mmol) was added to the mixture. Reaction stirred at room temperature for 18 hours. Reaction was quenched with 1N sodium hydroxide. Material was extracted twice with dichloromethane and the aqueous phase was discarded. Material was washed successively with 1N sodium hydroxide, water, and brine and the aqueous phases were discarded. Organics were dried MgSO$_4$, filtered and then concentrated to dryness. Silica gel chromatography eluting methanol-dichloromethane afforded the title compound as tan foam in 48% yield. MS (M−H)$^-$=291.2.

Intermediate 183

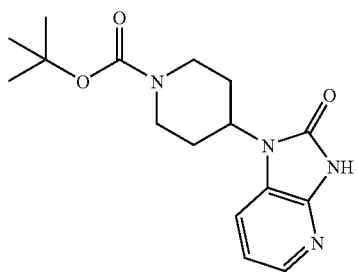

tert-butyl 4-(2-oxo-2,3-dihydroimidazo[4,5-b]pyridin-1-yl)piperidine-1-carboxylate. tert-Butyl 4-(2-aminopyridin-3-ylamino)piperidine-1-carboxylate (6.45 g, 22.06 mmol) was dissolved in acetonitrile (750 ml). N,N'-Carbonyldiimidazole (4.2 g, 25.9 mmol) was added to the mixture. Reaction stirred at room temperature for 23 hours. Additional N,N'-carbonyldiimidazole (4.2 g, 25.9 mmol) was added to the mixture. Reaction stirred at room temperature over 66 hours. Material was concentrated by roto-vap. Residue was dissolved in dichloromethane. Material was washed twice with water and the aqueous phase was discarded. Material was washed with brine and the aqueous phase was discarded. Organics were dried MgSO$_4$, filtered and then concentrated to dryness. Silica gel chromatography eluting ethyl acetate-hexanes afforded the title compound as white foam in 85% yield. MS (M−H)$^-$=317.2.

Intermediate 184

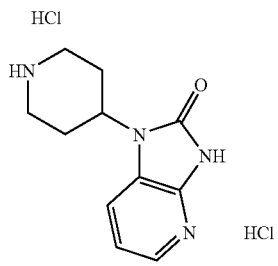

1-(piperidin-4-yl)-1H-imidazo[4,5-b]pyridin-2(3H)-one dihydrochloride. tert-Butyl 4-(2-oxo-2,3-dihydroimidazo[4,5-b]pyridin-1-yl)piperidine-1-carboxylate (5.97 g, 18.75 mmol) was dissolved in methanol (180 ml). 4M Hydrogen chloride in 1,4-dioxane (50 ml, 200 mmol) was added to the mixture. Reaction stirred at room temperature for 18 hours. Solids were filtered off and washed with methanol. Solids were collected and dried in vacuo. Title compound was obtained as white solid in 87% yield. MS (M+H)$^+$=219.1.

Intermediate 185

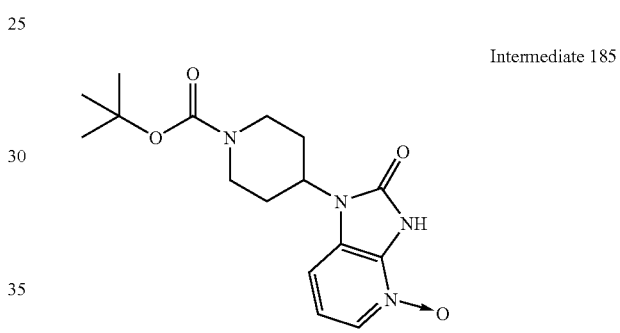

4-(4-oxy-2-oxo-2,3-dihydro-imidazo[4,5-b]pyridin-1-yl)-piperidine-1-carboxylic acid tert-butyl ester. tert-Butyl 4-(2-oxo-2,3-dihydroimidazo[4,5-b]pyridin-1-yl)piperidine-1-carboxylate (1.0 g, 3.14 mmol) was dissolved in 1,2-dichloroethane (50 ml). Mixture was cooled to 0° C. 3-Chloroperoxybenzoic acid (1.67 g, 9.68 mmol) was added to the mixture in one portion. Ice bath was removed and the mixture was warmed to room temperature. Reaction stirred at room temperature for 4 hours. Reaction was quenched with 1N sodium thiosulfate. Aqueous sodium bicarbonate was added to the mixture. Material was extracted three times with dichloromethane and the aqueous phase was discarded. Organics were dried MgSO$_4$, filtered and then concentrated to dryness. Title compound was obtained as white solid in 70% yield. MS (M−H)$^-$=333.3.

Intermediate 186

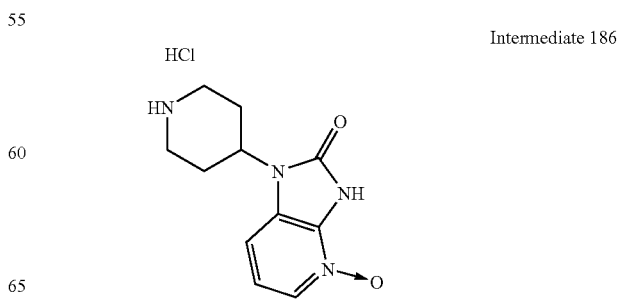

4-Oxy-1-piperidin-4-yl-1,3-dihydro-imidazo[4,5-b]pyridin-2-one hydrochloride. 4-(4-Oxy-2-oxo-2,3-dihydro-imidazo[4,5-b]pyridin-1-yl)-piperidine-1-carboxylic acid tert-butyl ester (730 mg, 2.183 mmol) was dissolved in a mixture of methanol (30 mL) and 4M hydrogen chloride in 1,4-dioxane (15 mL, 60.0 mmol). Reaction stirred at room temperature for 18 hours. Mixture was concentrated by roto-vap. Residue was triturated in 25 mL hot isopropanol. Mixture was allowed to cool to room temperature. Solids were filtered off and washed successively with isopropyl alcohol and diethyl ether. Solids were dried in vacuo. Title compound was obtained as white solid in 77% yield. MS (M+H)$^+$=235.3.

Intermediate 187

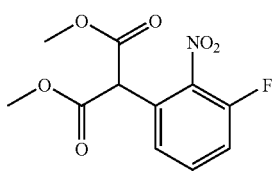

dimethyl 2-(3-fluoro-2-nitrophenyl)malonate. 1,3-Difluoro-2-nitrobenzene (2.83 g, 17.79 mmol) was dissolved in N,N-dimethylformamide (25 mL). Potassium carbonate (2.49 g, 18.02 mmol) was added to the mixture followed by dimethyl malonate (2.033 ml, 17.79 mmol). Mixture was warmed to 65° C. and held for 24 hours. Mixture was cooled to room temperature. Reaction was quenched with 1N hydrochloric acid. Material was extracted three times with diethyl ether and the aqueous phase was discarded. Material was washed twice with water and the aqueous phase was discarded. Material was washed with brine and the aqueous phase was discarded. Organics were dried MgSO$_4$, filtered and then concentrated to dryness. Residue was crystallized with hexanes. Solids were filtered off and washed with hexanes. Title compound was obtained as yellow crystals in 52% yield. MS (M−H)$^-$=270.1.

Intermediate 188

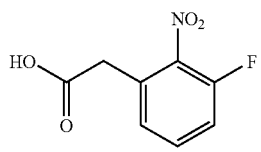

2-(3-fluoro-2-nitrophenyl)acetic acid. Dimethyl 2-(3-fluoro-2-nitrophenyl)malonate (2.53 g, 9.33 mmol) was suspended in water (20 mL). Concentrated hydrochloric acid (20 ml, 653 mmol) was added to the mixture. Reaction was heated to reflux and held with stirring for 5 hours. Mixture was cooled to room temperature. Material was extracted twice with diethyl ether and the aqueous phase was discarded. Organics were dried MgSO$_4$, filtered and then concentrated to dryness. Residue was crystallized from 5:1 hexanes:ethyl acetate. Solids were filtered off, washed with hexanes and then dried in vacuo. Title compound was obtained as white solid in 90% yield. 1H NMR (300 MHz, CHLOROFORM-D) δ ppm 3.85 (s, 2 H) 7.08-7.19 (m, 1 H) 7.20-7.28 (m, 1 H) 7.38-7.55 (m, 1 H).

Intermediate 189

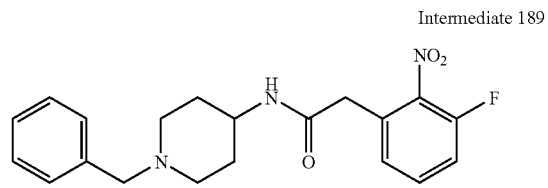

N-(1-benzylpiperidin-4-yl)-2-(3-fluoro-2-nitrophenyl)acetamide. 2-(3-Fluoro-2-nitrophenyl)acetic acid (1.17 g, 5.88 mmol) was dissolved in tetrahydrofuran (50 ml). N,N'-Carbonyldiimidazole (1.06 g, 6.54 mmol) was added to the mixture in one portion. Reaction stirred at room temperature for 30 minutes. 1-Benzylpiperidin-4-amine (1.15 ml, 6.09 mmol) was added to the mixture in one portion. Reaction stirred at room temperature for 1.25 hours. Reaction was quenched with water. Material was extracted twice with diethyl ether and the aqueous phase was discarded. Material was washed once with water and once with brine and the aqueous phases were discarded. Organics were dried MgSO$_4$, filtered and then concentrated to dryness. Title compound was obtained as amber oil in 99% yield. MS (M+H)$^+$=372.4.

Intermediate 190

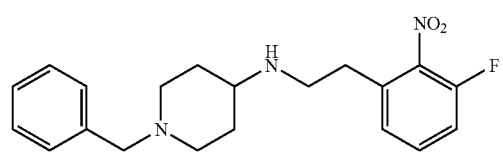

N-(3-fluoro-2-nitrophenethyl)-1-benzylpiperidin-4-amine. N-(1-Benzylpiperidin-4-yl)-2-(3-fluoro-2-nitrophenyl)acetamide (2.19 g, 5.90 mmol) was dissolved in tetrahydrofuran (40 ml). Mixture was warmed to 60° C. Chlorotrimethylsilane (2.7 ml, 21.27 mmol) was added to the mixture followed by lithium borohydride (7.2 ml, 14.40 mmol). Mixture was held at 60° C. for 2 hours with stirring. Reaction was quenched with 2 mL methanol. Water (4.0 ml, 222 mmol) was added to the mixture followed by concentrated hydrochloric acid (4.0 ml, 47.4 mmol). Mixture was warmed to reflux and held with stirring for 3 hours. Mixture was cooled to room temperature. Reaction was made basic with 5 mL 10N sodium hydroxide. Mixture stirred at room temperature for 15 minutes. Reaction layers were partitioned and the aqueous phase was discarded. Organic phase was concentrated by roto-vap. Silica gel chromatography eluting 2M ammonia in methanol-dichloromethane afforded the title compound as grey oil in 38% yield. MS (M+H)$^+$=358.4.

Intermediate 191

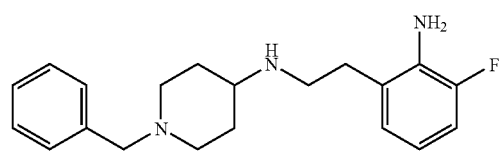

N-(2-amino-3-fluorophenethyl)-1-benzylpiperidin-4-amine. N-(3-Fluoro-2-nitrophenethyl)-1-benzylpiperidin-4-amine (800 mg, 2.238 mmol) was dissolved in methanol (30 mL). Platinum(IV) oxide (18.5 mg, 0.081 mmol) was added to the mixture. Reaction vessel was placed on a Parr apparatus and charged with 60 psi of hydrogen gas. Reaction shook at room temperature for 1 hour 20 minutes. Reaction was removed from the apparatus. Mixture was filtered through a 0.45 μm PVDF membrane. Filtrate was concentrated to dryness. Title compound was obtained as grey oil in 97% yield. MS (M+H)$^+$=328.5.

Intermediate 192

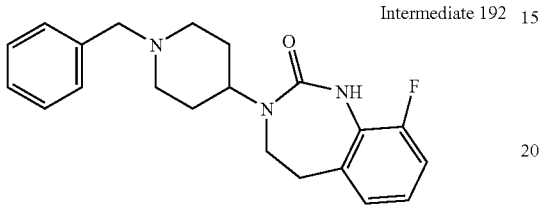

3-(1-benzylpiperidin-4-yl)-9-fluoro-4,5-dihydro-1H-benzo[d][1,3]diazepin-2(3H)-one. N-(2-Amino-3-fluorophenethyl)-1-benzylpiperidin-4-amine (700 mg, 2.138 mmol) was dissolved in acetonitrile (50 mL). N,N'-Carbonyldiimidazole (380 mg, 2.344 mmol) was added to the mixture in one portion. Reaction stirred at room temperature for 1 hour. Another 50 mg of N,N'-carbonyldiimidazole was added to the mixture. Reaction stirred at room temperature for 30 minutes. Reaction was concentrated by roto-vap. Residue was dissolved in dichloromethane. Mixture was washed twice with water and the aqueous phase was discarded. Organics were dried MgSO$_4$, filtered and then concentrated to dryness. Residue was dissolved in tetrahydrofuran. A few drops of concentrated aqueous hydrochloric acid were added to the mixture. Solids were triturated, filtered and then washed with tetrahydrofuran. Air was pulled through the filter cake for 15 minutes. Solids were dissolved in water. Mixture was made basic with 1N sodium hydroxide. Material was extracted twice with dichloromethane and the aqueous phase was discarded. Organics were dried MgSO$_4$, filtered and then concentrated to dryness. Title compound was obtained as purplish foam in 72% yield. MS (M+H)$^+$=354.4.

Intermediate 193

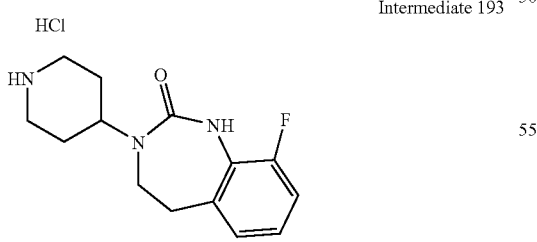

9-fluoro-3-(piperidin-4-yl)-4,5-dihydro-1H-benzo[d][1,3]diazepin-2(3H)-one hydrochloride. 3-(1-Benzylpiperidin-4-yl)-9-fluoro-4,5-dihydro-1H-benzo[d][1,3]diazepin-2(3H)-one (530 mg, 1.500 mmol) was suspended in 1,2-dichloroethane (10 mL). Mixture was cooled to 0° C. 1-Chloroethyl chloroformate (175 μl, 1.603 mmol) was added to the mixture drop-wise. Reaction was then warmed to reflux and held for 45 minutes. Mixture was concentrated by roto-vap. Residue was dissolved in methanol (10 mL). Reaction was warmed to reflux and held with stirring for 3 hours. Mixture was concentrated by roto-vap. Residue was treated with 20 mL acetone and warmed to reflux for 20 minutes. Resulting solids were filtered off and washed with acetone. Title compound was obtained as tan solid in 67% yield. MS (M+H)$^+$=264.4.

Intermediate 194

2-nitro-3-vinylpyridine. 3-Bromo-2-nitropyridine (1.015 g, 5.0 mmol), tetrabutylammonium chloride (1.390 g, 5.00 mmol), and bis(triphenylphosphine)palladium(II) chloride (0.351 g, 0.500 mmol) were combined. Mixture was suspended in acetonitrile (10 ml). The mixture was stirred at room temperature for 30 minutes while it was degassed by a flow of nitrogen. Tributyl(vinyl)tin (1.754 ml, 6.00 mmol) was added and the mixture was further degassed for 5 minutes. The vial was capped and heated at 90° C. for 4 hours. Solvents were removed from the mixture. The residue was dissolved with dichloromethane. Material was washed with brine and the aqueous phase was discarded. Organic layer was dried over Na$_2$SO$_4$, and filtered. Solvents were removed by roto-vap. Silica gel chromatography afforded the title compound as tan solid in 68% yield. 1H NMR (500 MHz, CHLOROFORM-D) δ ppm 8.39 (dd, J=4.58, 1.53 Hz, 1 H) 8.06 (dd, J=7.94, 1.53 Hz, 1 H) 7.55 (dd, J=7.93, 4.58 Hz, 1 H) 6.90 (dd, J=17.24, 11.14 Hz, 1 H) 5.82 (d, J=17.40 Hz, 1 H) 5.55 (d, J=10.99 Hz, 1 H).

Intermediate 195

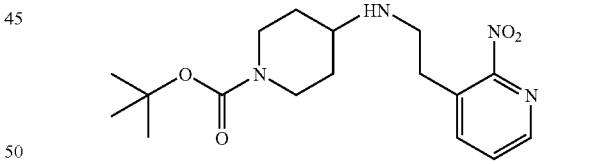

tert-butyl 4-(2-(2-nitropyridin-3-yl)ethylamino)piperidine-1-carboxylate. 2-Nitro-3-vinylpyridine (0.300 g, 2 mmol), tert-butyl 4-aminopiperidine-1-carboxylate (0.601 g, 3.00 mmol), and ethanol (5 ml) were combined. Triethylamine (0.836 ml, 6.00 mmol) was added. The vial was capped and heated at 90° C. for 62 hours. More tert-butyl 4-aminopiperidine-1-carboxylate (0.601 g, 3.00 mmol), and triethylamine (0.836 ml, 6.00 mmol) were added and the mixture was heated at 90° C. for 20 hours. Mixture was concentrated by roto-vap. Silica gel chromatography eluting ethyl acetate-hexanes afforded the title compound as tan solid in 48% yield. 1H NMR (500 MHz, CHLOROFORM-D) δ ppm 8.38 (dd, J=4.58, 1.53 Hz, 1 H) 7.84 (dd, J=7.63, 1.53 Hz, 1 H) 7.49 (dd, J=7.63, 4.58 Hz, 1 H) 3.92 (s, 2 H)

2.85-2.98 (m, 3 H) 2.75 (t, J=11.75 Hz, 2 H) 2.50-2.62 (m, 1 H) 1.75 (d, J=12.51 Hz, 2 H) 1.40 (s, 9 H) 1.00-1.27 (m, 4 H).

Intermediate 196

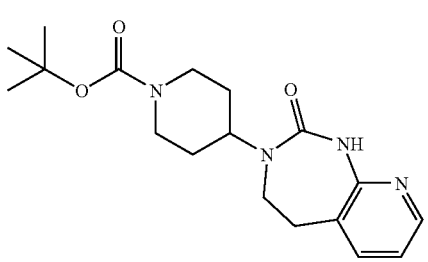

tert-butyl 4-(2-oxo-1,2,4,5-tetrahydropyrido[2,3-d][1,3]diazepin-3-yl)piperidine-1-carboxylate. tert-Butyl 4-(2-(2-nitropyridin-3-yl)ethylamino)piperidine-1-carboxylate (0.561 g, 1.601 mmol) was dissolved in methanol (60 mL). A catalytic amount of 10% palladium on carbon was added to the mixture. Reaction vessel was charged with 2 atm hydrogen gas. Reaction shook at room temperature for 16 hours. The reaction mixture was filtered through a pad of celite twice. Filtrate was concentrated in vacuo. Residue was dissolved in acetonitrile (100 mL). Triethylamine (0.672 ml, 4.82 mmol) was added to the mixture followed by N,N'-carbonyldiimidazole (0.32 g, 1.97 mmol. 1.2 equiv). After 1.5 hours more N,N'-carbonyldiimidazole (0.32 g, 1.97 mmol, 1.2 equiv) was added. Reaction stirred at room temperature for 16 hours. Additional N,N'-carbonyldiimidazole (0.32 g, 1.97 mmol) and triethylamine (0.672 ml, 4.82 mmol) were added and the clear solution was stirred at room temperature for 20 hours. Additional N,N'-carbonyldiimidazole (0.32 g, 1.97 mmol) and triethylamine (350 µL, 251 mmol) were added to the reaction mixture. The clear solution was stirred at room temperature for 68 hours. All solvents were removed by roto-vap. Silica gel chromatography eluting 2M ammonia in methanol-dichloromethane afforded the title compound as off white solid in 92% yield. 1H NMR (500 MHz, CHLOROFORM-D) δ ppm 8.20 (d, J=4.88 Hz, 1 H) 7.92 (s, 1 H) 7.33 (d, J=7.63 Hz, 1 H) 6.82 (dd, J=7.48, 4.73 Hz, 1 H) 4.35-4.50 (m, 1 H) 4.19 (bs, 2 H) 3.37-3.48 (m, 2 H) 2.87-2.92 (m, 2 H) 2.71-2.83 (m, 2 H) 1.72 (d, J=10.38 Hz, 2 H) 1.50-1.63 (m, 2 H) 1.44 (s, 9 H).

Intermediate 197

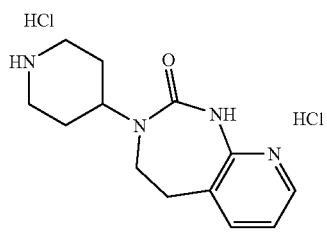

3-(piperidin-4-yl)-4,5-dihydro-1H-pyrido[2,3-d][1,3]diazepin-2(3H)-one dihydrochloride. tert-Butyl 4-(2-oxo-4,5-dihydro-1H-pyrido[2,3-d][1,3]diazepin-3(2H)-yl)piperidine-1-carboxylate (0.51 g, 1.472 mmol) was dissolved in dichloromethane (8 ml). Trifluoroacetic acid (2 ml, 26.0 mmol) was added to the solution. The mixture was stirred at room temperature for 4 hours. All volatiles were removed by roto-vap. Residue was dissolved in dichloromethane (10 mL). 2M Hydrogen chloride in diethyl ether (2.58 ml, 5.15 mmol) was added to the mixture. The mixture was stirred at room temperature for 15 minutes and then all volatiles were removed. The resulting off-white solid was washed with anhydrous diethyl ether four times to afford the title compound as white solid in 99% yield. 1H NMR (500 MHz, D₂O) δ ppm 8.01-8.29 (m, 2 H) 7.38 (t, J=6.71 Hz, 1 H) 4.63-4.88 (m, 2 H) 4.29-4.53 (m, 1 H) 3.61-3.71 (m, 2 H) 3.45-3.62 (m, 2 H) 3.01-3.27 (m, 4 H) 1.93-2.21 (m, 4 H).

Intermediate 198

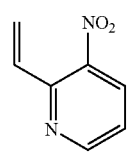

3-nitro-2-vinylpyridine. To an oven dried 20 mL of vial, was added 2-chloro-3-nitropyridine (0.793 g, 5 mmol), tetrabutylammonium chloride (1.390 g, 5.00 mmol), and bis(triphenylphosphine) palladium(II) chloride (0.351 g, 0.500 mmol). After addition of acetonitrile (10 ml) the resulting mixture was stirred at room temperature for 30 min while it was degassed by a flow of nitrogen through a needle inserted to the bottom of the vial. Tributyl(vinyl)tin (1.754 ml, 6.00 mmol) was added and the mixture was further degassed for 5 minutes. Vial was capped and heated at 90° C. for 2 hours. All solvents were removed. The residue was dissolved in dichloromethane and washed with brine. Organic layer was dried over Na₂SO₄, and filtered. Solvents were removed by roto-vap. Silica gel chromatography eluting ethyl acetate-hexanes afforded the title compound as dark brown oil in 67% yield. 1H NMR (500 MHz, CHLOROFORM-D) δ ppm 8.77 (dd, J=4.58, 1.53 Hz, 1 H) 8.18 (dd, J=8.24, 1.53 Hz, 1 H) 7.06-7.57 (m, 2 H) 6.63 (dd, J=16.79, 1.83 Hz, 1 H) 5.74 (dd, J=10.68, 1.83 Hz, 1 H).

Intermediate 199

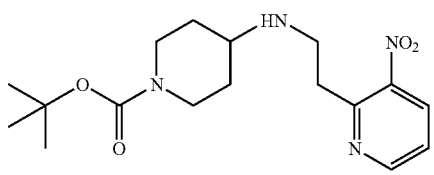

tert-butyl 4-(2-(3-nitropyridin-2-yl)ethylamino)piperidine-1-carboxylate. To an oven dried 10 mL of a vial, was added 3-nitro-2-vinylpyridine (0.300 g, 2 mmol), 4-amino-1-Boc-piperidine (0.601 g, 3.00 mmol), and ethanol (5 ml). Triethylamine (0.843 ml, 6.00 mmol) was added and the vial was capped and heated at 90° C. for 24 hours. Solvents were removed from the mixture by roto-vap. Silica gel chromatography eluting 2M ammonia in methanol-dichloromethane afforded the title compound in 74% yield. 1H NMR (500 MHz, CHLOROFORM-D) δ ppm 8.73 (dd, J=4.58, 1.53 Hz, 1 H) 8.19 (dd, J=8.24, 1.22 Hz, 1 H) 7.33 (dd, J=8.24, 4.58 Hz, 1 H) 3.95 (bs, 2 H) 3.30 (t, J=6.87 Hz, 2 H) 3.10 (t, J=6.71 Hz, 2 H) 2.78 (t, J=11.60 Hz, 2 H) 2.56-2.69 (m, 1 H) 1.76-1.84 (m, 2 H) 1.42 (s, 9 H) 1.13-1.27 (m, 2 H).

Intermediate 200

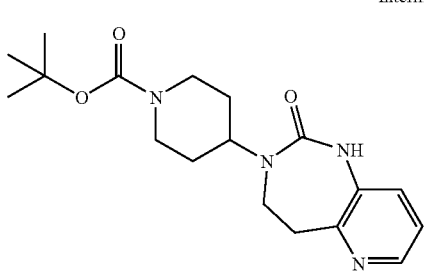

tert-butyl 4-(2-oxo-1,2,4,5-tetrahydropyrido[3,2-d][1,3]diazepin-3-yl)piperidine-1-carboxylate. tert-Butyl 4-(2-(3-nitropyridin-2-yl)ethylamino)piperidine-1-carboxylate (0.864 g, 2.466 mmol) was dissolved in methanol (50 ml). 10% Palladium on carbon (0.3 g, 0.28 mmol) was added to the mixture. Reaction vessel was placed on a Parr apparatus and charged with 2 atm hydrogen gas. Reaction shook at room temperature for 16 hours. The reaction mixture was twice filtered through a pad of celite. Filtrate was concentrated to yield tan solid. Residue (808 mg, 2.52 mmol) was dissolved in acetonitrile (200 mL). Triethylamine was added to the mixture (1.05 mL, 7.56 mmol) followed by N,N'-carbonyldiimidazole (0.50 g, 3.08 mmol). Reaction stirred at room temperature for 5 hours. More N,N'-carbonyldiimidazole (0.50 g, 3.08 mmol) was added to the mixture. Reaction stirred at room temperature for 16 hours. More N,N'-carbonyldiimidazole (0.50 g, 3.08 mmol) was added to the reaction mixture followed by triethylamine (1.05 mL, 7.56 mmol). Reaction stirred at room temperature for 20 hours. More N,N'-carbonyldiimidazole (0.50 g, 3.08 mmol) was added to the mixture followed by triethylamine (0.50 mL, 3.58 mmol). Reaction stirred at room temperature for 68 hours. Mixture was concentrated by roto-vap. Silica gel chromatography eluting 2M ammonia in methanol-dichloromethane afforded the title compound as off-white solid in 93% yield. 1H NMR (500 MHz, CHLOROFORM-D) δ ppm 8.05-8.13 (m, 2 H) 7.21 (d, J=7.94 Hz, 1 H) 7.01 (dd, J=8.24, 4.58 Hz, 1 H) 4.29-4.44 (m, 1 H) 4.19 (bs, 2 H) 3.44-3.51 (m, 2 H) 3.08-3.17 (m, 2 H) 2.76 (m, 2 H) 1.71 (d, J=10.99 Hz, 2 H) 1.53-1.65 (m, 2 H) 1.42 (s, 9 H).

Intermediate 201

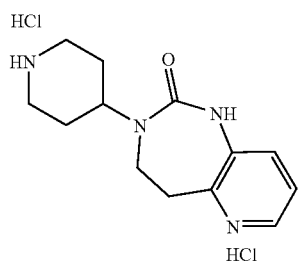

3-(piperidin-4-yl)-4,5-dihydro-1H-pyrido[3,2-d][1,3]diazepin-2(3H)-one dihydrochloride. tert-Butyl 4-(2-oxo-4,5-dihydro-1H-pyrido[3,2-d][1,3]diazepin-3(2H)-yl)piperidine-1-carboxylate (0.814 g, 2.350 mmol) was dissolved in dichloromethane (8.0 ml). Trifluoroacetic acid (2.0 ml, 26.0 mmol) was added to the mixture at room temperature. The mixture was stirred at room temperature for 4 hours. All volatiles were removed and the residue was dissolved in dichloromethane (10 mL). 2M Hydrogen chloride in diethyl ether (4.11 ml, 8.22 mmol) was added to the mixture. The reaction was stirred at room temperature for 15 minutes and all volatiles were removed. The resulting off-white solid was washed 4 times with anhydrous diethyl ether. Title compound was obtained as white solid in 88% yield. 1H NMR (500 MHz, D₂O) δ ppm 8.28 (d, J=4.88 Hz, 1 H) 8.05 (d, J=8.24 Hz, 1 H) 7.74-7.82 (m, 1 H) 4.30-4.41 (m, 1 H) 3.71-3.78 (m, 2 H) 3.51-3.62 (m, 2 H) 3.34-3.41 (m, 2 H) 3.09-3.20 (m, 2 H) 1.98-2.14 (m, 4 H).

Intermediate 202

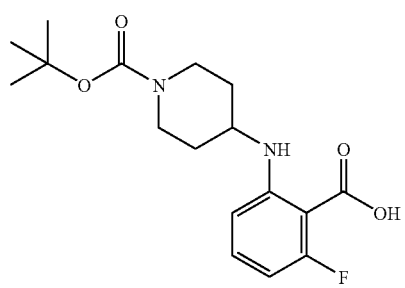

2-(1-(tert-butoxycarbonyl)piperidin-4-ylamino)-6-fluorobenzoic acid. 2-Amino-6-fluorobenzoic acid (2.01 g, 12.93 mmol) and tert-butyl 4-oxopiperidine-1-carboxylate (5.15 g, 25.9 mmol) were combined and dissolved in methanol (50 mL). Sodium cyanotrihydroborate (1.625 g, 25.9 mmol) was added in one portion at room temperature. Reaction stirred at room temperature for 1 hour. The solvent was removed in vacuo. The resulting foam was partitioned between dichloromethane (170 mL) and 1N sodium hydroxide (65 mL). Layers were separated. The dichloromethane layer was extracted with water (2×65 mL). The aqueous layers were combined and acidified with citric acid to pH around 3. The aqueous layer was extracted with ethyl acetate (3×100 mL). The ethyl acetate layers were combined, dried (Na₂SO₄), filtered and concentrated to dryness. Title compound was obtained as off-white solid in 92% yield. 1H NMR (400 MHz, MeOD) δ ppm 7.18-7.28 (m, 1 H) 6.57 (d, J=8.56 Hz, 1 H) 6.27 (dd, J=11.58, 8.06 Hz, 1 H) 3.83-3.95 (m, 2 H) 3.56-3.67 (m, 1 H) 3.00-3.15 (m, 2 H) 1.93-2.04 (m, 2 H) 1.44 (s, 9 H) 1.31-1.43 (m, 2 H).

Intermediate 203

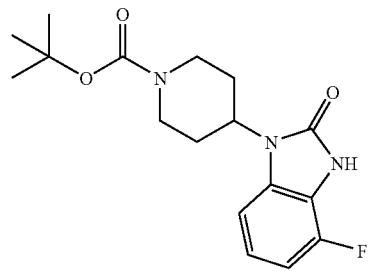

tert-butyl 4-(4-fluoro-2-oxo-2,3-dihydro-1H-benzo[d]imidazol-1-yl)piperidine-1-carboxylate. 2-(1-(tert-Butoxycarbonyl)piperidin-4-ylamino)-6-fluorobenzoic acid (1.081 g, 3.19 mmol) and triethylamine (0.534 ml, 3.83 mmol) were combined and suspended in toluene (20 mL). Diphenyl azidophosphate (0.826 ml, 3.83 mmol) was added to the mixture. Reaction stirred at room temperature for 35 minutes. The reaction was heated to 80° C. for 1 hour. Solvent was removed in vacuo. Silica gel chromatography eluting ethyl acetate-hexanes afforded the title compound as white solid in 97% yield. 1H NMR (500 MHz, CHLOROFORM-D) δ ppm 9.64 (s, 1 H) 6.94-7.02 (m, 1 H) 6.91 (d, J=8.24 Hz, 1 H) 6.82 (t, J=9.15 Hz, 1 H) 4.42-4.54 (m, 1 H) 4.31 (d, J=10.07 Hz, 2 H) 2.86 (t, J=12.67 Hz, 2 H) 2.21-2.35 (m, 2 H) 1.78-1.87 (m, 2 H) 1.49 (s, 9 H).

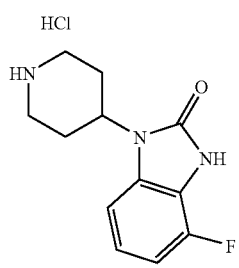

Intermediate 204

4-fluoro-1-(piperidin-4-yl)-1H-benzo[d]imidazol-2(3H)-one hydrochloride. tert-Butyl 4-(4-fluoro-2-oxo-2,3-dihydro-1H-benzo[d]imidazol-1-yl)piperidine-1-carboxylate (1.03 g, 3.07 mmol) was dissolved in dichloromethane (30 ml). 4N Hydrogen chloride in 1,4-dioxane (8 ml, 32 mmol) was added to the reaction at room temperature. The reaction stirred at room temperature for 5 hours. The solvent was removed in vacuo. Title compound was obtained as white solid in quantitative yield. 1H NMR (400 MHz, MeOD) δ ppm 7.14 (d, J=8.81 Hz, 1 H) 7.00-7.10 (m, 1 H) 6.80-6.92 (m, 1 H) 4.48-4.63 (m, 1 H) 3.52-3.60 (m, 2 H) 3.16-3.26 (m, 2 H) 2.64-2.82 (m, 2 H) 2.04 (dd, J=12.46, 1.89 Hz, 2 H).

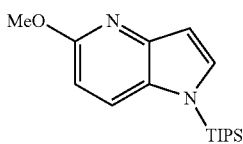

Intermediate 205

5-methoxy-1-(triisopropylsilyl)-1H-pyrrolo[3,2-b]pyridine. To a solution of 5-methoxy-1H-pyrrolo[3,2-b]pyridine (4.0 g, 27.0 mmol) in THF (50 mL) was added NaH (60%, 1.30 g, 32.4 mmol) in small portions at 0° C. over 10 min. The resulting mixture was stirred under $N_2$ for 1 hr, followed by dropwise addition of TIPS-Cl (6.86 mL, 32.4 mmol) in neat through an syringe at 0° C. over 2 min, and stirred for additional 1 hr. The reaction was quenched with sat. $NH_4Cl$ (50 mL), extracted with $Et_2O$ (500 mL). The extract was washed with brine (50 mL), dried ($MgSO_4$), concentrated on rotary vacuo, and the residue was purified on Biotage Flash Collector eluting with 20-75% EtOAc/Hexanes (1600 mL) to afford the expected product, 5-methoxy-1-(triisopropylsilyl)-1H-pyrrolo[3,2-b]pyridine (8.25 g, 100%). $^1$H NMR (400 MHz, CHLOROFORM-D) δ ppm 1.11 (d, J=7.55 Hz, 19 H) 1.57-1.67 (m, J=7.55, 7.55, 7.55, 7.55 Hz, 3 H) 3.98 (s, 3 H) 6.54 (d, J=9.06 Hz, 1 H) 6.67 (d, J=3.02 Hz, 1 H) 7.35 (d, J=3.27 Hz, 1 H) 7.65 (d, J=9.06 Hz, 1 H); Mass spec 305.1 (MH+) calc. for $C_{17}H_{28}N_2O$ Si 304.2.

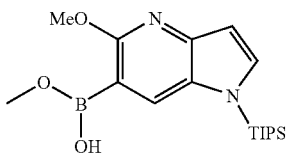

Intermediate 206 methyl hydrogen 5-methoxy-1-(triisopropylsilyl)-1H-pyrrolo[3,2-b]pyridin-6-ylboronate. To a colorless solution of 5-methoxy-1-(triisopropylsilyl)-1H-pyrrolo[3,2-b]pyridine (5.01 g, 16.45 mmol) in THF (100 mL) was dropwise added 2nd-BuLi (21.15 mL, 29.6 mmol) at −78° C. under $N_2$ over 5 min to give an orange solution, the mixture was stirred for 30 min, followed by dropwise addition of trimethyl borate (3.31 mL, 29.6 mmol) through a syringe over 1 min. The resulting light orange solution was stirred at −78° C. for 1 hr, quenched with sat. $NH_4Cl$ (30 mL), partitioned between $H_2O/Et_2O$ (100 mL/150 mL). After seperation, the organic layer was washed with brine (50 mL), dried on $MgSO_4$, concentrated on rotary vacuo and purified on Biotage Flash Collector eluting with 10~50% EtOAc/Hexanes (1300 mL) to afford the expected produce methyl hydrogen 5-methoxy-1-(triisopropylsilyl)-1H-pyrrolo[3,2-b]pyridin-6-ylboronate (2.5 g, 42%), as a colorless thick gum. Mass spec. 363.24 (MH+) calc. for $C_{18}H_{31}BN_2O_3$ Si 362.22.

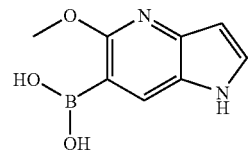

Intermediate 207

5-methoxy-1H-pyrrolo[3,2-b]pyridin-6-ylboronic acid. To a solution of methyl hydrogen 5-methoxy-1-(triisopropylsilyl)-1H-pyrrolo [3,2-b]pyridin-6-ylboronate (1.5 g, 4.14 mmol) (from 65236-015) in THF (10 mL) was treated with HCl (4M in 1,4-dioxane) for 1 hr at 0° C., checked with LC/MS: ~50% conversion, thus additional 1.3 ml HCl (4M in 1,4-dioxane) was added, stirred at rt over night. Most of the solvent was removed on rotary vacuo, and the residue as a white solid was triturated with $Et_2O$ (3 ml), filtration and washing with $Et_2O$ (2×3 mL) to afford the expected product, 5-methoxy-1H-pyrrolo[3,2-b]pyridin-6-ylboronic acid (0.78 g, 98%) as a white solid. $^1$H-NMR (500 MHz, MeOD) δ ppm 1.04-1.12 (m, 1 H) 1.18 (d, J=7.32 Hz, 1 H) 4.28-4.33 (m, 4 H) 6.74 (d, J=2.44 Hz, 1 H) 7.89 (d, J=3.05 Hz, 1 H) 8.42 (s, 1 H); Mass spec 193.20 Calc for $C_8H_9BN_2O_3$ 192.07.

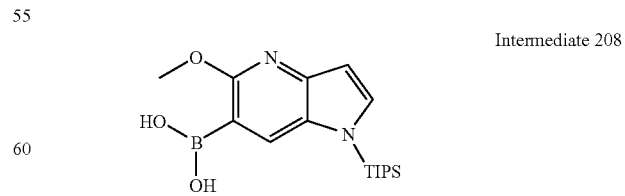

Intermediate 208

5-methoxy-1-(triisopropylsilyl)-1H-pyrrolo[3,2-b]pyridin-6-ylboronic acid. To a white suspension of 5-methoxy-1H-pyrrolo[3,2-b]pyridin-6-ylboronic acid (500 mg, 2.60 mmol) in tetrahydrofuran (25 mL) was added sodium hydride (281 mg, 11.72 mmol) in several portions at 0° C., the resulting light grey suspension was stirred for 30 min, followed by dropwise addition of chlorotriisopropylsilane (2260 mg, 11.72 mmol) through a syringe over 30 sec. under N₂. The mixture, as a suspension, was continued stirring at 0° C. for 2 hr, and the conversion was completed as determined by LC/MS. The reaction was carefully quenched with sat. NH₄Cl (10 mL), extracted with Et₂O (2×50 mL), the combined organic solution was washed with brine (20 mL), dried (Na₂SO₄), concentrated on rotary vacuo to afford the expected product, 5-methoxy-1-(triisopropylsilyl)-1H-pyrrolo[3,2-b]pyridin-6-ylboronic acid (900 mg, 99%), as a grey gum. ¹H-NMR (500 MHz, CHLOROFORM-D) s ppm 1.11 (d, J=7.63 Hz, 21 H) 1.62-1.72 (m, 3 H) 4.03-4.10 (m, 2 H) 6.67 (d, J=3.36 Hz, 1 H) 7.31 (s, 1 H) 7.43 (d, J=3.05 Hz, 1 H); Mass spec 349.21 (MH+) Calc for $C_{17}H_{29}BN_2O_3Si$ 348.2.

Intermediate 209

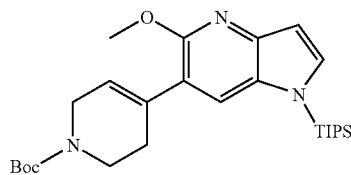

tert-butyl 4-(5-methoxy-1-(triisopropylsilyl)-1H-pyrrolo[3,2-b]pyridin-6-yl)-5,6-dihydropyridine-1(2H)-carboxylate. To 5-methoxy-1-(triisopropylsilyl)-1H-pyrrolo[3,2-b]pyridin-6-ylboronic acid (900 mg, 2.58 mmol) was added sodium carbonate (548 mg, 5.17 mmol), lithium chloride (219 mg, 5.17 mmol), tert-butyl 4-(trifluoromethylsulfonyloxy)-5,6-dihydropyridine-1(2H)-carboxylate (856 mg, 2.58 mmol) and deairared 1,4-dioxane (15 mL) at rt temperature, followed by tetrakis(triphenylphosphine)palladium(0) (149 mg, 0.1297 mol), and H₂O (1 mL). The resulting light brown mixture was stirred at 80° C. for 2 hr, and the conversion was completed as determined by LC/MS. After cooling down to rt, the mixture was partitioned between H₂O/EtOAc (50 mL/100 mL). After separation, the organic phase was washed with brine, dried (Na₂SO₄), concentrated on rotary vacuo, and purified on Biotage Flash Collector eluting with 30-80% EtOAc/Hexanes (1200 mL) to afford the expected product, tert-butyl 4-(5-methoxy-1-(triisopropylsilyl)-1H-pyrrolo[3,2-b]pyridin-6-yl)-5,6-dihydropyridine-1(2H)-carboxylate (998 mg, 80%) as a white solid. ¹H-NMR (400 MHz, MeOD) δ ppm 1.12 (s, 18 H) 1.49 (s, 9 H) 2.52 (s, 2 H) 3.47 (s, 3 H) 3.62 (s, 2 H) 4.00 (s, 3 H) 4.09 (s, 2 H) 5.78 (s, 1 H) 6.65 (s, 1 H) 7.33 (s, 1 H) 7.51 (s, 1 H). Mass spec 486.28 (MH+) Calc for $C_{27}H_{43}N_3O_3Si$ 485.31.

Intermediate 210

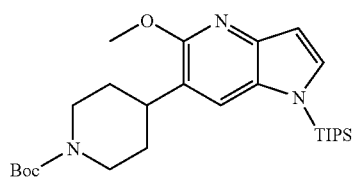

tert-butyl 4-(5-methoxy-1-(triisopropylsilyl)-1H-pyrrolo[3,2-b]pyridin-6-yl)piperidine-1-carboxylate. To colorless solution of tert-butyl 4-(5-methoxy-1-(triisopropylsilyl)-1H-pyrrolo[3,2-b]pyridin-6-yl)-5,6-dihydropyridine-1(2H)-carboxylate (998 mg, 2.055 mmol) in MeOH (30 mL) was added platinum(IV) oxide (98 mg, 0.432 mmol) at rt. The mixture was shaked on Par Shaker for 3 hr under H₂ (55 psi). The mixture was filtered with MeOH (20 mL), concentrated on rotary vacuo to afford the expected product, tert-butyl 4-(5-methoxy-1-(triisopropylsilyl)-1H-pyrrolo[3,2-b]pyridin-6-yl)piperidine-1-carboxylate (995 mg, 100%) as a light grey solid. Mass spec 488.27 Calc for $C_{27}H_{45}N_3O_3Si$ 487.32, which was pure enough to be used in next reaction.

Intermediate 211

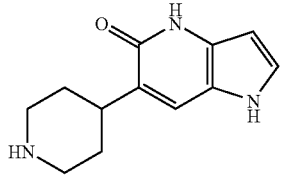

6-(piperidin-4-yl)-1H-pyrrolo[3,2-b]pyridin-5(4H)-one. To tert-butyl 4-(5-methoxy-1-(triisopropylsilyl)-1H-pyrrolo[3,2-b]pyridin-6-yl)piperidine-1-carboxylate (130 mg, 0.267 mmol) in CH₂Cl₂ (3 mL) was added TMS-I (163 μl, 1.20 mmol) at rt. The resulting brown solution was stirred at 60° C. over night. Partial of the solvent was removed on rotary vacuo, the residue was purified on reverse phase PrepHPLC to afford the expected product, 6-(piperidin-4-yl)-1H-pyrrolo[3,2-b]pyridin-5(4H)-one (49.3 mg, 85%). ¹H-NMR (400 MHz, MeOD) δ ppm 1.85 (dd, J=12.84, 3.53 Hz, 2 H) 2.12 (d, J=14.10 Hz, 3 H) 3.06-3.18 (m, 4 H) 3.42-3.52 (m, 3 H) 6.14 (t, J=2.14 Hz, 1 H) 7.20 (dt, J=2.96, 1.42 Hz, 1 H) 7.62 (s, 1 H); Mass spec 218.14 (MH+), Calc for $C_{12}H_{15}N_3O$ 217.12.

Intermediate 212

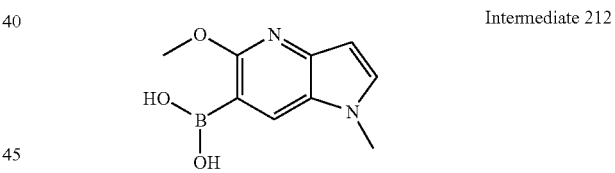

5-methoxy-1-methyl-1H-pyrrolo[3,2-b]pyridin-6-ylboronic acid. To a white suspension of 5-methoxy-1H-pyrrolo[3,2-b]pyridin-6-ylboronic acid (500 mg, 2.60 mmol) in tetrahydrofuran (25 mL) was added sodium hydride (281 mg, 11.72 mmol) in several portions at 0° C., the resulting light grey suspension was stirred for 30 min, followed by dropwise addition of iodomethane (1664 mg, 11.72 mmol) in syringe. The mixture was continued stirring at 0° C. for 2 hr and the reaction was quenched with conc. HCl at 0° C. to ~pH 6, MeOH (20 mL) was added, stirred for 2 min, the resulting suspension was passed through a thin layer silica gel with 10 mL MeOH. The collected solution was concentrated on rotary vacuo, and purified on PrepHPLC to afford the expected product, 5-methoxy-1-methyl-1H-pyrrolo[3,2-b]pyridin-6-ylboronic acid (398 mg, 74%) as a grey gum. ¹H-NMR (500 MHz, MeOD) δ ppm 3.33 (ddd, J=3.20, 1.83, 1.68 Hz, 3 H) 4.24 (s, 3 H) 6.62 (d, J=2.44 Hz, 1 H) 7.71 (d, J=3.36 Hz, 1 H) 8.39 (s, 1 H); Mass spec 207.16 (MH+) Calc for $C_9H_{11}BN_2O_3$ 206.09.

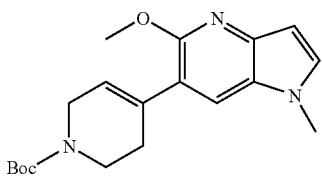

Intermediate 213 tert-butyl 4-(5-methoxy-1-methyl-1H-pyrrolo[3,2-b]pyridin-6-yl)-5,6-dihydropyridine-1(2H)-carboxylate. To 5-methoxy-1-methyl-1H-pyrrolo[3,2-b]pyridin-6-ylboronic acid (398 mg, 1.932 mmol) was added sodium carbonate (410 mg, 3.86 mmol), lithium chloride (164 mg, 3.86 mmol), tert-butyl 4-(trifluoromethylsulfonyloxy)-5,6-dihydropyridine-1(2H)-carboxylate (640 mg, 1.932 mmol) and deairared 1,4-Dioxane (15 mL) at rt temperature, followed by tetrakis(triphenylphosphine)pladdinum (0) (112 mg, 0.097 mol), and $H_2O$ (1 mL). The resulting light brown mixture was stirred at 80° C. for 2 hr. After cooling down to rt, the mixture was partitioned between $H_2O$/EtOAc (30 mL/50 mL), and separated. The organic layer was washed with brine (10 mL), dried ($Na_2SO_4$), concentrated on rotary vacuo, purified on Biotage Flash Collector eluting with 30~80% EtOAc/Hexanes (1200 mL) to afford the expected product, tert-butyl 4-(5-methoxy-1-methyl-1H-pyrrolo[3,2-b]pyridin-6-yl)-5,6-dihydropyridine-1(2H)-carboxylate (207 mg, 32%). $^1$H-NMR (400 MHz, MeOD) δ ppm 1.44-1.51 (m, 9 H) 2.51 (d, J=1.51 Hz, 2 H) 3.59 (s, 2 H) 3.78 (s, 3 H) 3.93 (s, 3 H) 4.04 (s, 2 H) 4.86 (s, 1 H) 5.82 (s, 1 H) 6.39 (d, J=2.52 Hz, 1 H) 7.27 (d, J=3.27 Hz, 1 H) 7.58 (s, 1 H); Mass spec 344.18 (MH+) Calc for $C_{19}H_{25}N_3O_3$ 343.19.

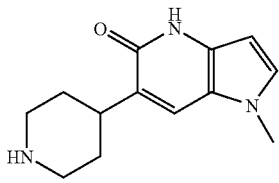

Intermediate 214

1-methyl-6-(piperidin-4-yl)-1H-pyrrolo[3,2-b]pyridin-5(4H)-one. To tert-butyl 4-(5-methoxy-1-methyl-1H-pyrrolo[3,2-b]pyridin-6-yl)piperidine-1-carboxylate (104 mg, 0.301 mmol) in $CH_2Cl_2$ (3 mL) was added TMS-I (123 µl, 0.903 mmol) at rt. The resulting brown solution was stirred at 60° C. over night. Partial of the solvent was removed on rotary vacuo, the residue was purified on reverse phase PrepHPLC to afford the expected product, 1-methyl-6-(piperidin-4-yl)-1H-pyrrolo[3,2-b]pyridin-5(4H)-one (65 mg, 94%). $^1$H-NMR (400 MHz, MeOD) δ ppm 2.05 (s, 3 H) 2.13 (s, 3 H) 3.20 (s, 4 H) 3.55 (s, 3 H) 6.25 (s, 1 H) 7.35 (s, 1 H) 8.01 (s, 1 H); Mass spec 232.19 Calc for $C_{13}H_{17}N_3O$ 231.14.

Intermediate 215

6-chloro-1-(triisopropylsilyl)-1H-pyrrolo[2,3-b]pyridine. To 6-chloro-1H-pyrrolo[2,3-b]pyridine (1.00 g, 6.55 mmol) in THF (1 mL) was added NaH (60%, 0.315 g, 7.86 mmoL) at 0° C. in several portions. The resulting mixture was stirred for 1 hr, followed by addition of triisopropylsilyl chloride (1.67 mL, 7.86 mmol) in neat at 0° C. The mixture was continued stirring at 0° C. under $N_2$ for 2 hr, quenched with $H_2O$ (40 mL), and extracted with $Et_2O$ (100 mL). After separation, the organic phase was washed with brine (30 mL), dried ($MgSO_4$), concentrated on rotary vacuo, and purified on Biotage Flash Collector eluting with 15~30% EtOAc/Hexanes (600 mL) to afford the expected product, 6-chloro-1-(triisopropylsilyl)-1H-pyrrolo[2,3-b]pyridine (1.51 g, 75%). $^1$H-NMR (400 MHz, CHLOROFORM-D) δ ppm 1.09-1.13 (m, 18 H) 1.80 (dt, J=14.92, 7.52 Hz, 3 H) 6.52 (d, J=3.53 Hz, 1 H) 7.02 (d, J=8.06 Hz, 1 H) 7.25 (d, J=3.53 Hz, 1 H) 7.77 (d, J=8.31 Hz, 1 H); Mass spec 309.19 Calc for $C_{16}H_{25}ClN_2Si$ 308.15.

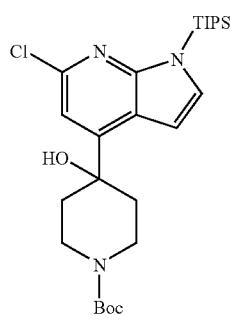

Intermediate 216 tert-butyl 4-(6-chloro-1-(triisopropylsilyl)-1H-pyrrolo[2,3-b]pyridin-4-yl)-4-hydroxypiperidine-1-carboxylate. To a colorless solution of 6-chloro-1-(triisopropylsilyl)-1H-pyrrolo[2,3-b]pyridine (500 mg, 1.63 mmol) in THF (16 mL) was dropwise added sec-BuLi at –78° C. under $N_2$ over 6 min, and the resulting tan solution was stirred for 2 hr. Tert-butyl 4-oxopiperidine-1-carboxylate (1.13 g, 5.70 mmol) in THF (3 mL) was dropwise added over 10 min to give a light tan solution at –78° C. under $N_2$, and continued stirring for 2 hr. The reaction was quenched with sat. $NH_4Cl$ (30 mL), extracted with $Et_2O$ (2×50 mL). The combined organic phase was washed with brine (30 mL), dried ($MgSO_4$), concentrated on rotary vacuo and purified on Biotage Flash Collector eluting with 20~50% EtOAc/Hexanes (800 mL) to give the expected product, tert-butyl 4-(6-chloro-1-(triisopropylsilyl)-1H-pyrrolo[2,3-b]pyridin-4-yl)-4-hydroxypiperidine-1-carboxylate (400 mg, 48%), as a light yellow solid. $^1$H-NMR (400 MHz, CHLOROFORM-D) δ ppm 1.25 (t, J=7.68 Hz, 18 H) 1.64 (s, 9 H) 1.94 (dt, J=15.17, 7.65 Hz, 5 H) 2.33-2.44 (m, 2 H) 3.42 (s, 2 H) 4.24 (d, J=7.05 Hz, 2 H) 6.88 (d, J=3.53 Hz, 1 H) 7.38-7.41 (m, 3 H); Mass spec. 508.25 (MH+) calc. for $C_{26}H_{42}ClN_3O_3Si$ 507.27.

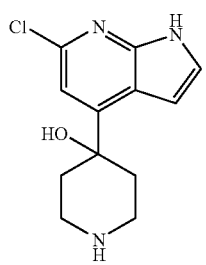

Intermediate 217

4-(6-chloro-1H-pyrrolo[2,3-b]pyridin-4-yl)piperidin-4-ol. To tert-butyl 4-(6-chloro-1-(triisopropylsilyl)-1H-pyrrolo[2,3-b]pyridin-4-yl)-4-hydroxypiperidine-1-carboxylate (510 mg, 1.00 mmol) in $CH_2Cl_2$ (6 mL) was slowly dropwise added TMS-I (0.43 mL, 3.01 mmol) at rt, and stirred at 60° C. overnight. Partial of the solvent was removed on rotary vacuo, and the residue was purified on reverse phase PrepHPLC to afford the expected product, 4-(6-chloro-1H-pyrrolo[2,3-b]pyridin-4-yl)piperidin-4-ol (310 mg, 63%), as a dark brown solid. $^1$H-NMR (400 MHz, CHLOROFORM-D) δ ppm 2.02 (d, J=14.35 Hz, 2 H) 2.65-2.76 (m, 2 H) 3.42 (d, J=11.33 Hz, 2 H) 3.58 (d, J=11.83 Hz, 2 H) 4.61 (s, 2 H) 6.91 (d, J=3.53 Hz, 1 H) 7.13 (s, 1 H) 7.28 (d, J=3.53 Hz, 1 H); Mass spec. 252.05 (MH+) calc. for $C_{12}H_{14}ClN_3O$ 251.08.

Intermediate 218

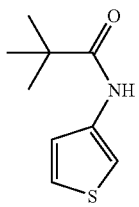

N-(thiophen-3-yl)pivalamide. To an oven dried flask was charged with methyl 3-aminothiophene-2-carboxylate (30 g, 191 mmol) and pyridine (300 ml), followed by addition of pivaloyl chloride (25.3 g, 210 mmol) at room temperature. A mild exotherm occurred, and solid was formed. 10 min later, the reaction mixture was refluxed under $N_2$ overnight (~20 hr), and stirred at rt on weekend. Most of the solvent was removed on rotary vacuo. The brown residue was partitioned between 1N HCl and $CH_2Cl_2$ (100 mL/150 mL). After seperation, the aqueous solution was extracted with $CH_2Cl_2$ (100 mL), the combined organic layers were washed with brine (70 mL), dried on $MgSO_4$, concentrated on rotary vacuo, the residue as a brown solid, was triturated with $Et_2O$ (30 mL), filtered and washed with $Et_2O$ (2×10 mL) to afford the expected product, N-(thiophen-3-yl)pivalamide (15.4 g, 50%) as an off white solid. $^1$H-NMR (400 MHz, CHLOROFORM-D) δ ppm 1.28 (s, 9 H) 6.98 (dd, J=5.16, 1.39 Hz, 1 H) 7.20 (dd, J=5.29, 3.27 Hz, 1 H) 7.57-7.66 (m, 2 H); Mass spec. C184.05 (MH+) calc. for $C_9H_{13}NOS$ 183.07.

Intermediate 219

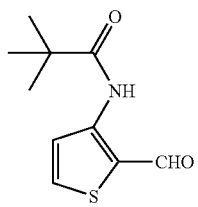

N-(2-formylthiophen-3-yl)pivalamide. To an oven dried flask was charged with N-(thiophen-3-yl)pivalamide (2.0 g, 10.91 mmol) and THF (50 mL) at rt, then the light tan solution was cooled down to −78° C., followed by dropwise addition of n-BuLi (2.4M in hexanes, 9.60 mL, 24.01 mmol) over 5 min under $N_2$. The resulting off-white suspension was stirred for 1 hr, followed by addition of DMF (3.21 mL, 41.5 mmol) through a syringe over 2 min. In 20 min, the suspension became tan solution and the reaction mixture was warmed to rt and continued stirring for 30 min. The conversion was completed as determined by TLC, thus the reaction was quenched with sat. $NH_4Cl$, partitioned between $Et_2O/H_2O$ (150 mL/50 mL), after separation, the organic solution was washed with brine, dried ($Na_2SO_4$), concentrated and purified on Biotage Fresh Collector eluting with 10~40% EtOAc/Hexanes to afford the expected product, N-(2-formylthiophen-3-yl)pivalamide (1.85 g, 80%) as a tan oil. $^1$H-NMR (500 MHz, CHLOROFORM-D) δ ppm 1.32 (s, 9 H) 7.68 (d, J=5.19 Hz, 1 H) 8.19 (d, J=5.19 Hz, 1 H) 9.71 (s, 1 H) 10.97 (s, 1 H); Mass spec. 212.09 (MH+) calc. for $C_{10}H_{13}NO_2S$ 211.07.

Intermediate 220

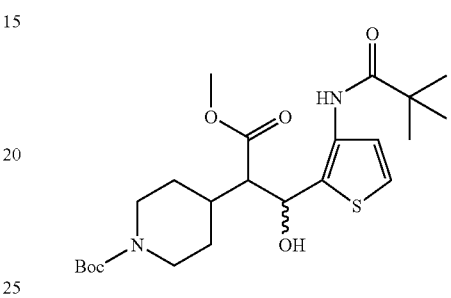

tert-butyl 4-(1-hydroxy-3-methoxy-3-oxo-1-(3-pivalamidothiophen-2-yl)propan-2-yl)piperidine-1-carboxylate. To a solution of diisopropylamine (5.84 g, 8.16 mL, 57.7 mmol) in THF (100 mL) was dropwise added n-BuLi (23.10 ml, 57.7 mmol) at −78° C. under $N_2$ over 5 min, and the resulting colorless solution was stirred for 20 min, followed by dropwise addition of tert-butyl 4-(2-methoxy-2-oxoethyl)piperidine-1-carboxylate (14.62 g, 56.8 mmol) in THF (20 mL) over 8 min, and stirred for 30 min.

On the other hand, to a light yellow solution of N-(2-formylthiophen-3-yl)pivalamide in THF was added NaH (1.99 g, 49.7 mmol) in several portions at 0° C., the resulting red orange solution was stirred for 30 min. Then it was dropwise added to the anion of tert-butyl 4-(2-methoxy-2-oxoethyl)piperidine-1-carboxylate through an addition funnel at −78° C. under $N_2$ over 15 min. The resulting red orange solution was stirred for 1 hr, checked with TLC. Conversion was completed, the reaction was quenched wit sat. $NH_4Cl$ (100 mL), partitioned between $H_2O/Et_2O$ (150 mL/300 mL), after seperation the organic phase was washed with brine (100 mL), dried with $MgSO_4$, concentrated on rotary vacuo, and the residue was purified on Biotage Flash Collector eluting with 15~60% EtOAc/Hexanes (1400 mL), 60% EtOAc/Hexanes (600 mL) to afford the expected diastereo mixture of tert-butyl 4-(1-hydroxy-3-methoxy-3-oxo-1-(3-pivalamidothiophen-2-yl)propan-2-yl)piperidine-1-carboxylate (21.1 g, 95% ) as a tan foam. Mass spec 469.20 (MH+) calc. for $C_{23}H_{36}N_2O_6S$ 468.23.

Intermediate 221

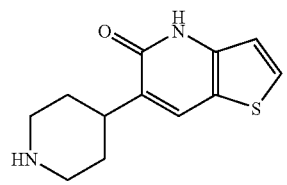

6-(piperidin-4-yl)thieno[3,2-b]pyridin-5(4H)-one. Tert-butyl 4-(1-hydroxy-3-methoxy-3-oxo-1-(3-pivalamidothiophen-2-yl)propan-2-yl)piperidine-1-carboxylate (10 g, 21.34 mmol) was dissolved in MeOH (20 mL), water (20.00 ml), hydrochloric acid (concentrated, 20 ml, 244 mmol), the resulting red pink solution was heated, the color changed to dark tan, and the mixture was refluxed in a oil bath under $N_2$ over night, conversion was completed as determined by LC/MS. Most of the solvent was removed on rotary vacuo, the resulting gum type residue was triturate with EtOAc/MeOH (10 mL/2 mL), filtered and washed with EtOAC/MeOH (10 mL/1 mL) to afford the expected product, 6-(piperidin-4-yl)thieno[3,2-b]pyridin-5(4H)-one (4.85 g, 97%), as a brown solid. $^1$H-NMR (400 MHz, MeOD) δ ppm 1.83-1.94 (m, J=13.41, 13.13, 13.13, 3.90 Hz, 2 H) 2.13 (d, J=13.85 Hz, 2 H) 3.08-3.19 (m, 4 H) 3.50 (dd, J=10.58, 2.01 Hz, 2 H) 7.08 (d, J=6.04 Hz, 1 H) 7.78 (d, J=5.54 Hz, 1 H) 7.96 (s, 1 H); Mass spec. 235.16 (MH$^+$), Calc. for $C_{12}H_{14}N_2OS$ 234.08.

Intermediates 222 and 223

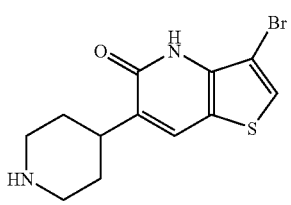

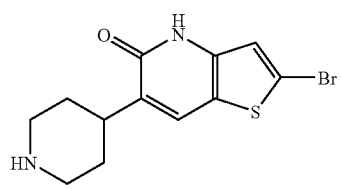

3-bromo-6-(piperidin-4-yl)thieno[3,2-b]pyridin-5(4H)-one and 2-bromo-6-(piperidin-4-yl)thieno[3,2-b]pyridin-5(4H)-one. To a suspesion of 6-(piperidin-4-yl)thieno[3,2-b]pyridin-5(4H)-one (250 mg, 1.067 mmol) in MeOH (10 mL) was added silica gel (750 mg) and NBS (220 mg, 1.236 mmol) at rt in one portion. The resulting yellow suspension was stirred for 2 hr to give ~85% conversion as determined by LC/MS, thus the reaction mixture was filtered with MeOH (10 mL), and concentrated on rotary vacuo. The crude compound was purified on reverse phase Prep HPLC to afford the expected products, an inseparable mixture of the regioisomers, 3-bromo-6-(piperidin-4-yl)thieno[3,2-b]pyridin-5(4H)-one and 2-bromo-6-(piperidin-4-yl)thieno[3,2-b]pyridin-5(4H)-one (68 mg, 21.6%). Mass spec 312.98 (MH+) calc. for $C_{12}H_{13}BrN_2OS$ 311.99.

Intermediates 224 and 225

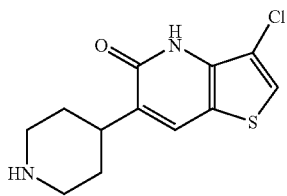

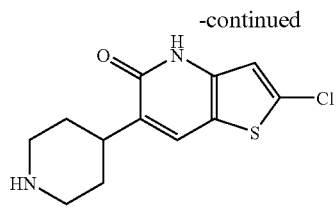

3-chloro-6-(piperidin-4-yl)thieno[3,2-b]pyridin-5(4H)-one and 2-chloro-6-(piperidin-4-yl)thieno[3,2-b]pyridin-5(4H)-one. To a suspension of 6-(piperidin-4-yl)thieno[3,2-b]pyridin-5(4H)-one (25 mg, 0.107 mmol) in MeOH (5 mL) and THF (10 mL) was added silica gel (750 mg), and NCS in one portion at rt. The resulting mixture was stirred at 60° C. over night. The suspension was filtered with MeOH (10 mL), concentrated and purified on reverse phase Prep HPLC to afford the expected products (13 mg, 45.3%), as a tan gum, an inseparable mixture of the regio isomers, 2-chloro-6-(piperidin-4-yl)thieno[3,2-b]pyridin-5(4H)-one and 3-chloro-6-(piperidin-4-yl)thieno[3,2-b]pyridin-5(4H)-one. Mass spec. 253.06 (MH+) Cal. for $C_{12}H_{13}ClN_2S$ 252.05.

Intermediate 226

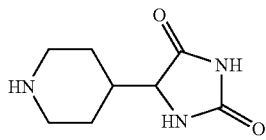

5-(piperidin-4-yl)imidazolidine-2,4-dione. To a solution of tert-butyl 4-formylpiperidine-1-carboxylate (1.0 g, 4.7 mmol) in a mixture of water (5 mL) and methanol (10 mL) were added sodium cyanide (345 mg, 7 mmol) and ammonium carbonate (902 mg, 9.4 mmol) and heated at reflux for 6 h. The reaction mixture was cooled, removed most of the solvent. The crude product was extracted with dichloromethane, dried (Na$_2$SO$_4$) and removed solvent. The crude product was dissolved in dichloromethane (5 mL) and treated with trifluoroacetic acid (5 mL) for 2 h. The solvent was removed and dried. MS (ESI) 184 (M+H); R$_f$=1.83.

Intermediate 227

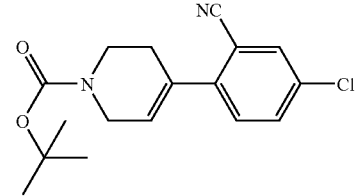

Tert-butyl 4-(4-chloro-2-cyanophenyl)-5,6-dihydropyridine-1(2H)-carboxylate. Tert-butyl 4-(4-chloro-2-cyanophenyl)-5,6-dihydropyridine-1(2H)-carboxylate was prepared as described by Boice et al. in Tetrahedron 2004, 60, 11367-11374.

Intermediate 228

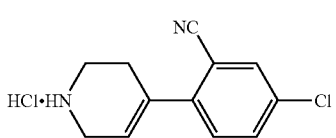

4-(4-chloro-2-cyanophenyl)-5,6-dihydropyridine hydrochloride. In a round bottom flask, tert-butyl 4-(4-chloro-2-cyanophenyl)-5,6-dihydropyridine-1(2H)-carboxylate (160 mg, 0.502 mmol) was dissolved in $CH_2Cl_2$ (10 mL). To this solution was added trifluoroacetic acid (2 mL, 26.0 mmol) and the reaction mixture turned bright yellow. The reaction was stirred at room temperature for 3 hours. Solvent was evaporated under high vacuum to give sticky green/grey residue. Treated with 2N HCl in ether (2.0 mL). Evaporated solvent and then triturated with $Et_2O$. Dried under vacuum to give 5-chloro-2-(1,2,3,6-tetrahydropyridin-4-yl)benzonitrile, HCl salt (135 mg, 0.529 mmol, 105% yield) as a maize colored solid. $^1H$ NMR (500 MHz, MeOD) δ ppm 2.81 (d, J=1.53 Hz, 2 H) 3.51 (t, J=5.95 Hz, 2 H) 3.92 (d, J=2.44 Hz, 2 H) 6.11 (s, 1 H) 7.51 (d, J=8.55 Hz, 1 H) 7.73 (dd, J=8.55, 2.14 Hz, 1 H) 7.88 (d, J=2.14 Hz, 1 H); MS (ESI): 219 (M+1H); $R_f$=1.01 (4 min run).

General procedure for the preparation of N-alkylated ester derivatives. The alkyl halide (MeI, EtI, n-PrI, or benzylbromide, 3-10 equivalents) was added to a stirred suspension of indazole 1 (0.5 mmol) and cesium carbonate (3.0 mmol) in 15 mL of dry acetonitrile. The resulting suspension was stirred at room temperature 24 h or until judged complete by tlc analysis. The reaction mixture was then concentrated under reduced pressure and the resulting residue partitioned between CH2Cl2 and H2O. The layers were separated and the organic portion washed with H2O, brine and dried over MgSO4. After filtration the filtrate was concentrated in vacuo to give a crude mixture of the N-alkylated adducts 2 and 3. These were purified by use of a Biotage@ SP-1 chromatography apparatus using a mixture of EtOAc and hexane solvents as eluants. The purified compounds were characterized by NMR either a Brucker AC 300 or a Brucker Avance 500 spectrometer in the solvents indicated. LC/MS data was obtained using a Schimadzu LC equipped with a 3.0×50 mm S1O column Phenomenex-Luna: 10-90% B at a flow rate of 4 mL/min over a period of 3 min. Mobile phase A=(10% MeOH, 90% H2O, 0.1% TFA); mobile phase B=(90% MeOH, 10% H2O, 0.1% TFA). A Schimadzu SPD-10$^a$ detector at 220 nm was used for peak detection and a Micromass ZMD spectrometer used for mass determination. The following products were isolated and characterized using this method:

Intermediate 229

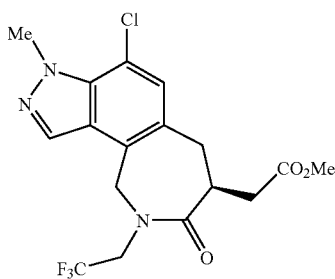

(S)-Methyl 2-(4-Chloro-3-methyl-8-oxo-9-(2,2,2-trifluoroethyl)-3,6,7,8,9,10-hexahydroazepino[3,4-e]indazol-7-yl) acetate. This compound was obtained as a colorless solid in 54% yield: 1HNMR (500 MHz, CDCl3) δ ppm 7.91 (s, 1H), 7.06 (s, 1H), 5.36 (d, 1H, J =17.0 Hz), 4.52 (d, 1H, J=17.0 Hz), 4.35 (s, 3H), 4.20 (m, 1H), 4.18 (m, 1H), 3.90 (m, 1H), 3.69 (s, 3H), 3.04 (m, 4H), 2.46 (m, 1H). LC/MS: single peak@ 2.28 min, (M+H)=404.

Intermediate 230

(S)-Methyl 2-(4-Chloro-3-ethyl-8-oxo-9-(2,2,2-trifluoroethyl)-3,6,7,8,9,10-hexahydroazepino[3,4-e]indazol-7-yl) acetate. This compound was obtained as a clear oil in 47% yield: 1HNMR (500 MHz, CDCl3) δ ppm 7.94 (s, 1H), 7.08 (s, 1H), 5.69 (d, 1H, J=17.0 Hz), 4.78 (q, 2H, J=7.5 Hz), 4.54 (d, 1H, J=17.0 Hz), 4.11 (m2H), 3.90 (m, 1H), 3.70 (s, 3H), 3.05 (m, 3H), 2.47 (m, 1H), 1.24 (t, 3H, J=7.5 Hz). LC/MS: single peak @ 2.41 min, (M+H)=418.

Intermediate 231

(S)-Methyl 2-(3-Benzyl-4-chloro-8-oxo-9-(2,2,2-trifluoroethyl)-3,6,7,8,9,10-hexahydroazepino[3,4-e]indazol-7-yl) acetate. This compound was obtained as a colorless oil in 42% yield: 1HNMR (500 MHz, CDCl3) δ ppm 8.03 (s, 1H), 7.24 (m, 3H), 7.12 (m, 2H), 7.07 (s, 1H), 5.94 (m, 2H), 5.38 (d, 1H, J=17.0 Hz), 4,56 (d, J=17 Hz), 4.10 (m, 3H), 3.89 (m, 1H), 3.70 (s, 3H), 3.05 (m, 3H), 2.46 (m, 1H). LC/MS: single peak @ 2.65 min, (M+H)=480.

Intermediate 232

(S)-Methyl 2-(4-Chloro-8-oxo-3-propyl-9-(2,2,2-trifluoroethyl)-3,6,7,8,9,10-hexahydroazepino[3,4-e]indazol-7-yl) acetate. This compound was obtained as a colorless oil in 25% yield: 1HNMR (500 MHz, CDCl3) δ ppm 7.93 (s, 1H), 7.06 (s, 1H), 5.35 (d, 1H, J=17.0 Hz), 4.65 (m, 2H), 4.53 (d, J=17

Hz), 4.08 (m, 2H), 4.11 (m, 2H), 3.88 (m, 1H), 3.68 (s, 3H), 3.02 (m, 3H), 2.47 (m, 1H), 1.24 1.90 (h, 2H), 0.89 (t, 3H, J=7.5 Hz). LC/MS: single peak @ 2.73 min, (M+H)=432.

Intermediate 233

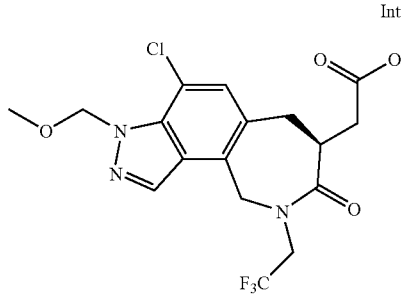

(S)-methyl 2-(4-chloro-3-(methoxymethyl)-8-oxo-9-(2,2,2-trifluoroethyl)-3,6,7,8,9,10-hexahydroazepino[3,4-e]indazol-7-yl)acetate. The compound was isolated as a white solid in 58% yield: 1H NMR (400 MHz, CHLOROFORM-D) δ ppm 2.47 (dd, J=17.00, 5.41 Hz, 1 H), 2.99-3.11 (m, 3 H), 3.71 (s, 3 H), 3.87-4.07 (m, 3 H), 4.14-4.25 (m, 2 H), 4.38 (s, 3 H), 4.48-4.58 (d, J=17.2 Hz, 1 H), 5.38 (d, J=17.12 Hz, 1 H), 7.09 (s, 1 H), 7.94 (s, 1 H); Mass spec. 434.02 (M+H) Calc. for $C_{18}H_{19}ClF_3N_3O_4$ 433.1

Intermediate 234

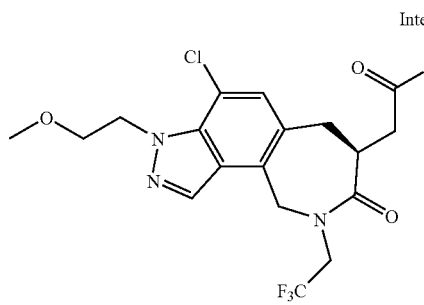

2-(S)-methyl 2-(4-chloro-3-(2-methoxyethyl)-8-oxo-9-(2,2,2-trifluoroethyl)-3,6,7,8,9,10-hexahydroazepino[3,4-e]indazol-7-yl)acetate. This compound was isolated as a white solid in 30.9% yield. 1H NMR (400 MHz, CHLOROFORM-D) δ ppm 2.46 (dd, J=16.87, 5.54 Hz, 1 H), 2.96-3.07 (m, 3 H), 3.31 (s, 3 H), 3.69 (s, 3 H), 3.81-3.92 (m, 3 H), 4.04-4.15 (m, 2 H), 4.34 (d, J=17.12 Hz, 1 H), 4.60 (dd, J=6.04, 3.78 Hz, 2 H), 5.38 (d, J=17.12 Hz, 1 H), 7.03 (s, 1 H), 8.01 (s, 1 H); Mass spec. 448.07 (M+H) Calc. for $C_{19}H_{21}ClF_3N_3O_4$ 447.12.

General procedure for the hydrolysis of N-alkylated acid derivatives. To a solution of ester (0.3 mmol) in 15 mL of THF was added a solution of LiOH (3.0 mmol) dissolved in 10 mL of H2O. The resulting solution was stirred at room temperature for 1 h or as judged complete by TLC analysis. The solution was then made acidic by the addition of a minimal amount of 0.1 N HCl, poured into 50 mL of H2O and extracted with CH2Cl2. The combined organic layers were washed with H2O and brine and dried over anhydrous MgSO4. After filtration the volatiles were removed in vacuo to generally give the free acids which were used without further purification. The acids were characterized in similar fashion to those above.

Intermediate 235

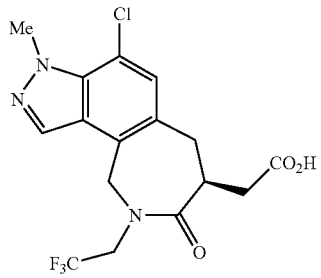

(S)-2-(4-Chloro-3-methyl-8-oxo-9-(2,2,2-trifluoroethyl)-3,6,7,8,9,10-hexahydroazepino[3,4-e]indazol-7-yl)acetic acid. This material was obtained as a colorless white solid in 98% yield: 1HNMR (500 MHz, DMSO-d6) δ ppm 12.2 (br s, 1H), 8.28 (s, 1H), 7.25 (s, 1H), 5.41 (d, J=17 Hz, 1H), 4.82 (d, J=17.0 Hz), 4.54 (m, 1H), 4.30 (s, 3H), 4.07 (m, 1H), 3.84 (m, 1H), 3.12 (d, J=18 Hz, 1H), 2.82 (d, J=18 Hz, 1H), 2.71 (m, 1H), 2.44 (m, 1H). LC/MS: single peak @ 2.12 min, (M+H) =390.

Intermediate 236

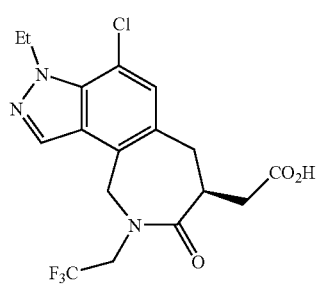

(S)-2-(4-Chloro-3-ethyl-8-oxo-9-(2,2,2-trifluoroethyl)-3,6,7,8,9,10-hexahydroazepino[3,4-e]indazol-7-yl)acetic acid. This material was isolated in 97% yield as a white solid: 1HNMR (500 MHz, DMSO-d6) δ ppm 12.2 (br s, 1H), 8.31 (s, 1H), 7.26 (s, 1H), 5.42 (d, J=17.0 Hz, 1H), 4.82 (d, J=17.0 Hz, 1H), 4.71 (m, 2H), 4.56 (m, 1H), 4.10 (m, 1H), 3.88 (m, 1H), 3.14 (d, J=17.5 Hz), 2.81 (m, 1 H), 2.74 (m, 1H), 2.41 (m, 1H), 1.40 (m, 3H). LC/MS: single peak @ 2.30 min, (M+H) =404.

Intermediate 237

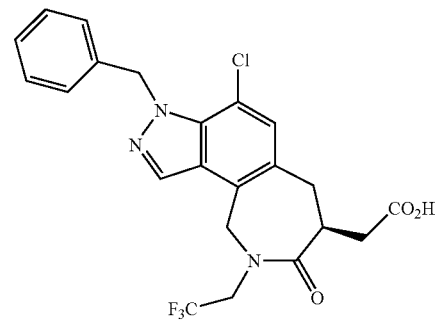

(S)-2-(4-Chloro-3-benzyl-8-oxo-9-(2,2,2-trifluoroethyl)-3,6,7,8,9,10-hexahydroazepino[3,4-e]indazol-7-yl)acetic acid. The acid was isolated as a colorless white solid in 89% yield: 1HNMR (500 MHz, DMSO-d6) δ ppm 12.2 (br s, 1H), 8.41 (s, 1H), 7.28 (m, 3H), 7.22 (s, 1H), 7.06 (m, 2H), 5.96 (d, J=16.5 Hz, 1H), 5.88 (d, J=16.5 Hz, 1H), 5.45 (d, J=17.0 Hz, 1H), 4.85 (d, J=17.0 Hz, 1H), 4.55 (m, 1H), 4.12 (m, 1H), 3.88 (m, 1H), 3.12 (d, J=17.5 Hz, 1H), 2.83 (m, 1H), 2.75 (m, 1H), 2.44 (m, 1H). LC/MS: single peak @ 2.51 min, (M+H)=466.

Intermediate 238

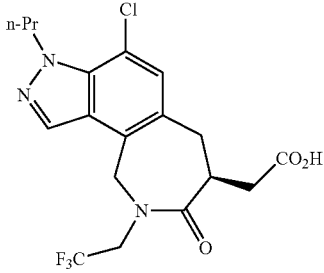

(S)-2-(4-Chloro-8-oxo-3-propyl-9-(2,2,2-trifluoroethyl)-3,6,7,8,9,10-hexahydroazepino[3,4-e]indazol-7-yl)acetic acid. This compound was isolated a colorless solid in 76% yield: 1HNMR (500 Mhz, DMSO-d6) δ ppm 12.2 (br s, 1H), 8.32 (s, 1H), 7.26 (s, 1H), 5.42 (d, J=17.0 Hz), 4.83 (d, J=17.0 Hz, 1H), 4.65 (m, 2H), 4.54 (m, 1H), 4.08 (m, 1H), 3.86 (m, 1H), 3.14 (d, J=17.0 Hz, 1H), 2.82 (m, 1H), 2.73 (m, 1H), 2.44 (m, 2H), 0.85 (t, J=7.0 Hz, 3H). LC/MS: single peak @ 2.46 min, (M+H)=418.

Intermediate 239

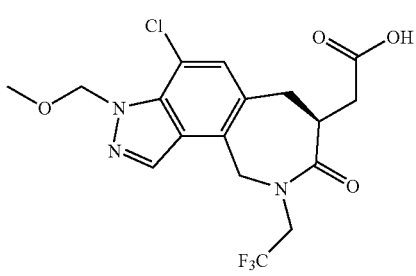

(S)-2-(4-chloro-3-(methoxymethyl)-8-oxo-9-(2,2,2-trifluoroethyl)-3,6,7,8,9,10-hexahydroazepino[3,4-e]indazol-7-yl)acetic acid. This compound was obtained as colorless crude white solid in 100% yield. Mass spec. 420.26 (M+H) Calc. for $C_{17}H_{17}ClF_3N_3O_4$ 419.09.

Intermediate 240

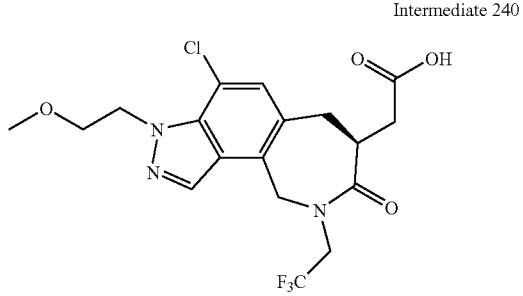

(S)-2-(4-chloro-3-(2-methoxyethyl)-8-oxo-9-(2,2,2-trifluoroethyl)-3,6,7,8,9,10-hexahydroazepino[3,4-e]indazol-7-yl)acetic acid. This compound was obtained as colorless crude white solid in 100% yield. Mass spec. 434.12 (M+H) Calc. for $C_{18}H_{19}ClF_3N_3O_4$ 433.1.

EXAMPLE 1

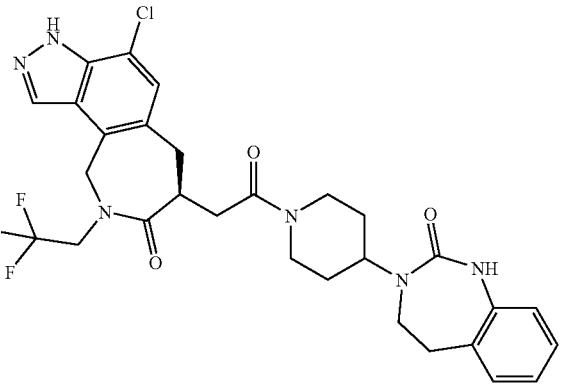

(S)-4-chloro-7-(2-oxo-2-(4-(2-oxo-1,2,4,5-tetrahydrobenzo[d][1,3]diazepin-3-yl)piperidin-1-yl)ethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (170 mg, 0.452 mmol) was dissolved in N,N-dimethylformamide (4.0 mL). N,N-Diisopropylethylamine (300 μl, 1.722 mmol) was added to the mixture followed by TBTU (152 mg, 0.473 mmol). 3-(Piperidin-4-yl)-4,5-dihydro-1H-benzo[d][1,3]diazepin-2(3H)-one (155 mg, 0.632 mmol) was then added to the mixture. Reaction stirred at room temperature for 45 minutes. Reaction was quenched with 50% acetonitrile-water. Mixture was purified by reverse phase prep HPLC (acetonitrile-water-trifluoroacetic acid). Acetonitrile was removed from the fractions by roto-vap. Remaining aqueous was made basic with sodium bicarbonate. Material was extracted twice with ethyl acetate. Organics were dried MgSO_4, filtered and concentrated to dryness. Title compound was obtained as white solid in 60% yield. 1H NMR (500 MHz, DMSO-D6) δ ppm 13.57 (s, 1 H) 8.50 (s, 1 H) 8.33 (s, 1 H) 7.23 (s, 1 H) 6.97-7.06 (m, 3 H) 6.73-6.84 (m, 1 H) 5.43 (d, J=16.79 Hz, 1 H) 4.85 (d, J=17.40 Hz, 1 H) 4.52-4.62 (m, 1 H) 4.41-4.52 (m, 1 H) 4.23-4.36 (m, 1 H) 4.00-4.14 (m, 2 H) 3.87-3.99 (m, 1 H) 3.34-3.39 (m, 2 H) 3.06-3.19 (m, 2 H) 2.94-3.04 (m, 1 H) 2.80-2.92 (m, 3 H) 2.53-2.62 (m, 1 H) 2.33-2.45 (m, 1 H) 1.58-1.84 (m, 3 H) 1.37-1.56 (m, 1 H). High resolution MS m/e (M+H)$^+$=603.2108.

EXAMPLE 2

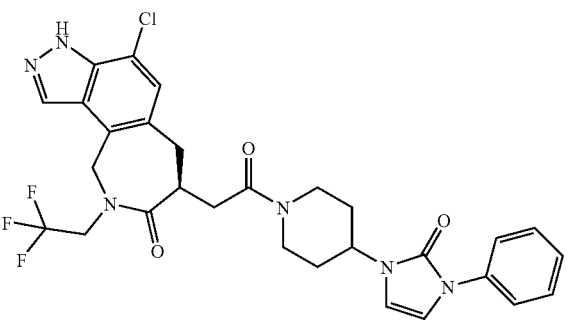

(S)-4-chloro-7-(2-oxo-2-(4-(2-oxo-3-phenyl-2,3-dihydroimidazol-1-yl)piperidin-1-yl)ethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (97 mg, 258 μmol) was dissolved in N,N-dimethylformamide (1.5 mL). N,N-Diisopropylethylamine (45 μl, 258 μmol) was added to the mixture followed by 3-phenyl-1-(piperidin-4-yl)-1H-imidazol-2(3H)-one hydrochloride (86 mg, 307 μmol). Reaction stirred at room temperature for 3.5 hours. Mixture was diluted with 50% water-acetonitrile. Mixture was purified by reverse phase prep HPLC (acetonitrile-water-ammonium acetate). Acetonitrile was removed from the fractions by roto-vap. Remaining aqueous was diluted with water. Solids were filtered off and washed with water. Solids were collected and dried in vacuo. Title compound was obtained as white solid in 24% yield. 1H NMR (500 MHz, DMSO-D6) δ ppm 13.56 (s, 1 H) 8.32 (s, 1 H) 7.72 (d, J=7.93 Hz, 2 H) 7.44 (t, J=8.09 Hz, 2 H) 7.19-7.28 (m, 2 H) 7.05 (t, J=2.75 Hz, 1 H) 6.86 (dd, J=8.55, 3.05 Hz, 1 H) 5.44 (d, J=17.09 Hz, 1 H) 4.86 (d, J=17.40 Hz, 1 H) 4.46-4.64 (m, 2 H) 4.14-4.26 (m, 1 H) 4.01-4.14 (m, 2 H) 3.88-4.00 (m, 1 H) 3.10-3.26 (m, 2 H) 3.02 (dd, J=16.33, 8.70 Hz, 1 H) 2.79-2.95 (m, 1 H) 2.61-2.73 (m, 1 H) 2.43 (dd, J=16.48, 4.27 Hz, 1 H) 1.73-1.95 (m, 3 H) 1.56-1.68 (m, 1 H). MS (M+H)$^+$=600.8.

EXAMPLE 3

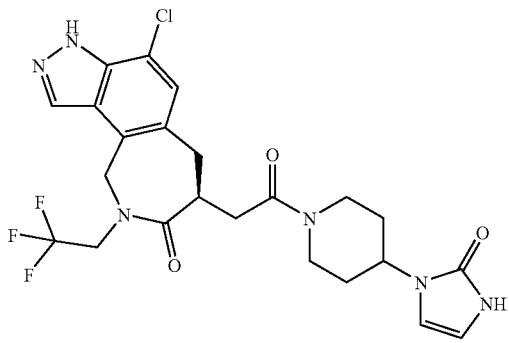

(S)-4-chloro-7-(2-oxo-2-(4-(2-oxo-2,3-dihydroimidazol-1-yl)piperidin-1-yl)ethyl)-9-(2,2,2-trifluoroethyl)-6,7,9,10-tetrahydroazepino[3,4-e]indazol-8(3H)-one. 1-(Piperidin-4-yl)-1H-imidazol-2(3H)-one hydrochloride (80 mg, 0.393 mmol) was suspended in a mixture of N,N-diisopropylethylamine (33.5 μl, 0.192 mmol) and N,N-dimethylformamide (2.0 mL). [4-Chloro-3,6,7,8,9,10-hexahydro-8-oxo-9-(2,2,2-trifluoroethyl)-2,3,9-triaza-(S)-cyclohepta[e]inden-7-yl] acetic acid (72 mg, 0.192 mmol) was then dissolved in the mixture. TBTU (61.5 mg, 0.192 mmol) was added to the mixture, which quickly became homogenous. Reaction stirred at room temperature for 3 hours. Reaction was quenched with 50% acetonitrile-water. Mixture was purified by reverse phase prep HPLC (acetonitrile-water-ammonium acetate). Acetonitrile was removed from the fractions by roto-vap. Residue was extracted twice with ethyl acetate. Organics were dried MgSO$_4$, filtered and then concentrated to dryness. Title compound was obtained as white solid in 42% yield. 1H NMR (500 MHz, DMSO-D6) δ ppm 13.56 (s, 1 H) 9.91 (s, 1 H) 8.32 (s, 1 H) 7.22 (s, 1 H) 6.48 (d, J=8.85 Hz, 1 H) 6.33 (d, J=2.44 Hz, 1 H) 5.43 (d, J=16.79 Hz, 1 H) 4.84 (d, J=16.79 Hz, 1 H) 4.52-4.63 (m, 1 H) 4.48 (d, J=12.51 Hz, 1 H) 3.99-4.15 (m, 3 H) 3.86-3.98 (m, 1 H) 3.08-3.22 (m, 2 H) 3.00 (dd, J=16.33, 8.70 Hz, 1 H) 2.79-2.91 (m, 1 H) 2.55-2.72 (m, 1 H) 2.32-2.48 (m, 1 H) 1.59-1.86 (m, 3 H) 1.43-1.60 (m, 1 H). High resolution MS m/e (M+H)$^+$=525.1629.

EXAMPLE 4

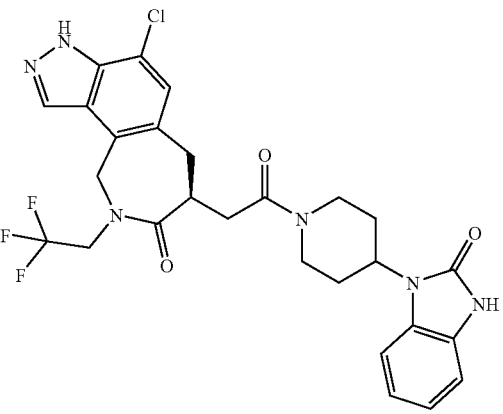

(S)-4-chloro-7-(2-oxo-2-(4-(2-oxo-2,3-dihydrobenzo[d]imidazol-1-yl)piperidin-1-yl)ethyl)-9-(2,2,2-trifluoroethyl)-6,7,9,10-tetrahydroazepino[3,4-e]indazol-8(3H)-one.
[4-Chloro-3,6,7,8,9,10-hexahydro-8-oxo-9-(2,2,2-trifluoroethyl)-2,3,9-triaza-(S)-cyclohepta[e]inden-7-yl]acetic acid (115 mg, 0.306 mmol) was dissolved in N,N-dimethylformamide (2.0 mL). N,N-Diisopropylethylamine (150 μl, 0.861 mmol) was added to the mixture followed successively by TBTU (103 mg, 0.321 mmol) and 4-(2-keto-1-benzimidazolinyl)piperidine (74 mg, 0.341 mmol). Reaction was stirred at room temperature for 2 hours. Reaction was quenched with 50% acetonitrile-water. Mixture was purified by reverse phase prep HPLC (acetonitrile-water-ammonium acetate). Acetonitrile was removed from the fractions by roto-vap. Remaining aqueous was extracted twice with ethyl acetate and the aqueous phase was discarded. Organics were dried MgSO$_4$, filtered and then concentrated to dryness. Title compound was obtained as white solid in 57% yield. 1H NMR (500 MHz, DMSO-D6) δ ppm 13.56 (s, 1 H) 10.84 (s, 1 H) 8.34 (d, J=5.80 Hz, 1 H) 7.40 (d, J=7.63 Hz, 1 H) 7.24 (s, 1 H) 6.97 (s, 2 H) 6.82-6.96 (m, 1 H) 5.45 (d, J=17.09 Hz, 1 H) 4.86 (dd, J=16.94, 5.95 Hz, 1 H) 4.34-4.71 (m, 3 H) 4.09-4.24 (m, 1 H) 3.91-4.10 (m, 1 H) 3.13-3.27 (m, 2 H) 2.96-3.13 (m, 1 H) 2.83-2.95 (m, 1 H) 2.62-2.78 (m, 1 H) 2.52-2.59 (m, 1 H) 2.26-2.46 (m, 1 H) 2.01-2.21 (m, 1 H) 1.58-1.85 (m, 2 H). High resolution MS m/e (M+H)$^+$=575.1785.

EXAMPLE 5

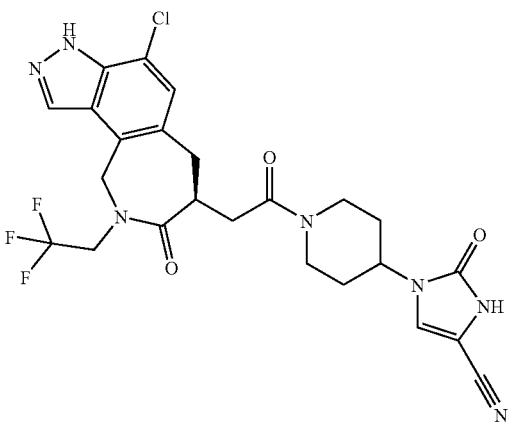

(S)-1-(1-(2-(4-chloro-8-oxo-9-(2,2,2-trifluoroethyl)-3,6,7,8,9,10-hexahydroazepino[3,4-e]indazol-7-yl)acetyl)piperidin-4-yl)-2-oxo-2,3-dihydro-1H-imidazole-4-carbonitrile. [4-Chloro-3,6,7,8,9,10-hexahydro-8-oxo-9-(2,2,2-trifluoroethyl)-2,3,9-triaza-(S)-cyclohepta[e]inden-7-yl] acetic acid (62 mg, 0.165 mmol) and 2-oxo-1-(piperidin-4-yl)-2,3-dihydro-1H-imidazole-4-carbonitrile hydrochloride (35 mg, 0.182 mmol) were combined and dissolved in a mixture of N,N-dimethylformamide (1.5 mL) and N,N-diisopropylethylamine (28.7 µL, 0.165 mmol). TBTU (53.0 mg, 0.165 mmol) was added to the mixture. Reaction stirred at room temperature for 1.5 hours. Reaction mixture was purified by reverse phase prep HPLC (acetonitrile-water-trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO4, filtered and then concentrated to dryness. Title compound was obtained as white solid in 10% yield. 1H NMR (500 MHz, DMSO-D6) δ ppm 13.55 (s, 1H) 11.13 (s, 1H) 8.32 (s, 1H) 7.81 (d, J=2.44 Hz, 1H) 7.22 (s, 1H) 5.43 (d, J=16.79 Hz, 1H) 4.85 (d, J=17.09 Hz, 1H) 4.52-4.62 (m, 1H) 4.48 (d, J=13.12 Hz, 1H) 4.03-4.18 (m, 3H) 3.87-3.99 (m, 1H) 3.08-3.22 (m, 2H) 2.95-3.05 (m, 1H) 2.80-2.92 (m, 1H) 2.60-2.70 (m, 1H) 2.37-2.45 (m, 1H) 1.83-1.93 (m, 1H) 1.76-1.83 (m, 1H) 1.64-1.75 (m, 1H) 1.49-1.61 (m, 1H). High resolution MS m/e (M+H)$^+$=550.1603.

EXAMPLE 6

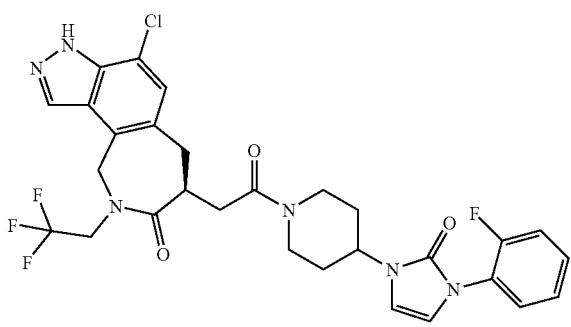

(S)-4-chloro-7-(2-(4-(3-(2-fluorophenyl)-2-oxo-2,3-dihydroimidazol-1-yl)piperidin-1-yl)-2-oxoethyl)-9-(2,2,2-trifluoroethyl)-6,7,9,10-tetrahydroazepino[3,4-e]indazol-8 (3H)-one. [4-Chloro-3,6,7,8,9,10-hexahydro-8-oxo-9-(2,2,2-trifluoroethyl)-2,3,9-triaza-(S)-cyclohepta[e]inden-7-yl] acetic acid (84mg, 0.224 mmol) was dissolved in N,N-dimethylformamide (1.5 mL). N,N-Diisopropylethylamine (200 µl, 1.1 mmol) was added to the mixture followed by TBTU (75 mg, 0.224 mmol). 3-(2-Fluorophenyl)-1-(piperidin-4-yl)-1H-imidazol-2(3H)-one hydrochloride (75 mg, 0.252 mmol) was added to the vessel with stirring. Reaction stirred at room temperature for 2 hours. Reaction mixture was purified by reverse phase prep HPLC (acetonitrile-water-ammonium acetate). Major peak was isolated. Acetonitrile was removed from the fractions in vacuo. The mixture was extracted 2 times with ethyl acetate and the aqueous phase was discarded. The material was dried over MgSO4, filtered, and concentrated to dryness. Title compound was obtained as white solid in 59% yield. 1H NMR (500 MHz, DMSO-D6) δ ppm 13.56 (d, J=1.53 Hz, 1H) 8.33 (s, 1H) 7.55 (t, J=7.78 Hz, 1H) 7.35-7.44 (m, 2H) 7.29 (t, J=7.32 Hz, 1H) 7.23 (s, 1H) 6.83 (d, J=5.49 Hz, 1H) 6.77 (s, 1H) 5.43 (d, J=17.09 Hz, 1H) 4.85 (d, J=17.70 Hz, 1H) 4.41-4.67 (m, 2H) 3.88-4.26 (m, 4H) 3.09-3.26 (m, 2H) 3.02 (dd, J=16.33, 8.70 Hz, 1H) 2.80-2.93 (m, 1 H) 2.67 (t, J=11.90 Hz, 1H) 2.38-2.47 (m, 1H) 1.72-1.94 (m, 3H) 1.54-1.70 (m, 1H). High resolution MS m/e (M+H)$^+$=619.1844.

EXAMPLE 7

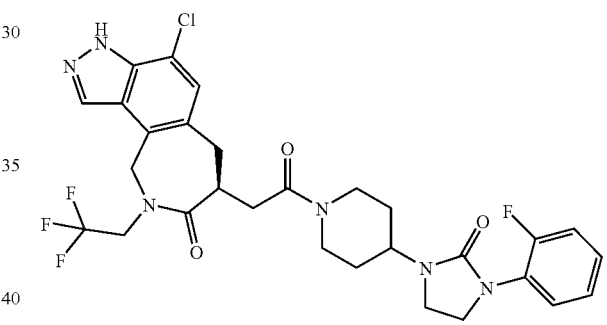

(S)-4-chloro-7-(2-(4-(3-(2-fluorophenyl)-2-oxoimidazolidin-1-yl)piperidin-1-yl)-2-oxoethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (90 mg, 0.24 mmol) was dissolved in N,N-dimethylformamide (1.5 mL). N,N-Diisopropylethylamine (150 µl, 0.86 mmol) was added to the mixture followed by TBTU (82 mg, 0.26 mmol). 1-(2-fluorophenyl)-3-(piperidin-4-yl)imidazolidin-2-one hydrochloride (80.5 mg, 0.27 mmol) was added to the vessel with stirring. Reaction was stirred at room temperature for 3 hours. Reaction was quenched with 50% acetonitrile-water. Mixture was purified by reverse phase prep HPLC (acetonitrile-water-ammonium acetate). Major peak was isolated. Acetonitrile was removed from the fractions in vacuo. Material was extracted from the remaining aqueous mixture twice with ethyl acetate and the aqueous phase was discarded. Organics were dried MgSO4, filtered and then concentrated to dryness. Title compound was obtained as white solid in 44% yield. 1H NMR (500 MHz, DMSO-D6) δ ppm 13.56 (s, 1H) 8.32 (s, 1H) 7.49 (t, J=7.93 Hz, 1H) 7.02-7.37 (m, 4H) 5.43 (d, J=17.09 Hz, 1H) 4.85 (d, J=17.40 Hz, 1H) 4.53-4.64 (m, 1H) 4.49 (d, J=12.51 Hz, 1H) 4.03-4.19 (m, 2H) 3.82-4.00 (m, 2H) 3.76 (t, J=7.78 Hz, 2H) 3.44 (t, J=7.63 Hz, 2H) 3.14 (d, J=14.34 Hz, 2H) 2.94-3.06 (m, 1H)

2.74-2.93 (m, 1H) 2.57-2.71 (m, 1H) 2.32-2.45 (m, 1H) 1.60-1.83 (m, 3H) 1.39-1.55 (m, 1H). High resolution MS m/e (M+H)⁺=621.2000.

EXAMPLE 8

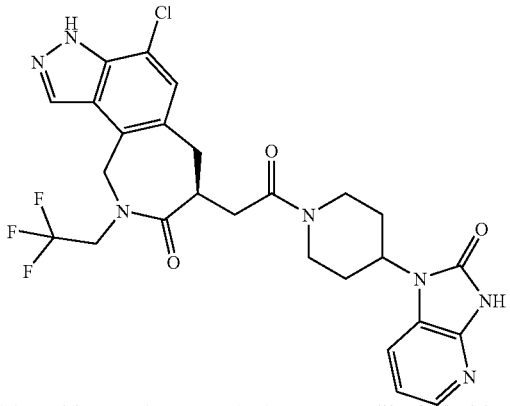

(S)-4-chloro-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (110 mg, 0.293 mmol) was dissolved in N,N-dimethylformamide (1.5 mL). N,N-Diisopropylethylamine (200 µl, 1.148 mmol) was added to the mixture followed by TBTU (104 mg, 0.324 mmol). 1-(Piperidin-4-yl)-1H-imidazo[4,5-b]pyridin-2(3H)-one dihydrochloride (101 mg, 0.347 mmol) was then added to the mixture. Reaction stirred at room temperature for 5 hours. Reaction was quenched with 50% acetonitrile-water. Mixture was purified by reverse phase prep HPLC (acetontrile-water-trifluoroacetic acid). Acetonitrile was removed from the mixture by roto-vap. Remaining aqueous was made basic with aqueous sodium bicarbonate. Material was extracted twice with ethyl acetate. Organics were dried MgSO₄, filtered and then concentrated to dryness. Title compound was obtained as white solid in 41% yield. 1H NMR (500 MHz, DMSO-D6) δ ppm 13.56 (s, 1H) 11.55 (s, 1H) 8.34 (d, J=9.77 Hz, 1H) 7.90 (d, J=5.19 Hz, 1H) 7.66 (dd, J=82.25, 8.09 Hz, 1H) 7.24 (s, 1H) 6.81-7.05 (m, 1H) 5.45 (dd, J=17.85, 5.34 Hz, 1H) 4.87 (dd, J=17.09, 5.49 Hz, 1H) 4.36-4.65 (m, 3H) 3.86-4.26 (m, 3H) 3.13-3.28 (m, 2H) 2.97-3.13 (m, 1H) 2.83-2.96 (m, 1H) 2.61-2.76 (m, 1H) 2.51-2.58 (m, 1H) 2.34-2.48 (m, 1H) 2.00-2.32 (m, 1H) 1.63-1.87 (m, 2H). High resolution MS m/e (M+H)⁺=576.1738.

EXAMPLE 9

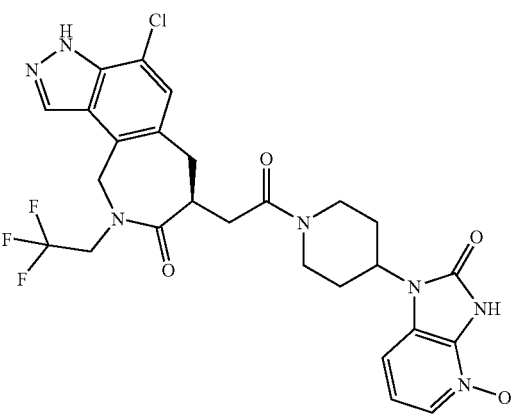

(S)-4-chloro-7-(2-oxo-2-(4-(4-oxy(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (87.3 mg, 0.232 mmol) was dissolved in N,N-dimethylformamide (1.5 mL). N,N-Diisopropylethylamine (120 µl, 0.689 mmol) was added to the mixture followed by TBTU (79.3 mg, 0.247 mmol). 4-Oxy-1-piperidin-4-yl-1,3-dihydro-imidazo[4,5-b]pyridin-2-one hydrochloride (70.5 mg, 0.260 mmol) was added to the mixture. Reaction stirred at room temperature for 4 hours. Reaction was quenched with 50% acetonitrile-water. Material was purified by reverse phase prep HPLC (water-acetonitrile-trifluoroacetic acid). Acetonitrile was removed from the fractions by roto-vap. Solids were filtered from the remaining aqueous. Air was pulled through the filter cake for 1.5 hours. Solids were collected and then dried under high vacuum. Title compound was obtained as white solid. 1H NMR (500 MHz, DMSO-D6) δ ppm 13.55 (s, 1H) 8.34 (d, J=9.46 Hz, 1H) 7.90 (t, J=7.48 Hz, 1H) 7.39 (dd, J=75.84, 8.09 Hz, 1H) 7.23 (s, 1H) 6.90-7.07 (m, 1H) 5.45 (dd, J=16.94, 5.95 Hz, 1H) 4.86 (dd, J=17.55, 6.26 Hz, 1H) 4.36-4.63 (m, 3H) 3.86-4.24 (m, 3H) 3.13-3.27 (m, 2H) 2.96-3.11 (m, 1H) 2.82-2.95 (m, 1H) 2.59-2.76 (m, 1H) 2.17-2.44 (m, 2H) 1.91-2.10 (m, 1H) 1.64-1.88 (m, 2H). High resolution MS m/e (M+H)⁺=592.1707.

EXAMPLE 10

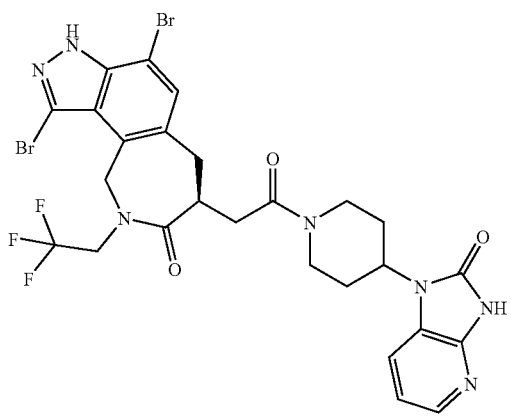

(S)-1,4-dibromo-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one. (S)-2-(1,4-Dibromo-8-oxo-9-(2,2,2-trifluoroethyl)-3,6,7,8,9,10-hexahydroazepino[3,4-e]indazol-7-yl)acetic acid (51 mg, 0.102 mmol) was dissolved in N,N-dimethylformamide (1.5 mL). N,N-Diisopropylethylamine (90 µl, 0.517 mmol) was added to the mixture followed by TBTU (36.1 mg, 0.112 mmol). 1-(Piperidin-4-yl)-1H-imidazo[4,5-b]pyridin-2(3H)-one dihydrochloride (36.5 mg, 0.125 mmol) was added to the mixture. Reaction stirred at room temperature for 2.5 hours. Reaction was quenched with 50% acetonitrile-water. Mixture was purified by reverse phase prep HPLC (acetonitrile-water-trifluoroacetic acid). Acetonitrile was removed from the fraction by roto-vap. Remaining aqueous was made basic with aqueous sodium bicarbonate. Material was extracted twice with ethyl acetate. Organics were dried MgSO₄, filtered and then concentrated to dryness. Title compound was obtained as white solid in 34% yield. 1H NMR (500 MHz, DMSO-D6) δ ppm 13.92 (s, 1H) 11.56 (d, J=6.41 Hz, 1H) 7.90 (d, J=5.19 Hz, 1H 7.65 (dd, J=69.89, 7.93 Hz, 1H) 7.49 (s, 1H) 6.81-7.06 (m, 1H) 5.54-5.68 (m, 1H) 5.35-5.50 (m, 1H) 4.49-4.63 (m, 1H) 4.32-4.42 (m, 1H) 4.20-4.49 (m, 1H) 4.13-4.20 (m, 1H) 3.93-4.14 (m, 1H) 3.22 (d, J=16.17 Hz, 2H) 2.97-3.12 (m, 1H) 2.86-2.97 (m, 1H) 2.67-2.79 (m, 1H) 2.52-2.66 (m, 1H) 2.42-2.48 (m, J=17.09 Hz, 1H) 2.34-2.42 (m, 1H) 1.93-2.32 (m, 1H) 1.74-1.85 (m, 1H) 1.65-1.74 (m, 1H). High resolution MS m/e (M+H)⁺=698.0314.

EXAMPLE 11

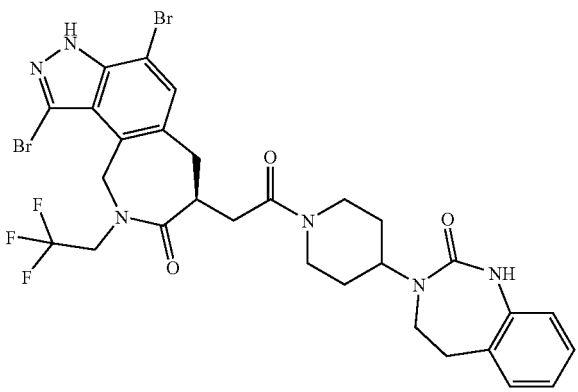

(S)-1,4-dibromo-7-(2-oxo-2-(4-(2-oxo-1,2,4,5-tetrahydrobenzo[d][1,3]diazepin-3-yl)piperidin-1-yl)ethyl)-9-(2,2,2-trifluoroethyl)-6,7,9,10-tetrahydroazepino[3,4-e]indazol-8(3H)-one. (S)-2-(1,4-Dibromo-8-oxo-9-(2,2,2-trifluoroethyl)-3,6,7,8,9,10-hexahydroazepino [3,4-e]indazol-7-yl)acetic acid (52 mg, 0.104 mmol) was dissolved in N,N-dimethylformamide (1.5 mL). N,N-Diisopropylethylamine (70 µl, 0.402 mmol) was added to the mixture followed by TBTU (34.8 mg, 0.108 mmol). 3-(Piperidin-4-yl)-4,5-dihydro-1H-benzo[d][1,3]diazepin-2(3H)-one (35.4 mg, 0.144 mmol) was then added to the mixture. Reaction stirred at room temperature for 1 hour. Reaction was quenched with 50% acetonitrile-water. Material was purified by reverse phase prep HPLC (acetonitrile-water-trifluoroacetic acid). Acetonitrile was removed from the fractions by roto-vap. Remaining aqueous was made basic with aqueous sodium bicarbonate. Material was extracted twice with ethyl acetate. Organics were dried MgSO$_4$, filtered and then concentrated to dryness. Title compound was obtained as white solid in 67% yield. 1H NMR (500 MHz, DMSO-D6) δ ppm 13.92 (s, 1H) 8.51 (s, 1H) 7.48 (s, 1H) 6.98-7.08 (m, 3H) 6.76-6.86 (m, 1H) 5.58 (d, J=17.40 Hz, 1H) 5.39 (d, J=17.09 Hz, 1H) 4.49 (d, J=13.12 Hz, 1H) 4.26-4.42 (m, 2H) 4.10-4.24 (m, 1H) 3.90-4.09 (m, 2H) 3.33-3.41 (m, 2H) 3.19 (d, J=16.79 Hz, 1H) 3.05-3.15 (m, 1 H) 2.95-3.02 (m, 1H) 2.83-2.94 (m, 3H) 2.53-2.65 (m, 1H) 2.33-2.46 (m, 1H) 1.58-1.85 (m, 3H) 1.40-1.57 (m, 1H). High resolution MS m/e (M+H)$^+$=725.0720.

EXAMPLE 12

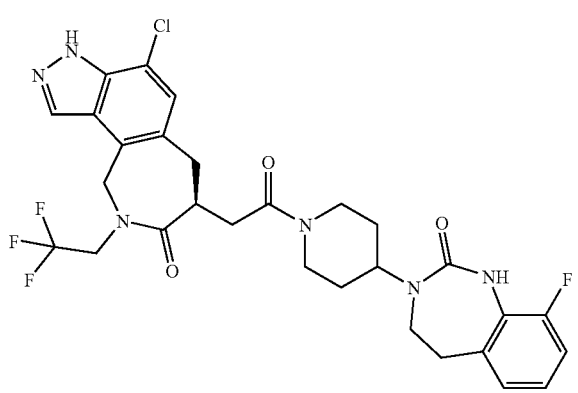

(S)-4-chloro-7-(2-(4-(9-fluoro-2-oxo-1,2,4,5-tetrahydrobenzo[d][1,3]diazepin-3-yl)piperidin-1-yl)-2-oxoethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (76 mg, 0.202 mmol) was dissolved in N,N-dimethylformamide (4.0 mL). N,N-Diisopropylethylamine (0.035 mL, 0.202 mmol) was added to the mixture followed by TBTU (64.9 mg, 0.202 mmol). 9-Fluoro-3-(piperidin-4-yl)-4,5-dihydro-1H-benzo[d][1,3]diazepin-2(3H)-one hydrochloride (60.6 mg, 0.202 mmol) was then added to the mixture. Reaction stirred at room temperature for 2 hours. Reaction was quenched with 50% acetonitrile-water. Mixture was purified by reverse phase prep HPLC (acetonitrile-water-trifluoroacetic acid). Acetonitrile was removed from the fractions by roto-vap. Remaining aqueous was made basic with aqueous sodium bicarbonate. Material was extracted twice with ethyl acetate. Organics were dried MgSO$_4$, filtered and then concentrated to dryness. Title compound was obtained as tan solid in 47% yield. 1H NMR (500 MHz, DMSO-D6) δ ppm 13.56 (s, 1H) 8.32 (s, 1H) 7.37 (d, J=4.88 Hz, 1H) 7.23 (s, 1H) 7.00-7.10 (m, 1H) 6.90-6.97 (m, 1H) 6.82-6.90 (m, 1H) 5.43 (d, J=17.40 Hz, 1 H) 4.85 (d, J=17.09 Hz, 1H) 4.52-4.66 (m, 1H) 4.41-4.52 (m, 1H) 4.19-4.32 (m, 1H) 4.00-4.15 (m, 2H) 3.86-3.99 (m, 1H) 3.39-3.48 (m, 2H) 3.06-3.20 (m, 2 H) 2.92-3.05 (m, 3H) 2.79-2.92 (m, 1H) 2.53-2.66 (m, 1H) 2.34-2.46 (m, 1H) 1.61-1.87 (m, 3H) 1.44-1.59 (m, 1H). High resolution MS m/e (M+H)$^+$=621.2015.

EXAMPLE 13

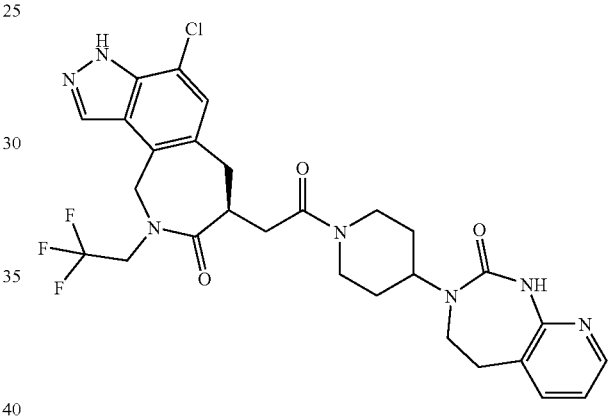

(S)-4-chloro-7-(2-oxo-2-(4-(2-oxo-1,2,4,5-tetrahydropyrido[2,3-d][1,3]diazepin-3-yl)piperidin-1-yl)ethyl)-9-(2,2,2-trifluoroethyl)-6,7,9,10-tetrahydroazepino[3,4-e]indazol-8 (3H)-one. [4-Chloro-3,6,7,8,9,10-hexahydro-8-oxo-9-(2,2,2-trifluoroethyl)-2,3,9-triaza-(S)-cyclohepta[e]inden-7-yl] acetic acid (78.3 mg, 0.208 mmol) was dissolved in N,N-dimethylformamide (1.5 mL). N,N-Diisopropylethylamine (120 µl, 0.689 mmol) was added to the mixture followed by TBTU (70.3 mg, 0.219 mmol). 3-(Piperidin-4-yl)-4,5-dihydro-1H-pyrido[2,3-d][1,3]diazepin-2(3H)-one dihydrochloride (71.0 mg, 0.222 mmol) was added to the mixture. Reaction stirred at room temperature for 2 hours. Reaction was quenched with 50% acetonitrile-water. Material was purified by reverse phase prep HPLC (water-acetonitrile 0.1% trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO$_4$, filtered and then concentrated to dryness. Title compound was obtained as white solid in 49% yield. 1H NMR (500 MHz, DMSO-D6) δ ppm 13.54 (s, 1H) 8.32 (s, 1H) 8.19 (s, 1H) 8.07 (d, J=4.58 Hz, 1H) 7.49 (d, J=5.80 Hz, 1H) 7.23 (s, 1H) 6.90 (dd, J=7.32, 4.88 Hz, 1H) 5.43 (d, J=18.01 Hz, 1H) 4.85 (d, J=17.40 Hz, 1H) 4.41-4.66 (m, 2H) 4.22-4.39 (m,1H) 3.99-4.16 (m, 2H) 3.83-3.98 (m, 1H) 3.42 (d, J=3.66 Hz, 2H) 3.06-3.17 (m, 2H) 2.93-3.05 (m, 1H)

2.77-2.93 (m, 3H) 2.53-2.67 (m, 1H) 2.31-2.44(m,1H) 1.57-1.87 (m, 3H) 1.39-1.57 (m, 1H). High resolution MS m/e (M+H)⁻=604.2070.

EXAMPLE 14

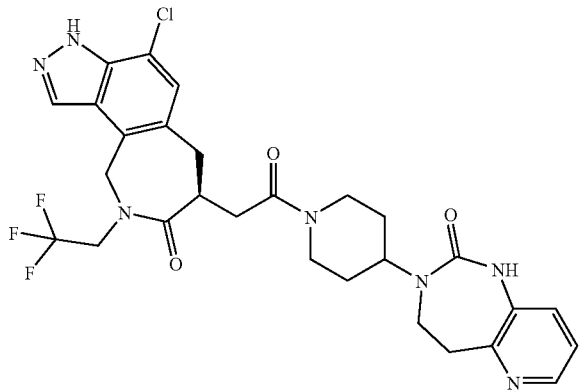

(S)-4-chloro-7-(2-oxo-2-(4-(2-oxo-1,2,4,5-tetrahydropyrido[3,2-d][1,3]diazepin-3-yl)piperidin-1-yl)ethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl] acetic acid (63.2 mg, 0.168 mmol) was dissolved in N,N-dimethylformamide (1.5 mL). N,N-Diisopropylethylamine (120 µl, 0.689 mmol) was added to the mixture followed by TBTU (57.5 mg, 0.179 mmol). 3-(Piperidin-4-yl)-4,5-dihydro-1H-pyrido[3,2-d][1,3]diazepin-2(3H)-one dihydrochloride (59.6 mg, 0.187 mmol) was added to the mixture. Reaction stirred at room temperature for 2 hours. Reaction was quenched with 50% acetonitrile-water. Material was purified by reverse phase prep HPLC (water-acetonitrile-trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO₄, filtered and then concentrated to dryness. Title compound was obtained as white solid in 39% yield. 1H NMR (500 MHz, DMSO-D6) δ ppm 13.54 (s, 1H) 8.61 (s, 1H) 8.32 (s, 1H) 8.03 (d, J=4.27 Hz, 1H) 7.42 (d, J=8.24 Hz, 1H) 7.23 (s, 1H) 7.11 (dd, J=8.24, 4.58 Hz, 1H) 5.43 (d, J=17.40 Hz, 1 H) 4.85 (d, J=17.09 Hz, 1H) 4.42-4.63 (m, 2H) 4.25-4.38 (m, 1H) 3.84-4.19 (m, 3H) 3.39-3.49 (m, 2H) 3.06-3.21 (m, 2H) 2.94-3.06 (m, 3H) 2.80-2.93 (m, 1H) 2.52-2.67 (m, 1H) 2.32-2.48 (m, 1H) 1.60-1.87 (m, 3H) 1.41-1.60 (m, 1H). High resolution MS m/e (M+H)⁺=604.2064.

EXAMPLE 15

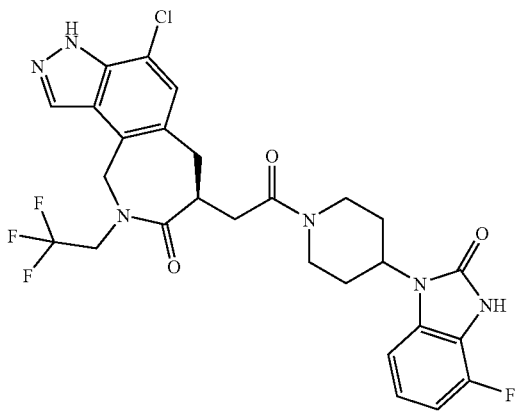

(S)-4-chloro-7-(2-(4-(4-fluoro-2-oxo-2,3-dihydrobenzo[d]imidazol-1-yl)piperidin-1-yl)-2-oxoethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl] acetic acid (65.7 mg, 0.175 mmol) was dissolved in N,N-dimethylformamide (1.5 mL). N,N-Diisopropylethylamine (120 µl, 0.689 mmol) was added to the mixture followed by TBTU (59.1 mg, 0.184 mmol). Fluoro-1-(piperidin-4-yl)-1H-benzo[d]imidazol-2(3H)-one hydrochloride (54.3 mg, 0.200 mmol) was added to the mixture. Reaction stirred at room temperature for 4 hours. Reaction was quenched with 50% acetonitrile-water. Material was purified by reverse phase prep HPLC (water-acetonitrile-trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO₄, filtered and then concentrated to dryness. Title compound was obtained as white solid in 61% yield. 1H NMR (500 MHz, DMSO-D6) δ ppm 13.54 (s, 1H) 11.41 (s, 1H) 8.33 (d, J=7.02 Hz, 1H) 7.24 (s, 1H) 7.20 (dd, J=81.18, 7.63 Hz, 1H) 6.80-7.05 (m, 2H) 5.45 (d, J=17.09 Hz, 1H) 4.86 (dd, J=17.24, 4.12 Hz, 1H) 4.37-4.69 (m, 3H) 3.85-4.28 (m, 3H) 3.13-3.27 (m, 2H) 2.96-3.13 (m, 1H) 2.81-2.95 (m, 1H) 2.69 (q, J=12.31 Hz, 1H) 2.51-2.58 (m, 1 H) 2.24-2.44 (m, 1H) 2.01-2.21 (m, 1H) 1.59-1.88 (m, 2H). High resolution MS m/e (M+H)⁺=593.1716.

EXAMPLE 16

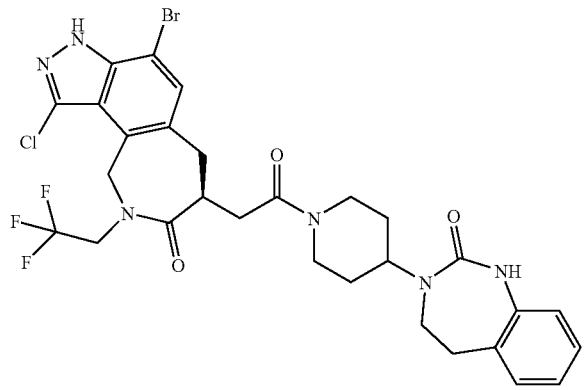

(S)-4-bromo-1-chloro-7-(2-oxo-2-(4-(2-oxo-1,2,4,5-tetrahydrobenzo[d][1,3]diazepin-3-yl)piperidin-1-yl)ethyl)-9-(2,2,2-trifluoroethyl)-6,7,9,10-tetrahydroazepino[3,4-e]indazol-8(3H)-one. (S)-2-(4-Bromo-1-chloro-9-neopentyl-8-oxo-3,6,7,8,9,10-hexahydroazepino[3,4-e]indazol-7-yl) acetic acid (73 mg, 0.161 mmol) was dissolved in N,N-dimethylformamide (1.5 ml). N,N-Diisopropylethylamine (100 µL, 0.574 mmol) was added to the mixture followed by TBTU (54.7 mg, 0.170 mmol). 3-(Piperidin-4-yl)-4,5-dihydro-1H-benzo[d][1,3]diazepin-2(3H)-one (50.0 mg, 0.204 mmol) was added to the mixture. Reaction stirred at room temperature for 2.5 hours. Reaction was quenched with 50% acetonitrile-water. Material was purified by reverse phase prep HPLC (water-acetonitrile-trifluoroacetic acid). Acetonitrile was removed from the fractions by roto-vap. Residue was treated with aqueous sodium bicarbonate. Material was extracted twice with ethyl acetate and the organic phase was discarded. Mixture was held at room temperature open to the air overnight. Solids were filtered off, washed with ethyl acetate and then dried in vacuo. Title compound was obtained as white solid in 23% yield. 1H NMR (500 MHz, DMSO-D6) δ ppm 13.76 (s, 1H) 8.48 (s, 1 H) 7.45 (s, 1H) 6.99-7.07 (m, 3H) 6.76-6.84 (m, 1H) 5.33-5.49 (m, 2H) 4.49 (d, J=12.21 Hz, 1H) 4.33-4.43 (m, 1H) 4.26-4.33 (m, 1H) 4.11-4.23 (m, 1H) 4.02-4.10 (m, 1H) 3.92-4.00 (m, 1H) 3.34-3.40 (m, 2H) 3.19 (d, J=17.70 Hz, 1H) 3.06-3.15 (m, 1H) 2.94-3.03 (m, 1H) 2.82-2.93 (m, 3H) 2.53-2.66 (m, 1H) 2.33-2.46 (m, 1H) 1.58-1.85 (m, 3H) 1.44-1.57 (m, 1H). High resolution MS m/e (M+H)$^+$=681.1219.

EXAMPLE 17

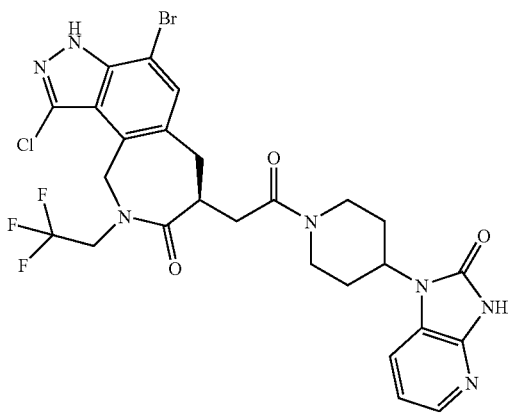

(S)-4-bromo-1-chloro-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one. (S)-2-(4-Bromo-1-chloro-9-neopentyl-8-oxo-3,6,7,8,9,10-hexahydroazepino[3,4-e]indazol-7-yl)acetic acid (125 mg, 0.275 mmol) was dissolved in N,N-dimethylformamide (3.0 ml). N,N-Diisopropylethylamine (150 μl, 0.861 mmol) was added to the mixture followed by TBTU (93.4 mg, 0.291 mmol). 1-(Piperidin-4-yl)-1H-imidazo[4,5-b]pyridin-2(3H)-one dihydrochloride (93.8 mg, 0.322 mmol) was added to the mixture. Reaction was stirred at room temperature for 4.0 hours. Reaction was quenched with 50% acetonitrile-water. Mixture was purified by reverse phase prep HPLC (water-acetonitrile-trifluoroacetic acid). Acetonitrile was removed from the fractions by roto-vap. Residue was treated with aqueous sodium bicarbonate. Material was extracted twice with ethyl acetate and the aqueous phase was discarded. Organics were dried MgSO$_4$, filtered and then concentrated to dryness. Title compound was obtained as white solid in 61% yield. 1H NMR (500 MHz, DMSO-D6) δ ppm 13.77 (s, 1H) 11.54 (s, 1H) 7.90 (d, J=4.27 Hz, 1H) 7.71 (d, J=8.24 Hz, 0.6H) 7.57 (d, J=7.63 Hz, 0.4H) 7.49 (s, 1H) 6.99 (dd, J=7.63, 5.49 Hz, 0.4H) 6.90 (dd, J=7.78, 5.34 Hz, 0.6H) 5.43 (d, J=4.27 Hz, 2H) 4.36-4.61 (m, 3H) 3.95-4.32 (m, 3H) 3.22 (dd, J=17.24, 3.51 Hz, 2H) 2.97-3.12 (m, 1H) 2.87-2.97 (m, 1H) 2.61-2.77 (m, 1H) 2.17-2.45 (m, 2H) 1.92-2.14 (m, 1H) 1.64-1.87 (m, 2H). High resolution MS m/e (M+H)$^+$=654.0853.

EXAMPLE 18

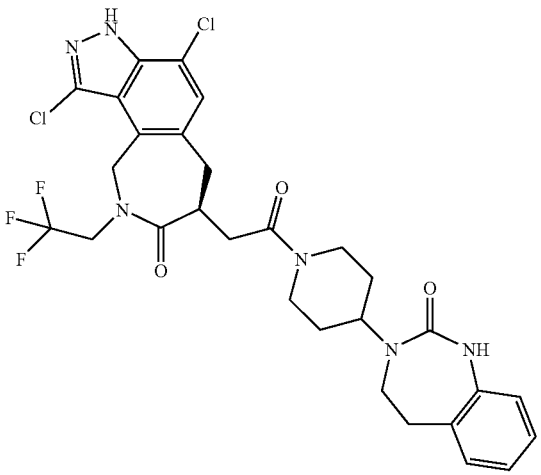

(S)-1,4-dichloro-7-(2-oxo-2-(4-(2-oxo-1,2,4,5-tetrahydrobenzo[d][1,3]diazepin-3-yl)piperidin-1-yl)ethyl)-9-(2,2,2-trifluoroethyl)-6,7,9,10-tetrahydroazepino[3,4-e]indazol-8(3H)-one. (S)-2-(1,4-Dichloro-8-oxo-9-(2,2,2-trifluoroethyl)-3,6,7,8,9,10-hexahydroazepino[3,4-e]indazol-7-yl)acetic acid(95 mg, 0.232 mmol) was dissolved in N,N-dimethylformamide (2.0 ml). TBTU (79 mg, 0.246 mmol) was added to the mixture followed by 3-(piperidin-4-yl)-4,5-dihydro-1H-benzo[d][1,3]diazepin-2(3H)-one (72 mg, 0.293 mmol) and then N,N-diisopropylethylamine (150 μl, 0.861 mmol). Reaction stirred at room temperature for 4 hours. Reaction was quenched with 50% acetonitrile-water. Material was purified by reverse phase prep HPLC (water-acetonitrile-trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO$_4$, filtered and then concentrated to dryness. Title compound was obtained as white solid in 59% yield. 1H NMR (500 MHz, DMSO-D6) δ ppm 13.88 (s, 1H) 8.49 (s, 1 H) 7.35 (s, 1H) 7.00-7.09 (m, 3H) 6.70-6.87 (m, 1H) 5.42 (s, 2H) 4.49 (d, J=12.51 Hz, 1H) 4.36-4.45 (m, 1H) 4.25-4.36 (m, 1H) 4.11-4.24 (m, 1H) 3.91-4.10 (m, 2H) 3.34-3.41 (m, 2H) 3.19 (d, J=18.01 Hz, 1H) 3.05-3.15 (m, 1H) 2.93-3.03 (m, 1H) 2.83-2.93 (m, 3H) 2.53-2.65 (m, 1H) 2.32-2.47 (m, 1H) 1.57-1.87 (m, 3H) 1.44-1.57 (m, 1H). High resolution MS m/e (M+H)$^-$=637.1735.

EXAMPLE 19

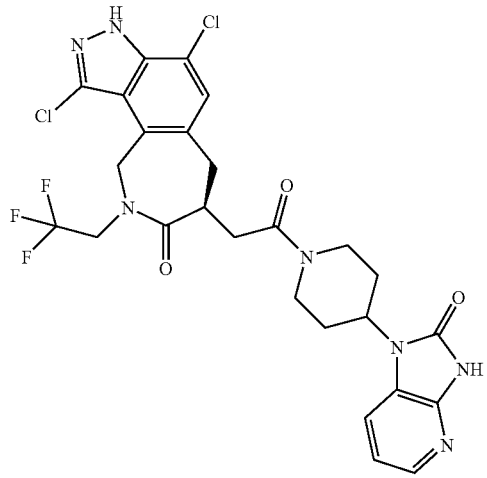

(S)-1,4-dichloro-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one. (S)-2-(1,4-Dichloro-8-oxo-9-(2,2,2-trifluoroethyl)-3,6,7,8,9,10-hexahydroazepino[3,4-e]indazol-7-yl)acetic acid (110 mg, 0.268 mmol) was dissolved in N,N-dimethylformamide (2.0 ml). N,N-Diisopropylethylamine (150 µl, 0.861 mmol) was added to the mixture followed successively by TBTU (92 mg, 0.287 mmol) and 1-(piperidin-4-yl)-1H-imidazo[4,5-b]pyridin-2(3H)-one dihydrochloride (92 mg, 0.316 mmol). Reaction stirred at room temperature for 5 hours. Reaction was quenched with 50% acetonitrile-water. Material was purified by prep HPLC (water-acetonitrile-trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO$_4$, filtered and then concentrated to dryness. Title compound was obtained as white solid in 70% yield. 1H NMR (500 MHz, DMSO-D6) δ ppm 13.89 (s, 1H) 11.55 (s, 1H) 7.90 (dd, J=5.19, 1.22 Hz, 1 H) 7.64 (dd, J=70.19, 7.93 Hz, 1H) 7.35 (s, 1H) 6.99 (dd, J=7.78, 5.34 Hz, 0.4H) 6.90 (dd, J=7.93, 5.19 Hz, 0.6H) 5.44 (d, J=4.88 Hz, 2H) 4.35-4.62 (m, 3H) 3.95-4.32 (m, 3H) 3.15-3.28 (m, 2H) 2.85-3.12 (m, 2H) 2.61-2.76 (m, 1H) 2.20-2.47 (m, 2H) 1.93-2.12 (m, 1H) 1.64-1.87 (m, 2H). High resolution MS m/e (M+H)$^+$=610.1328.

EXAMPLE 20

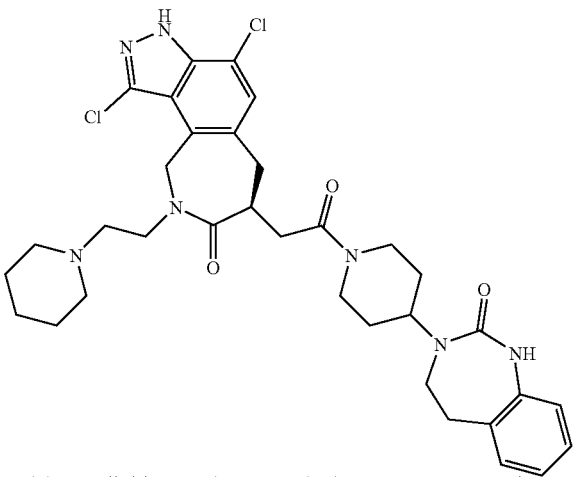

(S)-1,4-dichloro-7-(2-oxo-2-(4-(2-oxo-1,2,4,5-tetrahydrobenzo[d][1,3]diazepin-3-yl)piperidin-1-yl)ethyl)-9-(2-(piperidin-1-yl)ethyl)-6,7,9,10-tetrahydroazepino[3,4-e]indazol-8(3H)-one. (S)-2-(1,4-Dichloro-8-oxo-9-(2-(piperidin-1-yl)ethyl)-3,6,7,8,9,10-hexahydroazepino[3,4-e]indazol-7-yl)acetic acid (54 mg, 0.123 mmol) was dissolved in N,N-dimethylformamide (1.5 ml). N,N-Diisopropylethylamine (100 µL, 0.574 mmol) was added to the mixture followed successively by TBTU (42 mg, 0.131 mmol) and then 3-(piperidin-4-yl)-4,5-dihydro-1H-benzo[d][1,3]diazepin-2(3H)-one (43 mg, 0.175 mmol). Reaction stirred at room temperature for 4 hours. Reaction was quenched with 50% acetonitrile-water. Material was purified by reverse phase prep HPLC (water-acetonitrile-trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO$_4$, filtered and then concentrated to dryness. Title compound was obtained as white solid in 54% yield. 1H NMR (500 MHz, DMSO-D6) δ ppm 13.85 (s, 1H) 8.50 (s, 1H) 7.32 (s, 1H) 6.96-7.11 (m, 3H) 6.80 (s, 1H) 5.26 (s, 2H) 4.44-4.54 (m, 1H) 4.27-4.37 (m, 1H) 4.06 (d, J=14.04 Hz, 1H) 3.79-3.96 (m, 2H) 3.34-3.44 (m, 2H) 3.05-3.25 (m, 3H) 2.82-3.02 (m, 4H) 2.45-2.66 (m, 2H) 2.28-2.40 (m, 1H) 2.04-2.26 (m, 4H) 1.80-1.95 (m, 2H) 1.58-1.73 (m, 2H) 1.40-1.57 (m, 1H) 1.18 (bs, 6H). High resolution MS m/e (M+H)$^+$=666.2756.

EXAMPLE 21

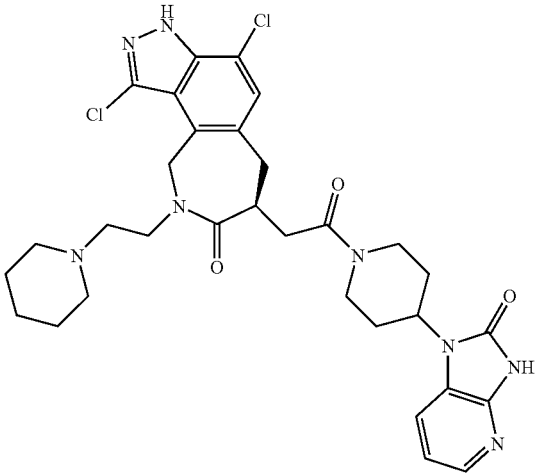

(S)-1,4-dichloro-7-(2-oxo-2-(4-(2-oxo-2,3-dihydroimidazo[4,5-b]pyridin-1-yl)piperidin-1-yl)ethyl)-9-(2-(piperidin-1-yl)ethyl)-6,7,9,10-tetrahydroazepino[3,4-e]indazol-8(3H)-one. (S)-2-(1,4-dichloro-8-oxo-9-(2-(piperidin-1-yl)ethyl)-3,6,7,8,9,10-hexahydroazepino[3,4-e]indazol-7-yl) acetic acid (74 mg, 0.168 mmol) was dissolved in N,N-dimethylformamide (2.0 ml). N,N-Diisopropylethylamine (120 µl, 0.689 mmol) was added to the mixture followed successively by TBTU (58 mg, 0.181 mmol) and 1-(piperidin-4-yl)-1H-imidazo[4,5-b]pyridin-2(3H)-one dihydrochloride (58 mg, 0.199 mmol). Reaction stirred at room temperature for 5 hours. Reaction was quenched with 50% acetonitrile-water. Material was purified by reverse phase prep HPLC (water-acetonitrile-trifluoroacetic acid). Acetonitrile was removed from the fractions by roto-vap. Remaining aqueous was made basic with aqueous sodium bicarbonate. Material was extracted twice with ethyl acetate and the aqueous phase was discarded. Organics were dried MgSO$_4$, filtered and then concentrated to dryness. Title compound was obtained as white solid in 71% yield. 1H NMR (500 MHz, DMSO-D6) δ ppm 13.86 (s, 1H) 11.55 (s, 1H) 7.90 (s, 1H) 7.84 (d, J=7.63 Hz, 0.6H) 7.59 (d, J=8.24 Hz, 0.4H) 7.33 (s, 1H) 6.84-7.06 (m, 1 H) 5.22-5.36 (m, 2H) 4.40-4.64 (m, 2H) 4.16 (t, J=14.65 Hz, 1H) 3.80-4.02 (m, 2H) 3.12-3.29(m,3H) 2.95-3.09(m, 1H) 2.84-2.96(m, 1H) 2.62-2.78(m, 1 H) 2.53-2.60 (m, 1H) 2.39-2.49 (m, 1H) 2.01-2.33 (m, 5H) 1.62-1.98 (m, 4H) 1.09-1.22 (m, 6H). High resolution MS m/e (M+H)$^+$= 639.2393.

EXAMPLE 22

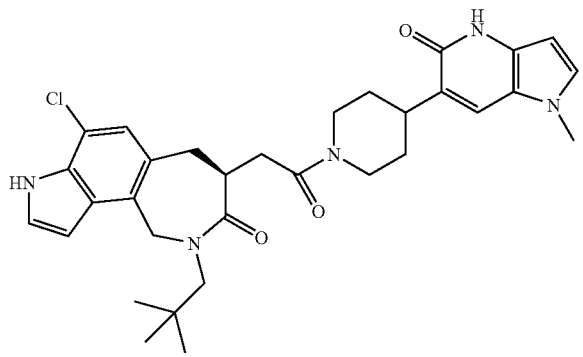

(S)-7-chloro-4-(2-(4-(1-methyl-5-oxo-4,5-dihydro-1H-pyrrolo[3,2-b]pyridin-6-yl)piperidin-1-yl)-2-oxoethyl)-2-neopentyl-1,2,4,5-tetrahydroazepino[3,4-e]indol-3(8H)-one. To a mixture of 1-methyl-6-(piperidin-4-yl)-1H-pyrrolo[3,2-b]pyridin-5(4H)-one (41 mg, 0.177 mmol), (S)-2-(4-chloro-9-neopentyl-8-oxo-3,6,7,8,9,10-hexahydroazepino[3,4-e]indazol-7-yl)acetic acid (64.5 mg, 0.177 mmol), HOBT (26.3 mg, 0.195 mmol) and EDC (37.4 mg, 0.195 mmol) in DMF (2 mL) was added diisopropylethylamine (108 µl, 0.620 mmol) at rt. The resulting mixture was stirred at rt over night, most of the solvent was removed under $N_2$, the residue was purified on reverse phase PrepHPLC to afford a grey gum which was triturated with $Et_2O$ (2 mL), filtered and washed with $Et_2O$ (2×0.5 mL) to afford the expected product, (S)-7-chloro-4-(2-(4-(1-methyl-5-oxo-4,5-dihydro-1H-pyrrolo [3,2-b]pyridin-6-yl)piperidin-1-yl)-2-oxoethyl)-2-neopentyl-1,2,4,5-tetrahydroazepino[3,4-e]indol-3(8H)-one (32 mg grey solid. Mass spec: 577.30 (MH+) calc. for $C_{31}H_{37}ClN_6O_3$ 576.26.

EXAMPLE 23

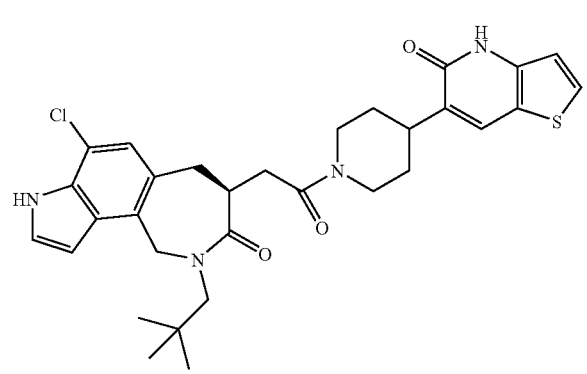

(S)-6-(1-(2-(7-chloro-2-neopentyl-3-oxo-1,2,3,4,5,8-hexahydroazepino[3,4-e]indol-4-yl)acetyl)piperidin-4-yl)thieno[3,2-b]pyridin-5(4H)-one. To a solution of (S)-2-(4-chloro-9-neopentyl-8-oxo-3,6,7,8,9,10-hexahydroazepino [3,4-e]indazol-7-yl)acetic acid (123 mg, 0.338 mmol), 6-(piperidin-4-yl)thieno[3,2-b]pyridin-5(4H)-one (79 mg, 0.338 mmol), HOBT (56.9 mg, 0.372 mmol), EDC (71.3 mg, 0.372 mmol) in DMF (5 mL) was added DIEA (0.295 mL, 1.690 mmol) at rt, and the mixture was stirred over night. Partial of the solvent was removed under $N_2$ at 60° C., and the residue was purified on reverse phase PrepHPLC to afford the expected product, (S)-6-(1-(2-(7-chloro-2-neopentyl-3-oxo-1,2,3,4,5,8-hexahydroazepino [3,4-e]indol-4-yl)acetyl)piperidin-4-yl)thieno[3,2-b]pyridin-5(4H)-one (113 mg, 57.6%) as a white solid. $^1$H-NMR (400 MHz, CHLOROFORM-D) δ ppm 0.80 (d, J=6.80 Hz, 11 H) 1.52 (ddd, J=12.46, 8.06, 4.41 Hz, 1H) 1.87-1.96 (m, 1H) 2.00 (s, 1H) 2.38-2.49 (m, 1H) 2.75 (td, J=12.84, 2.01 Hz, 1H) 2.94-3.04 (m, 1H) 3.07-3.18 (m, 4 H) 3.66 (dd, J=13.60, 2.77 Hz, 1H) 3.96-4.06 (m, 1H) 4.23 (s, 1H) 4.61-4.72 (m, 2H) 5.51 (d, J=17.37 Hz, 1H) 7.04 (dd, J=5.29, 2.01 Hz, 1H) 7.22 (s, 1H) 7.70 (dd, J=5.41, 2.14 Hz, 1H) 7.89 (d, J=18.38 Hz, 1H) 8.24 (s, 1H); Mass spec. 580.25 (MH$^+$), Calc. for $C_{30}H_{34}ClN_5O_3S$ 579.21.

EXAMPLES 24 AND 25

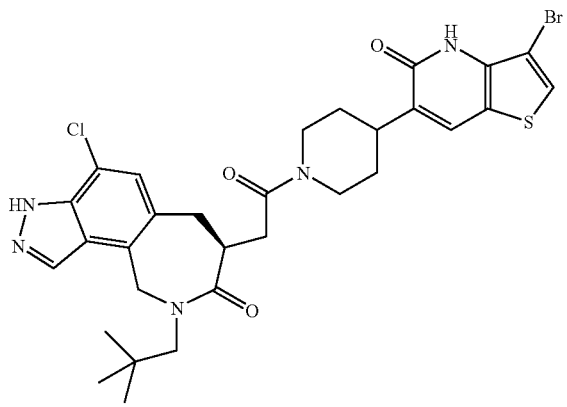

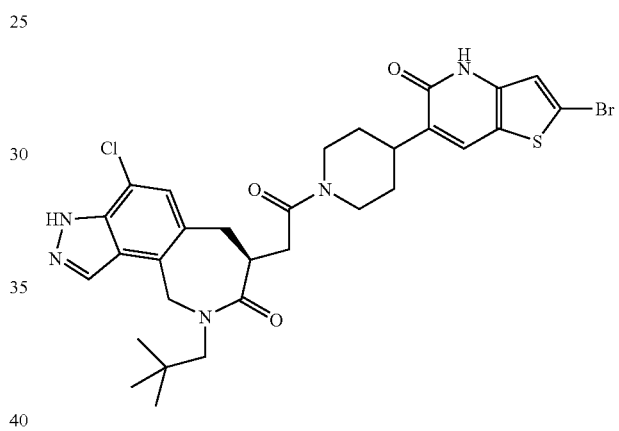

(S)-3-bromo-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one and (S)-2-bromo-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one. To a 10 mL vial was charged with (S)-2-(4-chloro-9-neopentyl-8-oxo-3,6,7,8,9,10-hexahydroazepino[3,4-e]indazol-7-yl)acetic acid (43.4 mg, 0.119 mmol), 2-bromo-6-(piperidin-4-yl)thieno[3,2-b]pyridin-5(4H)-one and 3-bromo-6-(piperidin-4-yl)thieno[3,2-b]pyridin-5(4H)-one (37.4 mg, 0.119 mmol), EDC (25.2 mg, 0.131 mmol), HOBT (20.11 mg, 0.131 mmol) and DMF (2 mL) respectively at rt, followed by DIEA (0.083 mL, 0.478 mmol). The resulting mixture was stirred at rt over night, most of the solvent was removed under $N_2$, and the residue was purified on reverse phase PrepHPLC to afford the expected products, an unseperable mixture of (S)-3-bromo-6-(1-(2-(4-chloro-9-neopentyl-8-oxo-3,6,7,8,9,10-hexahydroazepino [3,4-e]indazol-7-yl)acetyl)piperidin-4-yl)thieno[3,2-b]pyridin-5(4H)-one and (S)-2-bromo-6-(1-(2-(4-chloro-9-neopentyl-8-oxo-3,6,7,8,9,10-hexahydroazepino[3,4-e] indazol-7-yl)acetyl)piperidin-4-yl)thieno[3,2-b]pyridin-5 (4H)-one (31.2 mg, 39%). Mass spec. 658.11 (MH+), calc. for $C_{30}H_{33}BrClN_5O_3S$ 657.12.

EXAMPLES 26 AND 27

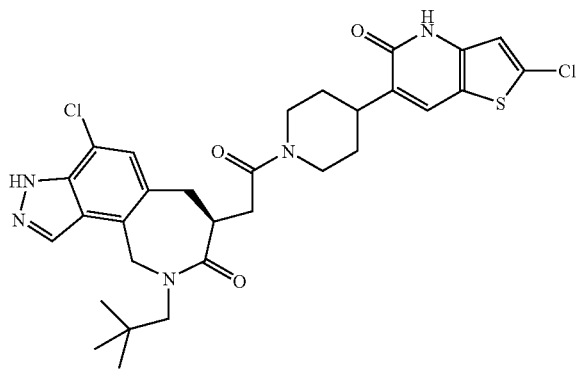

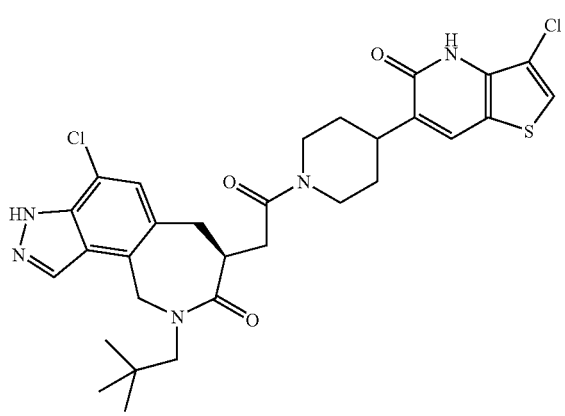

(S)-2-chloro-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one and (S)-3-chloro-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one. To 2-chloro-6-(piperidin-4-yl)thieno[3,2-b]pyridin-5(4H)-one and 3-chloro-6-(piperidin-4-yl)thieno[3,2-b]pyridin-5(4H)-one (3.0 mg, 0.011 mmol) were added (S)-2-(7-chloro-2-neopentyl-3-oxo-1,2,3,4,5,8-hexahydroazepino[3,4-e]indol-4-yl)acetic acid (4.6 mg, 0.011 mmol), EDC (2.247 mg, 0.012 mmol), HOBT (1.795 mg, 0.012 mmol), DMF (1.5 ml) at rt, followed by diisopropylethylamine (0.012 ml, 0.067 mmol). The resulting mixture was stirred at rt for 6 hr, checked with LC/MS: conversion was compleated. Partial of the solvent was removed under $N_2$, the residue was purified on reverse phase PrepHPLC to afford the expected products (2.3 mg), an unseperable mixture of (S)-2-chloro-6-(1-(2-(4-chloro-9-neopentyl-8-oxo-3,6,7,8,9,10-hexahydroazepino [3,4-e]indazol-7-yl)acetyl)piperidin-4-yl)thieno[3,2-b]pyridin-5 (4H)-one and (S)-3-chloro-6-(1-(2-(4-chloro-9-neopentyl-8-oxo-3,6,7,8,9,10-hexahydroazepino [3,4-e]indazol-7-yl) acetyl)piperidin-4-yl)thieno[3,2-b]pyridin-5(4H)-one, as a white solid. Mass spec 614.27 (MH+) calc for $C_{30}H_{33}Cl_2N_5O_3S$ 613.17.

EXAMPLE 28

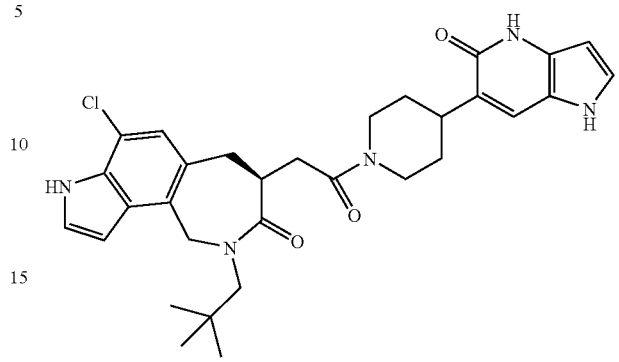

(S)-7-chloro-2-neopentyl-4-(2-oxo-2-(4-(5-oxo-4,5-dihydro-1H-pyrrolo[3,2-b]pyridin-6-yl)piperidin-1-yl)ethyl)-1,2,4,5-tetrahydroazepino[3,4-e]indol-3(8H)-one. To 6-(piperidin-4-yl)-1H-pyrrolo[3,2-b]pyridin-5(4H)-one (60.0 mg, 0.276 mmol) was added (S)-2-(7-chloro-2-neopentyl-3-oxo-1,2,3,4,5,8-hexahydroazepino[3,4-e]indol-4-yl) acetic acid (100 mg, 0.276 mmol), EDC (58.3 mg, 0.304 mmol), HOBT (41.0 mg, 0.304 mmol), DMF (2.0 ml) at rt, followed by diisopropylethylamine (0.192 ml, 1.10 mmol). The resulting mixture was stirred at rt over night, partial of the solvent was removed under $N_2$, and the residue was purified on reverse phase PrepHPLC to afford the expected products(25.2 mg, 16%), (S)-7-chloro-2-neopentyl-4-(2-oxo-2-(4-(5-oxo-4,5-dihydro-1H-pyrrolo [3,2-b]pyridin-6-yl)piperidin-1-yl) ethyl)-1,2,4,5-tetrahydroazepino [3,4-e]indol-3 (8H)-one, as a tan solid. $^1$H-NMR (400 MHz, MeOD) d 0.79 (d, J=5.29 Hz, 11H) 1.52-1.62 (m, 1H) 1.81 (s, 1H) 2.38-2.49 (m, 1H) 2.75 (s, 1H) 3.01 (d, J=13.35 Hz, 1H) 3.09-3.21 (m, 4H) 3.66 (d, J=13.85 Hz, 1H) 3.96 (s, 3H) 3.99-4.06 (m, 1H) 4.24 (s, 1H) 4.65 (d, J=17.37 Hz, 2H) 5.46-5.55 (m, 1H) 6.27 (dd, J=5.29, 3.02 Hz, 1H) 7.22 (s, 1H) 7.36 (dd, J=7.81, 3.02 Hz, 1H) 8.24 (s, 1H); Mass spec 562.48 (MH+) calc for $C_{31}H_{36}ClN_5O_3$ 561.25.

EXAMPLE 29

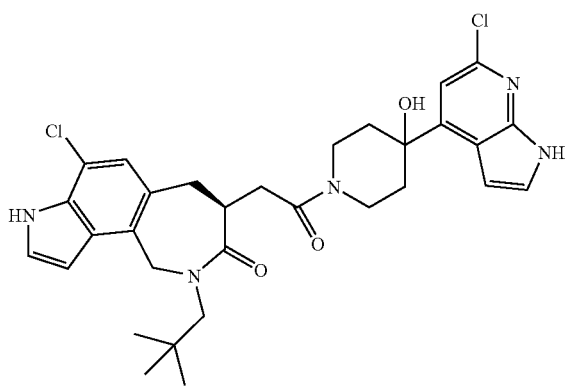

(S)-7-chloro-4-(2-(4-(6-chloro-1H-pyrrolo[2,3-b]pyridin-4-yl)-4-hydroxypiperidin-1-yl)-2-oxoethyl)-2-neopentyl-1,2,4,5-tetrahydroazepino[3,4-e]indol-3 (8H)-one. To 4-(6-chloro-1H-pyrrolo[2,3-b]pyridin-4-yl)piperidin-4-ol (69 mg, 0.304 mmol) in DMF (2 mL) was added (S)-2-(7-chloro-2-neopentyl-3-oxo-1,2,3,4,5,8-hexahydroazepino[3,4-e]indol-4-yl)acetic acid (100 mg, 0.276 mmol), EDC (58.3 mg, 0.304 mmol), HOBT (41.0 mg, 0.304 mmol), at rt, followed by diisopropylethylamine (0.192 ml, 1.10 mmol). The mixture was stirred at rt over night, partial of the solvent was removed under $N_2$, the residue was purified on reverse phase PrepH-PLC to afford the expected product, (S)-7-chloro-4-(2-(4-(6-chloro-1H-pyrrolo[2,3-b]pyridin-4-yl)-4-hydroxypiperidin-1-yl)-2-oxoethyl)-2-neopentyl-1,2,4,5-tetrahydroazepino[3,4-e]indol-3(8H)-one (126 mg, 57%) as a tan solid. $^1$H-NMR (400 MHz, MeOD) δ ppm 0.78-0.84 (m, 11H) 1.73 (s, 1H) 1.76-1.83 (m, 1H) 2.25-2.36 (m, 2H) 2.66-2.76 (m, 1H) 3.03 (d, J=13.35 Hz, 1H) 3.09-3.20 (m, 4H) 3.62-3.73 (m, 2H) 4.08 (d, J=12.84 Hz, 2H) 4.51 (d, J=10.83 Hz, 1H) 4.65 (d, J=17.12 Hz, 1H) 5.51 (d, J=17.12 Hz, 1H) 6.99 (d, J=3.53 Hz, 1H) 7.20-7.24 (m, 2H) 7.26-7.29 (m, 2H) 8.24 (s, 1H); Mass spec. 596.47 (MH+) calc. for $C_{31}H_{35}Cl_2N_5O_3$ 595.21.

EXAMPLE 30

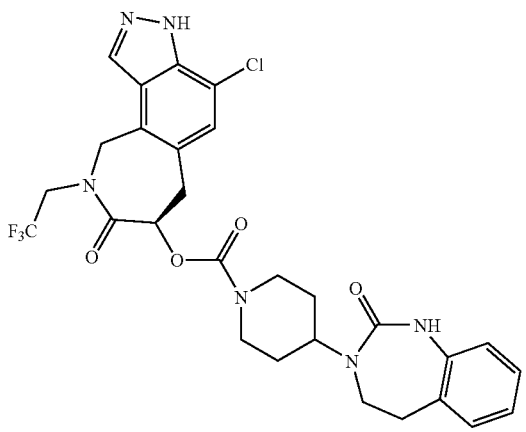

(R)-4-chloro-8-oxo-9-(2,2,2-trifluoroethyl)-3,6,7,8,9,10-hexahydroazepino[3,4-e]indazol-7-yl 4-(2-oxo-4,5-dihydro-1H-benzo[d][1,3]diazepin-3(2H)-yl)piperidine-1-carboxylate. (R)-4-chloro-8-oxo-9-(2,2,2-trifluoroethyl)-3,6,7,8,9,10-hexahydroazepino [3,4-e]indazol-7-yl 4-nitrophenyl carbonate (60 mg, 0.120 mmol) in dichloromethane (15 mL) was added 3-(piperidin-4-yl)-4,5-dihydro-1H-benzo[d][1,3]diazepin-2(3H)-one (32.5 mg, 0.132 mmol). The reaction mixture was stirred for 2 h. LC-MS analysis suggested formation of product ($R_f$=2.473, 605.22 (M+H)). The reaction mixture was washed with aqueous $NaHCO_3$ followed by 1.0 M HCl. THe crude product was purified by flash chromatography using 5% MeOH in dichloromethane to give (R)-4-chloro-8-oxo-9-(2,2,2-trifluoroethyl)-3,6,7,8,9,10-hexahydroazepino [3,4-e]indazol-7-yl 4-(2-oxo-4,5-dihydro-1H-benzo[d][1,3]diazepin-3 (2H)-yl)piperidine-1-carboxylate (29.00 mg, 0.048 mmol, 40% yield). $^1$H NMR (500 MHz, $CD_3OD$): in δ 8.30 (s, 1H), 7.32 (s, 1H), 7.09 (m, 3H), 6.93-6.87 (m, 3H), 6.09-6.05 (m, 1H), 5.50 (s, 2H), 5.44 (m, 1H), 4.68-4.54 (m, 1H), 4.39-4.35 (m, 2H), 4.32-4.19 (m, 1H), 4.16-4.05 (m, 3H), 3.55-3.50 (m, 3H), 3.12-2.92 (m, 2H), 1.87-1.74 (m, 4H); MS (ESI) 605 (M+H); $R_f$=2.47.

EXAMPLE 31

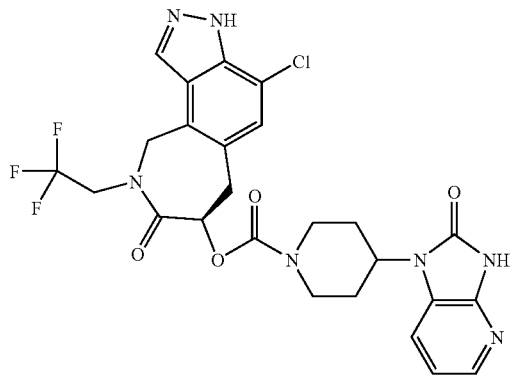

(R)-4-chloro-8-oxo-9-(2,2,2-trifluoroethyl)-3,6,7,8,9,10-hexahydroazepino[3,4-e]indazol-7-yl 4-(2-oxo-2,3-dihydro-1H-imidazo[4,5-b]pyridin-1-yl)piperidine-1-carboxylate. (R)-4-chloro-8-oxo-9-(2,2,2-trifluoroethyl)-3,6,7,8,9,10-hexahydroazepino[3,4-e]indazol-7-yl 4-nitrophenyl carbonate (115 mg, 0.23 mmol) in DMF (10.00 mL, 129 mmol) was added triethylamine (0.128 mL, 0.920 mmol) followed by 1-(piperidin-4-yl)-1H-imidazo[4,5-b]pyridin-2(3H)-one, 1.00HCl (70.3 mg, 0.276 mmol). After 12 h, the solvent was removed and the product was purified by flash chromatography using 5% methanol in dichloromethane to give (R)-4-chloro-8-oxo-9-(2,2,2-trifluoroethyl)-3,6,7,8,9,10-hexahydroazepino[3,4-e]indazol-7-yl 4-(2-oxo-2,3-dihydro-1H-imidazo[4,5-b]pyridin-1-yl)piperidine-1-carboxylate (106 mg, 0.183 mmol, 80% yield). $^1$H NMR (500 MHz, $CD_3OD$): in δ 8.29 (s, 1H), 8.03 (br, 1H), 7.96 (d, J=5.5 Hz, 1H), 7.71 (m, 1H), 7.27 (s, 1H), 7.13-7.12 (m, 1H), 6.10 (m, 1H), 5.44 (d, J=17 Hz, 1H), 4.88 (d, J=17 Hz, 1H), 4.72-4.60 (m, 2H), 4.50-4.39 (m, 1H), 4.38-4.22 (m, 1H), 4.21-4.02 (m, 1H), 3.40-3.40 (m, 1H), 3.39-3.27 (m, 2H), 3.23-2.97 (m, 2H), 2.71-2.23 (m, 2H), 1.95-1.74 (m, 2H); MS (ESI) 578 (M+H); $R_f$=2.15.

EXAMPLE 32

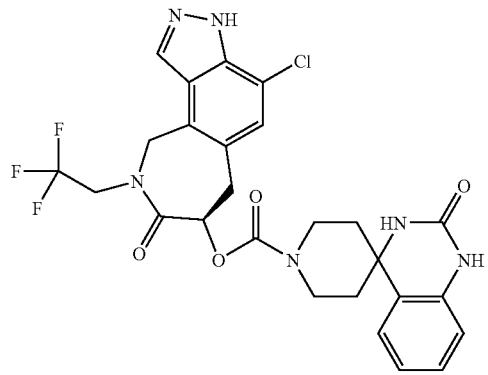

(S)-4-chloro-7-(2-oxo-2-(2'-oxo-2',3'-dihydro-1'H-spiro [piperidine-4,4'-quinazoline]-1-yl)ethyl)-9-(2,2,2-trifluoroethyl)-6,7,9,10-tetrahydroazepino[3,4-e]indazol-8(3H)-one. To a solution of (S)-2-(4-chloro-8-oxo-9-(2,2,2-trifluoroethyl)-3,6,7,8,9,10-hexahydroazepino[3,4-e]indazol-7-yl)acetic acid (50 mg, 0.133 mmol) in dichloromethane (25 mL) was added 1'H-spiro[piperidine-4,4'-quinazolin]-2'(3'H)-one (31 mg, 0.14 mmol) followed by 2-(1H-benzotriazol-1-yl)-1,1,3,3-tetramethyluronium tetrafluoroborate (47 mg, 0.15 mmol) and triethylamine (1.0 mL). After 12 h, the reaction mixture was washed with aqueous NaHCO$_3$ followed by 1.0 M HCl and dried (Na$_2$SO$_4$). The solvent was removed and the crude product was purified by flash chromatography using 7% MeOH in dichloromethane to give (S)-4-chloro-7-(2-oxo-2-(2'-oxo-2',3'-dihydro-1'H-spiro[piperidine-4,4'-quinazoline]-1-yl)ethyl)-9-(2,2,2-trifluoroethyl)-6,7,9,10-tetrahydroazepino[3,4-e]indazol-8(3H)-one (61 mg, 79%) as a white powder. MS (ESI) 575 (M+H); R$_f$=2.133.

EXAMPLE 33

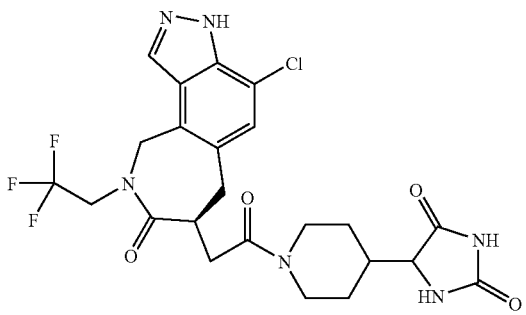

5-(1-(2-((S)-4-chloro-8-oxo-9-(2,2,2-trifluoroethyl)-3,6,7,8,9,10-hexahydroazepino[3,4-e]indazol-7-yl)acetyl)piperidin-4-yl)imidazolidine-2,4-dione. To a solution of (S)-2-(4-chloro-8-oxo-9-(2,2,2-trifluoroethyl)-3,6,7,8,9,10-hexahydroazepino[3,4-e]indazol-7-yl)acetic acid (50 mg, 0.133 mmol) in DMF (2.0 mL) was added 5-(piperidin-4-yl)imidazolidine-2,4-dione (37 mg, 0.2 mmol) followed by 2-(1H-benzotriazol-1-yl)-1,1,3,3-tetramethyluronium tetrafluoroborate (47 mg, 0.15 mmol) and triethylamine (1.0 mL). After 2 h, the solvent was removed under reduced pressure and the crude product was purified by Prep HPLC to give 5-(1-(2-((S)-4-chloro-8-oxo-9-(2,2,2-trifluoroethyl)-3,6,7,8,9,10-hexahydroazepino[3,4-e]indazol-7-yl)acetyl)piperidin-4-yl)imidazolidine-2,4-dione (30 mg) in 42% yield. $^1$H NMR (500 MHz, CD$_3$OD): in δ 8.27 (s, 1H), 7.21 (s, 1H), 5.54 (d, J=17 Hz, 1H), 4.82 (d, J=17 Hz, 1H), 4.69-4.54 (m, 1H), 4.18-3.95 (m, 4H), 3.30-2.96 (m, 4H), 2.71-2.62 (m, 1H), 2.58-2.48 (m, 1H), 2.21-2.12 (m, 1H), 1.91-1.84 (m, 2H), 1.66-1.31 (m, 2H); MS (ESI) 541 (M+H); R$_f$=2.05.

EXAMPLE 34

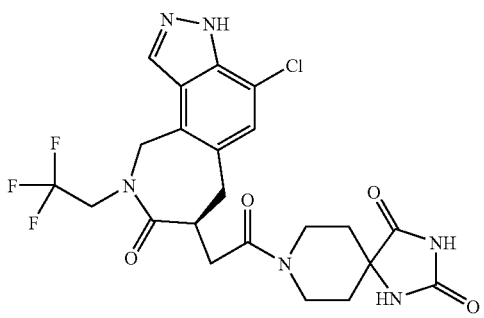

(S)-8-(2-(4-chloro-8-oxo-9-(2,2,2-trifluoroethyl)-3,6,7,8,9,10-hexahydroazepino[3,4-e]indazol-7-yl)acetyl)-1,3,8-triazaspiro[4.5]decane-2,4-dione. To a solution of (S)-2-(4-chloro-8-oxo-9-(2,2,2-trifluoroethyl)-3,6,7,8,9,10-hexahydroazepino[3,4-e]indazol-7-yl)acetic acid (50 mg, 0.133 mmol) in DMF (2.0 mL) were added 1,3,8-triazaspiro[4.5]decane-2,4-dione (34 mg, 0.2 mmol) followed by 2-(1H-benzotriazol-1-yl)-1,1,3,3-tetramethyluronium tetrafluoroborate (47 mg, 0.15 mmol) and triethylamine (1.0 mL). After 2 h, the solvent was removed under reduced pressure and the crude product was purified by PrepHPLC to give (S)-8-(2-(4-chloro-8-oxo-9-(2,2,2-trifluoroethyl)-3,6,7,8,9,10-hexahydroazepino[3,4-e]indazol-7-yl)acetyl)-1,3,8-triazaspiro[4.5]decane-2,4-dione (32 mg) in 46% yield. MS (ESI) 527 (M+H); R$_f$=1.66.

EXAMPLE 35

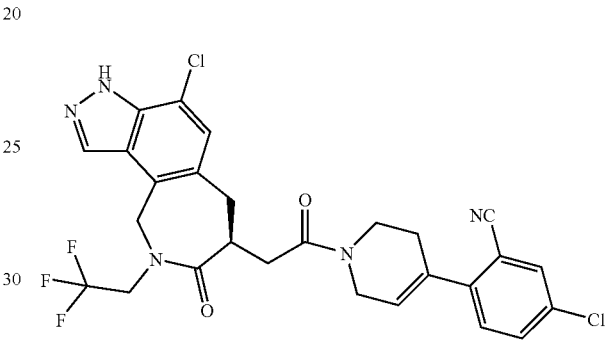

(S)-5-chloro-2-(1-(2-(4-chloro-8-oxo-9-(2,2,2-trifluoroethyl)-3,6,7,8,9,10-hexahydroazepino[3,4-e]indazol-7-yl)acetyl)-1,2,3,6-tetrahydropyridin-4-yl)benzonitrile. In an oven-dried round bottom flask, (S)-2-(4-chloro-8-oxo-9-(2,2,2-trifluoroethyl)-3,6,7,8,9,10-hexahydroazepino[3,4-e]indazol-7-yl)acetic acid (50 mg, 0.133 mmol) and 5-chloro-2-(1,2,3,6-tetrahydropyridin-4-yl)benzonitrile (44.1 mg, 0.173 mmol) were dissolved in DMF (2 ml). To this solution was added DIEA (0.093 ml, 0.532 mmol) followed by PyBOP (69.3 mg, 0.133 mmol). The reaction mixture was allowed to stir at room temperature under a nitrogen atmosphere for 3 hours during which time it became dark red in color. The DMF was evaporated under high vacuum. The residue was subjected to column chromatography (silica, 20:1 CH$_2$Cl$_2$/2M NH$_3$ in MeOH). The most pure fractions were collected, evaporated and again subjected to column chromatography (silica, 40:1 CH$_2$Cl$_2$/2M NH$_3$ in MeOH). The fractions were collected, evaporated and dried overnight under vacuum to give (S)-5-chloro-2-(1-(2-(4-chloro-8-oxo-9-(2,2,2-trifluoroethyl)-3,6,7,8,9,10-hexahydroazepino[3,4-e]indazol-7-yl)acetyl)-1,2,3,6-tetrahydropyridin-4-yl)benzonitrile (40 mg, 0.069 mmol, 52.1% yield) as a light tan solid. $^1$H NMR (500 MHz, MeOD) δ ppm 1.24-1.34 (m, 1H) 2.50-2.60 (m, 3H) 2.60-2.76 (m, 2H) 2.95-3.05 (m, 1H) 3.14-3.23 (m, 2H) 3.82-3.91 (m, 1H) 3.90-4.02 (m, 1H) 4.05-4.14 (m, 1H) 4.53-4.62 (m, 2H) 5.54 (d, J=17.4 Hz, 1H) 6.07 (d, J=13.7 Hz, 1H) 7.21 (s, 1H) 7.46 (d, J=8.3 Hz, 1H) 7.64 (d, J =8.5 Hz, 1H) 7.78 (s, 1H) 8.24 (s, 1H); MS (ESI): 575 (M-1H); R$_f$=1.90 (4 min run).

EXAMPLE 36

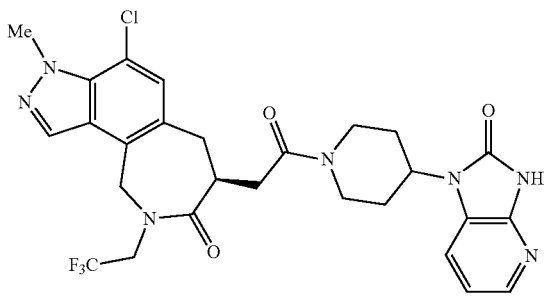

(S)-4-Chloro-3-methyl-7-(2-oxo-2-(4-(2-oxo-2,3-dihydro-1H-imidazo[4,5-b]pyridine-1-yl)piperidin-1-yl)ethyl)-9-(2,2,2-trifluoroethyl)-6,7,9,10-tetrahydroazepino[3,4-e]indazol-8(3H)-one. This material was isolated as a white solid in 47% yield: $^1$HNMR (500 MHz, DMSO-$d_6$) δ ppm 11.6 (br s, 1H), 8.29 (s, 0.6H), 8.27 (s, 0.4H), 5.43 (d, J=17.0 Hz, 1H), 4.88 (d, J=17.0 Hz, 1H), 4.58 (m, 3H), 4.47 (m, 0.6H), 4.30 (s, 3H), 4.13 (m, 2H), 4.04 (2H), 4.00 (m, 0.4H), 3.15 (m, 2H), 2.89 (m, 1H), 2.71 (m, 1H), 2.40 (m, 1H), 2.28 (m, 0.6H), 2.05 (m, 0.4H), 1.79 (m, 1H), 1.70 (m, 1H). LC/MS: single peak @ 2.35 min, (M+H)=590.

EXAMPLE 37

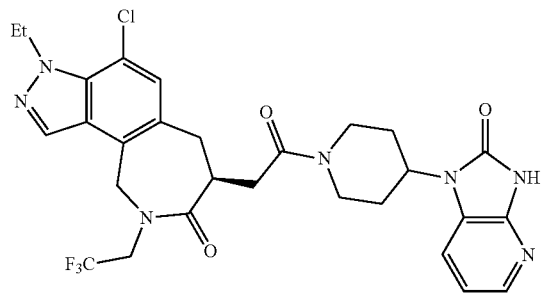

(S)-4-Chloro-3-ethyl-7-(2-oxo-2-(4-(2-oxo-2,3-dihydro-1H-imidazo[4,5-b]pyridine-1-yl)piperidin-1-yl)ethyl)-9-(2,2,2-trifluoroethyl)-6,7,9,10-tetrahydroazepino[3,4-e]indazol-8(3H)-one. This compound was isolated as a creamy white solid in 32% yield: $^1$HNMR (500 MHz, DMSO-$d_6$) δ ppm 11.6 (br s, 1H), 8.35 (s, 0.6H), 8.33 (s, 0.4H), 7.90 (m, 1H), 7.40 (d, J=7.5 Hz, 0.6H), 7.59 (d, J=8.5 Hz, 0.4H), 7.27 (s, 1H), 6.99 (m, 0.4H), 6.87 (m, 0.6H), 5.45 (d, J=17.5 Hz, 1H), 4.88 (d, J=17.5 Hz, 1H), 4.72 (m, 2H), 4.57 (m, 3H), 4.49 (m, 0.6H), 4.12 (m, 2H), 4.05 (m, 1H), 3.99 (m, 0.4H), 3.15 (m, 2H), 2.90 (m, 2H), 2.65 (m, 1H), 2.40 (m, 1H), 2.29 (m, 0.6H), 2.10 (m, 0.4H), 1.75 (m, 2H), 1.40 (t, J=7.5 Hz, 3H). LC/MS: single peak @ 2.45 min, (M+H)=604.

EXAMPLE 38

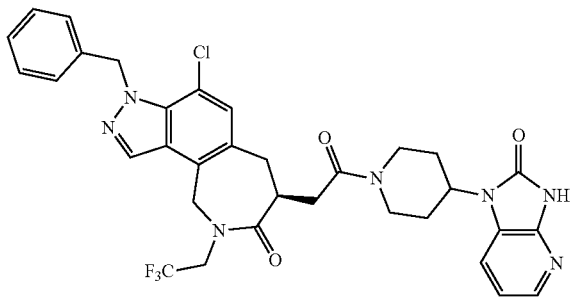

(S)-3-Benzyl-4-chloro-7-(2-oxo-2-(4-(2-oxo-2,3-dihydro-1H-imidazo[4,5-b]pyridine-1-yl)piperidin-1-yl)ethyl)-9-(2,2,2-trifluoroethyl)-6,7,9,10-tetrahydroazepino[3,4-e]indazol-8(3H)-one. This compound was isolated in 24% yield as a white solid: $^1$HNMR (500 MHz, DMSO-$d_6$) δ ppm 11.6 (br s, 1H), 8.45 (s, 0.6H), 8.43 (s, 0.4H), 7.79 (m, 1H), 7.51 (m, 0.6H), 7.31 (m, 0.4H), 7.25 (m, 3H), 7.09 (m, 2H), 6.77 (m, 0.4H), 6.70 (m, 0.6H), 5.96 (d, J=16.5 Hz, 1H), 5.88 (d, J=16.5 Hz, 1H), 5.47 (d, J=16.5 Hz, 1H), 4.93 (d, J=16.5 Hz, 1H), 4.55 (m, 3H), 4.45 (m, 0.6H), 4.16 (m, 2H), 4.05 (m, 1.4H), 3.35 (m, 2H), 3.20 (m, 2H), 3.05 (m, 2H), 2.89 (m, 1H), 2.65 (m, 1H), 2.45 (m, 1H), 2.25 (m, 0.6H), 2.00 (m, 1.4H), 1.70 (m, 2H). LC/MS: single peak @ 2.62 min, (M+H)=666.

EXAMPLE 39

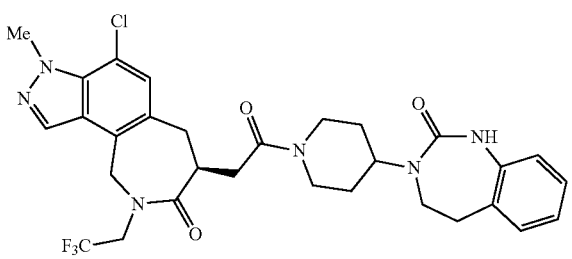

(S)-4-Chloro-3-methyl-7-(2-oxo-2-(4-(2-oxo-4,5-dihydro-1H-benzo[d][1,3]diazepin-3(2H)-yl)piperidin-1-yl)ethyl)-9-(2,2,2-trifluoroethyl)-6,7,9,10-tetrahydroazepino[3,4-e]indazol-8(3H)-one. This compound was isolated as a colorless solid in 72% yield: $^1$HNMR (500 MHz, DMSO-$d_6$) δ ppm 8.52 (s, 1H), 8.29 (s, 1H), 7.24 (s, 1H), 7.05 (s, 1H), 7.04 (m, 1H), 6.82 (m, 1H), 5.40 (d, J=17.0 Hz, 1H), 4.85 (d, J=17.0 Hz, 1H), 4.58 (m, 1H), 4.48 (m, 1H), 4.30 (s, 3H), 4.06 (m, 1H), 3.95 (m, 1H), 3.38 (m, 2H), 3.14 (m, 2H), 3.00 (m, 1H), 2.89 (m, 3H), 2.58 (m, 1H), 2.42 (m, 1H) 1.67 (m, 3H), 1.50 (m, 1H). LC/MS: single peak @ 2.44 min, (M+H) =617.

EXAMPLE 40

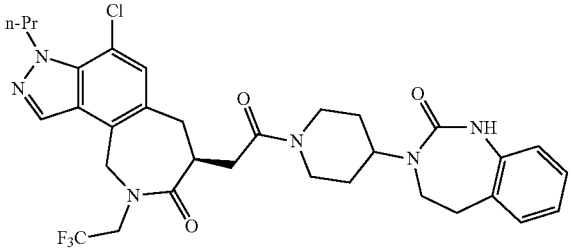

(S)-4-Chloro-3-propyl-7-(2-oxo-2-(4-(2-oxo-4,5-dihydro-1H-benzo[d][1,3]diazepin-3(2H)-yl)piperidin-1-yl)ethyl)-9-(2,2,2-trifluoroethyl)-6,7,9,10-tetrahydroazepino[3,4-e]indazol-8(3H)-one. This compound was isolatd in a 26% yield as a colorless, white solid: $^1$HNMR (500 MHz, DMSO-$d_6$) δ ppm 8.51 (s, 1H), 8.33 (s, 1H), 7.25 (s, 1H), 7.05 (s, 1H), 7.04 (m, 1H), 6.82 (m, 1H), 5.40 (d, J=17.0 Hz, 1H), 4.89 (d, J=17.0 Hz, 1H), 4.65 (m, 2H), 4.55 (m, 1H), 4.35 (m, 1H), 4.10 (m, 2H), 3.95 (m, 1H), 3.38 (m, 2H), 3.14 (m, 2H), 3.00 (m, 1H), 2.89 (m, 3H), 2.58 (m, 1H), 2.42 (m, 1H), 1.75 (m, 2H), 1.67 (m, 2H), 1.50 (m, 1H), 0.84 (t, J=7.0 Hz, 3H). LC/MS: single peak @ 2.77 min, (M+H)=645.

EXAMPLE 41

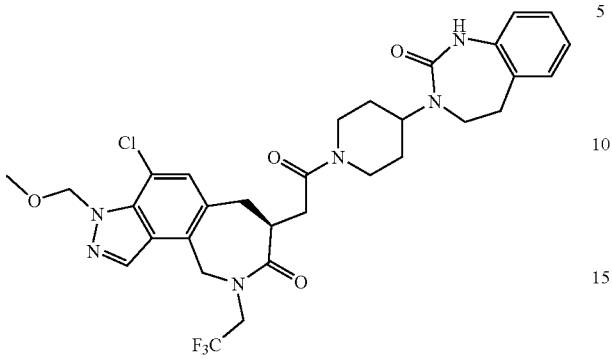

(S)-4-chloro-3-(methoxymethyl)-7-(2-oxo-2-(4-(2-oxo-4,5-dihydro-1H-benzo[d][1,3]diazepin-3(2H)-yl)piperidin-1-yl)ethyl)-9-(2,2,2-trifluoroethyl)-6,7,9,10-tetrahydroazepino[3,4-e]indazol-8(3H)-one. This compound was obtained in 26% yield as a colorless solid. $^1$H NMR (500 MHz, MeOD) δ ppm 1.71 (d, J=12.21 Hz, 2H) 1.84 (d, J=4.27 Hz, 2H) 2.03 (s, 1H) 2.48-2.65 (m, 1H) 2.68-2.75 (m, 1H) 2.88-2.93 (m, 1H) 2.98-3.06 (m, 4H) 3.15-3.23 (m, 3H) 3.26 (s, 1 H) 3.50-3.58 (m, 2H) 4.03-4.12 (m, 2H) 4.22 (s, 1H) 4.47 (s, 1H) 4.60-4.69 (m, 2H) 5.54-5.61 (m, 1H) 5.98 (q, J=11.19 Hz, 2H) 6.88-6.95 (m, 2H) 7.06-7.12 (m, 2H) 7.33 (s, 1H) 8.33 (d, J=1.83 Hz, 1H); Mass spec. 647.12 (M+H) Calc. for $C_{31}H_{34}ClF_3N_6O_4$ 646.23.

EXAMPLE 42

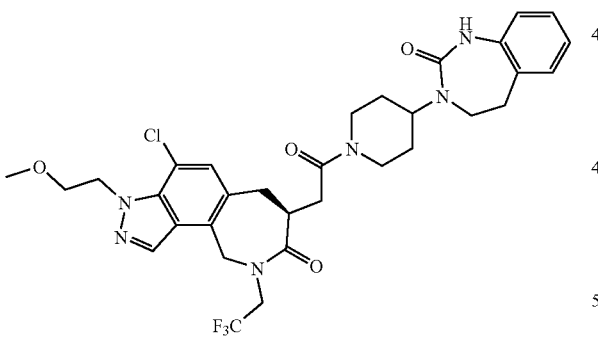

(S)-4-chloro-3-(2-methoxyethyl)-7-(2-oxo-2-(4-(2-oxo-4,5-dihydro-1H-benzo[d][1,3]diazepin-3(2H)-yl)piperidin-1-yl)ethyl)-9-(2,2,2-trifluoroethyl)-6,7,9,10-tetrahydroazepino[3,4-e]indazol-8(3H)-one. This compound was isolated as a white solid in 64.4% yield. $^1$H NMR (400 MHz, MeOD.) δ ppm 1.70 (d, J=14.86 Hz, 2H) 1.81 (s, 2H) 1.94-2.05 (m, 1H) 2.41-2.51 (m, 1H) 2.67 (s, 1 H) 2.97 (d, J=9.57 Hz, 4H) 3.10-3.22 (m, 4H) 3.45-3.55 (m, 3H) 3.80 (t, J=5.79 Hz, 2H) 4.01 (d, J=6.30 Hz, 2H) 4.18 (s, 1H) 4.43 (s, 1H) 4.56 (dd, J=15.36, 9.57 Hz, 2H) 4.88-4.94 (m, 2H) 5.49 (s, 1H) 6.83-6.91 (m, 2H) 7.06 (t, J=8.18 Hz, 2H) 7.19-7.25 (m, 1H) 8.23 (d, J=1.51 Hz, 1H); Mass psec. 661.14 (M+H) Calc. for $C_{32}H_{36}ClF_3N_6O_4$ 660.24.

What is claimed is:

1. A compound of Formula I

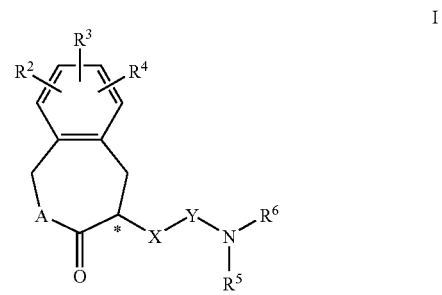

where:

A is O or $NR^1$;

$R^1$ is alkyl, alkenyl, cycloalkyl, $C_{5-7}$cycloalkenyl, (cycloalkyl)alkyl, haloalkyl, alkoxyalkyl, $(Ar^1)$alkyl, $(NR^7R^8)$alkyl, N—$(R^9)$-pyrrolidinyl or N—$(R^9)$-piperidinyl;

$R^2$ is hydrogen, halo, alkyl, or alkenyl;

$R^3$ is hydrogen, halo, alkyl, or alkenyl;

or $R^2$ and $R^3$ taken together is $N(R^{13})N=C(R^4)$;

$R^4$ is hydrogen, halo, alkyl, or alkenyl;

$NR^5R^6$ taken together is

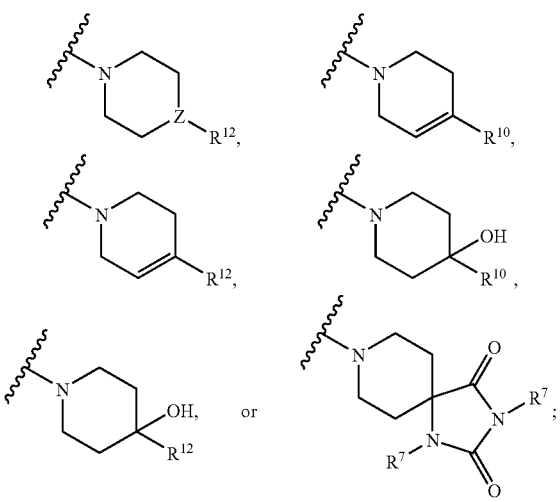

$R^7$ is hydrogen or alkyl;

$R^8$ is hydrogen or alkyl;

or $NR^7R^8$ taken together is selected from the group consisting of pyrrolidinyl, piperidinyl, N—$(R^9)$-piperazinyl, morpholinyl, and thiomorpholinyl;

$R^9$ is hydrogen, alkyl, alkylcarbonyl, or alkoxycarbonyl;

$R^{10}$ is phenyl, naphthyl, pyridinyl, pyridinyl N-oxide, quinolinyl, quinolinyl N-oxide, isoquinolinyl, or isoquinolinyl N-oxide, and is substituted with 0-2 substituents selected from the group consisting of halo, alkyl, haloalkyl, alkoxy, hydroxy, and phenyl;

or $R^{10}$ is selected from the group consisting of

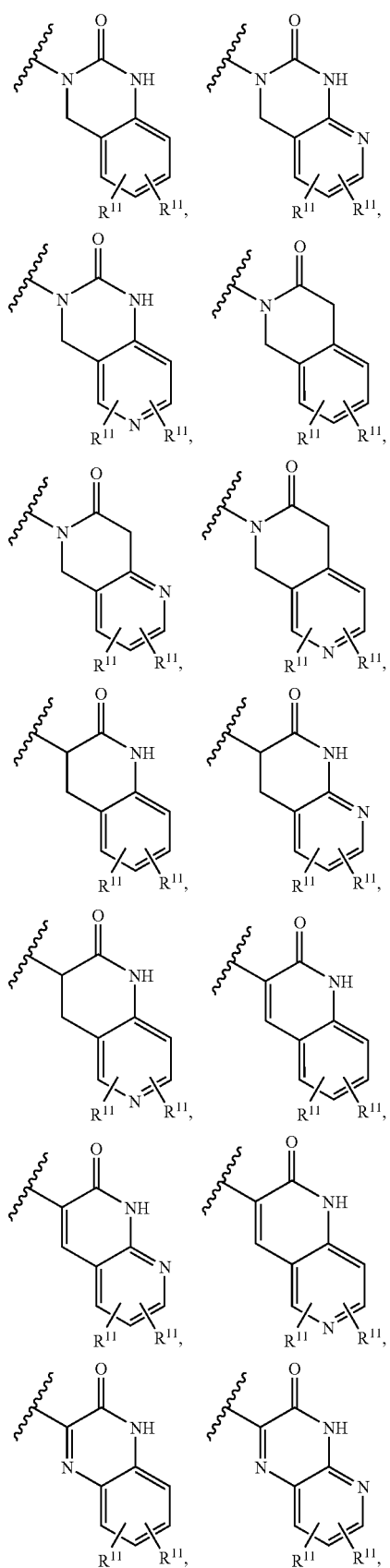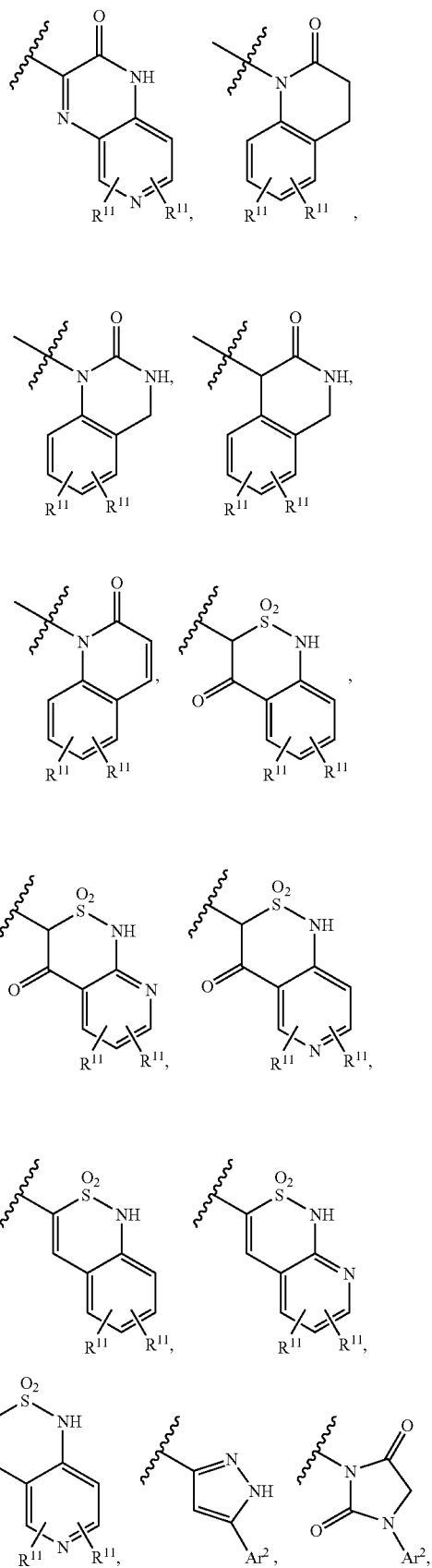

-continued

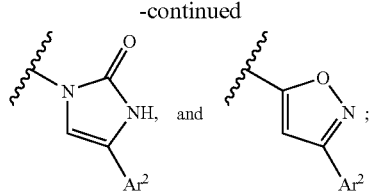

$R^{11}$ is hydrogen, halo, alkyl, haloalkyl, or alkoxy;
$R^{12}$ is selected from the group consisting of

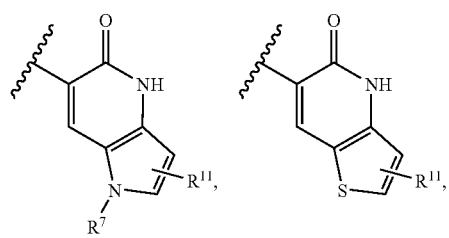

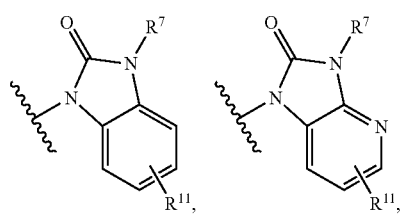

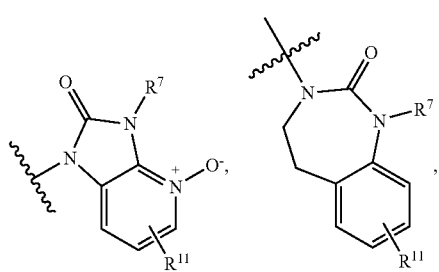

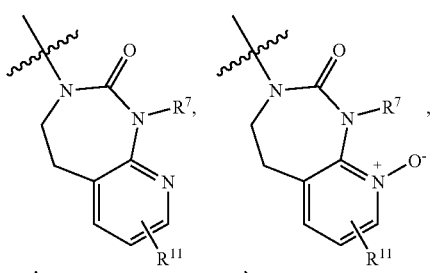

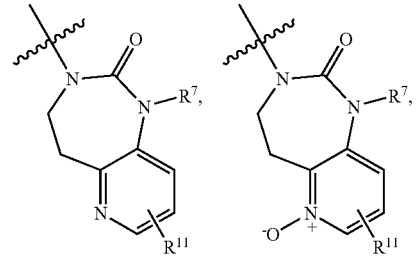

-continued

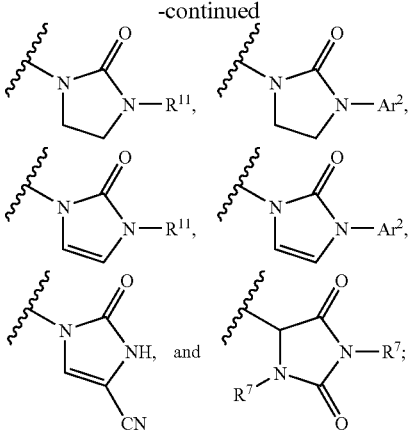

$R^{13}$ is hydrogen, alkyl, alkenyl, alkoxyalkyl, or benzyl;
$Ar^1$ is phenyl, naphthyl, pyridinyl, or imidazolyl, and is substituted with 0-2 substituents selected from the group consisting of halo, alkyl, and haloalkyl;
$Ar^2$ is phenyl, naphthyl, or pyridinyl, and is substituted with 0-2 substituents selected from the group consisting of halo, alkyl, and haloalkyl;
X—Y is aminocarbonyl, oxycarbonyl, methylenecarbonyl, ethylene, or amino(cyano)iminomethyl;
Z is N or CH; and
the carbon bearing the asterisk is either the (S) configuration or the (R) configuration;
or a pharmaceutically acceptable salt thereof.

2. A compound of formula II

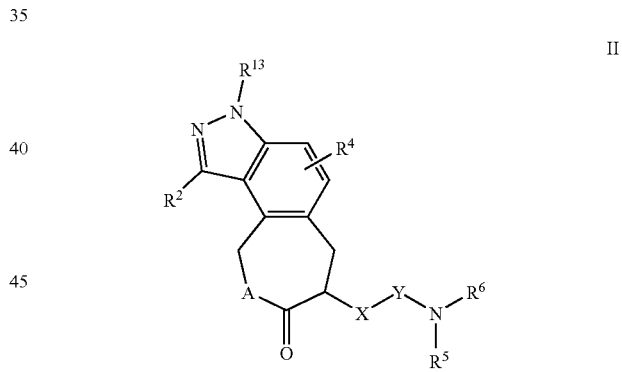

II where:
A is O or $NR^1$;
$R^1$ is alkyl, alkenyl, cycloalkyl, $C_{5-7}$cycloalkenyl, (cycloalkyl)alkyl, haloalkyl, alkoxyalkyl, $(Ar^1)$alkyl, $(NR^7R^8)$alkyl, N—$(R^9)$-pyrrolidinyl or N—$(R^9)$-piperidinyl;
$R^2$ is hydrogen, halo, alkyl, or alkenyl;
$R^4$ is hydrogen, halo, alkyl, or alkenyl;
$NR^5R^6$ taken together is

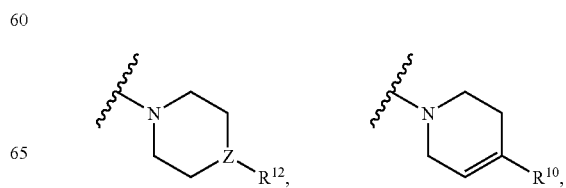

-continued

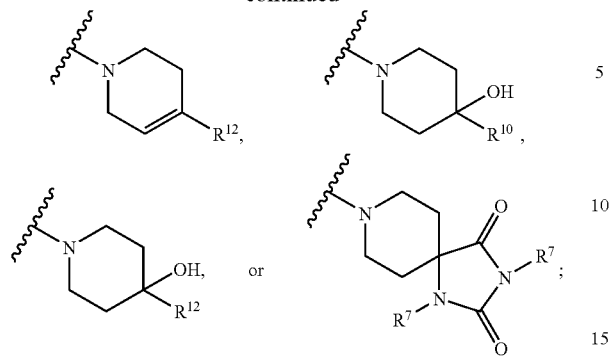

R[7] is hydrogen or alkyl;
R[8] is hydrogen or alkyl;
or NR[7]R[8] taken together is selected from the group consisting of pyrrolidinyl, piperidinyl, N—(R[9])-piperazinyl, morpholinyl, and thiomorpholinyl;
R[9] is hydrogen, alkyl, alkylcarbonyl, or alkoxycarbonyl;
R[10] is phenyl, naphthyl, pyridinyl, pyridinyl N-oxide, quinolinyl, quinolinyl N-oxide, isoquinolinyl, or isoquinolinyl N-oxide, and is substituted with 0-2 substituents selected from the group consisting of halo, alkyl, haloalkyl, alkoxy, hydroxy, and phenyl;
or R[10] is selected from the group consisting of

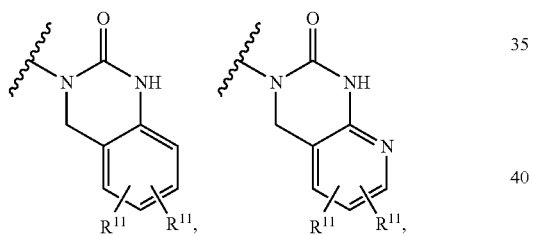

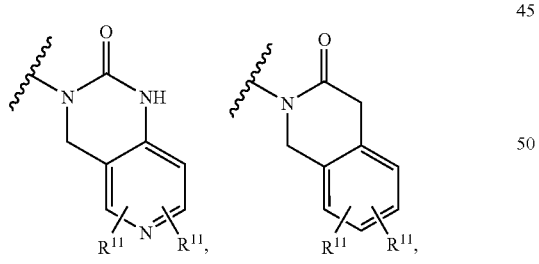

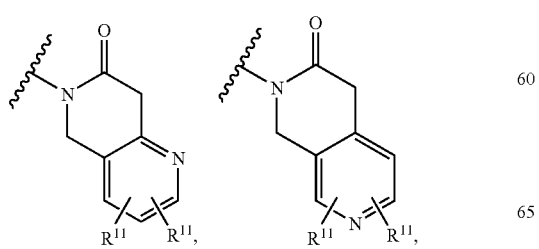

-continued

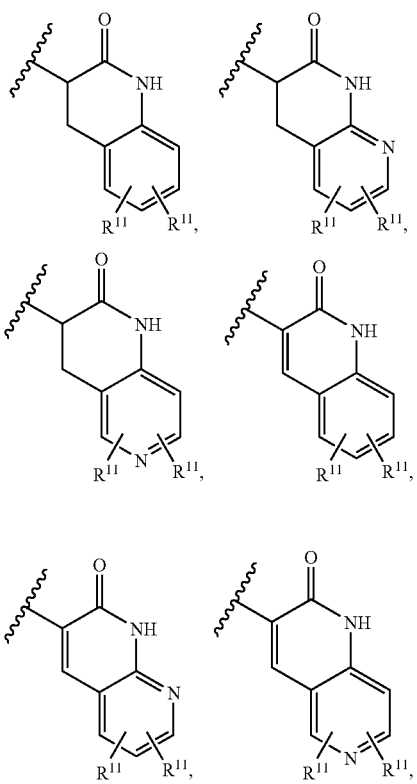

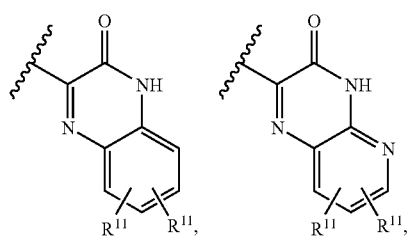

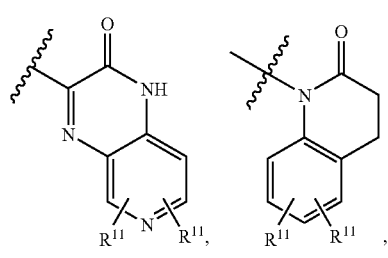

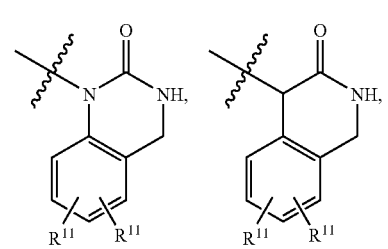

-continued
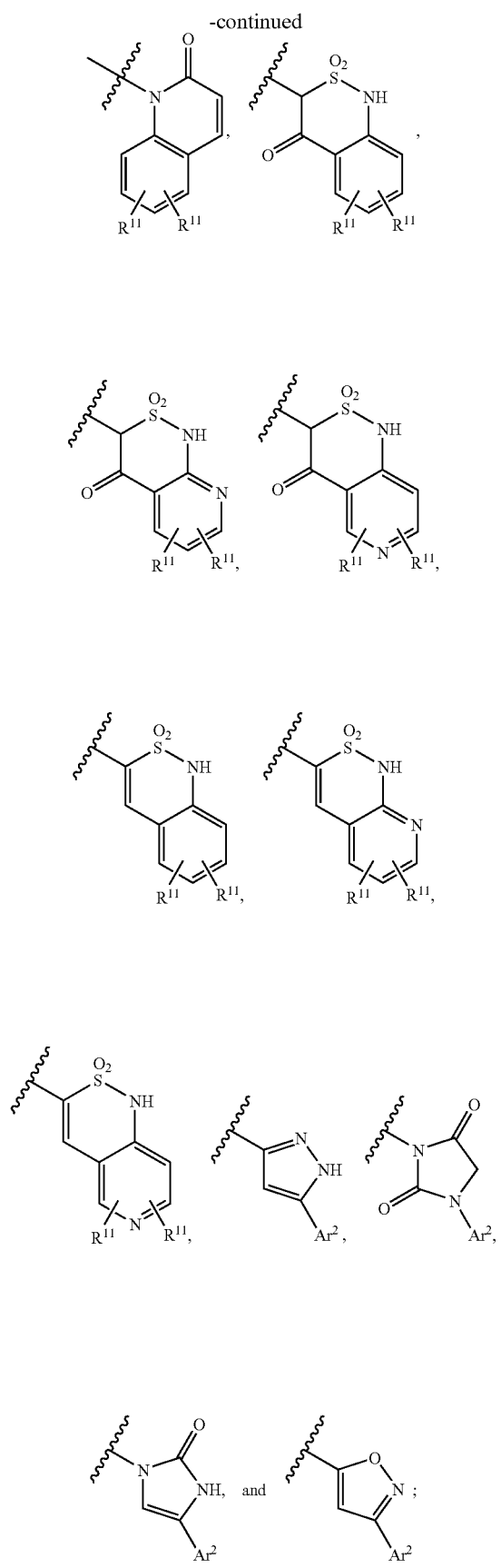
$R^{11}$ is independently hydrogen, halo, alkyl, haloalkyl, or alkoxy;
$R^{12}$ is selected from the group consisting of
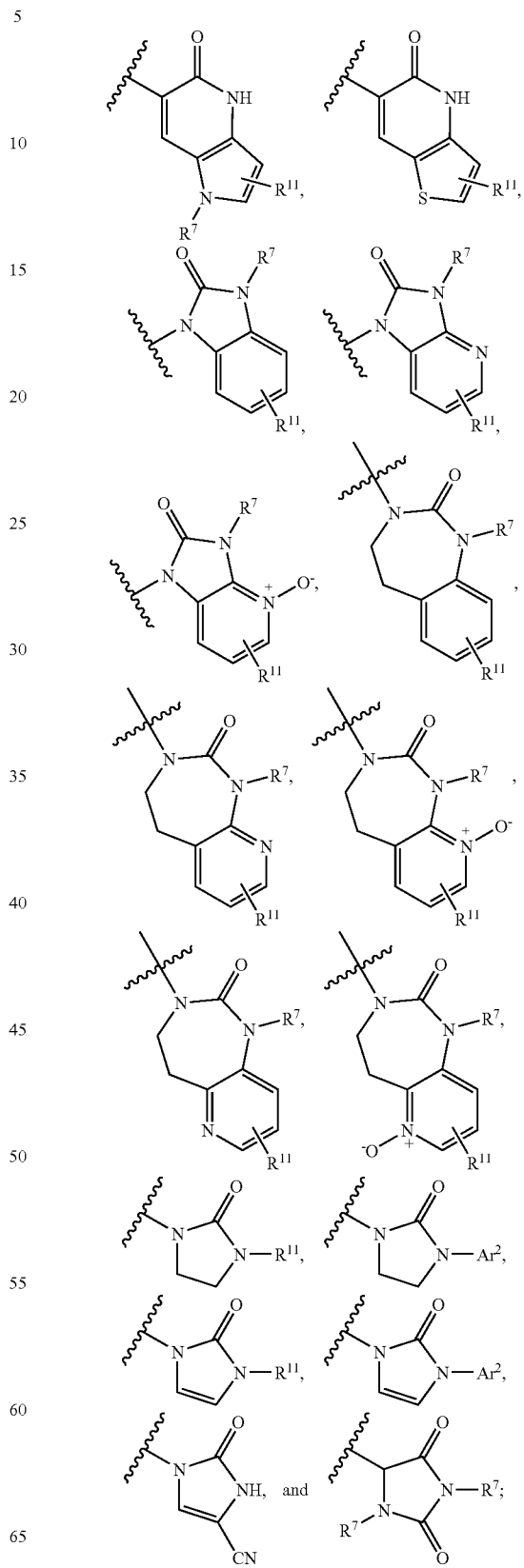

R¹³ is hydrogen, alkyl, alkenyl, alkoxyalkyl, or benzyl;
Ar¹ is phenyl, naphthyl, pyridinyl, or imidazolyl, and is substituted with 0-2 substituents selected from the group consisting of halo, alkyl, and haloalkyl;
Ar² is phenyl, naphthyl, or pyridinyl, and is substituted with 0-2 substituents selected from the group consisting of halo, alkyl, and haloalkyl;
X—Y is aminocarbonyl, oxycarbonyl, methylenecarbonyl, ethylene, or amino(cyano)iminomethyl;
Z is N or CH; and
the carbon bearing the asterisk is either the (S) configuration or the (R) configuration;
or a pharmaceutically acceptable salt thereof.

3. A compound of claim 2 where R¹ is alkyl or haloalkyl.
4. A compound of claim 2 where R² is 2,2,2-trifluoroethyl.
5. A compound of claim 2 where NR⁵R⁶ taken together is

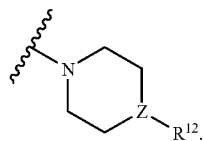

6. A compound of claim 2 selected from the group consisting of
(S)-4-chloro-7-(2-oxo-2-(4-(2-oxo-1,2,4,5-tetrahydrobenzo[d][1,3]diazepin-3-yl)piperidin-1-yl)ethyl)-9-(2,2,2-trifluoroethyl)-6,7,9,10-tetrahydroazepino[3,4-e]indazol-8(3H)-one;
(S)-4-chloro-7-(2-oxo-2-(4-(2-oxo-3-phenyl-2,3-dihydroimidazol-1-yl)piperidin-1-yl)ethyl)-9-(2,2,2-trifluoroethyl)-6,7,9,10-tetrahydroazepino[3,4-e]indazol-8(3H)-one;
(S)-4-chloro-7-(2-oxo-2-(4-(2-oxo-2,3-dihydroimidazol-1-yl)piperidin-1-yl)ethyl)-9-(2,2,2-trifluoroethyl)-6,7,9,10-tetrahydroazepino[3,4-e]indazol-8(3H)-one;
(S)-4-chloro-7-(2-oxo-2-(4-(2-oxo-2,3-dihydrobenzo[d]imidazol-1-yl)piperidin 1-yl)ethyl)-9-(2,2,2-trifluoroethyl)-6,7,9,10-tetrahydroazepino[3,4-e]indazol-8(3H)-one;
(S)-1-(1-(2-(4-chloro-8-oxo-9-(2,2,2-trifluoroethyl)-3,6,7,8,9,10-hexahydroazepino[3,4-e]indazol-7-yl)acetyl)piperidin-4-yl)-2-oxo-2,3-dihydro-1H-imidazole-4-carbonitrile;
(S)-4-chloro-7-(2-(4-(3-(2-fluorophenyl)-2-oxo-2,3-dihydroimidazol-1-yl)piperidin-1-yl)-2-oxoethyl)-9-(2,2,2-trifluoroethyl)-6,7,9,10-tetrahydroazepino[3,4-e]indazol-8(3H)-one;
(S)-4-chloro-7-(2-(4-(3-(2-fluorophenyl)-2-oxoimidazolidin-1-yl)piperidin-1-yl)-2-oxoethyl)-9-(2,2,2-trifluoroethyl)-6,7,9,10-tetrahydroazepino[3,4-e]indazol-8(3H)-one;
(S)-4-chloro-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one;
(S)-4-chloro-7-(2-oxo-2-(4-oxy(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one;
(S)-1,4-dibromo-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one;
(S)-1,4-dibromo-7-(2-oxo-2-(4-(2-oxo-1,2,4,5-tetrahydrobenzo[d][1,3]diazepin-3-yl)piperidin-1-yl)ethyl)-9-(2,2,2-trifluoroethyl)-6,7,9,10-tetrahydroazepino[3,4-e]indazol-8(3H)-one;
(S)-4-chloro-7-(2-(4-(9-fluoro-2-oxo-1,2,4,5-tetrahydrobenzo[d][1,3]diazepin-3-yl)piperidin-1-yl)-2-oxoethyl)-9-(2,2,2-trifluoroethyl)-6,7,9,10-tetrahydroazepino[3,4-e]indazol-8(3H)-one;
(S)-4-chloro-7-(2-oxo-2-(4-(2-oxo-1,2,4,5-tetrahydropyrido[2,3-d][1,3]diazepin-3-yl)piperidin-1-yl)ethyl)-9-(2,2,2-trifluoroethyl)-6,7,9,10-tetrahydroazepino[3,4-e]indazol-8(3H)-one;
(S)-4-chloro-7-(2-oxo-2-(4-(2-oxo-1,2,4,5-tetrahydropyrido[3,2-d][1,3]diazepin-3-yl)piperidin-1-yl)ethyl)-9-(2,2,2-trifluoroethyl)-6,7,9,10-tetrahydroazepino[3,4-e]indazol-8(3H)-one;
(S)-4-chloro-7-(2-(4-(4-fluoro-2-oxo-2,3-dihydrobenzo[d]imidazol-1-yl)piperidin-1-yl)-2-oxoethyl)-9-(2,2,2-trifluoroethyl)-6,7,9,10-tetrahydroazepino[3,4-e]indazol-8(3H)-one;
(S)-4-bromo-1-chloro-7-(2-oxo-2-(4-(2-oxo-1,2,4,5-tetrahydrobenzo [d][1,3]diazepin-3-yl)piperidin-1-yl)ethyl)-9-(2,2,2-trifluoroethyl)-6,7,9,10-tetrahydroazepino[3,4-e]indazol-8(3H)-one;
(S)-4-bromo-1-chloro-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one;
(S)-1,4-dichloro-7-(2-oxo-2-(4-(2-oxo-1,2,4,5-tetrahydrobenzo[d][1,3]diazepin-3-yl)piperidin-1-yl)ethyl)-9-(2,2,2-trifluoroethyl)-6,7,9,10-tetrahydroazepino[3,4-e]indazol-8(3H)-one;
(S)-1,4-dichloro-7-(2-oxo-2-(4-(2-oxo-2,3-dihydroimidazo[4,5-b]pyridin-1-yl)piperidin-1-yl)ethyl)-9-(2,2,2-trifluoroethyl)-6,7,9,10-tetrahydroazepino[3,4-e]indazol-8(3H)-one;
(S)-1,4-dichloro-7-(2-oxo-2-(4-(2-oxo-1,2,4,5-tetrahydrobenzo[d][1,3]diazepin-3-yl)piperidin-1-yl)ethyl)-9-(2-(piperidin-1-yl)ethyl)-6,7,9,10-tetrahydroazepino[3,4-e]indazol-8(3H)-one;
(S)-1,4-dichloro-7-(2-oxo-2-(4-(2-oxo-2,3-dihydroimidazo[4,5-b]pyridin-1-yl)piperidin-1-yl)ethyl)-9-(2-(piperidin-1-yl)ethyl)-6,7,9,10-tetrahydroazepino[3,4-e]indazol-8(3H)-one;
(S)-7-chloro-4-(2-(4-(1-methyl-5-oxo-4,5-dihydro-1H-pyrrolo[3,2-b]pyridin-6-yl)piperidin-1-yl)-2-oxoethyl)-2-neopentyl-1,2,4,5-tetrahydroazepino[3,4-e]indol-3(8H)-one;
(S)-6-(1-(2-(7-chloro-2-neopentyl-3-oxo-1,2,3,4,5,8-hexahydroazepino[3,4-e]indol-4-yl)acetyl)piperidin-4-yl)thieno[3,2-b]pyridin-5(4H)-one;
(S)-3-bromo-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one;
(S)-2-bromo-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one;
(S)-2-chloro-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one;
(S)-3-chloro-6-(1-(2-(4-chloro-9-neopentyl-8-oxo-3,6,7,8,9,10-hexahydroazepino[3,4-e]indazol-7-yl)acetyl)piperidin-4-yl)thieno[3,2-b]pyridin-5(4H)-one;
(S)-7-chloro-2-neopentyl-4-(2-oxo-2-(4-(5-oxo-4,5-dihydro-1H-pyrrolo[3,2-b]pyridin-6-yl)piperidin-1-yl)ethyl)-1,2,4,5-tetrahydroazepino[3,4-e]indol-3(8H)-one;

(S)-7-chloro-4-(2-(4-(6-chloro-1H-pyrrolo[2,3-b]pyridin-4-yl)-4-hydroxypiperidin-1-yl)-2-oxoethyl)-2-neopentyl-1,2,4,5-tetrahydroazepino[3,4-e]indol-3(8H)-one;

(R)-4-chloro-8-oxo-9-(2,2,2-trifluoroethyl)-3,6,7,8,9,10-hexahydroazepino[3,4-e]indazol-7-yl 4-(2-oxo-4,5-dihydro-1H-benzo[d][1,3]diazepin-3(2H)-yl)piperidine-1-carboxylate;

(R)-4-chloro-8-oxo-9-(2,2,2-trifluoroethyl)-3,6,7,8,9,10-hexahydroazepino[3,4-e]indazol-7-yl 4-(2-oxo-2,3-dihydro-1H-imidazo[4,5-b]pyridin-1-yl)piperidine-1-carboxylate;

(S)-4-chloro-7-(2-oxo-2-(2'-oxo-2',3'-dihydro-1'H-spiro[piperidine-4,4'-quinazoline]-1-yl)ethyl)-9-(2,2,2-trifluoroethyl)-6,7,9,10-tetrahydroazepino[3,4-e]indazol-8(3H)-one;

5-(1-(2-((S)-4-chloro-8-oxo-9-(2,2,2-trifluoroethyl)-3,6,7,8,9,10-hexahydroazepino[3,4-e]indazol-7-yl)acetyl)piperidin-4-yl)imidazolidine-2,4-dione;

(S)-8-(2-(4-chloro-8-oxo-9-(2,2,2-trifluoroethyl)-3,6,7,8,9,10-hexahydroazepino[3,4-e]indazol-7-yl)acetyl)-1,3,8-triazaspiro[4.5]decane-2,4-dione;

(S)-5-chloro-2-(1-(2-(4-chloro-8-oxo-9-(2,2,2-trifluoroethyl)-3,6,7,8,9,10-hexahydroazepino[3,4-e]indazol-7-yl)acetyl)-1,2,3,6-tetrahydropyridin-4-yl)benzonitrile;

(S)-4-Chloro-3-methyl-7-(2-oxo-2-(4-(2-oxo-2,3-dihydro-1H-imidazo[4,5-b]pyridine-1-yl)piperidin-1-yl)ethyl)-9-(2,2,2-trifluoroethyl)-6,7,9,10-tetrahydroazepino[3,4-e]indazol-8(3H)-one;

(S)-4-Chloro-3-ethyl-7-(2-oxo-2-(4-(2-oxo-2,3-dihydro-1H-imidazo[4,5-b]pyridine-1-yl)piperidin-1-yl)ethyl)-9-(2,2,2-trifluoroethyl)-6,7,9,10-tetrahydroazepino[3,4-e]indazol-8(3H)-one;

(S)-3-Benzyl-4-chloro-7-(2-oxo-2-(4-(2-oxo-2,3-dihydro-1H-imidazo[4,5-b]pyridine-1-yl)piperidin-1-yl)ethyl)-9-(2,2,2-trifluoroethyl)-6,7,9,10-tetrahydroazepino[3,4-e]indazol-8(3H)-one;

(S)-4-Chloro-3-methyl-7-(2-oxo-2-(4-(2-oxo-4,5-dihydro-1H-benzo[d][1,3]diazepin-3 (2H)-yl)piperidin-1-yl)ethyl)-9-(2,2,2-trifluoroethyl)-6,7,9,10-tetrahydroazepino[3,4-e]indazol-8(3H)-one;

(S)-4-Chloro-3-propyl-7-(2-oxo-2-(4-(2-oxo-4,5-dihydro-1H-benzo[d][1,3]diazepin-3(2H)-yl)piperidin-1-yl)ethyl)-9-(2,2,2-trifluoroethyl)-6,7,9,10-tetrahydroazepino[3,4-e]indazol-8(3H)-one;

(S)-4-chloro-3-(methoxymethyl)-7-(2-oxo-2-(4-(2-oxo-4,5-dihydro-1H-benzo[d][1,3]diazepin-3(2H)-yl)piperidin-1-yl)ethyl)-9-(2,2,2-trifluoroethyl)-6,7,9,10-tetrahydroazepino[3,4-e]indazol-8(3H)-one; and (S)-4-chloro-3-(2-methoxyethyl)-7-(2-oxo-2-(4-(2-oxo-4,5-dihydro-1H-benzo[d][1,3]diazepin-3(2H)-yl)piperidin-1-yl)ethyl)-9-(2,2,2-trifluoroethyl)-6,7,9,10-tetrahydroazepino[3,4-e]indazol-8(3H)-one;

or a pharmaceutically acceptable salt thereof.

7. A compound of 2 where the carbon bearing the asterisk is of the (S) configuration.

8. A composition comprising a compound of claim 1, or a pharmaceutically acceptable salt thereof, and a pharmaceutically acceptable adjuvant, carrier, or diluent.

9. A method of treating migraine comprising the administration of a therapeutically effective amount of a compound of claim 1, or a pharmaceutically acceptable salt thereof, to a patient.

* * * * *